United States Patent
Bailey et al.

(10) Patent No.: US 7,470,715 B2
(45) Date of Patent: Dec. 30, 2008

(54) ESTROGEN MODULATORS

(75) Inventors: Simon Bailey, San Diego, CA (US); Stephen Douglas Barrett, Hartland, MI (US); Raj Kumar Raheja, Ann Arbor, MI (US); Veerabahu Shanmugasundaram, Novi, MI (US)

(73) Assignee: Pfizer Inc., New York, NY (US)

(*) Notice: Subject to any disclaimer, the term of this patent is extended or adjusted under 35 U.S.C. 154(b) by 11 days.

(21) Appl. No.: 11/612,582

(22) Filed: Dec. 19, 2006

(65) Prior Publication Data

US 2007/0149564 A1 Jun. 28, 2007

Related U.S. Application Data

(60) Provisional application No. 60/805,233, filed on Jun. 20, 2006, provisional application No. 60/752,780, filed on Dec. 22, 2005.

(51) Int. Cl.
*C07D 261/02* (2006.01)
*A61K 31/42* (2006.01)

(52) U.S. Cl. .................. 514/378; 514/341; 514/183

(58) Field of Classification Search ........... 514/378, 514/183, 341
See application file for complete search history.

(56) References Cited

U.S. PATENT DOCUMENTS

| | | | |
|---|---|---|---|
| 4,933,464 A | 6/1990 | Markofsky | |
| 5,151,441 A | 9/1992 | Mueller et al. | |
| 5,256,632 A | 10/1993 | Wolf et al. | |
| 5,256,666 A | 10/1993 | Mueller et al. | |
| 5,580,893 A | 12/1996 | Ishihara et al. | |
| 5,859,257 A | 1/1999 | Talley | |
| 5,902,719 A | 5/1999 | Baba et al. | |
| 6,136,839 A | 10/2000 | Isakson et al. | |
| 6,255,489 B1 | 7/2001 | Klintz et al. | |
| 6,436,923 B1 | 8/2002 | Bhagwat et al. | 514/213.01 |
| 6,657,093 B2 | 12/2003 | Meudt et al. | |
| 6,743,815 B2 | 6/2004 | Huebner et al. | 514/378 |
| 6,869,969 B2 | 3/2005 | Huebner et al. | 514/378 |
| 2002/0117662 A1 | 8/2002 | Nil | |
| 2003/0171412 A1 | 9/2003 | Malamas et al. | 514/367 |
| 2003/0207927 A1 | 11/2003 | Malamas et al. | 514/373 |
| 2003/0220384 A1 | 11/2003 | Seibert et al. | |
| 2003/0225155 A1 | 12/2003 | Fernandez-Pol | |
| 2004/0102498 A1 | 5/2004 | Heubner et al. | |
| 2005/0009799 A1 | 1/2005 | Jain et al. | 514/179 |
| 2005/0256210 A1 | 11/2005 | Olsson et al. | 514/734 |

FOREIGN PATENT DOCUMENTS

| | | |
|---|---|---|
| CA | 2372912 A1 | 4/1998 |
| CN | 1117080 A | 1/1995 |
| EP | 0339899 A2 | 11/1989 |
| EP | 0378111 B1 | 7/1990 |
| EP | 0480659 B1 | 4/1992 |
| EP | 0611760 A1 | 8/1994 |
| EP | 0707000 A1 | 4/1996 |
| EP | 1051994 A2 | 11/2000 |
| EP | 1064948 A2 | 1/2001 |
| EP | 1064964 A2 | 1/2001 |
| EP | 1251126 A2 | 10/2002 |
| EP | 1577288 | 9/2005 |
| GB | 012182 | 2/1973 |
| GB | 2201672 A | 12/1986 |
| JO | 2042061 A | 8/1988 |
| JO | 2042062 A | 8/1988 |
| JP | 63108339 A | 10/1986 |
| JP | 04338387 A | 5/1991 |
| JP | 06236057 A | 2/1993 |
| JP | 07267931 A | 3/1994 |
| JP | 07287409 A | 4/1994 |
| JP | 08073436 A | 7/1994 |
| JP | 11124306 A | 10/1997 |
| JP | 2001158787 A | 9/1999 |
| JP | 2001302662 A | 4/2000 |
| WO | WO92/01679 A1 | 2/1992 |
| WO | WO9417059 A1 | 8/1994 |
| WO | WO9551896 A1 | 5/1995 |
| WO | WO96/03385 A1 | 2/1996 |
| WO | WO9612706 A1 | 5/1996 |
| WO | WO9633994 A1 | 10/1996 |
| WO | WO97/14679 A2 | 4/1997 |
| WO | WO97/29774 A1 | 8/1997 |
| WO | WO97/38986 A1 | 10/1997 |
| WO | WO00/19994 A1 | 4/2000 |
| WO | WO01/40223 A2 | 6/2001 |
| WO | WO01/81333 A2 | 11/2001 |
| WO | 0241835 | 5/2002 |
| WO | 02079163 | 10/2002 |
| WO | WO03/053948 A1 | 7/2003 |
| WO | WO03/055860 A1 | 7/2003 |
| WO | WO03057215 A1 | 7/2003 |
| WO | 04005314 | 1/2004 |
| WO | 04026887 | 4/2004 |
| WO | 04073610 | 9/2004 |
| WO | 04073612 | 9/2004 |
| WO | 05033056 | 4/2005 |

OTHER PUBLICATIONS

Gendimenico, G.J., et al., "Topical estrogens: their effects on connective tissue synthesis in hairless mouse skin", *Arch. Dermatol. Res.*, vol. 294, pp. 231-236, Jun. 7, 2002 (XP002436331).

Patriarca, Marisa T., Effects of topical estradiol on the facial skin collagen of postmenopausal women under oral hormone therapy: A pilot study, European Journal of Obstetrics & Gynecology and Reporoductive Biology, 130(2007) 202-205.

Demyttenaere-Kovatcheva, et al., J. Med. Chem., vol. 48, pp. 7628-7636 (2005).

Waldo, et al., Organic Letters, vol. 7, No. 23, pp. 5203-5205 (2005).

*Primary Examiner*—Ardin Marschel
*Assistant Examiner*—Zohreh Vakili
(74) *Attorney, Agent, or Firm*—Gregg C. Benson; J. Michael Dixon

(57) ABSTRACT

The present application is directed to a new class of isoxazoles and their use as estrogen modulators.

5 Claims, No Drawings

ESTROGEN MODULATORS

CROSS REFERENCE TO RELATED APPLICATION

This application claims priority to U.S. Provisional Application Ser. Nos. 60/752,780, filed Dec. 22, 2005 and U.S. Provisional Application 60/805,233, filed Jun. 20, 2006, the contents of each which are hereby incorporated by reference.

FIELD OF THE INVENTION

This application is directed to a new class of isoxazole derivatives, to their use as estrogen modulators, and to pharmaceutical compositions containing these compounds.

BACKGROUND OF THE INVENTION

Human skin consists of two major layers, the dermis and the epidermis. The dermis is the thicker inner layer. It is the layer which provides strength, elasticity and thickness to the skin. The main cell type of the dermis is the fibroblast, which is responsible for synthesis and secretion of dermal matrix components such as collagen, elastin and glycosaminoglycans. Collagen provides strength, elastin the elasticity, and glycosaminoglycans the moistness and plumpness of the skin. With ageing, the thickness of the dermal layer is reduced and this is believed to be partially responsible for the formation of wrinkles in ageing skin.

The top layer of human skin, the epidermis, provides a barrier to the external environment and is composed of many different cell types including keratinocytes, melanocytes and langerhan cells. Keratinocytes are the major cell type of the epidermis (75-80% of the total number of cells in the human epidermis).

Changes in the skin associated with menopause, such as dryness, loss of elasticity, thinning, wrinkles, etc., are attributed to lack of estrogen production. Estrogen therapy prevents, slows down, or reverses many of the changes associated with ageing. Some of the effects of estrogen on the skin include: increase in skin thickness, disappearance of fine wrinkles, increase of the mitotic rate of the epidermis, stimulation of collagen turnover, increases in the production of hyaluronic acid, and synthesis of glycosaminoglycans by the fibroblasts.

While topical estrogen will alleviate wrinkles and other problems associated with aging, such therapy is typically inappropriate due to systemic absorption of the hormone and the corresponding pharmacological effects. A need in the art exists for synthetic estrogens suitable for topical administration to alleviate wrinkles.

SUMMARY OF THE INVENTION

In accordance with the present invention a new class of estrogen modulators has been discovered. These estrogen modulators, their salts and solvates, may be represented by Formula I below:

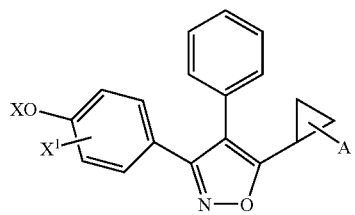

I in which:
X is represented by hydrogen, $X^1$ is absent, or is represented by a substituent selected from the group consisting of halogen, $C_1$-$C_6$ alkyl, $C_1$-$C_6$ alkoxy, $C_1$-$C_6$ thioalkyl, trifluoromethyl, hydroxy, amino, and cyano;

A is represented by a substituent selected from the group consisting of:
  i) hydrogen,
  ii) cyano,
  iii) ($C_1$-$C_6$)alkyl, optionally substituted,
  iv) ($C_3$-$C_{10}$)cycloalkyl, optionally substituted,
  v) ($C_3$-$C_{10}$) cycloalkyl($C_1$-$C_6$)alkyl, in which the alkyl and cycloalkyl moieties may each be optionally substituted,
  vi) ($C_6$-$C_{10}$)aryl optionally substituted,
  vii) ($C_6$-$C_{10}$)aryl ($C_1$-$C_6$)alkyl, in which the alkyl and aryl moieties may each be optionally substituted,
  viii) heteroaryl, optionally substituted,
  ix) heteroaryl($C_1$-$C_6$)alkyl, in which the heteroaryl and alkyl moieties may each be optionally substituted,
  x) heterocyclic, optionally substituted,
  xi) heterocyclic($C_1$-$C_6$)alkyl, in which the alkyl and heterocyclic moieties may each be substituted,
  xii) $(CH_2)_z Y^1—Y^2$,
  xiii) $(CH_2)_z—S(O)_t R$,
  xiv) $(CH_2)_z—OR$,
  xv) $(CH_2)_z—NRR^1$,
  xvi) $(CH_2)_z—COOR$,
  xvii) $(CH_2)_z OCOR$, and;
  xviii) $(CH_2)_z COR$, $Y^1$ and $Y^2$ are each independently represented by a substituent selected from the group consisting of:
  i) ($C_3$-$C_{10}$)cycloalkyl, optionally substituted,
  ii) ($C_6$-$C_{10}$)aryl optionally substituted,
  iii) heteroaryl, optionally substituted, and;
  iv) heterocyclic, optionally substituted, z is represented by an integer from 0 to 5, t is represented by the integer 0, 1, or 2, $R^1$ is represented by hydrogen or ($C_1$-$C_6$)alkyl, optionally substituted, R is represented by a substituent selected from the group consisting of:
  i) hydrogen,
  ii) ($C_1$-$C_6$)alkyl, optionally substituted,
  iii) ($C_3$-$C_{10}$)cycloalkyl, optionally substituted,
  iv) ($C_3$-$C_{10}$) cycloalkyl($C_1$-$C_6$)alkyl, in which the alkyl and cycloalkyl moieties may each be optionally substituted,
  v) ($C_6$-$C_{10}$)aryl optionally substituted,
  vi) ($C_6$-$C_{10}$)aryl ($C_1$-$C_6$)alkyl, in which the alkyl and aryl moieties may each be optionally substituted,
  vii) heteroaryl, optionally substituted,
  viii) heteroaryl($C_1$-$C_6$)alkyl, in which the heteroaryl and alkyl moieties may each be optionally substituted,
  ix) heterocyclic, optionally substituted,
  x) heterocyclic($C_1$-$C_6$)alkyl, in which the alkyl and heterocyclic moieties may each be substituted, and;
  xi) ($C_1$-$C_6$)alkylene-$Y^3$—($C_1$-$C_6$)alkyl, in which the alkylene and alkyl moieties may be substituted;
and;
$Y^3$ is represented by O or S.

The compounds of Formula I are estrogen receptor modulators. The compounds will cause a biological effect by interacting with the estrogen receptor. Typically, the compounds will act as agonists. In selected embodiments they will act as partial agonists, tissue selective agonists, or antagonists. As estrogen receptor modulators, the compounds can be used to treat, or alleviate, conditions associated with inappropriate, or inadequate, activation of the estrogen receptor.

Examples of such conditions include uterine cancer, adjuvant breast cancer, breast disorder, male breast cancer, migraine, incontinence, vaginal atrophy, bladder infection, senile gynecomastia, diabetes, hypoglycemia, melanoma, impotence, inflammatory bowel disease, CNS and GI disorders caused by an excess of tackykinins, decreased libido, immune system disorders, decreased fertility, pulmonary hypertensive disease, autoimmune disease, Turner's syndrome, alopecia, hirsutism, disorders related to an excess of neurokinin, obsessive-compulsive disorders including smoking and alcohol abuse. Alternatively, the compounds can be used as estrogen replacement therapy for females experiencing menopause. The compounds may also be utilized in postmenopausal females to stimulate bone mass, thereby alleviating osteoporosis. The compounds may also be combined with a synthetic progesterone and utilized as part of a birth control regimen as is known in the art.

Typically, the compounds will be used topically to alleviate wrinkles, promote wound healing, decrease sebum secretion, alleviate photo damaged skin, treat acne, etc.

The invention is also directed to pharmaceutical compositions containing at least one of the compounds, in an amount effective to modulate activation of the estrogen receptor. In a further embodiment, the invention is directed to a kit containing at least one of the compounds packaged for retail distribution, in association with instructions advising the consumer on how to use the compound to alleviate a condition associated with inappropriate activation of the estrogen receptor. An additional embodiment is directed to the use of a compound as a diagnostic agent to detect inappropriate activation of the estrogen receptor.

DETAILED DESCRIPTION OF THE INVENTION

The headings within this document are only being utilized expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "halogen" refers to a chlorine, fluorine or bromine atom.

b. "$C_1$-$C_6$ alkyl" refers to a branched or straight chained alkyl group containing from 1 to 6 carbon atoms, such as methyl, ethyl, n-propyl, isopropyl, n-butyl, isobutyl, pentyl, etc.

c. "$C_1$-$C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 6 hydrogen atoms are replaced by a substituent selected from the group consisting of halogen, haloalkyl, hydroxy, thiol, cyano, and $NR^2R^3$ in which $R^2$ and $R^3$ are each independently represented by hydrogen or $C_1$-$C_6$ alkyl.

d. "$C_1$-$C_6$alkylene, optionally substituted" refers to a branched or straight chained alkylene group containing from 1 to 6 carbon atoms, such as methylene, ethylene, n-propylene, isopropylene, n-butylene, isobutylene, hexylene, etc. Such an alkylene group may be optionally substituted, in which up to 6 hydrogen atoms are replaced by a substituent selected from the group consisting of halogen, haloalkyl, hydroxy, thiol, cyano, and $NR^2R^3$, in which $R^2$ and $R^3$ are as defined above.

e. "hydroxyalkyl" refers to a branched or straight chained alkyl group containing from 1 to 6 carbon atoms, in which at least one hydrogen atom is replaced with a hydroxyl group (i.e. —OH). Examples of suitable hydroxyalkyl's include hydroxymethyl, 1-hydroxy-ethyl, 2-hydroxy-ethyl, 2-hydroxy-propyl, 5-hydroxy-hexyl, 3-hydroxy-isopropyl, 3-hydroxy-isobutyl, etc.

f. "haloalkyl" refers to a branched or straight chained alkyl group containing from 1 to 6 carbon atoms, in which at least one hydrogen atom is replaced with a halogen (i.e. $C_1$-$C_6$ haloalkyl). Examples of suitable haloalkyl's include chloromethyl, difluoromethyl, trifluoromethyl, 1-fluoro-2-chloro-ethyl, 5-fluoro-hexyl, 3-difluoro-isopropyl, 3-chloro-isobutyl, etc.

g. "($C_1$-$C_2$)alkyl substituted with one or more halogen atoms" refers to a straight chained alkyl group containing 1 or 2 carbon atoms, i.e., methyl or ethyl in which at least one hydrogen atom is replaced with a halogen (i.e. for example trifluromethyl, dichloromethyl, etc.).

h. "($C_1$-$C_2$)alkoxy substituted with one or more halogen atoms" refers to a straight chained alkoxy group containing 1 or 2 carbon atoms, i.e., methoxy or ethoxy in which at least one hydrogen atom is replaced with a halogen (i.e. for example trifluoromethoxy, difluromethoxy, etc.)

i. "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc.

j. "haloalkoxy" refers to a branched or straight chained alkoxy group containing from 1 to 6 carbon atoms, in which at least one hydrogen atom is replaced with a halogen (i.e. $C_1$-$C_6$ haloalkoxy). Examples of suitable haloalkoxy's include chloromethoxy, difluoromethoxy, trifluoromethoxy, 1-fluoro-2-chloro-ethoxy, 5-fluoro-hexoxy, 3-difluoro-isopropoxy, 3-chloro-isobutoxy, etc.

k. "$C_1$-$C_6$ thioalkyl," refers to a straight or branched chain alkyl group containing from 1 to 6 carbon atoms, that is connected to the indicated phenyl ring by a sulfur atom, (i.e. —S-methyl, —S-ethyl, S-isopropyl, etc.)

l. "($C_6$-$C_{10}$)aryl" optionally substituted means a cyclic, aromatic hydrocarbon containing from 6 to 10 carbon atoms. Examples of aryl groups include phenyl, naphthyl and biphenyl. Such an aryl moiety may be optionally substituted with up to 4 non-hydrogen substituents, each substituent is independently selected from the group consisting of halogen, nitro, cyano, hydroxy, ($C_1$-$C_6$)alkyl, ($C_1$-$C_6$)alkoxy, ($C_1$-$C_2$)alkyl substituted with one or more halogens, ($C_1$-$C_2$)alkoxy substituted with one or more halogens, —C(O)—$R^2$, —C(O)—O—$R^2$, $SR^2$, $SO_2R^2$ and $NR^2R^3$. $R^2$ and $R^3$ are each independently represented by $C_1$-$C_6$ alkyl or hydrogen. These substituents may be the same or different and may be located at any position of the ring, that is chemically permissible.

m. "($C_3$-$C_{10}$) cycloalkyl" optionally substituted refers to a saturated or partially saturated monocyclic, bicyclic or tricyclic alkyl moiety wherein each cyclic moiety has 3 to 10 carbon atoms. Examples of cycloalkyl moieties include cyclopropyl, cyclobutyl, cyclopentyl, cyclohexyl, cyclooctyl, and the like. Such a cycloalkyl group may be optionally substituted, in which up to 4 hydrogen atoms are replaced by a substituent selected from the group consisting of halogen, cyano, nitro, hydroxy, ($C_1$-$C_6$)alkyl, ($C_1$-$C_6$)alkoxy, ($C_1$-$C_2$)alkyl substituted with one or more halogens, ($C_1$-$C_2$)alkoxy substituted with one or more halogens, —C(O)—$R^2$, —C(O)—O—$R^2$, $SR^2$, $SO_2R^2$ and $NR^2R^3$, in which $R^2$ and $R^3$ are as defined above.

n. "heteroaryl" refers to an aromatic ring having one, or more, heteroatoms selected from oxygen, nitrogen and sulfur. More specifically, it refers to a 5- or 6-, membered ring containing 1, 2, 3, or 4 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. The 5-membered ring has 2 double bonds and the 6-membered ring has 3 double bonds. The term heteroaryl also includes bicyclic groups in which the heteroaryl ring is fused to a benzene ring, heterocyclic ring, a cycloalkyl ring, or another heteroaryl ring. Examples of such heteroaryl ring systems include, but are not limited to, pyrrolyl, furanyl, thienyl, imidazolyl, oxazolyl, indolyl, thiazolyl, pyrazolyl, pyridinyl, pyrimidinyl, purinyl, quinolinyl, benzofuran, tetrazole, isoquinolinyl, oxadiazolyl, thiadiazolyl, isothiazolyl, isoxazolyl, triazolyl, benzo[b]thienyl, 2-, 4-, 5-, 6-, or 7-benzoxazolyl, 7-benzimidazolyl, or benzothiazolyl.

o. "heteroaryl, optionally substituted," refers to a heteroaryl moiety as defined immediately above, in which up to 4 carbon atoms of the heteroaryl moiety may be substituted with a substituent, each substituent is independently selected from the group consisting of halogen, cyano, nitro, hydroxy, $(C_1-C_6)$alkyl, $(C_1-C_6)$alkoxy, $(C_1-C_2)$alkyl substituted with one or more halogens, $(C_1-C_2)$alkoxy substituted with one or more halogens, $SO_2R^2$—C(O)—$R^2$, —C(O)—O—$R^2$, $SR^2$, and $NR^2R^3$, in which $R^2$ and $R^3$ are as defined above.

p. "heterocycle" or "heterocyclic ring" refers to any 3- or 4-membered ring containing a heteroatom selected from oxygen, nitrogen and sulfur; or a 5-, 6-, 7-, 8-, 9-, or 10-membered ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, the 6- and 7-membered rings have 0 to 2 double bonds, and the 8, 9, or 10 membered rings may have 0, 1, 2, or 3 double bonds. The term "heterocyclic" also includes bicyclic groups in which any of the above heterocyclic rings is fused to a benzene ring, a cyclohexane or cyclopentane ring or another heterocyclic ring (for example, indolyl, quinolyl, isoquinolyl, tetrahydroquinolyl, benzofuryl, dihydrobenzofuryl or benzothienyl and the like). Heterocyclics include: pyrrolidinyl, tetrahydrofuranyl, tetrahydrothiophenyl, piperidinyl, piperazinyl, azepane, azocane, morpholinyl, isochromyl, quinolinyl, tetrahydrotriazine, tetrahydropyrazole, dihydro-oxathiol-4-yl, dihydro-1H-isoindole, tetrahydro-oxazolyl, tetrahydro-oxazinyl, thiomorpholinyl, tetrahydropyrimidinyl, dioxolinyl, octahydrobenzofuranyl, octahydrobenzimidazolyl, and octahydrobenzothiazolyl.

q. "heterocyclic, optionally substituted" refers to a heterocyclic moiety as defined immediately above, in which up to 4 carbon atoms of the heterocycle moiety may be substituted with a substituent, each substituent is independently selected from the group consisting of halogen, cyano, nitro, hydroxy, $(C_1-C_6)$alkyl, $(C_1-C_6)$alkoxy, $(C_1-C_2)$alkyl substituted with one or more halogens, $(C_1-C_2)$alkoxy substituted with one or more halogens, —C(O)—$R^2$, —C(O)—O—$R^2$, $SR^2$, $SO_2R^2$ and $NR^2R^3$, in which $R^2$ and $R^3$ are as defined above. Any nitrogen atom within such a heterocyclic ring may optionally be substituted with $(C_1-C_6)$ alkyl, if such substitution is chemically permissible.

r. Estrogen agonists are herein defined as chemical compounds capable of binding to the estrogen receptor sites in mammalian tissue, and mimicking the actions of estrogen in one or more tissues.

s. Estrogen antagonists are herein defined as chemical compounds capable of binding to the estrogen receptor sites in mammalian tissue, and blocking the actions of estrogen in one or more tissues.

t. Estrogen partial agonists are defined as chemical compounds capable of binding to the estrogen receptor sites in mammalian tissue, and eliciting pharmacologic response(s) consistent with that of an estrogen-like substance with weaker estrogen receptor affinity.

u. Estrogen tissue selective agonists are defined as chemical compounds capable of binding to the estrogen receptor sites in mammalian tissue, and eliciting pharmacologic response(s) in some but not all tissues, or to greater or lesser degrees in some tissues, consistent with that of an estrogen receptor agonist.

v. "pharmaceutically acceptable" means suitable for use in, or on, mammals.

w. "salts" is intended to refer pharmaceutically acceptable salts and to salts suitable for use in industrial processes, such as the preparation of the compound.

x. "pharmaceutically acceptable salts" is intended to refer to either pharmaceutically acceptable acid addition salts" or "pharmaceutically acceptable basic addition salts" depending upon actual structure of the compound.

y. "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents.

z. "pharmaceutically acceptable basic addition salts" is intended to apply to any non-toxic organic or inorganic basic addition salt of the compounds represented by Formula I, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

aa. "compound of Formula I", "compounds of the invention", and "compounds" are used interchangeably throughout the application and should be treated as synonoms.

bb. "patient" refers to warm blooded animals such as, for example, guinea pigs, mice, rats, gerbils, cats, rabbits, dogs, monkeys, chimpanzees, stump tail macques, and humans.

cc. "treat" refers to the ability of the compounds to either relieve, alleviate, or slow the progression of the patient's disease (or condition) or any tissue damage associated with the disease.

dd. "isomer" means "stereoisomer" and "geometric isomer" as defined below.

ee. "stereoisomer" means compounds that possess one or more chiral centers and each center may exist in the R or S configuration. Stereoisomers includes all diastereomeric, enantiomeric and epimeric forms as well as racemates and mixtures thereof.

ff. "geometric isomer" means compounds that may exist in cis, trans, anti, entgegen (E), and zusammen (Z) forms as well as mixtures thereof.

Certain of the compounds of the formula (I) may exist as geometric isomers. The compounds of the formula (I) may possess one or more asymmetric centers, thus existing as two, or more, stereoisomeric forms. The present invention includes all the individual stereoisomers and geometric isomers of the compounds of formula (I) and mixtures thereof. Individual enantiomers can be obtained by chiral separation, by using available synthetic building blocks incorporating the relevant asymmetric center with the appropriate stereochemistry in the synthesis, or by asymmetric synthesis starting with achiral synthetic building blocks.

In addition, the compounds of the present invention can exist in unsolvated as well as solvated forms with pharmaceutically acceptable solvents such as water, ethanol, and the like. The compounds may also exist in one or more crystalline states, i.e. polymorphs, or they may exist as amorphous solids. All such forms are encompassed by the claims.

All of the compounds of Formula I are isoxazole derivatives. To further exemplify the invention, the numbering system for this ring and its substitution pattern is shown below:

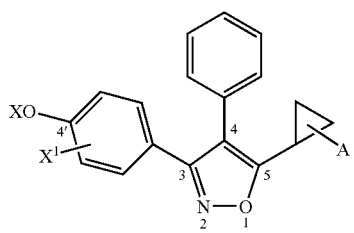

Position 3 of the isoxazole ring will always be substituted with a phenyl ring, substituted at the 4'-position with a hydroxyl group (or any other suitable protecting group known in the art). This phenyl ring may optionally be further substituted as described above. Position 4 of the isoxazole ring will also be substituted with a phenyl ring. As depicted above, this phenyl ring will not be substituted. Position 5 of the isoxazole ring will be substituted with a cyclopropyl moiety. This cyclopropyl moiety may optionally be substituted as depicted above by substituent A. A may be bonded to any of positions 1', 2', or 3' of the cyclopropyl ring (typically position 1').

More specific embodiments of the invention include compounds of Formula I in which:

i) in which $X^1$ is absent and X is represented by hydrogen, ii) in which $X^1$ is absent, X is represented by hydrogen, and A is represented by $C_1$-$C_6$ alkyl, optionally substituted, iii) in which $X^1$ is absent, X is represented by hydrogen, and A is represented by hydroxyalkyl, iv) in which $X^1$ is absent, X is represented by hydrogen, and A is bonded to the 1' position and is represented by methyl, ethyl, n-propyl, isopropyl, n-butyl, isobutyl, or sec-butyl, in which any alkyl group may be optionally substituted by hydroxyl or halogen, v) in which $X^1$ is absent, X is represented by hydrogen, and A is bonded to the 1' position and is represented by $(CH_2)_z$—COOR, in which z is 0 or 1, and R is ($C_1$-$C_6$) alkyl, optionally substituted, vi) in which $X^1$ is absent, X is represented by hydrogen, and A is bonded to the 1' position and is represented by $(CH_2)_z$OCOR, in which z is 1 or 2, and R is ($C_1$-$C_6$)alkyl, optionally substituted, or ($C_3$-$C_{10}$) cycloalkyl, vii) in which $X^1$ is absent, X is represented by hydrogen, and A is bonded to the 1' position and represented by $(CH_2)_z$—OR, in which z is 1, 2, or 3 and R is ($C_1$-$C_6$) alkyl, optionally substituted.

Synthesis

The compounds of Formula I can be prepared using methods analogous to those known in the art for the preparation of isoxazoles. The reader's attention is directed to Wakefield, B. J. Product class 9: isoxazoles. *Science of Synthesis*, 11, 2002, 229-288 for a description of such reactions. Scheme I below provides an overview of one such technique:

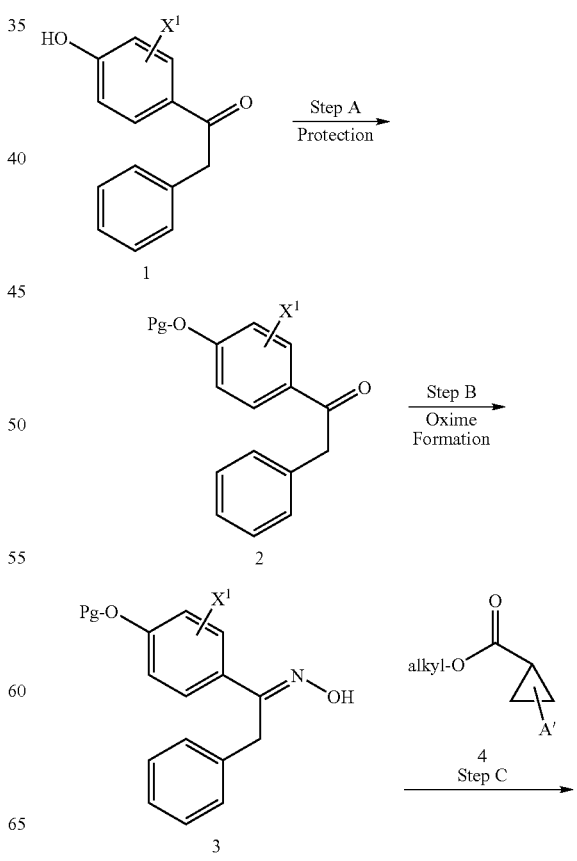

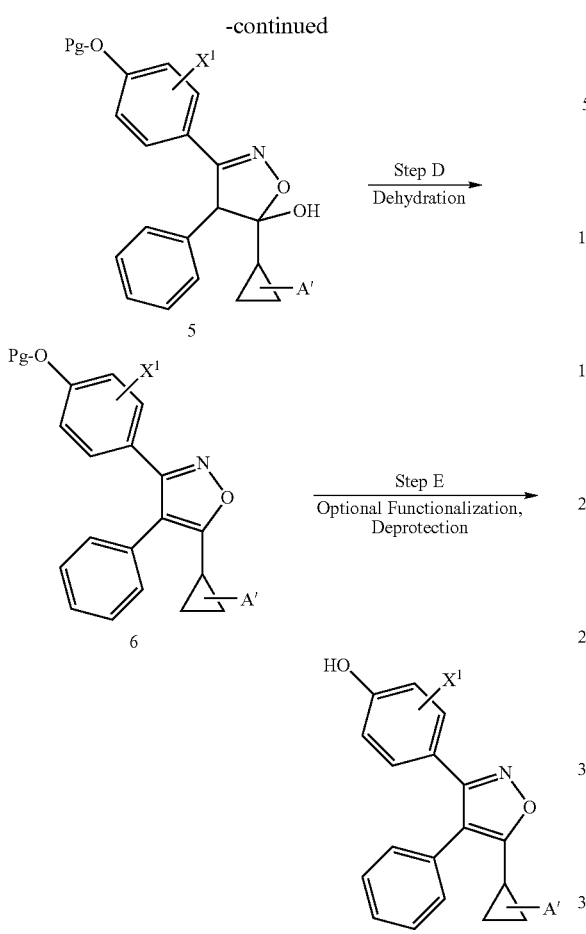

The starting material in Reaction Scheme I is benzyl 4-hydroxyphenyl ketone ($X^1$ is H), whose structure is depicted above as compound 1. This compound is available commercially. Methods for its synthesis are described in *Synthetic Communications*, 33(14), 2003, 2519-2530; *Journal of Organic Chemistry*, 65(8), 2000, 2322-2330; *Tetrahedron*, 56(37), 2000, 7199-7203; *Synlett*, (12), 2000, 1777-1778.

The initial step in the synthesis is to place a protecting group (Pg) on the hydroxyl function of compound 1, as depicted above in Step A. Any number of known protecting groups may be utilized. Examples include tert-butyldimethylsilyl ("TBDMS"), methoxymethyl("MOM"), methyl, benzyl, etc. The reader's attention is directed to, T. W. Greene, *Protective Groups in Organic Synthesis*, John Wiley & Sons, New York, 1991, for a description of potential protecting groups and methods for placing such groups onto compound 1. Alternatively, the protection reaction may be omitted and the oxime formation reaction depicted in Step B may be carried out directly on the compound 1.

In Step B, the ketone of compound 2 is converted into an oxime function using techniques know in the art. The reader's attention is directed to Recent advances in the chemistry of oximes, Organic Preparations and Procedures International (2000), 32(3), 235-264 for a description of such reactions. Typically, compound 2 is contacted with an excess of a base, such as sodium acetate, at room temperatures in a protic solvent, such as ethanol. An excess of hydroxylamine hydrochloride is then introduced and the reactants are stirred for a sufficient period of time to allow the reaction to proceed to completion. The desired product, compound 3, may be recovered from the reaction zone by extraction, evaporation, filtration, etc., as is known in the art. Compound 3 may be optionally purified or the crude may be used directly in Step C. Any number of known purification techniques may be utilized (e.g. HPLC, MPLC, crystallization, recrystallization, etc).

In Step C, a reaction is carried out which forms the precursor to the isoxazole ring that is a component of all of the compounds of Formula I (i.e. a 5-hydroxyisoxazoline). The isoxazole ring may be formed using techniques analogously known in the art. The reader's attention is directed to *Chemical & Pharmaceutical Bulletin*, 36(8), 1988, 3142-6; *Journal of Heterocyclic Chemistry*, 22(2), 1985, 501-4; *Heterocycles*, 23(3), 1985, 571-83 for a description of such reactions. Typically compound 3 is initially contacted with an excess of a strong base, such as n-butyl lithium, at depressed temperatures, in an aprotic solvent, to allow deprotonation of the oxime. Once compound 3 is deprotonated, one or more equivalents of the cyclopropyl derivative described by compound 4 is added to the reaction. The reactants are stirred at reduced temperatures until the reaction is completed. The desired product, compound 5, may be isolated from the reaction by extraction, evaporation, distillation, etc. as is known in the art. Compound 5 may optionally be purified by chromatography or other techniques known in the art.

The cyclopropyl derivative, as described by compound 4, provides the substituent at the 5-position of the isoxazole ring in the final compounds. A' should either be represented by the moiety desired in the final product, or a moiety that can readily be transformed into the desired substituent in optional Step E. Such cylopropyl derivatives are known in the art.

In Step D, the hydroxyl moiety located at the 5 position of the 5-hydroxyisoxazoline ring is eliminated, allowing generation of the desired isoxazole. This may be accomplished by contacting compound 5 with a strong acid, such as para-toluene sulfonic acid, at elevated temperatures (i.e. reflux) for a sufficient period of time to allow the reaction to proceed to completion. The desired product, which is described by compound 6, may be isolated from the reaction by extraction, evaporation, distillation, etc. as is known in the art. Compound 6 may optionally be purified by chromatography or other techniques known in the art.

The number of reactions carried out in Step E and the order in which these reactions are carried out will depend upon the desired final product and whether A' represents the substituent required in the final product. If A' represents the moiety desired in the final product, then compound 6 is subjected to a deprotection reaction in which the protecting group, Pg, is removed from the molecule. This deprotection may be carried out as is known in the art. Typically compound 6 is contacted with an acid, such as hydrochloric acid, at elevated temperatures for a sufficient period of time to allow the reaction to proceed to completion. The desired product of Formula I may be isolated from the reaction by extraction, evaporation, distillation, etc. as is known in the art. The compound may then be purified by chromatography or other techniques known in the art.

If A' does not represent the final moiety, then one, or more, reactions will be carried out to generate the final product. Methods for incorporating such functional groups onto a cyclopropyl ring are known in the art. By way of illustrative example, Scheme II below described the preparation of alcohols, esters, thioethers, sulfonates, amines, ketones, amides, etc and provides literature citations which provide generalized methods for carrying out such reactions.

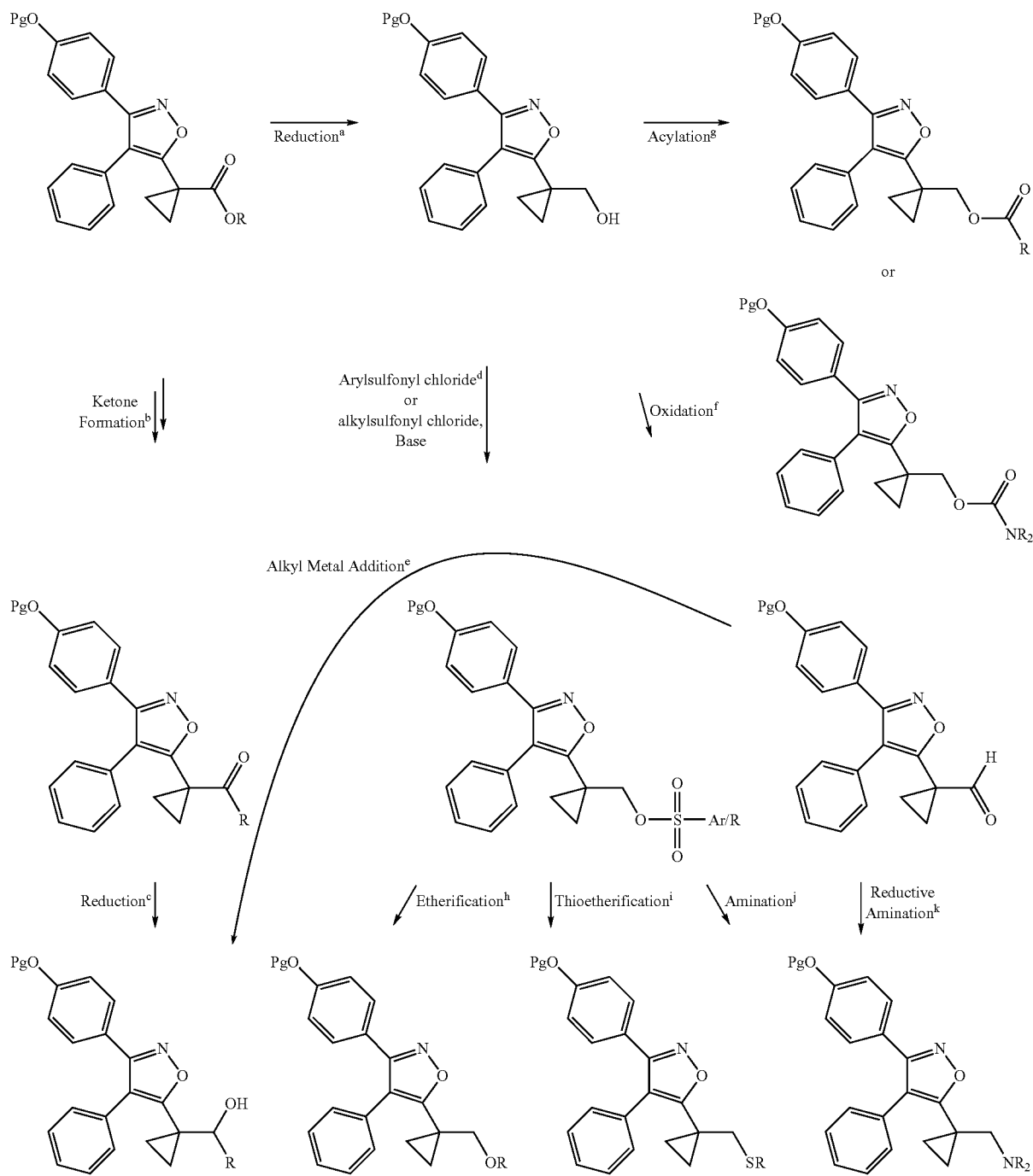

Scheme II. General Optional Functionalization (Step E from Scheme I)

[a]Zakharkin, L. I.; Khorlina, I. M. Tetrahedron Letters, 1962, 619-20.
[b]Singh, Jaimala; et al. Journal fuer Praktische Chemie (Weinheim, Germany), 2000, 342(4), 340-347.
[c]Wills, Martin; Hannedouche, Jerome. Current Opinion in Drug Discovery & Development, 2002, 5(6), 881-891.
[d]March, J. Advanced Organic Chemistry, Third Edition, John Wiley & Sons, 1985, p. 444.
[e]March, J. Advanced Organic Chemistry, Third Edition, John Wiley & Sons, 1985, pp. 816-822.
[f]Tidwell, Thomas T. Organic Reactions (New York) (1990), 39, 297-572.
[g]Hudson, R. F. Chimia, 1961, 15, 394-399.
[h]March, J. Advanced Organic Chemistry, Third Edition, John Wiley & Sons, 1985, pp. 342-343.
[i]March, J. Advanced Organic Chemistry, Third Edition, John Wiley & Sons, pp. 360-362.
[j]March, J. Advanced Organic Chemistry, Third Edition, John Wiley & Sons, pp. 364-366.
[k]March, J. Advanced Organic Chemistry, Third Edition, John Wiley & Sons, pp. 798-800.

Medical and Cosmetic Uses

As noted above, the compounds of Formula I are estrogen receptor modulators and may be used to alleviate estrogen responsive conditions, diseases, etc. In order to exhibit the therapeutic properties described above, the compounds need to be administered in a quantity sufficient to modulate activation of the estrogen receptor. This amount can vary depending upon the particular disease/condition being treated, the severity of the patient's disease/condition, the patient, the particular compound being administered, the route of administration, and the presence of other underlying disease states within the patient, etc. When administered systemically, the compounds typically exhibit their effect at a dosage range of from about 0.1 mg/kg/day to about 1000 mg/kg/day for any of the diseases or conditions listed above. Repetitive daily administration may be desirable and will vary according to the conditions outlined above.

The compounds of the present invention may be administered by a variety of routes. They may be administered orally. The compounds may also be administered parenterally (i.e., subcutaneously, intravenously, intramuscularly, intraperitoneally, or intrathecally), rectally, or topically.

In a typical embodiment, the compounds are administered topically. Topical administration is especially appropriate for dermal conditions such as wrinkles, photo-damage, excess sebum, etc. The dose will vary, but as a general guideline, the compound will be present in a dermatologically acceptable carrier in an amount of from about 0.01 to 50 w/w %, and more typically from about 0.1 to 10 w/w %. The dermatological preparation will be applied to the affected area from 1 to 4 times daily. "Dermatologically acceptable" refers to a carrier which may be applied to the skin or hair, and which will allow the drug to diffuse to the site of action. More specifically, it refers the site where modulation of activation of an estrogen receptor is desired.

As mentioned above, aging may have a detrimental impact on the appearance of the skin. This can be exacerbated by environmental factors such as frequent sun bathing, use of tanning salons, smoking, etc. Age and decreased estrogen levels may result in skin that appears wrinkled, withered, spotty, photo damaged, etc.

Age and decreased estrogen levels are also associated with physiological and biochemical changes in the dermal and epidermal tissues. These include decreases in the mitotic rate of keratinocytes, changes in dermal thickness, decrease in glycosaminoglycans, decreases in soluble collagen, and a decrease in the urinary excretion of hydroxyproline, a measure of decreases in collagen turnover. The decreases in the synthesis of extracellular components leads to the cosmetic problems described above.

The compounds of Formula I may be used to counter act the effects of age and diminished estrogen levels. The compounds will stimulate mitosis in fibroblasts, leading to increased levels of collagen, elastin, and glycosaminoglycans. This in turn will gradually lead to an increase in dermal thickness, enhanced elasticity, improved moisture, etc. This in turn will lead to enhanced subjective appearance (i.e. an alleviation of wrinkles).

The compounds may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the lumenal duct so that it may be deposited on the surface of the skin.

In some individuals, an excessive quantity of sebum is secreted onto the skin. This can have a number of adverse consequences. It can exacerbate acne, since sebum is the primary food source for *Propionbacterium acnes*, the causative agent of acne. It can cause the skin to have a greasy appearance, typically considered cosmetically unappealing.

Formation of sebum is regulated by growth factors and a variety of hormones including estrogen. The cellular and molecular mechanism by which estrogens exert their influence on the sebaceous gland has not been fully elucidated. However, clinical experience documents the impact estrogens have on sebum production. Thus, the compounds of formula I inhibit the secretion of sebum and thus reduce the amount of sebum on the surface of the skin. The compounds can be used to treat a variety of dermal diseases such as acne or seborrheic dermatitis.

In addition to treating diseases associated with excess sebum production, the compounds can also be used to achieve a cosmetic effect. Some consumers believe that they are afflicted with overactive sebaceous glands. They feel that their skin is oily and thus unattractive. These individuals can utilize the compounds of Formula I to decrease the amount of sebum on their skin. Decreasing the secretion of sebum will alleviate oily skin in individuals afflicted with such conditions.

The compounds may also be used to treat sebaceous hyperplasia. Sebaceous hyperplasia is the term used for enlarged sebaceous glands seen on the skin of the middle-aged and elderly. Most typically they occur on the forehead or cheeks. While these enlarged glands are not harmful, many individuals feel that they are cosmetically unattractive. Isotretinoin, which reduces sebum secretion, has been shown to reduce the size of these enlarged glands. Thus, by reducing sebum secretion, these compounds will also alleviate sebaceous hyperplasia.

In addition to treating dermal conditions, the compounds may be used systemically to treat conditions, disorders, or disease states that are at least partially mediated by an estrogen deficiency or excess. The compounds of this invention are useful in treating a peri-menopausal, menopausal, or post-menopausal patient in which the levels of endogenous estrogens produced are greatly diminished. Menopause is generally defined as the last natural menstrual period and is characterized by the cessation of ovarian function, leading to the substantial diminution of circulating estrogen in the bloodstream. As used herein, menopause also includes conditions of decreased estrogen production that may be surgically, chemically, or be caused by a disease state which leads to premature diminution or cessation of ovarian function.

The compounds of this invention are also useful in inhibiting or treating other effects of estrogen deprivation including, hot flushes, vaginal or vulvar atrophy, atrophic vaginitis, vaginal dryness, pruritus, dyspareunia, dysuria, frequent urination, urinary incontinence, urinary tract infections. Other reproductive tract uses include the treatment or inhibition of dysfunctional uterine bleeding. The compounds are also useful in treating or inhibiting endometriosis.

The compounds of this invention are also useful for inhibiting or treating Alzheimer's disease, cognitive decline, decreased libido, senile dementia, neurodegenerative disorders, depression, anxiety, insomnia, schizophrenia, and infertility. The compounds of this invention are also useful in treating or inhibiting benign or malignant abnormal tissue growth including, glomerulosclerosis, prostatic hypertrophy, uterine leiomyomas, breast cancer, scleroderma, fibromatosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage. The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis, uveitis, psoriasis, multiple sclerosis, systemic lupus erythematosus and sepsis.

The compounds of this invention are also useful in treating or inhibiting ocular disorders including cataracts, uveitis, and macular degeneration. The compounds of this invention are also useful in treating or inhibiting metabolic disorders such as type-II diabetes, of lipid metabolism, appetite (e.g. anorexia nervosa and bulimia). Compounds in this invention are also useful in treating or inhibiting bleeding disorders such as hereditary hemorrhagic telangiectasia, dysfunctional uterine bleeding, and combating hemorrhagic shock. The compounds of this invention are useful in disease states where amenorrhea is advantageous, such as leukemia, endometrial ablations, chronic renal or hepatic disease or coagulation diseases or disorders. The compounds of this invention can be used as a contraceptive agent, particularly when combined with a progestin. The compounds may also be used to stimulate the healing of wounds.

Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly on the skin or hair. Pharmaceutical and cosmetic compositions can be manufactured utilizing techniques known in the art. Typically an effective amount of the compound will be admixed with a pharmaceutically/cosmetically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention will typically be administered topically. As used herein, topical refers to application of the compounds (and optional carrier) directly to the skin and/or hair. The topical composition according to the present invention can be in the form of solutions, lotions, salves, creams, ointments, liposomes, sprays, gels, foams, roller sticks, or any other formulation routinely used in dermatology.

Thus, a further embodiment relates to cosmetic or pharmaceutical compositions, in particular dermatological compositions, which comprise at least one of the compounds corresponding to Formula I above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily. The reader's attention is directed to *Remington's Pharmaceutical Science*, Edition 17, Mack Publishing Co., Easton, Pa. for a discussion of how to prepare such formulations. These compositions are prepared according to the usual methods. The amounts of the various constituents in the dermatological compositions according to the invention are those conventionally used in the fields considered.

The medicinal and cosmetics containing the compounds of the invention will typically be packaged for retail distribution (i.e. an article of manufacture). Such articles will be labeled and packaged in a manner to instruct the patient how to use the product. Such instructions will include the condition to be treated, duration of treatment, dosing schedule, etc.

The compounds of Formula I may also be admixed with any inert carrier and utilized in laboratory assays in order to determine the concentration of the compounds within the serum, urine, etc., of the patient as is known in the art. The compounds may also be used as a research tool.

EXAMPLES

In the discussion above and in the examples below, the following abbreviations have the following meanings. If an abbreviation is not defined, it has its generally accepted meaning.

| Chemical Reagents and Solvents | |
|---|---|
| ACN = | acetonitrile |
| BuLi or nBuLi = | n-butyllithium |
| CDI = | 1,1'-carbonyldiimidazole |
| DCC = | 1,3-dicyclohexylcarbodiimide |
| DCM = | dichloromethane |
| DIBAL-H = | diisobutylaluminum hydride |
| DMA = | N,N-dimethylacetamide |
| DMAP = | 4-dimethylaminopyridine |
| DMF = | N,N-dimethylformamide |
| DMSO = | dimethylsulfoxide |
| EtOAc = | ethyl acetate |
| EtOH = | ethanol |
| HCl = | hydrochloric acid |
| IPA = | isopropyl alcohol |
| IBx = | 1-hydroxy-1,2-benziodoxol-3(1H)-one 1-oxide |
| LDA = | lithium diisopropylamide |
| MeOH = | methanol |
| MTBE = | methyltertbutyl ether |

-continued

| | |
|---|---|
| NaOAc = | sodium acetate |
| NMP = | 1-methyl-2-pyrrolidinone |
| p-TsOH = | para-toluenesulfonic acid |
| p-TsOH•H$_2$O = | para-toluenesulfonic acid monohydrate |
| pyr = | pyridine |
| TBAF = | tetrabutylammonium fluoride |
| TBDMSCl = | tert-butyldimethylsilyl chloride |
| TFA = | trifluoroacetic acid |
| TFAA = | trifluoroacetic anhydride |
| THF = | tetrahydrofuran |
| MSOH = | methane sulfonic acid |
| TSOH = | toluene sulfonic acid |

Chemical Functional Groups

| | |
|---|---|
| Ac = | acetyl |
| AcO = | acetoxy |
| BOC or Boc = | tert-butoxycarbonyl |
| CBZ = | benzyloxycarbonyl |
| Et = | ethyl |
| EtO = | ethoxy |
| LG = | leaving group |
| Me = | methyl |
| MeO = | methoxy |
| MOM = | methoxymethyl |
| Pg = | protecting group |
| TBDMS or TBS = | tert-butyldimethylsilyl |

Chromatography

| | |
|---|---|
| HPLC = | high pressure liquid chromatography |
| LC/MS or LCMS = | liquid chromatography-mass spectrometry |
| MPLC = | medium pressure liquid chromatography |
| p-TLC = | preparative thin layer chromatography |
| TLC = | thin layer chromatography |

Mass Spectrometry

| | |
|---|---|
| APCI = | atmospheric pressure chemical ionization |
| APCI$^+$ = | atmospheric pressure chemical ionization, positive ionization |
| APCI$^-$ = | atmospheric pressure chemical ionization, negative ionization |
| ESI = | electrospray ionization |
| ES$^+$ = | electrospray positive ionization |
| ES$^-$ = | electrospray negative ionization |
| max = | maximum |
| MS = | mass spectrometry |
| m/z = | mass-to-charge ratio |

Nuclear Magnetic Resonance

| | |
|---|---|
| bd = | broad doublet |
| bm = | broad multiplet |
| bs = | broad singlet |
| d = | doublet |
| dd = | doublet of doublets |
| dq = | doublet of quartets |
| dt = | doublet of triplets |
| Hz = | hertz |
| J = | coupling constant |
| m = | multiplet |
| MHz = | megahertz |
| NMR = | nuclear magnetic resonance |
| q = | quartet |
| s = | singlet |

Units of Measure

| | |
|---|---|
| eq. = | equivalents |
| g = | grams |
| h = | hours |
| M = | molar |
| M % = | mole percent |
| meq = | milliequivalents |
| mg = | milligrams |
| min = | minutes |
| mL = | milliliters |
| mm = | millimeters |
| mmol = | millimoles |
| N = | normal |
| μL = | microliters |

Other

| | |
|---|---|
| o/n = | overnight |
| rt = | room temperature |
| v/v = | volume-to-volume ratio |

The general analytical methods used in the Examples are set forth below, unless specifically stated otherwise:

Melting points are determined on either a Thomas-Hoover Uni-Melt or Mettler Toledo melting point apparatus and are uncorrected.

400 MHz $^1$H (and 100 MHz $^{13}$C) NMR spectra are obtained on a Varian Inova spectrometer equipped with an ATB probe, two RF channels, and a SMS-100 sample changer by Zymark. Spectra are generally acquired at 25° C. Automated H2 gradient shimming, automated locking autogain routines are employed. Samples are usually spun at 20 Hz for 1 D experiments. $^1$H NMR spectra are acquired using 45° tip angle pulses, 1.0 second recycle delay, and 16 scans at a resolution of 0.2 Hz/point. The acquisition window is typically 6400 Hz from +14 to −2 ppm (Reference TMS @ 0 ppm), and processing is without line broadening. Typical acquisition time is 100 seconds. $^{19}$F NMR spectra are acquired using 30-degree tip angle pulses, 1.0 second recycle delay, and 16 scans at a resolution of 0.6 Hz/point. The acquisition window is typically 82 KHz from +20 to −200 ppm (Reference CFCl$_3$=0 ppm) and processing is with 0.6 Hz line broadening. Typical acquisition time is 40 seconds. Regular $^{13}$C NMR spectra are acquired using 45° tip angle pulses, 0.2 second recycle delay, and 512 scans at a resolution of 0.7 Hz/point. Spectral width is typically 23 KHz from +220 to −10 ppm (Reference TMS @ 0 ppm). Proton decoupling is applied continuously, and 0.7 Hz line broadening is applied during processing. Typical acquisition time is 102 minutes.

Positive and negative ion atmospheric pressure chemical ionization (APCI) mass spectra are obtained on a Micromass Platform LC mass spectrometer operating in Open Access mode. Samples are introduced by loop injection using a Gilson 215 autosampler into a mobile phase of 80:20 acetonitrile:water flowing at 200 μL/min delivered by a Hewlett-Packard HP1100 HPLC. The mass spectrometer source and probe temperatures are 150° C. and 450° C., respectively. The cone voltage is typically 15 V while the corona pin is held at 3.5 kV in positive ion and 3.0 kV in negative ion mode. Positive and negative ion electrospray ionization (ES) mass spectra are obtained on a Waters Micromass ZQ single quadrupole mass spectrometer.

Specific rotations are measured at 589 nm on either a Perkin Elmer Model 341 or a Rudolph Research Analytical Model Autopol IV polarimeter at 25° C.

Liquid chromatographic mass spectrometry is performed on Agilent LC-MSD instruments using 50×4.6 mm Phenomenex Develosil Combi RP3 columns at 45° C. and a gradient (either 98, 90, 70, 50, 25 or 10 to 2% water over 3.5 min then holding for 0.5 min) of acetonitrile and water with 0.1% formic acid measuring absorbance at 254 and 214 nm.

HPLC is performed using either a 150×4.6 mm Phenomenex Luna 5 micron C18 reverse phase column or a 150×4.6 mm ACE 5 micron C18 reverse phase column and a gradient of water and acetonitrile with 0.1% TFA or formic acid (typically 80:20 to 90:10 over 15 minutes) with a 1.5 mL/min flow rate measuring absorbance at 280, 254, and 214 nm.

Preparative HPLC on arrays is performed on either 150× 21.2 mm Phenomenex Luna C18 column eluting with a gradient of acetonitrile and water with 0.1% formic acid or a 150×21.2 mm Gemini C18 column eluting with a gradient of acetonitrile and water with 0.1% ammonium hydroxide.

Analytical chiral HPLC is performed using a 150×4.6 mm Chiralcel OJ-H column and a gradient of hexanes and isopropanol.

Preparative chiral HPLC is performed using either a 250× 21.2 mm Chiralcel OJ-H column and a gradient of hexanes and isopropanol or by supercritical fluid chromatography on a 250×21.2 mm Chilralcel OJ-H column and a gradient of methanol and carbon dioxide.

Flash chromatography is carried out using prepacked silica gel columns (Analogix, Isco, or Biotage) typically eluting with a gradient of hexanes and ethyl acetate unless otherwise indicated.

Example 1

Example 1 illustrates Steps A-E of Reaction Scheme I, in which A' is modified in Step E to introduce the desired moiety onto the cyclopropyl ring. The intermediates produced in this Example are utilized in subsequent examples and are referred to by the letters shown below in subsequent examples.

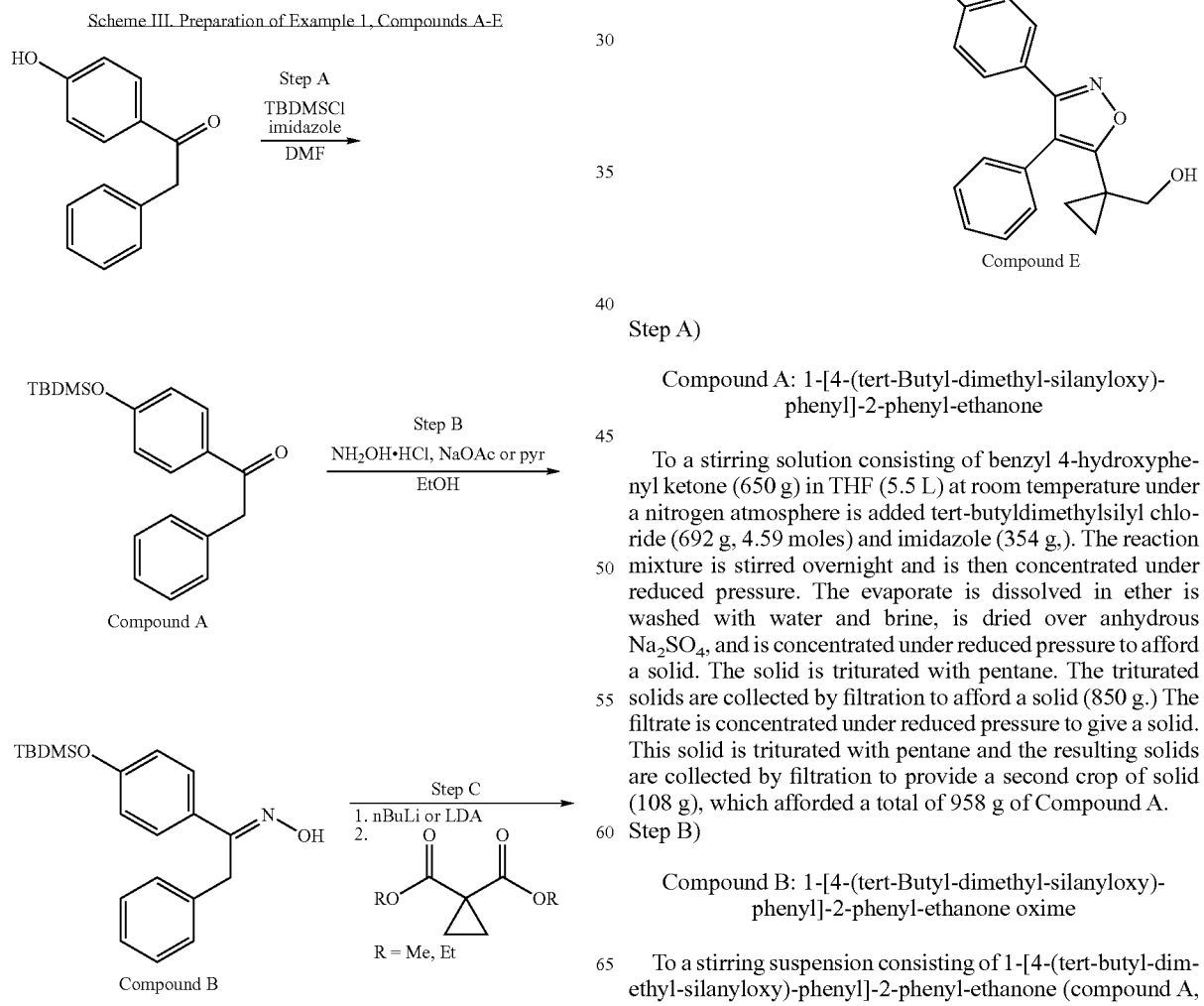

Step A)

Compound A: 1-[4-(tert-Butyl-dimethyl-silanyloxy)-phenyl]-2-phenyl-ethanone

To a stirring solution consisting of benzyl 4-hydroxyphenyl ketone (650 g) in THF (5.5 L) at room temperature under a nitrogen atmosphere is added tert-butyldimethylsilyl chloride (692 g, 4.59 moles) and imidazole (354 g,). The reaction mixture is stirred overnight and is then concentrated under reduced pressure. The evaporate is dissolved in ether is washed with water and brine, is dried over anhydrous $Na_2SO_4$, and is concentrated under reduced pressure to afford a solid. The solid is triturated with pentane. The triturated solids are collected by filtration to afford a solid (850 g.) The filtrate is concentrated under reduced pressure to give a solid. This solid is triturated with pentane and the resulting solids are collected by filtration to provide a second crop of solid (108 g), which afforded a total of 958 g of Compound A.

Step B)

Compound B: 1-[4-(tert-Butyl-dimethyl-silanyloxy)-phenyl]-2-phenyl-ethanone oxime To a stirring suspension consisting of 1-[4-(tert-butyl-dimethyl-silanyloxy)-phenyl]-2-phenyl-ethanone (compound A, 955 g) in ethanol (8 L) is added pyridine (4 L) and hydroxylamine hydrochloride (610 g). The resulting mixture is heated at 100° C. for two hours and subsequently stirred at room temperature overnight. The reaction mixture is concentrated under reduced pressure to afford a residue that is dissolved in ethyl acetate. The solution is washed with 5% aqueous citric acid and brine. The organic layer is separated, is dried over anhydrous $Na_2SO_4$, and is concentrated under reduced pressure. The concentrate is triturated with pentane. The triturated solids are collected by filtration to afford the solid product (480 g.) The filtrate is concentrated under reduced pressure and that concentrate is triturated with pentane. The solids are collected by filtration to provide another crop of solid product (320 g), which afforded a total of 800 g of Compound B.
Step C)

Compound C: 1-{3-[4-(tert-Butyl-dimethyl-silanyloxy)-phenyl]-5-hydroxy-4-phenyl-4,5-dihydro-isoxazol-5-yl}-cyclopropanecarboxylic acid methyl ester An oven-dried 1 L three-neck flask equipped with magnetic stir bar, nitrogen gas inlet valve, and digital thermometer probe, and addition funnel had been charged with 1-[4-(tert-butyl-dimethyl-silanyloxy)-phenyl]-2-phenyl-ethanone oxime (Compound B, 26.6 g) and anhydrous THF (140 mL.) The reaction vessel is submerged in an ice-methanol bath equipped with a thermometer reading –18° C. The internal solution temperature is cooled to –9.0° C. A solution consisting of 2.5 $\underline{M}$ n-butyllithium in hexane (31 mL, 78 mmol) is added dropwise over 25 minutes (bath temperature –18 to –16° C., internal mixture temperature –9.0 to –0.6° C.), over which time the solution color turned from yellow after addition of the first few drops to orange at the first endpoint. The reaction mixture is stirred for three minutes as the internal mixture temperature cooled to –3.3° C. (bath temperature –14° C.) Another 31 mL of 2.5 $\underline{M}$ n-butyllithium in hexane is added over 11 minutes (bath temperature –14 to –16° C., internal mixture temperature –3.3 to –0.3° C. with a peak temperature in that time period of +0.2° C.) The reaction mixture is stirred for 31 minutes as the internal mixture temperature cooled to –10.1° C. (bath temperature –14° C.) Cyclopropane-1,1-dicarboxylic acid dimethyl ester (26.0 mL) is added over less than one minute to give an internal mixture temperature of +4.6° C. (bath temperature –13° C.) The reaction mixture is stirred for one hour and is quenched with the addition of brine solution (100 mL.) The layers are separated and the organic phase is dried over anhydrous magnesium sulfate and is concentrated under reduced pressure to afford an oil (59.9 g.) The product is purified by flash silica gel column chromatography to afford the foam product (24.0 g.)
Step D)

Compound D: 1-{3-[4-(tert-Butyl-dimethyl-silanyloxy)-phenyl]-4-phenyl-isoxazol-5-yl}-cyclopropanecarboxylic acid methyl ester Methyl 1-[3-(4-{[tert-butyl(dimethyl)silyl]oxy}phenyl)-5-hydroxy-4-phenyl-4,5-dihydroisoxazol-5-yl]cyclopropanecarboxylate (Compound C, 42 g) is dissolved in toluene (100 mL) and p-toluenesulfonic acid hydrate (1.7 g) is added with swirling. The mixture is heated over a steam bath until the internal mixture temperature, measured with a digital thermometer, is raised to 80° C. The mixture is then removed from the steam bath and is treated with water (50 mL.) The layers are shaken and separated and the toluene phase is dried over anhydrous magnesium sulfate and is concentrated under reduced pressure to afford an oil that is purified by flash silica gel column chromatography. Elution through a 400 g Analogix silica cartridge with a gradient (100% hexanes to 35% ethyl acetate over 1800 mL, or three column volumes) afforded an oily product. The product is dissolved in chloroform and is reconcentrated under reduced pressure to afford a residue that solidified overnight under high vacuum to the solid product (32 g.)
Step E)

Compound E: (1-{3-[4-(tert-Butyl-dimethyl-silanyloxy)-phenyl]-4-phenyl-isoxazol-5-yl}-cyclopropyl)-methanol To a stirring solution consisting of methyl 1-[3-(4-{[tert-butyl(dimethyl)silyl]oxy}phenyl)-4-phenylisoxazol-5-yl]cyclopropanecarboxylate (Compound D, 29.9 g) in dichloromethane (200 mL) at –78° C. under an argon atmosphere is added a solution consisting of 1.0 M diisobutyl aluminum hydride in hexanes. The reaction mixture is stirred as it gradually warmed to 10° C. overnight. The stirring reaction mixture is cooled with an ice-water bath and is quenched cautiously with the slow addition of methanol (50 mL.) Within five minutes of methanol addition, a thick white precipitate formed. The reaction mixture is then poured into a saturated aqueous sodium bicarbonate solution (250 mL.) Dichloromethane is added to dilute the biphasic mixture, and the insolubles are removed by vacuum filtration. The layers are separated and the dichloromethane layer is dried over anhydrous magnesium sulfate and vacuum filtered. The filtrate is concentrated under reduced pressure to an oil that solidified under high vacuum to afford the solid product (25.3 g); MS (APCI$^+$) m/z 422 (MH$^+$); HPLC: wavelength (% purity) 214 nm (100%), 254 nm (100%), 280 nm (100%); retention time: 1.5 min; mobile phase: 50-2% H2O in 3.5 min, hold 0.5 min, run time 4 min; stationary phase: Phenomenex Develosil Combi RP3 50×4.6 mm Column; 45° C.

Example 2

4-[5-(1-Hydroxymethyl-cyclopropyl)-4-phenyl-isoxazol-3-yl]-phenol

To a stirring solution consisting of (1-{3-[4-(tert-butyl-dimethyl-silanyloxy)-phenyl]-4-phenyl-isoxazol-5-yl}-cyclopropyl)-methanol (compound E, Example 1) (18.2 g) in tetrahydrofuran (200 mL) at room temperature under a nitrogen atmosphere is added a 1.0 M solution consisting of tetrabutylammonium fluoride in tetrahydrofuran (45.3 mL.) The reaction mixture is stirred at room temperature overnight. The reaction mixture is concentrated under reduced pressure. The concentrate is purified by flash silica gel column chromatography. Elution with hexanes-ethyl acetate (1:1 v/v) afforded 12 g of a residue. The residue is dissolved in warm methanol. Addition of hexanes caused precipitation of a solid that is collected by filtration (11 g.) The solid is redissolved in warm methanol and again is precipitated with hexanes to afford a new crop of solid product (8.1 g); melting point 210-211° C.; MS (APCI$^+$) m/z 308 (MH$^+$.)

Example 3

4-[5-(1-Isopropoxymethyl-cyclopropyl)-4-phenyl-isoxazol-3-yl]-phenol-

Preparation of the reagent: methyl tris(2-propanolato)phosphorus(1+) tetrafluoroborate To a stirring solution consisting of trimethyloxonium tetrafluoroborate (6.0 g) in dichloromethane (50 mL) at room temperature is slowly added triisopropyl phosphite (11 mL.) The resulting mixture is stirred for three hours. The mixture is concentrated under reduced pressure to afford methyltris(2-propanolato)phosphorus(1+) tetrafluoroborate (7.0 g); $^1$H NMR (400 MHz, CDCl$_3$) δ 5.10 (m, 3H), 2.20 (m, 3H), 1.50 (d, 18H.)

Preparation of the Title Compound

A mixture comprising 4-{5-[1-(hydroxymethyl)cyclopropyl]-4-phenyl-isoxazol-3-yl}phenol (which may be produced as in Example 2, 0.50 g) and methyltris(2-propanolato)phosphorus(1+) tetrafluoroborate (7.0 g) is stirred at room temperature for one day. The mixture is then treated with methanol (3 mL) and the mixture is poured into ice water. Saturated aqueous sodium bicarbonate is added and the mixture is extracted with ethyl acetate. The organic layer is separated and dried over anhydrous sodium sulfate, is filtered, and is concentrated under reduced pressure. The concentrate is purified by flash silica column chromatography to afford 4-[5-(1-isopropoxymethyl-cyclopropyl)-4-phenyl-isoxazol-3-yl]-phenol (0.43 g); MS (ES$^+$) m/z 350 (MH$^+$); elemental microanalysis for C$_{22}$H$_{23}$NO$_3$: % C(calculated/found) 75.62/75.19, % H, 6.63/6.76; % N, 4.01/4.10.

Examples 4-13 General Procedures

Unless otherwise described, Examples 4-13 are prepared by the following general procedures: Coupling of a protected phenol such as (1-{3-[4-(tert-butyl-dimethyl-silanyloxy)-phenyl]-4-phenyl-isoxazol-5-yl}-cyclopropyl)-methanol (Example 1, Compound E) or {1-[3-(4-methoxymethoxy-phenyl)-4-phenyl-isoxazol-5-yl]-cyclopropyl}-methanol (this example, Coupling Method C, Step iii) with a reagent according to one of Coupling Methods A-D afforded a synthetic intermediate. Deprotection of the synthetic intermediate according to either Deprotection Method A or Deprotection Method B afforded the desired product:

Coupling Method A:

To a stirring mixture consisting of excesses of alcohol derivative and triphenylphosphine in tetrahydrofuran at 0° C. under an inert atmosphere is added dropwise an excess of diisopropyl azodicarboxylate. The mixture is stirred for a time and the limiting reagent, (1-{3-[4-(tert-butyl-dimethyl-silanyloxy)-phenyl]-4-phenyl-isoxazol-5-yl}-cyclopropyl)-methanol (Example 1, Compound E) is added. The resultant mixture is agitated at room temperature overnight. The mixture is then concentrated under reduced pressure and the concentrate is dissolved in an organic solvent such as dichloromethane or ethyl acetate. The resultant mixture is washed with aqueous sodium bicarbonate solution. In some experiments, the organic mixture is further washed with water and with brine solution and is then separated. The organic layer is dried over a drying agent such as anhydrous sodium sulfate or anhydrous magnesium sulfate and is filtered and concentrated under reduced pressure. The concentrate is purified by flash silica gel chromatography in which the mobile phase consisted of a hexanes-ethyl acetate mixture to afford the desired synthetic intermediate.

Coupling Method B:

Method A is carried out except the excess of alcohol derivative is added in combination with Example 1, Compound E to a mixture consisting of excesses of triphenylphosphine and diisopropyl azodicarboxylate.

Coupling Method C:

Step i) Preparation of 1-[3-(4-hydroxy-phenyl)-4-phenyl-isoxazol-5-yl]-cyclopropanecarboxylic acid methyl ester To a mixture consisting of 1-{3-[4-(tert-butyl-dimethyl-silanyloxy)-phenyl]-4-phenyl-isoxazol-5-yl}-cyclopropanecarboxylic acid methyl ester (Example 1, Compound C, 7.16 g) in dioxane (120 mL) is added concentrated aqueous hydrochloric acid (30 mL.) The mixture is brought to 100° C. for three hours. The mixture is cooled and is poured into ice water. The mixture is treated with sodium bicarbonate and is extracted with ethyl acetate. The organic layer is dried over anhydrous sodium sulfate and is filtered and concentrated under reduced pressure. The concentrate is purified by flash silica gel column chromatography. Elution with hexanes-ethyl acetate (9:1 v/v) afforded the solid synthetic intermediate 1-[3-(4-hydroxy-phenyl)-4-phenyl-isoxazol-5-yl]-cyclopropanecarboxylic acid methyl ester (3.23 g, 9.63 mmol.)

Step ii) Preparation of 1-[3-(4-methoxymethoxy-phenyl)-4-phenyl-isoxazol-5-yl]-cyclopropanecarboxylic acid methyl ester To a mixture consisting of this synthetic intermediate (1.20 g) in tetrahydrofuran (30 mL) at 0° C. is added 60% sodium hydride in mineral oil suspension (0.22 g) The resulting mixture is stirred for 40 minutes at 0° C. A solution consisting of chloromethyl methyl ether (0.33 mL) in tetrahydrofuran (3 mL) is then added dropwise. The resultant mixture is stirred for two hours at 0° C. The mixture is then treated with saturated aqueous ammonium chloride and is extracted with ethyl acetate. The organic layer is dried over anhydrous sodium sulfate and is concentrated under reduced pressure to afford the synthetic intermediate 1-[3-(4-methoxymethoxy-phenyl)-4-phenyl-isoxazol-5-yl]-cyclopropanecarboxylic acid methyl ester (1.54 g.)

Step iii) Preparation of {1-[3-(4-methoxymethoxy-phenyl)-4-phenyl-isoxazol-5-yl]-cyclopropyl}-methanol To a mixture consisting of this synthetic intermediate (1.50 g) in tetrahydrofuran (30 mL) at 0° C. is added a solution consisting of lithium aluminum hydride in tetrahydrofuran (1 M, 5.7 mL) The mixture is stirred at 0° C. for one hour and is then treated with saturated aqueous ammonium chloride solution. The mixture is extracted with ethyl acetate. The organic layer is separated and is dried over anhydrous sodium sulfate and filtered. The filtrate is concentrated under reduced pressure to obtain the synthetic intermediate {1-[3-(4-methoxymethoxy-phenyl)-4-phenyl-isoxazol-5-yl]-cyclopropyl}-methanol.

Step iv) Electrophilic addition to {1-[3-(4-methoxymethoxy-phenyl)-4-phenyl-isoxazol-5-yl]-cyclopropyl}-methanol To a mixture consisting of {1-[3-(4-methoxymethoxy-phenyl)-4-phenyl-isoxazol-5-yl]-cyclopropyl}-methanol (Examples 4-13 General Procedures, Coupling Method C, Step iii) in a solvent such as tetrahydrofuran or dichloromethane at 0° C. is added an excess of base such as 60% sodium hydride in mineral oil suspension or triethylamine. The mixture is stirred for a time and then a liquid comprising an excess of an electrophile such as iodomethane or methanesulfonyl chloride is added dropwise. The mixture is stirred overnight at room temperature. The mixture is then subjected to workup by first treating with water or an aqueous solution such as saturated ammonium chloride and is extracted with an organic solvent such as ethyl acetate or dichloromethane. The organic layer is dried over a drying agent such as anhydrous sodium sulfate and is concentrated under reduced pressure to afford the desired synthetic intermediate.

[Optional] Step v) Nucleophilic substitution of methanesulfonate functional group of synthetic intermediate methanesulfonic acid 1-[3-(4-methoxymethoxy-phenyl)-4-phenyl-isoxazol-5-yl]-cyclopropylmethyl ester To a mixture consisting of an excess of a nucleophile such as 2,2,2-trifluoroethanol in a solvent such as N,N-dimethylformamide cooled to 0° C. under an inert atmosphere is added an excess of a base such as 60% sodium hydride in mineral oil suspension to give the original reaction mixture. This mixture is stirred for less than one hour and a second mixture, consisting of the limiting reagent methanesulfonic acid 1-[3-(4-methoxymethoxy-phenyl)-4-phenyl-isoxazol-5-yl]-cyclopropylmethyl ester (Examples 4-13 General Procedures, Coupling Method C, Step iv) in a solvent such as N,N-dimethylformamide or another solvent miscible with the solvent of the original reaction mixture, is added dropwise at 0° C. to give the combined reaction mixture. The combined reaction mixture is heated to a temperature such as 70° C. for at least one hour. The combined reaction mixture is then diluted with a solvent such as ethyl acetate and is washed with a dilute aqueous acid such as 1 N hydrochloric acid, water, and brine solution. The organic layer is separated and dried over a drying agent such as anhydrous sodium sulfate and is filtered and concentrated under reduced pressure to afford the desired synthetic intermediate.

Coupling Method D:

To a stirring mixture consisting of the limiting reagent (1-{3-[4-(tert-butyl-dimethyl-silanyloxy)-phenyl]-4-phenyl-isoxazol-5-yl}-cyclopropyl)-methanol (Example 1, Compound E) in a solvent such as tetrahydrofuran at 0° C. is added an excess of a base such as diisopropylethylamine. To this mixture is added dropwise an excess of an electrophile such as chloromethyl methyl ether. This mixture is stirred for more than one hour. The mixture is then diluted with an organic solvent such as ethyl acetate and is washed with a dilute aqueous acid such as 1 N hydrochloric acid, water, and brine solution. The organic layer is separated and is dried over a drying agent such as anhydrous sodium sulfate, is filtered, and is concentrated under reduced pressure. The concentrate is purified by flash silica gel column chromatography. Elution with a hexanes-ethyl acetate mixture afforded the desired synthetic intermediate.

Deprotection Method A:

To a stirring mixture consisting of any synthetic intermediate prepared by Coupling Methods A, B, and D (Examples 4-13 General Procedures) in an organic solvent such as dichloromethane or tetrahydrofuran at room temperature under an inert atmosphere is added an excess of tetrabutylammonium fluoride as a solid or a 1 M solution in tetrahydrofuran. The mixture is stirred for at least 30 minutes. Optionally, to the vigorously stirring mixture is then added an aqueous base solution such as a 2 M sodium bicarbonate solution and the organic layer is separated, dried over a drying agent such as anhydrous sodium sulfate or anhydrous magnesium sulfate, and filtered. In all cases, the aqueous-treated or non-treated organic mixture is concentrated under reduced pressure. The concentrate is purified by flash silica gel column chromatography, crystallization, or recrystallization. In the cases involving chromatography, elution with a solvent mixture such as hexanes-ethyl acetate afforded the desired product. In the cases involving crystallization or recrystallization, crystallization or recrystallization from a solvent or a solvent mixture such as hexanes-ethyl acetate afforded the desired product.

Deprotection Method B:

To a stirring mixture consisting of any synthetic intermediate prepared by Coupling Method C (Examples 4-13 General Procedures) in an organic solvent such as methanol or a solvent mixture such as methanol-isopropanol at room temperature is added excess 6 N hydrochloric acid solution. The resultant mixture is stirred for at least one hour at room temperature. The mixture is then treated with an aqueous base solution such as aqueous sodium bicarbonate and is extracted with an organic solvent such as ethyl acetate. The organic layer is optionally washed sequentially with water and brine solution. The organic layer is dried with a drying agent such as anhydrous sodium sulfate or magnesium sulfate and is filtered and concentrated under reduced pressure. The concentrate is purified by flash silica gel column chromatography, crystallization, or recrystallization. In the cases involving chromatography, elution with a solvent mixture such as hexanes-ethyl acetate afforded the desired product. In the cases involving crystallization or recrystallization, crystallization or recrystallization from a solvent or a solvent mixture such as hexanes-dichloromethane afforded the desired product.

Example 4

4-{5-[1-(2-Ethoxy-phenoxymethyl)-cyclopropyl]-4-phenyl-isoxazol-3-yl}-phenol

The title compound is prepared using the general procedures described in Coupling Method A and Deprotection Method A with the following specifications:

Coupling Method A:

alcohol derivative: 2-ethoxyphenol (0.15 g), triphenylphosphine (0.56 g), diisopropyl azodicarboxylate (0.28 mL), (1-{3-[4-(tert-butyl-dimethyl-silanyloxy)-phenyl]-4-phenyl-isoxazol-5-yl}-cyclopropyl)-methanol (0.30 g), synthetic intermediate afforded: 3-[4-(tert-butyl-dimethyl-silanyloxy)-phenyl]-5-[1-(2-ethoxy-phenoxymethyl)-cyclopropyl]-4-phenyl-isoxazole (0.20 g)

Deprotection Method A synthetic intermediate (0.20 g)

solvent: dichloromethane (20 mL)

tetrabutylammonium fluoride (0.12 g)

title compound afforded: 0.12 g

Melting point 148-149° C.;

MS (ES$^+$) m/z 428 (MH$^+$).

Example 5

4-{5-[1-(2-Fluoro-6-trifluoromethoxy-phenoxymethyl)-cyclopropyl]-4-phenyl-isoxazol-3-yl}-phenol The title compound is prepared according to the procedure described in Example 4, except 2-fluoro-6-trifluoromethoxyphenol is substituted for 2-ethoxyphenol; melting point 132-133° C.; MS (ES$^+$) m/z 486 (MH$^+$.)

Example 6

4-{5-[1-(2-Ethoxy-pyridin-3-yloxymethyl)-cyclopropyl]-4-phenyl-isoxazol-3-yl}-phenol The title compound (0.052 g) is prepared according to the procedure described in Example 4, 2-ethoxy-pyridin-3-ol is substituted for 2-ethoxyphenol; melting point 190-192° C.; MS (ES$^+$) m/z 429 (MH$^+$.)

Example 7

4-{5-[1-(2-Fluoro-6-methoxy-phenoxymethyl)-cyclopropyl]-4-phenyl-isoxazol-3-yl}-phenol The title compound is prepared using the general procedures described in Coupling Method B and Deprotection Method A with the following specifications:
Coupling Method B
alcohol derivative: 2-fluoro-6-methoxy-phenol (0.15 g),
triphenylphosphine (0.50 g),
diisopropyl azodicarboxylate (0.3 mL),
(1-{3-[4-(tert-butyl-dimethyl-silanyloxy)-phenyl]-4-phenyl-isoxazol-5-yl}-cyclopropyl)-methanol (0.40 g),
synthetic intermediate afforded: 3-[4-(tert-butyl-dimethyl-silanyloxy)-phenyl]-5-[1-(2-fluoro-6-methoxy-phenoxymethyl)-cyclopropyl]-4-phenyl-isoxazole (0.28 g)
Subsequent utilization of Deprotection Method A afforded the title compound; $^1$H NMR (400 MHz, CDCl$_3$): δ 7.35-7.26 (m, 7H), 6.95-6.89 (m, 1H), 6.76-6.75 (m, 2H), 6.68-6.60 (m, 2H), 4.87 (s, 1H), 4.11 (s, 2H), 3.73 (s, 3H), 1.01-0.99 (m, 4H); MS (ES$^+$) m/z 432 (MH$^{+\cdot}$)

Example 8

4-[5-(1-Methoxymethyl-cyclopropyl)-4-phenyl-isoxazol-3-yl]-phenol

The title compound is prepared using the general procedures described in Coupling Method B and Deprotection Method A with the following specifications:
Coupling Method C
Step iv)
{1-[3-(4-methoxymethoxy-phenyl)-4-phenyl-isoxazol-5-yl]-cyclopropyl}-methanol (0.406 g)
solvent: tetrahydrofuran (15 mL)
base: 60% sodium hydride in mineral oil suspension (0.052 g)
electrophile: iodomethane (0.075 mL)
Deprotection Method B
synthetic intermediate from Coupling Method C (0.170 g)
solvent mixture: methanol-isopropanol (2:1 v/v, 6 mL)
title compound afforded: 0.120 g
$^1$H NMR (400 MHz, CDCl$_3$) δ: 7.30 (m, 7H), 6.72 (d, 2H), 5.10 (s, 1H), 3.42 (s, 2H), 3.20 (s, 3H), 1.00 (m, 2H), (0.85 (m, 2H);
MS (ES$^+$) m/z 322 (MH$^+$)

Example 9

4-[4-Phenyl-5-(1-propoxymethyl-cyclopropyl)-isoxazol-3-yl]-phenol

The title compound (0.21 g) is prepared according to the procedure described in Example 8, except iodopropane is substituted for iodomethane; melting point 111-112° C.; $^1$H-NMR (400 MHz, CDCl$_3$) δ 7.38 (m, 4H), 7.26 (m, 3H), 6.76 (d, 2H), 3.51 (s, 2H), 3.26 (t, 2H), 1.56 (m, 2H), 0.98 (m, 2H), 0.84 (m, 5H.)

Example 10

4-[5-(1-Methoxymethoxymethyl-cyclopropyl)-4-phenyl-isoxazol-3-yl]-phenol

The title compound is prepared using the general procedures described in Coupling Method D and Deprotection Method A with the following specifications:
Coupling Method D
(1-{3-[4-(tert-butyl-dimethyl-silanyloxy)-phenyl]-4-phenyl-isoxazol-5-yl}-cyclopropyl)-methanol (0.21 g)
solvent: tetrahydrofuran (2 mL)
base: diisopropylethylamine (0.1 mL)
electrophile: chloromethyl methyl ether (0.056 mL)
Deprotection Method A
synthetic intermediate from Coupling Method D (0.23 g)
solvent: tetrahydrofuran (4 mL)
tetrabutylammonium fluoride (0.14 g)
title compound afforded: 0.15 g
$^1$H-NMR (400 MHz, CDCl$_3$) δ 7.38-7.22 (m, 7H), 6.78 (d, 2H), 4.44 (s, 2H), 3.38 (s, 2H), 3.24 (s, 3H), 0.99 (m, 2H), 0.92 (m, 2H

Example 11

4-{4-Phenyl-5-[1-(2,2,2-trifluoro-ethoxymethyl)-cyclopropyl]-isoxazol-3-yl}-phenol The title compound is prepared using the general procedures described in Coupling Method C and Deprotection Method B with the following specifications:
Coupling Method C (with optional Step v)
Step iv)
{1-[3-(4-methoxymethoxy-phenyl)-4-phenyl-isoxazol-5-yl]-cyclopropyl}-methanol (4.42 g)
solvent: dichloromethane (50 mL)
base: triethylamine (2.18 mL)
electrophile: methanesulfonyl chloride (1.24 mL)
synthetic intermediate afforded: methanesulfonic acid 1-[3-(4-methoxymethoxy-phenyl)-4-phenyl-isoxazol-5-yl]-cyclopropylmethyl ester (product of this step, 5.40 g)
Step v)
methanesulfonic acid 1-[3-(4-methoxymethoxy-phenyl)-4-phenyl-isoxazol-5-yl]-cyclopropylmethyl ester (product of Step iv, 0.33 g)
nucleophile: 2,2,2-trifluoro-ethanol (0.28 mL)
solvent: N,N-dimethylformamide
base: 60% sodium hydride in mineral oil suspension (0.07 g)
synthetic intermediate afforded (product of this step, 0.35 g)
Deprotection Method B
synthetic intermediate from Coupling Method C (product of Step v, 0.35 g)
title compound afforded: 0.23 g
Melting point 112-113° C.;
$^1$H-NMR (400 MHz, CDCl$_3$) δ 7.41-7.32 (m, 7H), 6.87 (d, 2H), 5.20 (s, 1H), 3.62 (m, 4H), 1.02 (m, 2H), 0.96 (m, 2H).

Example 12

4-{5-[1-(2-Methyl-pyridin-3-yloxymethyl)-cyclopropyl]-4-phenyl-isoxazol-3-yl}-phenol The title compound (0.26 g) is prepared according to the procedure described in Example 11, except 2-methyl-pyridin-3-ol is substituted for 2,2,2-trifluoro-ethanol; melting point 194-195° C.; $^1$H-NMR (400 MHz, DMSO-d$_6$) δ 9.91 (s, 1H), 7.98 (s, 1H), 7.40-7.32 (m, 5H), 7.10 (m, 4H), 6.64 (d, 2H), 4.04 (s, 2H), 2.34 (s, 3H), 1.02 (m, 2H), 0.96 (m, 2H.)

Example 13

4-{5-[1-(2-Methoxy-pyridin-3-yloxymethyl)-cyclopropyl]-4-phenyl-isoxazol-3-yl}-phenol The title compound (0.22 g) is prepared according to the procedure described in Example 11, except 2-methoxy-pyridin-3-ol is substituted for 2,2,2-trifluoro-ethanol; melting point 189-190° C.; $^1$H-NMR (400 MHz, DMSO-$d_6$) δ 9.91 (s, 1H), 7.72 (d, 1H), 7.43 (m, 2H), 7.38 (m, 3H), 7.17-7.12 (m, 3H), 6.82 (m, 1H), 6.68 (d, 2H), 4.04 (s, 2H), 3.91 (s, 3H), 1.03 (m, 2H), 0.96 (m, 2H.)

Examples 14-17 General Procedure

Examples 14-17 are prepared according to the following general procedure:
Step A)

1-{3-[4-(tert-Butyl-dimethyl-silanyloxy)-phenyl]-4-phenyl-isoxazol-5-yl}-cyclopropanecarbaldehyde
(common synthetic intermediate for Examples 14-17, 20-30, 32-33, 45, and 47)

To a mixture consisting of (1-{3-[4-(tert-butyl-dimethyl-silanyloxy)-phenyl]-4-phenyl-isoxazol-5-yl}-cyclopropyl)-methanol (Example 1, Compound E, 4.0 g) in dichloromethane (60 mL) is added 1,1,1-triacetoxy-1,1-dihydro-1,2-benziodoxol-3(1H)-one (7.0 g.) The mixture is stirred overnight at room temperature. The mixture is treated with aqueous sodium thiosulfate (20 mL) and the layers are thoroughly mixed and separated. The organic layer is washed sequentially with water and brine solution and is dried over anhydrous sodium sulfate. The mixture is filtered and the filtrate is concentrated under reduced pressure to afford the solid common synthetic intermediate (4.1 g.)
Step B)

General Method for addition of alkylmagnesium bromide to 1-{3-[4-(tert-butyl-dimethyl-silanyloxy)-phenyl]-4-phenyl-isoxazol-5-yl}-cyclopropanecarbaldehyde To a mixture consisting of the common synthetic intermediate prepared in Step A in tetrahydrofuran cooled to a temperature such as 0° C. or −78° C. is added a mixture consisting of an alkylmagnesium bromide (excess) in tetrahydrofuran. The mixture is stirred for at least one hour at room temperature and is then cooled to 0° C. To the cooled stirring mixture is added a saturated aqueous ammonium chloride dropwise. The resulting mixture is extracted with an organic solvent such as ethyl acetate. The organic layer is separated and is washed sequentially with a dilute aqueous acid such as 1 $\underline{N}$ hydrochloric acid, water, and brine. The organic layer is then dried over a drying agent such as anhydrous sodium sulfate and is filtered and concentrated under reduced pressure. Optionally, the concentrate is purified by flash silica gel column chromatography. Elution with a solvent mixture such as hexanes-ethyl acetate afforded the desired synthetic intermediate.
Step C)
General Method for Deprotection of Synthetic Intermediate Prepared in Step B To a mixture consisting of the synthetic intermediate prepared in Step B in tetrahydrofuran at room temperature is added an excess of tetrabutylammonium fluoride. The mixture is stirred for at least 30 minutes and is then diluted with an organic solvent such as ethyl acetate. The organic mixture is washed sequentially with water and brine and is then dried over a drying agent such as anhydrous sodium sulfate. The mixture is filtered and the filtrate is concentrated under reduced pressure. The concentrate is purified by flash silica gel column chromatography. Elution with a solvent mixture such as dichloromethane-methanol-ammonia or hexanes-ethyl acetate afforded the desired product.

Example 14

(±)-4-{5-[1-(Cyclopropyl-hydroxy-methyl)-cyclopropyl]-4-phenyl-isoxazol-3-yl}-phenol Example 14 is prepared according to the general procedure described above with the following specifications:
Step B)
common synthetic intermediate (0.45 g)
temperature: 0° C.
alkylmagnesium bromide: cyclopropylmagnesium bromide (1 $\underline{M}$ in tetrahydrofuran, 2.7 mL)
synthetic intermediate isolated: (±)-(1-{3-[4-(tert-butyl-dimethyl-silanyloxy)-phenyl]-4-phenyl-isoxazol-5-yl}-cyclopropyl)-cyclopropyl-methanol (0.27 g)
Step C)
synthetic intermediate prepared in Step B (0.27 g)
tetrabutylammonium fluoride (0.17 g)
title compound afforded: 0.065 g
$^1$H-NMR (400 MHz, CDCl$_3$) δ 7.39-7.27 (m, 5H), 7.22 (m, 2H), 6.77 (d, 2H), 2.84 (d, 1H), 0.99 (m, 3H), 0.80 (m, 2H), 0.52 (m, 2H), 0.28 (m, 1H), 0.18 (m, 1H)

Example 15

(±)-4-{5-[1-(1-Hydroxy-butyl)-cyclopropyl]-4-phenyl-isoxazol-3-yl}-phenol

The title compound (0.132 g) is prepared according to the general procedure described above. The alkylmagnesium bromide used in Step B is n-propylmagnesium bromide; melting point 139-140° C.; $^1$H-NMR (400 MHz, CDCl$_3$) δ 7.36-7.28 (m, 5H), 7.20 (m, 2H), 6.77 (d, 2H), 3.36 (m, 1H), 1.64-1.23 (m, 5H), 0.91-0.76 (m, 6H.)

Example 16

(±)-4-{5-[1-(Hydroxy-phenyl-methyl)-cyclopropyl]-4-phenyl-isoxazol-3-yl}-phenol

The title compound (0.24 g) is prepared according to the general procedure described above. The alkylmagnesium bromide used in Step B is phenylmagnesium bromide; $^1$H-NMR (400 MHz, CDCl$_3$) δ 7.36-7.12 (m, 11H), 6.70 (m, 3H), 4.79 (s, 1H), 1.04 (m, 2H), 0.81-0.72 (m, 2H.)

Example 17

(±)-4-{5-[1-(1-Hydroxy-2-methyl-propyl)-cyclopropyl]-4-phenyl-isoxazol-3-yl}-phenol Example 17 is prepared according to the general procedure described above with the following specifications:
Step B)
common synthetic intermediate (0.5 g)
temperature: −78° C.
alkylmagnesium bromide: isopropylmagnesium bromide (2 $\underline{M}$ in tetrahydrofuran, 1.5 mL)

synthetic intermediate isolated: (±)-1-(1-{3-[4-(tert-butyl-dimethyl-silanyloxy)-phenyl]-4-phenyl-isoxazol-5-yl}-cyclopropyl)-2-methyl-propan-1-ol (0.21 g)
Step C)
Title compound afforded: 0.12 g
¹H-NMR (400 MHz, CDCl₃+CD₃OD) δ 7.38 (m, 3H), 7.28 (m, 2H), 7.20 (d, 2H), 7.76 (d, 2H), 3.02 (d, 1H), 1.80 (m, 1H), 0.99-0.81 (m, 10H).

Example 18

4-{5-[1-(4-Methyl-piperazin-1-ylmethyl)-cyclopropyl]-4-phenyl-isoxazol-3-yl}-phenol The title compound is prepared according to the following procedure:
Step A)
To a mixture consisting of the substrate {1-[3-(4-methoxymethoxy-phenyl)-4-phenyl-isoxazol-5-yl]-cyclopropyl}-methanol (Examples 4-13 General Procedures, Coupling Method C, Step iii, 0.500 g) in dichloromethane (8 mL) is added 1-hydroxy-1,2-benziodoxol-3(1H)-one 1-oxide (1.19 g.) The stirring mixture is brought to reflux till the substrate is not detected by methods such as thin layer chromatography or mass spectrometry. The mixture is then cooled to room temperature and filtered. The filtrate is concentrated under reduced pressure to afford the solid 1-[3-(4-methoxymethoxy-phenyl)-4-phenyl-isoxazol-5-yl]-cyclopropanecarbaldehyde.
Step B)
To a mixture consisting of 1-[3-(4-methoxymethoxy-phenyl)-4-phenyl-isoxazol-5-yl]cyclopropanecarbaldehyde (this example, Step A, 0.490 g) in dichloromethane (15 mL) is added 1-methyl-piperazine (0.173 mL) and sodium triacetoxyborohydride (0.420 g.) The mixture is stirred for two hours. Another portion of 1-methyl-piperazine (0.08 mL) and sodium triacetoxyborohydride (0.18 g) are added to the mixture and the mixture is stirred overnight. The mixture is treated with water and is extracted with dichloromethane. The organic layer is separated and is dried over anhydrous sodium sulfate. The mixture is filtered and the filtrate is concentrated under reduced pressure. The concentrate is purified by flash silica gel column chromatography to afford 1-{1-[3-(4-methoxymethoxy-phenyl)-4-phenyl-isoxazol-5-yl]-cyclopropylmethyl}-4-methyl-piperazine (0.500 g.)
Step C)
To a mixture consisting of 1-{1-[3-(4-methoxymethoxy-phenyl)-4-phenyl-isoxazol-5-yl]-cyclopropylmethyl}-4-methyl-piperazine (this example, Step B) in isopropanol is added 6 N hydrochloric acid solution. The mixture is stirred at room temperature overnight. The mixture is titrated to pH 8 with an aqueous sodium hydroxide solution and is extracted with ethyl acetate. The organic layer is separated and dried over anhydrous sodium sulfate. The mixture is filtered and the filtrate is concentrated under reduced pressure. The concentrate is purified to afford the title compound ¹H NMR (400 MHz, CDCl₃) δ 7.40-7.20 (m, 7H), 6.70 (d, 2H), 2.45 (m, 8H), 2.25 (s, 3H), 1.05 (m, 2H), 0.78 (m, 2H); MS (EH+) m/z 390 (MH+.)

Example 19

4-[5-(1-Cyclopentylaminomethyl-cyclopropyl)-4-phenyl-isoxazol-3-yl]-phenol

The title compound (0.52 g) is prepared according to the procedure described in Example 18, except cyclopentylamine is substituted for 1-methyl-piperazine; ¹H NMR (400 MHz, CDCl₃) δ 7.38 (m, 5H), 7.20 (m, 2H) 6.60 (d, 2H), 3.10 (bs, 1H), 3.00 (m, 1H), 2.70 (s, 2H), 1.80 (m, 2H), 1.62 (m, 2H), 1.50 (m, 2H), 1.25 (m, 2H), 1.00 (m, 2H), 0.80 (m, 2H); MS (EH+) m/z 375 (MH+.)

Example 20

4-[5-(1-Dimethylaminomethyl-cyclopropyl)-4-phenyl-isoxazol-3-yl]-phenol hydrochloride salt Step A)
To a mixture consisting of 1-{3-[4-(tert-butyl-dimethyl-silanyloxy)-phenyl]-4-phenyl-isoxazol-5-yl}-cyclopropanecarbaldehyde (Examples 14-17 General Procedure, Step A, 0.51 g) in dichloromethane (20 mL) is added sequentially a solution consisting of dimethylamine in tetrahydrofuran (2.0 M, 2 mL) followed by sodium triacetoxyborohydride (0.75 g.) The mixture is agitated overnight at room temperature under a nitrogen atmosphere. The mixture is diluted with dichloromethane (20 mL) and is washed twice with brine solution. The organic layer is separated, dried over anhydrous sodium sulfate, filtered, and concentrated under reduced pressure. The concentrate is purified by flash silica gel column chromatography to afford the synthetic intermediate (1-{3-[4-(tert-butyl-dimethyl-silanyloxy)-phenyl]-4-phenyl-isoxazol-5-yl}-cyclopropylmethyl)-dimethyl-amine (0.251 g)
Step B)
To a mixture consisting of the synthetic intermediate prepared in Step A (0.246 g) in dichloromethane is added tetrabutylammonium fluoride (0.15 g.) The mixture is stirred at room temperature for twenty minutes and is then treated with a solution consisting of hydrogen chloride (1 M) in diethyl ether until precipitation is observed. The precipitate is collected by filtration, is washed with dichloromethane (3×5 mL), and is dried under high vacuum overnight to afford the title compound (0.070 g); melting point 234° C.; MS (ES⁺) m/z 335 (MH⁺.)

Example 21

4-[5-(1-[1,4]Diazepan-1-ylmethyl-cyclopropyl)-4-phenyl-isoxazol-3-yl]-phenol hydrochlorid salt The title compound (0.115 g) is prepared according to the procedure described in Example 20, except [1,4]diazepane-1-carboxylic acid tert-butyl ester (0.21 mL) is substituted for dimethylamine in tetrahydrofuran solution; melting point 193-194° C.; MS (ES⁺) m/z 390 (MH⁺.)

Example 22

4-(5-{1-[(3-Methoxy-propylamino)-methyl]-cyclopropyl}-4-phenyl-isoxazol-3-yl)-phenol The title compound is prepared according to the procedure described in Example 20, except 3-methoxypropylamine is substituted for dimethylamine in tetrahydrofuran solution and the product is not isolated by precipitating as a hydrochloride salt in the second step; instead, the mixture is treated with a dilute aqueous base such as sodium bicarbonate solution. The organic layer is separated and is washed sequentially with water and with brine solution. The organic layer is then dried over a drying agent such as anhydrous sodium sulfate, filtered, and concentrated under reduced pressure. The concentrate is purified by flash silica gel column chromatography. Elution with a solvent mixture such as a mixture of dichloromethane-methanol or dichloromethane-methanol-ammonia affords the title compound.

Example 23

4-{5-[1-(Indan-5-ylaminomethyl)-cyclopropyl]-4-phenyl-isoxazol-3-yl}-phenol hydrochloride salt The title compound (0.101 g) is prepared according to the procedure described in Example 20, except indan-5-ylamine (0.17 g) is substituted for dimethylamine in tetrahydrofuran solution; melting point 204-205° C.; MS (ES$^+$) m/z 423 (MH$^+$.)

Example 24

(±)-4-(5-{1-[(1,2-Dimethyl-propylamino)-methyl]-cyclopropyl}-4-phenyl-isoxazol-3-yl)-phenol The title compound is prepared according to the procedure described in Example 22, except (±)-1,2-dimethyl-propylamine is substituted for 3-methoxypropylamine.

Example 25

(±)-4-(4-Phenyl-5-{1-[(1-phenyl-propylamino)-methyl]-cyclopropyl}-isoxazol-3-yl)-phenol The title compound (0.126 g) is prepared according to the procedure described in Example 20, except (±)-1-phenyl-propylamine (0.16 mL) is substituted for dimethylamine in tetrahydrofuran solution and the reaction mixture from Step A is treated directly with tetrabutylammonium fluoride without being subjected to aqueous workup. The mixture is stirred at room temperature for one hour and is washed with 2 M aqueous sodium bicarbonate solution. The organic layer is separated, dried over anhydrous sodium sulfate, filtered, and concentrated under reduced pressure. The concentrate is purified by flash silica gel column chromatography to afford the title compound; melting point 126-127° C.; MS (ES$^+$) m/z 425 (MH$^+$.)

Example 26

4-[4-Phenyl-5-(1-{[(1R)-1-phenyl-propylamino]-methyl}-cyclopropyl)-isoxazol-3-yl]-phenol The title compound is prepared according to the procedure described in Example 22, except (R)-1-phenyl-propylamine is substituted for (±)-1-phenyl-propylamine.

Example 27

4-[4-Phenyl-5-(1-pyrrolidin-1-ylmethyl-cyclopropyl)-isoxazol-3-yl]-phenol

The title compound is prepared according to the procedure described in Example 22, except pyrrolidine is substituted for 3-methoxypropylamine.

Example 28

4-(5-{1-[(3-Dimethylamino-propylamino)-methyl]-cyclopropyl}-4-phenyl-isoxazol-3-yl)-phenol The title compound is prepared according to the procedure described in Example 22 except N',N',-dimethyl-propane-1,3-diamine is substituted for 3-methoxypropylamine.

Example 29

4-(4-Phenyl-5-{1-[(3-trifluoromethyl-phenylamino)-methyl]-cyclopropyl}-isoxazol-3-yl)-phenol The title compound is prepared according to the procedure described in Example 22, except 3-trifluoromethyl-phenylamine is substituted for 3-methoxypropylamine.

Example 30

(±)-4-[4-Phenyl-5-(1-{[(tetrahydro-furan-2-ylmethyl)-amino]-methyl}-cyclopropyl)-isoxazol-3-yl]-phenol The title compound (0.192 g) is prepared according to the procedure described in Example 20, except (±)-(tetrahydro-furan-2-yl)-methylamine is substituted for dimethylamine in tetrahydrofuran solution. A precipitate is not collected; instead, the mixture treated with hydrogen chloride in ether solution is concentrated under reduced pressure. The concentrate is purified by flash silica gel column chromatography to afford the title compound; melting point 276-277° C.; MS (ES$^+$) m/z 391 (MH$^+$)

Example 31

4-[5-(1-Morpholin-4-ylmethyl-cyclopropyl)-4-phenyl-isoxazol-3-yl]-phenol

The title compound (0.18 g) is prepared according to the procedure described in Example 18, except morpholine is substituted for 1-methyl-piperazine; $^1$H NMR (400 MHz, CDCl$_3$) δ 7.40-7.20 (m, 7H), 6.70 (d, 2H), 5.30 (bs, 1H), 3.60 (m, 4H), 2.40 (m, 6H), 1.05 (m, 2H), 0.70 (m, 2H); MS (ES$^+$) m/z 377 (MH$^+$.)

Example 32

4-[4-Phenyl-5-(1-thiomorpholin-4-ylmethyl-cyclopropyl)-isoxazol-3-yl]-phenol hydrochloride salt Step A)

To a mixture consisting of (1-{3-[4-(tert-butyl-dimethyl-silanyloxy)-phenyl]-4-phenyl-isoxazol-5-yl}-cyclopropyl)-methanol (Example 1, Compound E, 2.0 g) in dichloromethane (30 mL) is added sequentially pyridine (0.60 mL), methanesulfonyl chloride (0.55 mL), and 4-dimethylaminopyridine (0.06 g) at 0° C. under a nitrogen atmosphere. The mixture is stirred at 0° C. for 30 minutes and is warmed to room temperature. The mixture is stirred at room temperature for four hours and is then diluted with dichloromethane (30 mL.) The mixture is washed 0.5 N hydrochloric acid solution and with brine solution. The organic layer is separated, dried over anhydrous sodium sulfate, filtered, and concentrated under reduced pressure. The concentrate is purified by flash silica gel column chromatography to afford the synthetic intermediate methanesulfonic acid 1-{3-[4-(tert-butyl-dimethyl-silanyloxy)-phenyl]-4-phenyl-isoxazol-5-yl}-cyclopropylmethyl ester (2.35 g.)

Step B)

To a mixture consisting of the synthetic intermediate prepared in Step A (0.2 g) in dimethyl sulfoxide (3 mL) is added sequentially sodium carbonate (0.043 g) and thiomorpholine (0.04 mL) at room temperature under a nitrogen atmosphere. The mixture is stirred for 18 hours and is then diluted with dichloromethane (20 mL.) The mixture is washed with brine solution and the organic layer is dried over anhydrous sodium sulfate, filtered, and concentrated under reduced pressure. The concentrate is purified by flash silica gel column chromatography to afford the synthetic intermediate 4-(1-{3-[4-(tert-butyl-dimethyl-silanyloxy)-phenyl]-4-phenyl-isoxazol-5-yl}-cyclopropylmethyl)-thiomorpholine (0.081 g.)

Step C)

To a mixture consisting of the synthetic intermediate prepared in Step B (0.075 g) in dichloromethane (6 mL) is added a solution consisting of 1 $\underline{M}$ hydrogen chloride in diethyl ether to precipitate a solid. The solid is collected by filtration, is washed with dichloromethane (3×5 mL), and is dried under high vacuum overnight to afford the title compound (0.029 g); melting point 249-250° C.; MS m/z (ES$^+$) 393 (MH$^+$.)

Example 33

4-{4-Phenyl-5-[1-(pyridin-4-ylaminomethyl)-cyclopropyl]-isoxazol-3-yl}-phenol hydrochloride salt The title compound is prepared according to the procedure described in Example 32, except 4-aminopyridine (0.173 g) is substituted for thiomorpholine; moreover, the mixture in Step B is heated to 60° C. for six hours following the stirring at room temperature for 18 hours. In addition, in Step C, the synthetic intermediate (1-{3-[4-(tert-butyl-dimethyl-silanyloxy)-phenyl]-4-phenyl-isoxazol-5-yl}-cyclopropylmethyl)-pyridin-4-yl-amine formed in Step B is dissolved in methanol instead of dichloromethane. This mixture is concentrated under reduced pressure. The concentrate is crystallized from acetone-ethyl acetate (5:1 v/v, 5 mL.) The solid is collected by filtration and is dried under high vacuum to afford the title compound (0.075 g); melting point 316-317° C.; MS (ES$^+$) m/z 384 (MH$^+$.)

Example 34

1-{1-[3-(4-Hydroxy-phenyl)-4-phenyl-isoxazol-5-yl]-cyclopropylmethyl}-pyridinium; chloride Step A)

To a stirring solution consisting of Example 1, Compound E (0.3 g) in dichloromethane (20 mL) is added sequentially pyridine (0.062 mL) and trifluoromethanesulfonyl anhydride (0.13 mL) at −70° C. under a nitrogen atmosphere. The mixture is stirred at −70° C. for three hours. Additional pyridine (0.02 mL) is subsequently added and the stirring mixture is allowed to warm to −20° C. overnight. The mixture is diluted with dichloromethane (20 mL) and is washed with brine solution. The organic layer is separated, dried over anhydrous sodium sulfate, filtered, and concentrated under reduced pressure. The concentrate is purified by flash silica gel column chromatography to afford the synthetic intermediate 1-(1-{3-[4-(tert-butyl-dimethyl-silanyloxy)-phenyl]-4-phenyl-isoxazol-5-yl}-cyclopropylmethyl)-pyridinium; trifluoro-methanesulfonate (0.216 g.)

Step B)

To a stirring mixture consisting of the synthetic intermediate prepared in Step A (0.169 g) in dichloromethane is added tetrabutylammonium fluoride (0.15 g.) The mixture is stirred at room temperature for twenty minutes. A solution consisting of 1 $\underline{M}$ hydrogen chloride in diethyl ether is added to precipitate a solid. The precipitate is collected by filtration, washed with dichloromethane (3×5 mL), and dried under high vacuum overnight to afford the title compound (0.061 g); melting point 244-245° C.; MS (ES$^+$) m/z 369 (M$^+$.)

Example 35

4-(5-Cyclopropyl-4-phenyl-isoxazol-3-yl)-phenol

Step A)

To a mixture consisting of Example 1, Compound B (3.0 g) in anhydrous tetrahydrofuran (14 mL) at −5° C. under a nitrogen atmosphere is added a solution consisting of 1.6 $\underline{M}$ n-butyllithium in hexanes (12 mL.) The mixture is stirred between −5 and 0° C. for 30 minutes. To the stirring mixture at 0° C. is added a mixture consisting of cyclopropanecarboxylic acid methyl ester (1.3 g) in tetrahydrofuran (7 mL) and the resultant mixture is stirred for two hours. The mixture is raised to room temperature and is stirred for 18 hours. The mixture is then treated with saturated aqueous ammonium chloride (50 mL) and diluted with ethyl acetate (300 mL.) The organic layer is separated and is washed sequentially with an additional portion of saturated aqueous ammonium chloride (50 mL) and brine solution (50 mL.) The organic layer is separated and is dried over anhydrous sodium sulfate, filtered, and concentrated under reduced pressure. The concentrate is purified by flash silica gel column chromatography. Elution with dichloromethane then with a mixture of hexanes-ethyl acetate (4:1 v/v) afforded the synthetic intermediate 3-[4-(tert-butyl-dimethyl-silanyloxy)-phenyl]-5-cyclopropyl-4-phenyl-4,5-dihydro-isoxazol-5-ol (1.15 g.)

Step B)

To a mixture consisting of the synthetic intermediate prepared in this example, Step A (0.30 g) in anhydrous tetrahydrofuran (10 mL) is added sequentially molecular sieves and para-toluenesulfonic acid monohydrate (0.01 g.) The mixture is stirred at reflux for two hours and is then cooled to room temperature. The mixture is diluted with tetrahydrofuran (30 mL) and is then treated with tetrabutylammonium fluoride (0.38 g.) The mixture is stirred at room temperature for two hours and is treated with saturated aqueous ammonium chloride (30 mL) and diluted with ethyl acetate (200 mL.) The organic layer is separated and is washed sequentially with another portion of saturated aqueous ammonium chloride (50 mL) and brine solution (50 mL.) The organic layer is dried over anhydrous sodium sulfate, filtered, and concentrated under reduced pressure. The concentrate is purified by flash silica gel column chromatography. Elution with hexanes-ethyl acetate (7:3 v/v) afforded the title compound (0.160 g); melting point 197-200° C.;

MS (APCI$^+$) m/z 278 (MH$^+$.)

Example 36

4-[5-(1-methyl-cyclopropyl)-4-phenyl-isoxazol-3-yl] phenol

Step A)

The synthetic intermediate 3-[4-(tert-butyl-dimethyl-silanyloxy)-phenyl]-5-(1-methyl-cyclopropyl)-4-phenyl -4,5-dihydro-isoxazol-5-ol (0.833 g) is prepared from Example 1, Compound B and 1-methyl-cyclopropanecarboxylic acid methyl ester by the general method described in Step A of Example 35.

Step B)

The title compound (0.454 g) is prepared from the synthetic intermediate in Step A above, by the general method

Example 37

Thioacetic acid S-{1-[3-(4-hydroxy-phenyl)-4-phenyl-isoxazol-5-yl]-cyclopropylmethyl} ester Step A)

To a mixture consisting of potassium thioacetate (0.55 g) in N,N-dimethylformamide (15 mL) at 0° C. is added a mixture consisting of Example 32, Step A (1.63 g) in N,N-dimethylformamide (30 mL.) The mixture is stirred at room temperature overnight and is then diluted with ethyl acetate (60 mL.) The mixture is washed sequentially with 1 N hydrochloric acid (3×20 mL), water (20 mL), and brine solution (20 mL) and is dried over anhydrous sodium sulfate and concentrated under reduced pressure. The concentrate is purified by flash silica gel column chromatography. Elution with hexanes-ethyl acetate (9:1 v/v) afforded the synthetic intermediate thioacetic acid S-(1-{3-[4-(tert-butyl-dimethyl-silanyloxy)-phenyl]-4-phenyl-isoxazol-5-yl}-cyclopropylmethyl)ester (0.71 g.)

Step B)

To a mixture consisting of the synthetic intermediate prepared in this example, Step A (0.71 g) in tetrahydrofuran (10 mL) is added sequentially acetic acid (0.092 mL) and tetrabutylammonium fluoride (0.42 g.) The mixture is stirred at room temperature for 30 minutes and is then diluted with ethyl acetate (30 mL.) The mixture is washed sequentially with 1 N hydrochloric acid (15 mL), water (15 mL), and brine solution (15 mL.) The mixture is then dried over anhydrous sodium sulfate, filtered, and concentrated under reduced pressure. The concentrate is purified by flash silica gel column chromatography. Elution with hexanes-ethyl acetate mixture (9:1 to 4:1 v/v stepwise) afforded the title compound (0.38 g);

$^1$H-NMR (400 MHz, CDCl$_3$) δ 7.40 (m, 3H), 7.22 (m, 5H), 6.72 (d, 2H), 5.14 (s, 1H), 3.16 (s, 2H), 2.30 (s, 3H), 1.02 (m, 2H), 0.96 (m, 2H).

Example 38

4-[5-(1-Methylsulfanylmethyl-cyclopropyl)-4-phenyl-isoxazol-3-yl]-phenol

Step A)

To a mixture consisting of sodium thiomethoxide (0.33 g) in N,N-dimethylformamide (3 mL) is added a mixture consisting of methanesulfonic acid 1-[3-(4-methoxymethoxy-phenyl)-4-phenyl-isoxazol-5-yl]-cyclopropylmethyl ester (synthetic intermediate prepared in Example 11, Step iv, 1 g) in N,N-dimethylformamide at 0° C. The mixture is stirred at 80° C. for four hours and is cooled to room temperature. The mixture is then diluted with ethyl acetate (50 mL) and is sequentially washed with 1 N hydrochloric acid solution (3×15 mL), water (15 mL), and brine solution (15 mL.) The mixture is dried over anhydrous sodium sulfate, filtered, and concentrated under reduced pressure to afford the synthetic intermediate 3-(4-methoxymethoxy-phenyl)-5-(1-methylsulfanylmethyl-cyclopropyl)-4-phenyl-isoxazole (0.89 g.)

Step B)

The title compound is prepared from the synthetic intermediate prepared in this example, Step A using Deprotection Method B (Examples 4-13 General Procedures.) The product is precipitated from hexanes-dichloromethane (4:1 v/v) to afford the desired product (0.24 g); melting point 176-177° C.; $^1$H-NMR (400 MHz, CDCl$_3$) δ 7.42-7.22 (m, 7H), 6.74 (d, 2H), 5.24 (br. s, 1H), 2.75 (s, 2H), 2.01 (s, 3H), 1.04 (m, 2H), 0.82 (m, 2H).

Example 39

4-[5-(1-Methanesulfonylmethyl-cyclopropyl)-4-phenyl-isoxazol-3-yl]-phenol

Step A)

To a mixture consisting of the synthetic intermediate prepared in Example 38, Step A (0.46 g) in tetrahydrofuran-methanol-water (2:1:1 v/v, 12 mL) is added potassium peroxymonosulfate (OXONE®, 2.96 g.) The mixture is stirred at room temperature overnight and is filtered. The collected solids are rinsed with ethyl acetate (30 mL) and the filtrate is sequentially washed with water (15 mL), aqueous iron(II) sulfate (2×15 mL), and brine solution (15 mL.) The organic mixture is dried over anhydrous sodium sulfate, filtered, and concentrated under reduced pressure to afford a synthetic intermediate.

Step B)

The concentrate (synthetic intermediate from Step A) is subjected to the conditions described in Example 38, Step B to afford the title compound (0.29 g); melting point 172-173° C.;

$^1$H-NMR (400 MHz, CDCl$_3$) δ 7.42 (m, 3H), 7.32-7.18 (m, 5H), 6.74 (d, 2H), 5.16 (s, 1H), 3.22 (s, 2H), 2.76 (s, 3H), 1.36 (m, 2H), 1.18 (m, 2H.)

Example 40

4-[4-Phenyl-5-(1-phenylsulfanylmethyl-cyclopropyl)-isoxazol-3-yl]-phenol

The title compound (0.146 g) is prepared using the procedure described in Example 38, except benzenethiol sodium salt is substituted for sodium thiomethoxide; melting point 180-181° C.; $^1$H-NMR (400 MHz, CDCl$_3$) δ 7.41 (m, 3H), 7.22 (m, 7H), 7.06 (m, 2H), 6.73 (d, 2H), 3.18 (s, 2H), 0.98-0.86 (m, 4H.)

Example 41

4-[5-(1-Benzenesulfonylmethyl-cyclopropyl)-4-phenyl-isoxazol-3-yl]-phenol

The title compound (0.29 g) is prepared from 3-(4-methoxymethoxy-phenyl)-4-phenyl-5-(1-phenylsulfanylmethyl-cyclopropyl)-isoxazole (synthetic intermediate prepared in Example 40) using the procedure described in Example 39; melting point 174-175; $^1$H-NMR (400 MHz, CDCl$_3$) δ 7.78 (m, 2H), 7.59 (m, 1H), 7.48 (m, 2H), 7.39 (m, 3H), 7.08 (m, 4H), 6.78 (m, 2H), 5.17 (s, 1H), 3.18 (s, 2H), 1.38 (m, 2H), 1.12 (m, 2H.)

Example 42

{1-[3-(4-Hydroxy-phenyl)-4-phenyl-isoxazol-5-yl]-cyclopropyl}-acetonitrile

Step A)

To a mixture consisting of methanesulfonic acid 1-[3-(4-methoxymethoxy-phenyl)-4-phenyl-isoxazol-5-yl]-cyclopropylmethyl ester (synthetic intermediate prepared in Example 11, Step iv, 0.45 g) in N,N-dimethylformamide (4 mL) is added potassium cyanide (0.17 g.) The mixture is stirred at 80° C. for five hours and is subsequently diluted with ethyl acetate (30 mL.) The mixture is sequentially washed with water (15 mL) and brine solution (15 mL), dried over anhydrous sodium sulfate, filtered, and concentrated under reduced pressure to afford the synthetic intermediate {1-[3-(4-methoxymethoxy-phenyl)-4-phenyl-isoxazol-5-yl]-cyclopropyl}-acetonitrile (0.38 g.)

Step B)

The title compound (0.23 g) is prepared from the synthetic intermediate prepared in this example, Step A using the procedure described in Example 38, Step B; melting point 189-190° C.;

$^1$H-NMR (400 MHz, DMSO-d$_6$) δ 9.92 (s, 1H), 7.44 (m, 3H), 7.34 (m, 2H), 7.16 (d, 2H), 6.72 (d, 2H), 2.92 (s, 2H), 0.98-0.94 (m, 4H.)

Example 43

4-{4-Phenyl-5-[1-(1H-tetrazol-5-ylmethyl)-cyclopropyl]-isoxazol-3-yl}-phenol

Step A)

To a mixture consisting of {1-[3-(4-methoxymethoxy-phenyl)-4-phenyl-isoxazol-5-yl]-cyclopropyl}-acetonitrile (the synthetic intermediate prepared in Example 42, Step A, 0.7 g) in toluene (10 mL) are added di-n-butyltin oxide (0.48 g) and azidotrimethylsilane (0.51 mL.) The stirring mixture is brought to reflux and continued stirring overnight. The mixture is subsequently cooled to room temperature, diluted with ethyl acetate (40 mL), and sequentially washed with water (20 mL) and brine solution (20 mL), dried over anhydrous sodium sulfate, filtered, and concentrated under reduced pressure. The concentrate is purified by flash silica gel column chromatography. Elution with hexanes-ethyl acetate (1:1 v/v) and further elution with ethyl acetate afforded the synthetic intermediate 5-{1-[3-(4-methoxymethoxy-phenyl)-4-phenyl-isoxazol-5-yl]-cyclopropylmethyl}-1H-tetrazole (0.6 g.)

Step B)

The title compound is prepared from the synthetic intermediate prepared in this example, Step A (0.6 g) using the procedure described in Example 38, Step B. The desired product is precipitated from diethyl ether-acetone (4:1 v/v) to afford the title compound as a solid (0.28 g);

$^1$H-NMR (400 MHz, DMSO-d$_3$) δ 10.36 (br. s, 1H), 7.38 (m, 3H), 7.08 (m, 4H), 6.68 (d, 2H), 3.02 (s, 2H), 0.78 (m, 2H), 0.61 (m, 2H.)

Example 44

4-[5-(1-{[(2R)-Morpholin-2-ylmethoxy]methyl}cyclopropyl)-4-phenylisoxazol-3-yl]-phenol Step A)

To a mixture consisting of 2R-hydroxymethyl-morpholine-4-carboxylic acid tert-butyl ester (0.61 g, preparation of unprotected (S)-enantiomer is described in *Organic Letters*, 7(5), 937-939; 2005) in N,N-dimethylformamide (6 mL) at 0° C. is added 60% sodium hydride suspension in mineral oil (0.09 g.) The mixture is stirred at room temperature for ten minutes and a mixture consisting of methanesulfonic acid 1-[3-(4-methoxymethoxy-phenyl)-4-phenyl-isoxazol-5-yl]-cyclopropylmethyl ester (Example 11, Step iv, 0.8 g) in N,N-dimethylformamide (4 mL) is subsequently added dropwise. The mixture is stirred at 80° C. for five hours and is subsequently cooled to room temperature and diluted with ethyl acetate (50 mL.) The mixture is washed sequentially with water (20 mL) and brine solution (20 mL), dried over anhydrous sodium sulfate, filtered, and concentrated under reduced pressure. The concentrate is purified by flash silica column chromatography. Elution with hexanes-ethyl acetate (4:1 v/v, 7:3 v/v stepwise) afforded the first synthetic intermediate (2R)-{1-[3-(4-methoxymethoxy-phenyl)-4-phenyl-isoxazol-5-yl]-cyclopropylmethoxymethyl}-morpholine-4-carboxylic acid tert-butyl ester (0.62 g.)

Step B)

Subjection of the synthetic intermediate prepared in this example, Step A, to Deprotection Method B (Examples 4-13 General Procedures) afforded the second synthetic intermediate (2R)-{1-[3-(4-hydroxy-phenyl)-4-phenyl-isoxazol-5-yl]-cyclopropylmethoxymethyl}-morpholine-4-carboxylic acid tert-butyl ester (0.19 g.) This intermediate is dissolved in dichloromethane (4 mL) and the resultant mixture is cooled to 0° C. and treated with trifluoroacetic acid (1 mL.) The mixture is stirred at room temperature for one hour and is subsequently concentrated under reduced pressure. The concentrate is dissolved in a solution consisting of ammonia in methanol, and the mixture is concentrated under reduced pressure. The concentrate is purified by flash silica gel column chromatography. Elution with dichloromethane-methanol (9:1 v/v) treated with ammonia afforded the title compound (0.06 g); $^1$H-NMR (400 MHz, CDCl$_3$+CD$_3$OD) δ 7.40-7.38 (m, 3H), 7.34 (m, 2H), 7.20 (d, 2H), 6.78 (d, 2H), 3.94 (m, 1H), 3.76-3.64 (m, 2H), 3.60-3.48 (m, 2H), 3.43-3.34 (m, 3H), 3.02-2.82 (m, 2H), 2.73 (t, 1H), 0.98 (m, 2H), 0.84 (m, 2H.)

Example 45

(±)-4-{5-[1-(1-Hydroxy-ethyl)-cyclopropyl]-4-phenyl-isoxazol-3-yl}-phenol

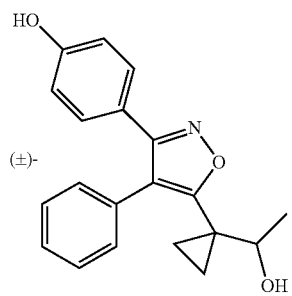

Example 45 is prepared according to the general procedure described for the preparation of Examples 14-17 with the following specifications:

Step B)

common synthetic intermediate (0.25 g)

temperature: 0° C.

alkylmagnesium bromide: methylmagnesium bromide (3.0 M in diethyl ether, 0.22 mL)

purification: flash silica gel column chromatography; elution with hexanes-ethyl acetate (4:1 v/v)

synthetic intermediate afforded: (±)-1-(1-{3-[4-(tert-butyl-dimethyl-silanyloxy)-phenyl]-4-phenyl-isoxazol-5-yl}-cyclopropyl)-ethanol (0.184 g)

Step C)
synthetic intermediate prepared in Step B (0.184 g)
tetrabutylammonium fluoride (0.46 mL, 1.0 M in tetrahydrofuran)
purification: precipitated from hexanes-absolute ethanol
title compound afforded: 0.065 g
   Melting point 196-197° C.;
   LC/MS (APCI+) m/z 322 (MH+)

Example 46

(R)-(–)-4-{5-[1-(1-Hydroxy-ethyl)-cyclopropyl]-4-phenyl-isoxazol-3-yl}-phenol

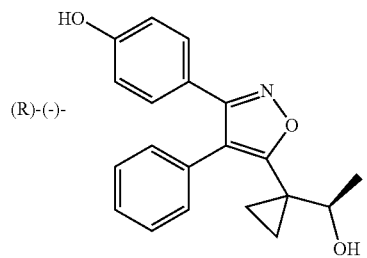

Step A)
To a solution consisting of 1-(4-methoxy-phenyl)-2-phenyl-ethanone (commercially available, 1011 g, 4468 mmoles) in absolute ethanol (2 gallons) is added hydroxylamine hydrochloride (373 g, 5362 mmoles) and sodium acetate (440 g, 5362 mmoles.) The reaction mixture is stirred at room temperature for two days. The mixture is diluted with water (8 L) and the resultant mixture is stirred at room temperature for one hour. The mixture is subsequently filtered to give a solid, which is rinsed with water (3×4 L.) The product is dried to afford the synthetic intermediate 1-(4-methoxy-phenyl)-2-phenyl-ethanone oxime (948 g.)

Step B)
To a stirring solution consisting of the synthetic intermediate prepared in Step A (1051 g) in tetrahydrofuran (8 L) at –14° C. is added a solution consisting of 2.5 M n-butyllithium (593 g) in hexane over a two hour period. The mixture is stirred for an additional 30 minutes and is subsequently added to a cold (–5° C.) solution consisting of cyclopropane-1,1-dicarboxylic acid dimethyl ester (832 g) in tetrahydrofuran (1 L.) The mixture is stirred for 30 minutes and is subsequently added to a cold (0° C.) mixture of acetic acid (650 mL) and water (1 L.) The stirring mixture is warmed to room temperature over 30 minutes. The aqueous layer is removed and the organic layer is washed with water (2 L), is separated, and is concentrated under reduced pressure to afford the synthetic intermediate 1-[5-hydroxy-3-(4-methoxy-phenyl)-4-phenyl-4,5-dihydro-isoxazol-5-yl]-cyclopropanecarboxylic acid methyl ester (2354 g.)

Step C)
To a solution consisting of 1-[5-hydroxy-3-(4-methoxy-phenyl)-4-phenyl-4,5-dihydro-isoxazol-5-yl]-cyclopropanecarboxylic acid methyl ester (2354 g) in toluene (8 L) is added p-toluenesulfonic acid monohydrate (40.8 g.) The mixture is stirred at 64° C. for 6.5 hours and is subsequently filtered over Celite filter aid. The Celite cake is washed with toluene (2×1 L) and the filtrate is diluted with a mixture of isopropanol (6 L) and heptane (6 L) to form a precipitate. The precipitate is triturated to afford a solid. The solid is triturated in a mixture of isopropanol (6 L) and heptane (2 L) for 3.5 hours and is subsequently collected by filtration. The solid is dried to afford the synthetic intermediate 1-[3-(4-methoxy-phenyl)-4-phenyl-isoxazol-5-yl]-cyclopropanecarboxylic acid methyl ester (889 g.)

Step D)
To a solution consisting of morpholine (15 g) in anhydrous tetrahydrofuran (300 mL) at 0° C. is added a solution (110 mL) consisting of 1.4 M methylmagnesium bromide (18 g) in toluene-tetrahydrofuran (3:1 v/v.) The stirring mixture warmed to 2° C. over 15 minutes and a solution consisting of the synthetic intermediate prepared in Step C (20 g) in tetrahydrofuran (100 mL) is subsequently added. The stirring mixture warmed to room temperature over 2.25 hours. The mixture is subsequently cooled to 0° C. and is quenched with saturated aqueous ammonium chloride (100 mL) and diluted with ethyl acetate (100 mL.) The layers are separated and the aqueous layer is extracted with a fresh portion of ethyl acetate (100 mL.) The organic layers are combined and washed sequentially with saturated aqueous ammonium chloride and brine solution. The organic layer is dried over anhydrous sodium sulfate and filtered through a plug of silica gel. The filtrate is concentrated under reduced pressure to afford the synthetic intermediate {1-[3-(4-methoxy-phenyl)-4-phenyl-isoxazol-5-yl]-cyclopropyl}-morpholin-4-yl-methanone (25.4 g.)

Step E)
To a solution consisting of the synthetic intermediate prepared in Step D (13 g) in anhydrous toluene (300 mL) is added aluminum chloride (26 g.) The stirring mixture is brought to reflux for one hour and is subsequently cooled to room temperature. To this mixture is added ethyl acetate (600 mL) followed by the dropwise addition of ice cubes until the insolubles dissolved completely in the resulting biphasic mixture. The organic layer is separated and the aqueous layer is extracted with a fresh portion of ethyl acetate (200 mL.) The ethyl acetate extracts are combined and washed with brine solution (200 mL.) The organic layer is separated, dried, filtered, and the filtrate is concentrated under reduced pressure. The concentrate is purified by flash silica gel column chromatography. Elution with a gradient (0-100% ethyl acetate in hexanes) followed by precipitation from dichloromethane afforded the synthetic intermediate {1-[3-(4-hydroxy-phenyl)-4-phenyl-isoxazol-5-yl]-cyclopropyl}-morpholin-4-yl-methanone (9.6 g.)

Step F)
To a stirring solution consisting of the synthetic intermediate prepared in Step E (20.3 g) in anhydrous tetrahydrofuran (174 mL) at 0° C. is added sequentially triethylamine (12 g), 4-dimethylaminopyridine (1.6 g) and a solution consisting of tetrabutyldimethylsilyl chloride (12 g) in anhydrous tetrahydrofuran (87 mL.) The mixture is allowed to warm to room temperature as it continued to stir for 18 hours. The mixture is diluted with ethyl acetate and washed sequentially with saturated aqueous ammonium chloride and brine solution. The organic layer is separated, dried over anhydrous magnesium sulfate, filtered, and concentrated under reduced pressure. The concentrate is purified by flash silica gel column chromatography. Elution with a gradient (0-60% ethyl acetate in hexanes) afforded the synthetic intermediate (1-{3-[4-(tert-butyl-dimethyl-silanyloxy)-phenyl]-4-phenyl-isoxazol-5-yl}-cyclopropyl)-morpholin-4-yl-methanone (22.9 g.)

Step G)
To a stirring solution consisting of the synthetic intermediate prepared in Step F (21 g) in anhydrous tetrahydrofuran (200 mL) at –10° C. is added a solution consisting or 1.4 M methylmagnesium bromide in toluene-tetrahydrofuran (3:1 v/v, 200 mL) over 30 minutes. The mixture is allowed to warm to room temperature as it continued stirring for 18 hours. The mixture is treated with saturated aqueous ammonium chloride (100 mL) and is diluted with ethyl acetate (500 mL.) The organic layer is separated and washed sequentially with a fresh portion of saturated aqueous ammonium chloride (100 mL) and brine solution (100 mL.) The organic layer is separated, dried over anhydrous sodium sulfate, filtered, and concentrated under reduced pressure. The concentrate is purified by flash silica gel column chromatography. Elution with hexanes-ethyl acetate (4:1 v/v) afforded the synthetic intermediate 1-(1-{3-[4-(tert-butyl-dimethyl-silanyloxy)-phenyl]-4-phenyl-isoxazol-5-yl}-cyclopropyl)-ethanone (15.14 g.)
Step H)

To a mixture consisting of 1 M borane-tetrahydrofuran complex in tetrahydrofuran stabilized with 0.005 M1,2,2,6,6-pentamethylpiperidine (35 mL) and a solution consisting of 1 M (S)-2-methyl-CBS-oxazaborolidine in toluene (7.9 mL) is added dropwise over 110 minutes a mixture consisting of the synthetic intermediate prepared in Step G (17 g) in toluene (120 mL) at room temperature under a nitrogen atmosphere. The mixture is stirred for fifteen minutes and is subsequently cooled to 0° C. To this mixture is added a solution consisting of 1 M tetrabutylammonium fluoride in tetrahydrofuran (53 mL) over 25 minutes. The mixture is stirred for an additional fifteen minutes and is subsequently treated with saturated aqueous ammonium chloride (500 mL) and diluted with ethyl acetate (800 mL.) The layers are separated and the organic layer is washed with brine solution (100 mL.) The organic layer is separated, dried over anhydrous magnesium sulfate, filtered, and concentrated under reduced pressure to give a solid. The solid is triturated in hexanes-dichloromethane (1:1 v/v, 140 mL) for five minutes and the resulting solids are collected by filtration and dried to afford a solid (11.9 g.) The solid is dissolved in hot acetonitrile (250 mL.) Hot water (300 mL) is added with stirring and the mixture is cooled with agitation to precipitate a solid. The solid is collected by filtration and dried in a vacuum oven (70° C.) overnight to afford the title compound (8.16 g); melting point 213° C.; specific rotation (Rudolph Research Analytical Model AutoPol IV): $[\alpha]=-25.2°$ (methanol.)

Example 47

(±)-4-{5-[1-(1-Hydroxy-propyl)-cyclopropyl]-4-phenyl-isoxazol-3-yl}-phenol

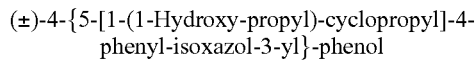

Example 47 (0.068 g) is prepared according to the general procedure described for the preparation of Example 45 except ethylmagnesium bromide is substituted for methylmagnesium bromide; melting point 175-176° C.; LC/MS (APCI$^+$) m/z 336 (MH$^+$).

Example 48

(R)-(-)-4-{5-[1-(1-Hydroxy-propyl)-cyclopropyl]-4-phenyl-isoxazol-3-yl}-phenol

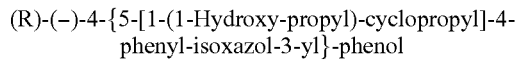

Step A)

To a stirring solution consisting of oxalyl chloride (5.0 mL) in dichloromethane (115 mL) at −78° C. is added dropwise a solution consisting of dimethyl sulfoxide (8.2 mL) in dichloromethane (25 mL) over ten minutes. The mixture is stirred at −78° C. for 40 minutes and a solution consisting of (±)-1-(1-{3-[4-(tert-butyl-dimethyl-silanyloxy)-phenyl]-4-phenyl-isoxazol-5-yl}-cyclopropyl)-propan-1-ol (synthetic intermediate prepared in Example 47, 18.70 g) in dichloromethane (150 mL) is subsequently added dropwise over one hour. The mixture is stirred at −78° C. for an additional 30 minutes and excess triethylamine is subsequently added dropwise. The stirring mixture is allowed to warm gradually to room temperature overnight. The stirring mixture is treated with water. The layers are separated and the aqueous layer is extracted with a fresh portion of dichloromethane. The combined organic extracts are washed with brine solution, dried over anhydrous magnesium sulfate, filtered, and concentrated under reduced pressure. The concentrate is purified by flash silica gel column chromatography. Elution with hexanes-ethyl acetate (17:3 v/v) afforded the synthetic intermediate 1-(1-{3-[4-(tert-butyl-dimethyl-silanyloxy)-phenyl]-4-phenyl-isoxazol-5-yl}-cyclopropyl)-propan-1-one (17.90 g.)
Step B)

To a solution consisting of 1 M borane-tetrahydrofuran complex in tetrahydrofuran (13 mL, stabilized with 1,2,2,6,6-pentamethylpiperidine) in tetrahydrofuran is added a solution consisting of 1 M (S)-2-methyl-CBS-oxazaborolidine in toluene (2.9 mL.) To this mixture is added dropwise a mixture consisting of the synthetic intermediate prepared in Step A (6.54 g) in toluene (50 mL.) The mixture is stirred for twenty minutes and is subsequently cooled to 0° C. To this mixture is added a solution consisting of 1 M tetrabutylammonium fluoride in tetrahydrofuran (20 mL.) The mixture is stirred for an additional fifteen minutes. A few milliliters of methanol are added to the mixture and the mixture is subsequently diluted with ethyl acetate and washed with saturated aqueous ammonium chloride and brine solution. The organic layer is separated, dried over anhydrous magnesium sulfate, filtered, and concentrated under reduced pressure. The concentrate is triturated in hexanes-chloroform until a solid formed. The suspension is concentrated under reduced pressure and the solid is triturated with chloroform. The resulting solids are collected by filtration are precipitated twice from ethanol-hexanes to afford the title compound (3.95 g); melting point 163-164° C.; MS (APCI$^+$) m/z 336 (MH$^+$); $[\alpha]^{25.2°\,C.}_{589nm}=-43.7$ (methanol)

Example 49

4-{5-[1-(1-Hydroxy-1-methyl-ethyl)-cyclopropyl]-4-phenyl-isoxazol-3-yl}-phenol

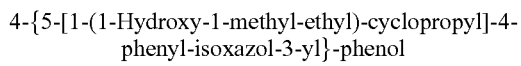

Step A)

To a stirring solution consisting of 1-{3-[4-(tert-butyl-dimethyl-silanyloxy)-phenyl]-4-phenyl-isoxazol-5-yl}-cyclopropanecarboxylic acid methyl ester (Example 1, Step D, 1.0 g) in anhydrous tetrahydrofuran (5 mL) at 0° C. is added dropwise a solution consisting of 1.4 M methylmagnesium bromide in toluene-tetrahydrofuran (3:1 v/v, 3.2 mL.) The stirring mixture is allowed to gradually warm to room temperature overnight. The mixture is subsequently cooled to 0° C. and quenched with water. The subsequent mixture is extracted with ethyl acetate. The organic extract is washed sequentially with saturated aqueous ammonium chloride and brine solution, is dried over anhydrous magnesium sulfate, is filtered, and is concentrated under reduced pressure. The concentrate is purified by flash silica gel column chromatography. Elution with a gradient (0-15% ethyl acetate in hexanes) afforded the synthetic intermediate 2-(1-{3-[4-(tert-butyl-dimethyl-silanyloxy)-phenyl]-4-phenyl-isoxazol-5-yl}-cyclopropyl)-propan-2-ol (0.480 g.)
Step B)

The title compound (0.313 g) is prepared from the synthetic intermediate prepared in Step A using the procedure described in Example 45, Step C; melting point 212-213° C., LC/MS (APCI⁺) m/z 336 (MH⁺.)

Example 50

4-{5-[1-(1-Ethyl-1-hydroxy-propyl)-cyclopropyl]-4-phenyl-isoxazol-3-yl}-phenol

The title compound is prepared according to the procedure described in Example 49 except ethylmagnesium bromide is substituted for methylmagnesium bromide; melting point 118-119° C.; LC/MS (APCI⁺) m/z 346 (MH⁺.)

Examples 51-59

Examples 51-59 are prepared using the following combinatorial synthesis. In a 2 dram reaction vial is added a solution consisting of 0.045 M Compound E, Example 1, in dichloromethane (3.3 mL.). To this solution is added triethylamine (0.035 mL) and 0.2 mmol of the acid chloride identified below (in Table A, column 2) in dichloromethane. The reactions mixtures are agitated at room temperature overnight, then at 40° C. for 20 hours. An additional 0.2 mmol of both the acid chloride and triethylamine are added and the reaction mixtures are further agitated at ambient temperature for three days. The reactions are quenched with Si-propylamine resin (Aldrich, Loading: 1.0 mmol/g, 600 mg/reaction) and the subsequent mixtures are agitated overnight. The resin is removed by filtration and the filtrate concentrated in the Genevac. Each reaction is subsequently diluted with tetrahydrofuran (2 mL) and a solution consisting of 1.0 M tetrabutylammonium fluoride in tetrahydrofuran is added. The reaction vials are agitated for 1.5 hours. The reactions are purified by preparatory HPLC.

The final products are characterized by one of the following LC/MS techniques, as identified in column 4 below: The MS value generated is reported in column 5.

MS Methods

Method #1)—OA machines: Phenomenex Develosil Combi RP3, 50×4.6 mm column, 45° C., X-2% H₂O over 3.5 min, hold 0.5 min)

Method #2—Waters Xterra MS C-18, 150×4.6 mm, 5 µM, 90-10% H₂O over 8.0 min, hold 1.5 min, flow rate=1.5 mL/min, injection volume, 20 µL)

TABLE A

| Example Number | Acid chloride | Final Product | | MS |
|---|---|---|---|---|
| 51 | | | 1 | 70-2% H₂O, 254 nm, 3.560 min (100%, M + 1 376.2) |
| 52 | | | 1 | 70-2% H₂O, 254 nm, 3.746 min (100%, M + 1 378.2) |
| 53 | | | 1 | 70-2% H₂O, 254 nm, 3.161 min (100%, M + 1 380.2) |

TABLE A-continued
| Example Number | Acid chloride | Final Product | MS |
|---|---|---|---|
| 54 | 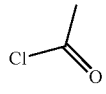 | 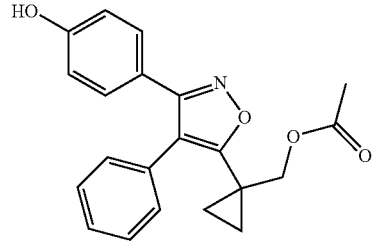 | 1 70-2% H$_2$O, 254 nm, 3.256 min (100%, M + 1 350.2) |
| 55 | 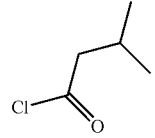 | 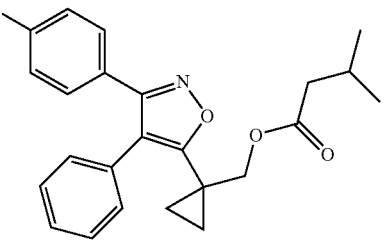 | 1 70-2% H$_2$O, 254 nm, 3.922 min (100%, M + 1 392.2) |
| 56 | 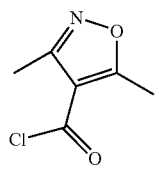 | 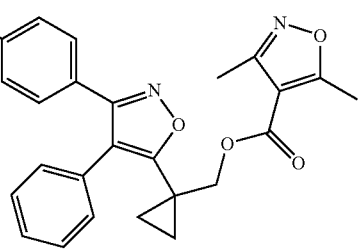 | 1 70-2% H$_2$O, 254 nm, 3.664 min (99%, M + 1 431.2) |
| 57 | 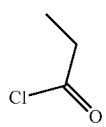 | 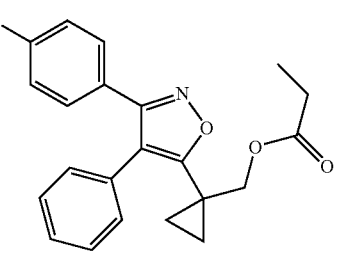 | 2 8.05 min (100%, M + 1 363.4) |

TABLE A-continued

| Example Number | Acid chloride | Final Product | MS |
|---|---|---|---|
| 58 | | | 2  8.53 min (100%, M + 1 377.4) |
| 59 | | | 2  6.75 min, (100%, M + 1 460.0) |

Example 60

1-[3-(4-Hydroxy-phenyl)-4-phenyl-isoxazol-5-yl]-cyclopropanecarboxylic acid isobutyl ester

To a stirring solution consisting of Example 87 (1.5 g) in isobutanol (10 mL) is carefully added thionyl chloride (3 mL.) The stirring mixture is heated to 60° C. for 7.5 hours. The reaction mixture is cooled to ambient temperature, diluted with ethyl acetate and washed successively with 5% aqueous sodium bicarbonate, water, and brine solution. The organic layer is dried over anhydrous magnesium sulfate and concentrated under reduced pressure. The concentrate is purified by flash silica gel column chromatography. Elution with a gradient (0-25% ethyl acetate in hexanes) afforded a residue. The residue is precipitated from hexanes-diethyl ether to afford the title compound (0.98 g); melting point 109-110° C.; LC/MS (APCI$^+$) m/z 378 (MH$^+$.)

Example 61

1-[3-(4-Hydroxy-phenyl)-4-phenyl-isoxazol-5-yl]-cyclopropanecarboxylic acid isopropyl ester

The title compound (2.0 g) is prepared using the general procedure described in Example 60 except isopropanol is substituted for isobutanol; melting point 175° C.; LC/MS (APCI$^+$) m/z 350 (MH$^+$.)

Examples 62-86

Examples 62-86 are prepared using the following combinatorial synthesis. In a 2 dram vial is added 0.1 mmol of the appropriate amine as identified in column 2, to this is added a solution consisting of 0.1 mmol of the aldehyde, 1-{3-[4-(tert-butyl-dimethyl-silanyloxy)-phenyl]-4-phenyl-isoxazol-5-yl}-cyclopropanecarbaldehyde (Examples 14-17 General Procedure, Step A) in DCM (1 mL) and a solution consisting of 0.3 mmol of tetramethylammonium triacetoxyborohydride in DCM (1 mL) The reaction mixtures are stirred at room temperature for 4 h and then 0.3 mmol of acetic acid is added. The reactions are stirred at room temperature overnight and subsequently a solution consisting of 0.3 mmol of tetramethylammonium triacetoxyborohydride in DCM (1 mL) is added. The reaction mixtures are stirred at room temperature overnight and a solution consisting of 1 $\underline{M}$ tetrabutylammonium fluoride in tetrahydrofuran (0.15 mL) is subsequently added. The reaction mixtures are stirred at room temperature for two hours and water (3 mL) is subsequently added. The DCM dichloromethane layer is separated by passing through phase separation columns and then concentrated in the Genevac. The samples are purified by HPLC. The final products are characterized by LCMS, which is carried out in the following manner.

| | |
|---|---|
| Column: | Atlantis C18, 100 mm × 4.6 mm, 3 micron |
| Flow rate: | 1 ml/min |
| Solvent: | A = acetonitrile |
| | B = water with 10 mM NH$_4$ OAC |
| Method: | 0-3 min. 25% A, 75% B; 3-8 min 95% A, 5% B |
| | 8-10 min. 25% A, 75% B |

| Example Number | Amine | Final Product | LCMS |
|---|---|---|---|
| 62 | (CH3)2NH | [4-hydroxyphenyl-phenyl-isoxazole-cyclopropyl-CH2-N(CH3)2] | LCMS: 254 nM, 3.52 min (100%, M + 1 335.4) |
| 63 | 5,6,7,8-tetrahydropyrido[4,3-d]pyrimidine | [4-hydroxyphenyl-phenyl-isoxazole-cyclopropyl-CH2-N(tetrahydropyrido-pyrimidine)] | LCMS: 254 nM, 3.95 min (100%, M + 1 425.5) |
| 64 | CH3NH-CH2CH2-OH | [4-hydroxyphenyl-phenyl-isoxazole-cyclopropyl-CH2-N(CH3)-CH2CH2-OH] | LCMS: 254 nM, 3.37 min (100%, M + 1 365.4) |
| 65 | CH3NH-CH2-(5-methyl-1,3,4-oxadiazol-2-yl) | [4-hydroxyphenyl-phenyl-isoxazole-cyclopropyl-CH2-N(CH3)-CH2-(5-methyl-1,3,4-oxadiazol-2-yl)] | LCMS: 254 nM, 3.82 min (100%, M + 1 417.5) |

-continued
| Example Number | Amine | Final Product | LCMS |
|---|---|---|---|
| 66 | 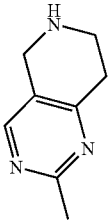 | 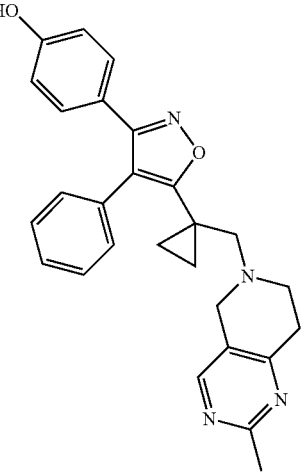 | LCMS: 254 nM, 3.88 min (80%, M + 1 439.5) |
| 67 | 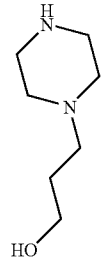 | 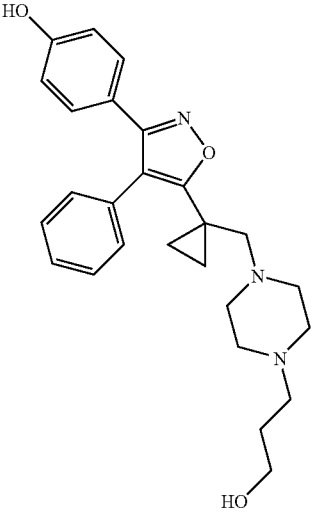 | LCMS: 254 nM, 3.42 min (100%, M + 1 434.5) |
| 68 | 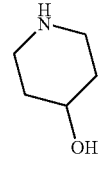 | 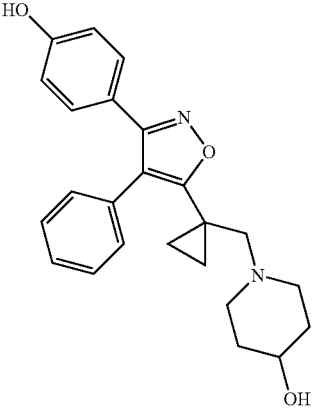 | LCMS: 254 nM, 3.33 min (100%, M + 1 391.5) |

-continued

| Example Number | Amine | Final Product | LCMS |
|---|---|---|---|
| 69 | methylaminopropionitrile | isoxazole derivative with N-methyl-N-(2-cyanoethyl)aminomethyl cyclopropyl | LCMS: 254 nM, 4.18 min (100%, M + 1 374.5) |
| 70 | 4-(2-hydroxyethyl)piperidine | isoxazole derivative with 4-(2-hydroxyethyl)piperidinylmethyl cyclopropyl | LCMS: 254 nM, 3.33 min (100%, M + 1 419.5) |
| 71 | azetidine | isoxazole derivative with azetidinylmethyl cyclopropyl | LCMS: 254 nM, 3.30 min (100%, M + 1 347.4) |
| 72 | N-ethyl-4-picolylamine | isoxazole derivative with N-ethyl-N-(4-pyridylmethyl)aminomethyl cyclopropyl | LCMS: 254 nM, 4.72 min (100%, M + 1 426.5) |

-continued
| Example Number | Amine | Final Product | LCMS |
|---|---|---|---|
| 73 | 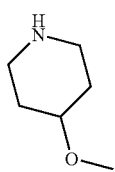 | 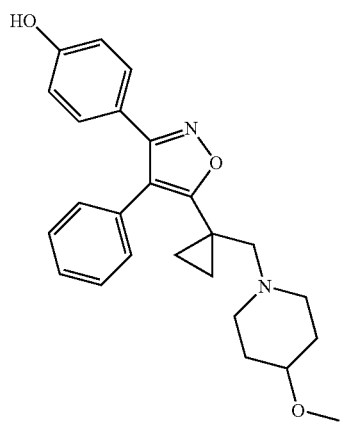 | LCMS: 254 nM, 4.14 min (95%, M + 1 405.5) |
| 74 | 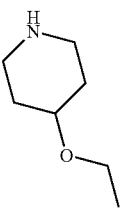 | 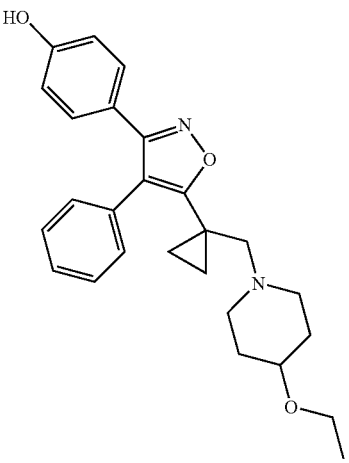 | LCMS: 254 nM, 4.42 min (100%, M + 1 419.5) |
| 75 | 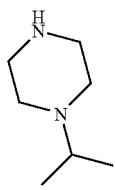 | 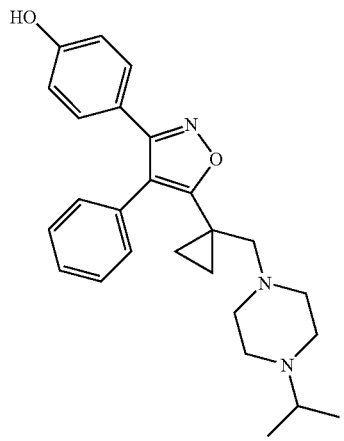 | LCMS: 254 nM, 3.77 min (100%, M + 1 418.5) |

-continued
| Example Number | Amine | Final Product | LCMS |
|---|---|---|---|
| 76 | 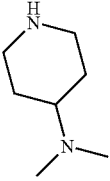 | 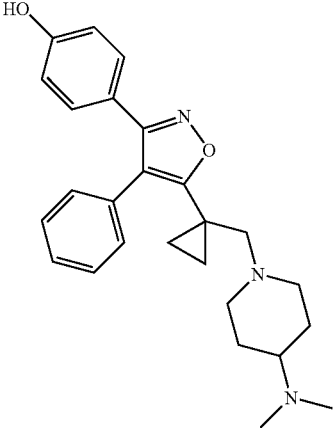 | LCMS: 254 nM, 3.87 min (98%, M + 1 418.5) |
| 77 | 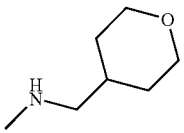 | 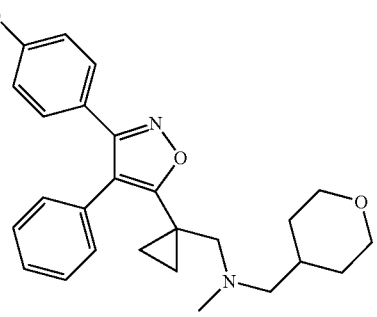 | LCMS: 254 nM, 4.57 min (100%, M + 1 419.5) |
| 78 | 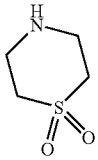 | 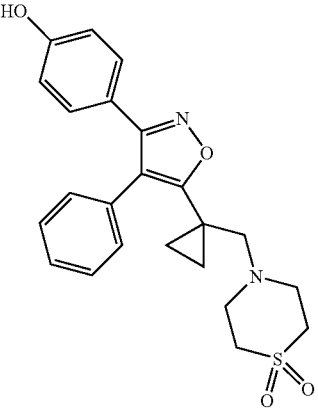 | LCMS: 254 nM, 3.80 min (100%, M + 1 425.5) |
| 79 | 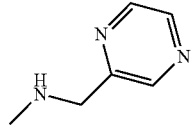 | 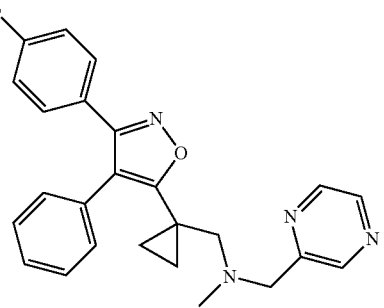 | LCMS: 254 nM, 4.07 min (100%, M + 1 413.5) |

| Example Number | Amine | Final Product | LCMS |
|---|---|---|---|
| 80 | 1-ethylpiperazine | (structure) | LCMS: 254 nM, 3.72 min (100%, M + 1 404.5) |
| 81 | ((3R,4R)-4-methylpyrrolidin-3-yl)methanol | (structure) | LCMS: 254 nM, 3.45 min (100%, M + 1 405.5) |
| 82 | (R)-3-(2-methoxyethoxy)pyrrolidine | (structure) | LCMS: 254 nM, 3.78 min (100%, M + 1 435.5) |

-continued
| Example Number | Amine | Final Product | LCMS |
|---|---|---|---|
| 83 | 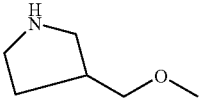 | 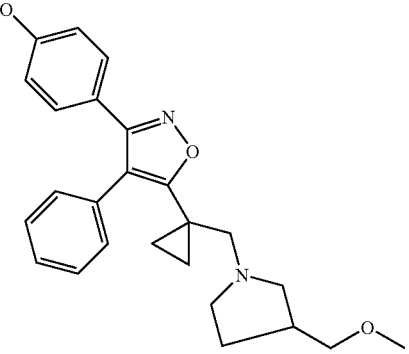 | LCMS: 254 nM, 3.94 min (100%, M + 1 405.5) |
| 84 | 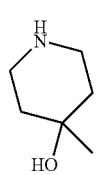 | 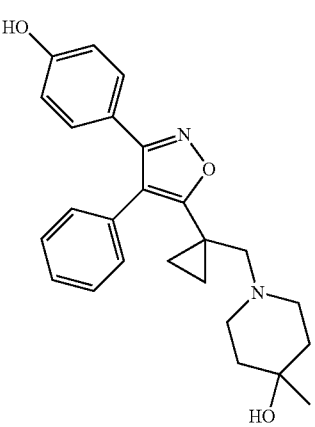 | LCMS: 254 nM, 3.38 min (89%, M + 1 405.5) |
| 85 | 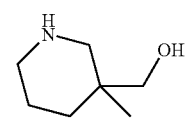 | 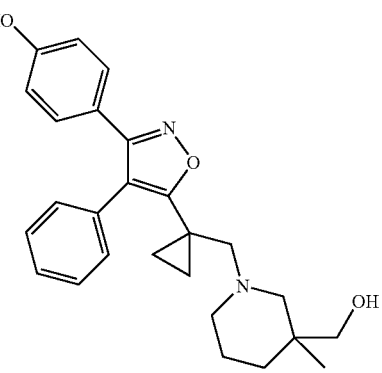 | LCMS: 254 nM, 4.15 min (100%, M + 1 419.5) |
| 86 | 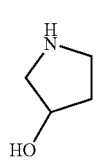 | 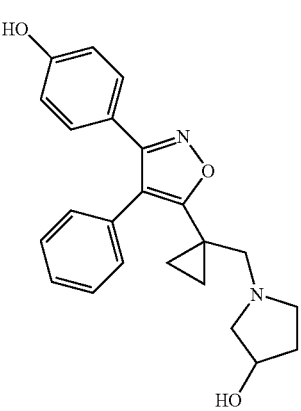 | LCMS: 254 nM, 3.28 min (100%, M + 1 377.5) |

Example 87

1-[3-(4-Hydroxy-phenyl)-4-phenyl-isoxazol-5-yl]-cyclopropanecarboxylic acid

To a solution consisting of 1-{3-[4-(tert-butyl-dimethyl-silanyloxy)-phenyl]-4-phenyl-isoxazol-5-yl}-cyclopropanecarboxylic acid methyl ester (Example 1, Compound D, 10 g) in tetrahydrofuran (100 mL) is added a 50 wt % sodium hydroxide in water solution (10 mL). The mixture is heated to 60° C. for 18 hours. The reaction mixture is concentrated under reduced pressure and partitioned between diethyl ether and water. The aqueous layer is washed with diethyl ether and acidified to pH 5 with concentrated aqueous hydrochloric acid. The aqueous phase is extracted with ethyl acetate. The combined extracts are washed with water and brine solution, dried over anhydrous sodium sulfate, and concentrated under reduced pressure to afford the title compound (5.64 g); MS (APCI$^+$) m/z 322 (MH$^+$.)

Example 88

1-[3-(4-Hydroxy-phenyl)-4-phenyl-isoxazol-5-yl]-cyclopropanecarboxylic acid 2-methoxy-ethyl ester To a solution consisting of the product of Example 87 (0.50 g) in 2-methoxyethanol (5 mL) is added thionyl chloride (1.0 mL.) The mixture is heated to 60° C. for 18 h is and is subsequently cooled, diluted with ethyl acetate, washed with water and brine solution, dried over anhydrous sodium sulfate, and concentrated under reduced pressure. The concentrate is purified by flash silica gel column chromatography. Elution with a gradient (0 to 50% ethyl acetate in hexanes) afforded the title compound (0.37 g); MS (APCI$^+$) m/z 380 (MH$^+$.)

Example 89

1-[3-(4-Hydroxy-phenyl)-4-phenyl-isoxazol-5-yl]-cyclopropanecarboxylic acid cyclopentyl ester The title compound (0.31 g) is prepared according to the general procedure described in Example 88, except cyclopentanol is substituted for 2-methoxyethanol; MS (APCI$^+$) m/z 390 (MH$^+$.)

Example 90

1-[3-(4-Hydroxy-phenyl)-4-phenyl-isoxazol-5-yl]-cyclopropanecarboxylic acid isobutyl ester The title compound (0.37 g) is prepared according to the general procedure described in Example 88, except isobutanol is substituted for 2-methoxyethanol; MS (APCI$^+$) m/z 378 (MH$^+$.)

Example 91

1-[3-(4-Hydroxy-phenyl)-4-phenyl-isoxazol-5-yl]-cyclopropanecarboxylic acid propyl ester The title compound (0.43 g) is prepared according to the general procedure described in Example 88, except n-propanol is substituted for 2-methoxyethanol; MS (APCI$^+$) m/z 364 (MH$^+$.)

Example 92

1-[3-(4-Hydroxy-phenyl)-4-phenyl-isoxazol-5-yl]-cyclopropanecarboxylic acid benzyl ester The title compound (0.22 g) is prepared according to the general procedure described in Example 88, except benzyl alcohol is substituted for 2-methoxyethanol; MS (APCI$^+$) m/z 412 (MH$^+$.)

Example 93

1-[3-(4-Hydroxy-phenyl)-4-phenyl-isoxazol-5-yl]-cyclopropanecarboxylic acid 2,2-dimethyl-propyl ester The title compound (0.43 g) is prepared according to the general procedure described in Example 88, except 2,2-dimethylpropanol is substituted for 2-methoxyethanol; MS (APCI$^+$) m/z 392 (MH$^+$.)

Example 94

1-[3-(4-Hydroxy-phenyl)-4-phenyl-isoxazol-5-yl]-cyclopropanecarboxylic acid butyl ester The title compound (0.41 g) is prepared according to the general procedure described in Example 88, except n-butanol is substituted for 2-methoxyethanol; MS (APCI$^+$) m/z 378 (MH$^+$.)

Example 95

1-[3-(4-Hydroxy-phenyl)-4-phenyl-isoxazol-5-yl]-cyclopropanecarboxylic acid cyclobutylmethyl ester The title compound (0.20 g) is prepared according to the general procedure described in Example 88, except cyclobutylmethanol is substituted for 2-methoxyethanol; MS (APCI$^+$) m/z 378 (MH$^+$.)

Example 96

1-[3-(3-Fluoro-4-methoxy-phenyl)-4-phenyl-isoxazol-5-yl]-cyclopropanecarboxylic acid ethyl ester Step A)

To a stirring suspension consisting of aluminum trichloride (15.9 g) in dichloromethane (200 mL) cooled to an internal temperature of −10° C. under a nitrogen atmosphere is added 2-fluoroanisole (10 g) over one minute. Phenylacetyl chloride (11.6 mL) is subsequently added to the mixture at a rate that maintained the internal temperature below 0° C. The reaction mixture is allowed to warm to room temperature overnight. Water (100 mL) is cautiously added to the stirring mixture. The layers are subsequently separated and the dichloromethane layer is concentrated under reduced pressure. The concentrate is dissolved in ethyl acetate and washed with water, 1 M sodium hydroxide, water, and brine. The organic layer is dried over anhydrous sodium sulfate, filtered, and concentrated under reduced pressure to afford the synthetic intermediate 1-(3-fluoro-4-methoxy-phenyl)-2-phenyl-ethanone (14.1 g.)

Step B)

To a mixture consisting of the synthetic intermediate prepared in Step A (14.1 g) in ethanol (200 mL) is added hydroxylamine hydrochloride (4.81 g) and sodium acetate (5.92 g.) The mixture is stirred at room temperature for 18 hours and is subsequently partitioned between ethyl acetate and water. The organic layer is separated and is washed with water and brine solution, is dried over anhydrous sodium sulfate, is filtered, and is concentrated under reduced pressure. The concentrate is purified by flash silica gel column chromatography. Elution with a gradient (0 to 50% ethyl acetate in hexanes) afforded the synthetic intermediate 1-(3-fluoro-4-methoxy-phenyl)-2-phenyl-ethanone oxime (9.81 g.)

Steps C and D)

The synthetic intermediate 1-[3-(3-fluoro-4-methoxy-phenyl)-4-phenyl-isoxazol-5-yl]-cyclopropanecarboxylic acid ethyl ester (0.60 g) is prepared from the synthetic intermediate prepared in Step B using the general procedure described in Example 1, Steps C and D.

Example 97

1-[3-(3-Fluoro-4-hydroxy-phenyl)-4-phenyl-isoxazol-5-yl]-cyclopropanecarboxylic acid ethyl ester To a stirring mixture consisting of Example 96 (0.60 g) in dichloromethane (10 mL) cooled to −10° C. under a nitrogen atmosphere is added boron tribromide (0.60 mL.) The mixture is stirred at −10° C. for one hour and is subsequently treated with saturated aqueous ammonium chloride. The mixture is extracted with ethyl acetate. The organic layer is separated, washed with water and brine solution, dried over anhydrous sodium sulfate, filtered, and concentrated under reduced pressure. The concentrate is purified by flash silica gel column chromatography. Elution with a gradient (0 to 20% ethyl acetate in hexanes) afforded the title compound (0.028 g); MS (APCI$^+$) m/z 368 (MH$^+$.)

Example 98

2-Fluoro-4-[5-(1-hydroxymethyl-cyclopropyl)-4-phenyl-isoxazol-3-yl]-phenol

Step A)

To a stirring solution consisting of Example 96 (3.00 g) in tetrahydrofuran (50 mL) cooled to −10° C. under nitrogen atmosphere is added a 1.0 $\underline{M}$ lithium aluminum hydride in tetrahydrofuran solution (15.7 mL) over five minutes. The mixture is stirred at −10° C. for 45 minutes and is carefully quenched with saturated aqueous ammonium chloride (25 mL.) The mixture is extracted with ethyl acetate and the organic layer is washed with water and brine solution, dried over anhydrous sodium sulfate, filtered, and concentrated under reduced pressure to afford the synthetic intermediate {1-[3-(3-fluoro-4-methoxy-phenyl)-4-phenyl-isoxazol-5-yl]-cyclopropyl}-methanol.

Step B)

To a stirring solution consisting of the synthetic intermediate prepared in Step A (0.50 g) in dichloromethane (10 mL) under a nitrogen atmosphere is added boron trifluoride-dimethyl sulfide complex (1.86 mL.) The mixture is stirred at room temperature for two days and is subsequently partitioned between ethyl acetate and water. The organic layer is washed with water and brine solution, dried over anhydrous sodium sulfate, filtered, and concentrated under reduced pressure. The concentrate is purified by flash silica gel column chromatography. Elution with a gradient (0 to 50% ethyl acetate in hexanes) afforded the title compound (0.25 g); MS (APCI$^+$) m/z 326 (MH$^+$.)

Example 99

4-{5-(1-(Dicyclopropyl-hydroxy-methyl)-cyclopropyl]-4-phenyl-isoxazol-3-yl}-phenol Step A)

The synthetic intermediate 1-{3-[4-(tert-butyl-dimethyl-silanyloxy)-phenyl]-4-phenyl-isoxazol-5-yl}-cyclopropanecarboxylic acid ethyl ester is prepared according to the general procedure described in Example 1, Steps A-D, except cyclopropane-1,1-dicarboxylic acid diethyl ester is substituted for cyclopropane-1,1-dicarboxylic acid dimethyl ester in Step C.

Step B)

To a stirring solution consisting of the synthetic intermediate prepared in Step A (2.0 g) in anhydrous tetrahydrofuran (10 mL) cooled to 0° C. is added a solution consisting of 0.5 $\underline{M}$ cyclopropylmagnesium bromide in tetrahydrofuran (9.5 mL.) The mixture is stirred at 0° C. for two hours and subsequently at room temperature for 18 hours. The mixture is subsequently treated with saturated aqueous ammonium chloride (25 mL) and extracted with ethyl acetate (200 mL.) The organic layer is separated and is washed with a fresh portion of saturated aqueous ammonium chloride (50 mL) and brine solution (50 mL.) The organic layer is dried over anhydrous sodium sulfate, filtered, and concentrated under reduced pressure. The concentrate is purified by flash silica gel column chromatography. Elution with dichloromethane afforded the synthetic intermediate (1-{3-[4-(tert-butyl-dimethyl-silanyloxy)-phenyl]-4-phenyl-isoxazol-5-yl}-cyclopropyl)-dicyclopropyl-methanol (0.337 g.)

Step C)

To a stirring solution consisting of the synthetic intermediate prepared in Step B (0.30 g) in anhydrous tetrahydrofuran (10 mL) is added tetrabutylammonium fluoride hydrate (0.30 g.) The mixture is stirred at room temperature for two hours. The mixture is treated with saturated aqueous ammonium chloride (20 mL) and subsequently extracted with ethyl acetate (200 mL.) The organic layer is separated and is washed with a fresh portion of saturated aqueous ammonium chloride (50 mL) and brine solution (50 mL.) The organic layer is dried over anhydrous sodium sulfate, filtered, and concentrated under reduced pressure. The concentrate is purified by flash silica gel column chromatography. Elution with hexanes-ethyl acetate (7:3 v/v) afforded the title compound (0.192 g); melting point 169-170° C.; MS (APCI$^+$) m/z 388 (MH$^+$.)

Example 100

Example 100 provides a number of alternative syntheses of the compound, 4-{5-[1-(1-hydroxy-ethyl)-cyclopropyl]-4-phenyl-isoxazol-3-yl}-phenol, which is the product of Example 45, and its individual enantiomers (R)-(−)-4-{5-[1-(1-Hydroxy-ethyl)-cyclopropyl]-4-phenyl-isoxazol-3-yl}-phenol and (S)-(+)-4-{5-[1-(1-Hydroxy-ethyl)-cyclopropyl]-4-phenyl-isoxazol-3-yl}-phenol. This example also illustrate the preparation of the enantiomers of (±)-4-{5-[1-(1-Hydroxy-propyl)-cyclopropyl]-4-phenyl-isoxazol-3-yl}-phenol.

Alternative Synthesis A (R)-(-)-4-{5-[1-(1-Hydroxy-ethyl)-cyclopropyl]-4-phenyl-isoxazol-3-yl}-phenol

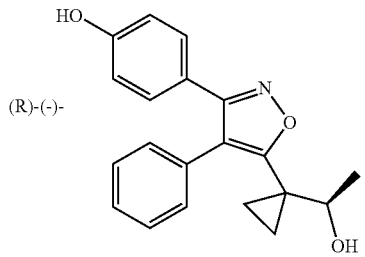

(R)-(-)-

Step A)

A five-liter four-neck reaction flask with a mechanical stirrer, constant addition funnel, nitrogen line, cooling bath and temperature probe is assembled. The flask is purged with nitrogen and charged with anisole (1050 mL.) The liquid is stirred and cooled to −8.6° C. using a dry-ice/acetone bath. Aluminum trichloride (474.0 g) is added in portions over 25 minutes while the internal temperature is maintained below +2.4° C. The mixture is stirred and cooled to −5.0° C. and phenylacetyl chloride (433 mL) is subsequently added over 75 minutes using a constant addition funnel while the temperature is maintained below +4.5° C. The reaction mixture continued stirring cold. A ten-liter rotary evaporator flask with a mechanical stirrer and digital thermometer is assembled. The flask is charged with toluene (2.25 L), water (3.5 L) and ice (840 g) and with stirring the reaction mixture is slowly added over 30 minutes while maintaining the temperature below +50° C. The reaction flask is rinsed with a mixture of toluene (1.0 L) and water (0.5 L) and the rinsate is transferred to the rotary evaporator flask. The biphasic mixture is stirred for 30 minutes and is subsequently allowed to stand. The aqueous layer is removed by vacuum and the organic layer is washed with a fresh portion of water (1.5 L), 5% aqueous potassium carbonate (1.5 L), and another portion of water (1.5 L.) The organic layer is concentrated under reduced pressure (50 Torr) on the rotary evaporator with a bath temperature of 50° C. About 1 L of toluene is removed and the mixture is allowed to stand for the evening. The mixture is concentrated further on the rotary evaporator until pressure is reduced to 34 Torr and very little solvent is distilling over. The total amount of solvent removed is about 3 L. The flask is removed from the rotary evaporator and equipped with a mechanical stirrer. Heptane (2.0 L) is added with stirring. A precipitate formed and the suspension thickened with time. The suspension is diluted further with heptane (3.0 L.) The resulting suspension is stirred for 30 minutes and subsequently filtered. The solids are washed with heptane (2×1 L) and dried in a vacuum oven at 45° C. for 19 hours, 45 minutes to afford the synthetic intermediate 1-(4-methoxy-phenyl)-2-phenyl-ethanone (561.67 g.)

Step B)

To a solution of the product of Step A, 1-(4-methoxy-phenyl)-2-phenyl-ethanone, (1011 g, 4468 mmoles) in absolute ethanol (2 gallons) is added hydroxylamine hydrochloride (373 g, 5362 mmoles) and sodium acetate (440 g, 5362 mmoles.) The reaction mixture is stirred at room temperature for two days. The mixture is diluted with water (8 L) and the resultant mixture is stirred at room temperature for one hour. The mixture is subsequently filtered to give a solid, which is rinsed with water (3×4 L.) The product is dried to afford the synthetic intermediate 1-(4-methoxy-phenyl)-2-phenyl-ethanone oxime (948 g.)

Step C)

To a stirring solution consisting of the synthetic intermediate prepared in Step B (1051 g) in tetrahydrofuran (8 L) at −14° C. is added a solution consisting of 2.5 M n-butyllithium (593 g) in hexane over a two hour period. The mixture is stirred for an additional 30 minutes and is subsequently added to a cold (−5° C.) solution consisting of cyclopropane-1,1-dicarboxylic acid dimethyl ester (832 g) in tetrahydrofuran (1 L.) The mixture is stirred for 30 minutes and is subsequently added to a cold (0° C.) mixture of acetic acid (650 mL) and water (1 L.) The stirring mixture is warmed to room temperature over 30 minutes. The aqueous layer is removed and the organic layer is washed with water (2 L), is separated, and is concentrated under reduced pressure to afford the synthetic intermediate 1-[5-hydroxy-3-(4-methoxy-phenyl)-4-phenyl-4,5-dihydro-isoxazol-5-yl]-cyclopropanecarboxylic acid methyl ester (2354 g.)

Step D)

To a solution of the product of Step C, 1-[5-hydroxy-3-(4-methoxy-phenyl)-4-phenyl-4,5-dihydro-isoxazol-5-yl]-cyclopropanecarboxylic acid methyl ester, (2354 g) in toluene (8 L) is added p-toluenesulfonic acid monohydrate (40.8 g.) The mixture is stirred at 64° C. for 6.5 hours and is subsequently filtered over Celite filter aid. The Celite cake is washed with toluene (2×1 L) and the filtrate is diluted with a mixture of isopropanol (6 L) and heptane (6 L) to form a precipitate. The precipitate is triturated to afford a solid. The solid is triturated in a mixture of isopropanol (6 L) and heptane (2 L) for 3.5 hours and is subsequently collected by filtration. The solid is dried to afford the synthetic intermediate 1-[3-(4-methoxy-phenyl)-4-phenyl-isoxazol-5-yl]-cyclopropanecarboxylic acid methyl ester (889 g.)

Step E)

Each of two twenty-liter ChemGlass reactors, Reactor A and Reactor B, are equipped with a mechanical stirrer, nitrogen gas line, Huber Chiller, and temperature probe. Reactor A is purged with nitrogen for 30 minutes and is charged with the synthetic intermediate prepared above in Step D (869 g) and dichloromethane (4.0 L.) The Huber Chiller is set to −25° C. and the stirring mixture is cooled to an internal temperature of −14.1° C. and boron tribromide (5×500 g) is subsequently added in portions over one hour while maintaining the temperature below −12° C. Upon completion of boron tribromide addition, the internal mixture temperature is −13.6° C. The mixture is stirred cold for 90 minutes and is transferred over 40 minutes to stirring water (10 L) in Reactor B (Huber Chiller set to assist in exotherm control in Reactor B as temperature is maintained below +37° C.), which had two rear open ports to facilitate gas escape. Reactor A is rinsed with dichloromethane (2.0 L) and the rinsate is transferred to Reactor B. The stirring mixture in Reactor B is diluted with the slow addition of water (5.0 L.) The biphasic mixture is stirred for 30 minutes and is allowed to stand. The layers are separated and the organic layer is washed with water (4×5 L.) The organic layer is separated and is concentrated under reduced pressure. The concentrate is subjected to atmospheric pressure to afford the solid synthetic intermediate 1-[3-(4-hydroxy-phenyl)-4-phenyl-isoxazol-5-yl]-cyclopropanecarboxylic acid methyl ester (1004 g.)

Step F)

To a mixture consisting of the synthetic intermediate prepared in Step E above (980 g) in dichloromethane (4.5 L) maintained between 16-25° C. under a nitrogen atmosphere is added tert-butyldimethylsilyl chloride (464 g.) 1-Methylimidazole (245 mL) is subsequently added over about a five minute period followed by dichloromethane (0.5 L.) and the mixture is stirred for five days. The mixture is concentrated under reduced pressure. The concentrate is partitioned between water (4.0 L) and methyl tert-butyl ether (8.0 L.) The mixture is stirred for ten minutes and the layers are separated. The organic layer is washed with water (2×2 L) and is concentrated under reduced pressure. The concentrate is taken up into methyl tert-butyl ether (1.0 L) and the mixture is concentrated under reduced pressure. This is repeated once more to afford the synthetic intermediate 1-{3-[4-(tert-butyl-dimethyl-silanyloxy)-phenyl]-4-phenyl-isoxazol-5-yl}-cyclopropanecarboxylic acid methyl ester (1302 g.)

Step G)

To a stirring mixture consisting of O,N-dimethyl-hydroxylamine hydrochloride (43.6 g) in THF (435 mL) at −25° C. under a nitrogen atmosphere is added 1.6 $\underline{M}$ n-butyllithium in hexanes (560 mL) over fifty minutes while maintaining the internal temperature below −16° C. The addition funnel is rinsed with THF (25 mL) and the rinseate is drained into the stirring reaction mixture. A solution consisting of the synthetic intermediate prepared in Step F (100 g) in THF (236.6 g total solution mass, 42.4 wt. % synthetic intermediate in THF) is added over approximately one minute, maintaining the internal reaction mixture temperature between −19° C. and +1° C. The reaction mixture is stirred cold for 50 minutes and is subsequently treated with saturated aqueous ammonium chloride (250 mL) and water (250 mL.), maintaining reaction mixture temperature between 4° C. and 18° C. The mixture is stirred for ten minutes and is diluted with methyl tert-butyl ether (1 L.) The layers are mixed and separated, and the organic layer is washed with water (2×250 mL), dried over anhydrous magnesium sulfate, and filtered through Celite. The filtrate is concentrated under reduced pressure to afford the synthetic intermediate 1-{3-[4-(tert-butyl-dimethyl-silanyloxy)-phenyl]-4-phenyl-isoxazol-5-yl}-cyclopropanecarboxylic acid methoxy-methyl-amide (103.5 g.)

Step H)

To a stirring mixture consisting of the synthetic intermediate prepared in Step G (103.5 g) in THF (500 mL) at room temperature under a nitrogen atmosphere is added a solution consisting of 3 $\underline{M}$ methylmagnesium bromide in diethyl ether (110 mL) over twenty minutes. The reaction mixture temperature increased to 43° C. over the period of addition of methylmagnesium bromide solution and is subsequently stirred for an additional twenty minutes after addition is complete. The reaction mixture is added over nine minutes to a stirring mixture consisting of saturated aqueous ammonium chloride (500 mL) and water (500 mL) and the flask containing the reaction mixture is rinsed with THF (2×50 mL) and the rinseate added to the aqueous mixture. The combined mixture is stirred for five minutes and is diluted with methyl tert-butyl ether (1.0 L.) The layers are separated and the organic layer is dried over anhydrous magnesium sulfate, filtered through Celite, and concentrated under reduced pressure. Residual THF is chased with hexanes and the crude product is purified by flash silica gel (230-400 mesh, 350 g) column chromatography. Elution with hexanes-ethyl acetate (10:1 v/v) afforded the synthetic intermediate 1-(1-{3-[4-(tert-butyl-dimethyl-silanyloxy)-phenyl]-4-phenyl-isoxazol-5-yl}-cyclopropyl)-ethanone (72.9 g.)

Step I)

To a stirring mixture consisting of borane-diethylaniline complex (23 mL) in THF (125 mL) and a solution consisting of 1 $\underline{M}$ (S)-2-methyl-CBS-oxazaborolidine in toluene (28 mL) is added dropwise over one hour a mixture consisting of the synthetic intermediate prepared in Step H (61.2 g) in toluene (400 mL) under a nitrogen atmosphere while maintaining the reaction mixture temperature below 25° C. The mixture is stirred for ten minutes and is subsequently added to a mixture consisting of saturated aqueous ammonium chloride (200 mL) and water (200 mL) over ten minutes. The subsequent mixture is stirred for five minutes and the layers are separated. The organic layer is washed with brine solution, dried over anhydrous magnesium sulfate, filtered through Celite, and concentrated under reduced pressure. The concentrate is purified by flash silica gel column chromatography. Elution with hexanes followed by a 7:3 v/v hexanes-ethyl acetate mixture afforded the synthetic intermediate (R)-1-(1-{3-[4-(tert-butyl-dimethyl-silanyloxy)-phenyl]-4-phenyl-isoxazol-5-yl}-cyclopropyl)-ethanol (66.7 g.)

Step J)

To a stirring mixture consisting of the synthetic intermediate prepared in Step 1 (77.7 g) in THF (160 mL) is added a 48 wt. % aqueous tetrafluoroboric acid solution (93 mL) over ten minutes. The reaction mixture is stirred for one hour and is subsequently treated with water (160 mL.) The mixture is cooled with an ice-water bath to +4° C. for about one hour and a precipitate formed. The precipitate is collected by filtration, washed with water (2×200 mL), and dried in a vacuum oven (50° C.) overnight to give a solid (45.7 g.) Several batches of solid from repeat experiments are combined to give a total of 172.9 g. The solids are dissolved in hot acetonitrile (4 L.) To the hot solution is added water (3.2 L) over nineteen minutes and the mixture is allowed to cool to 40° C. before cooling further over an ice-water bath to form a precipitate. The precipitate is collected by filtration, washed with acetonitrile-water (5:4 v/v, 500 mL), and dried to afford the title compound (126.4 g); MS (ES$^+$) m/z 322 (MH$^+$);

Chiral Purity:

The chiral purity of the title compound is quantified by normal phase HPLC and ultraviolet detection at 254 nm. The comparison of peak retention times and detector responses of the title compound in the sample solutions and the standard solutions achieved identification and quantitation.

High Performance Liquid Chromatography (HPLC) System consisting of:

a. Mobile Phase Delivery System, capable of uniformly delivering 1.2 mL/min., e.g., Agilent Model G1311A or equivalent b. Sample injector, e.g., Agilent Model G1313A or equilvalent c. Analytical column, Diacel Chiralpak OJ 4.6×250 mm d. UV detector, capable of providing linear response at 254 nm, e.g., Agilent Model G1314A or equilvalent e. Column oven (if not part of pump system), e.g. Agilent Model G1316A f. Electronic Integrator, e.g. Waters Empower or equilvalent Instrumentation: Apparatus and parameters (Use the apparatus and principles as described in the USP under Pressurized Liquid Chromatography).

Chromatographic Conditions:

| Column: | Diacel Chiralpak OJ 4.6 × 250 mm |
|---|---|
| Column Temperature: | 30° C. |
| Injection Volume: | 10 µL |
| Flow Rate: | 1.2 mL/min |
| Detection: | UV @ 254 nm |
| Mobile phase | 90:10 n-Heptane:Ethanol isocratic for 20 minutes |
| Diluent: | Ethanol |

| % RSD (Area) | % RSD of Retention Time | Retention Time | Peak Asymmetry | Column Efficiency | Signal-to-noise (S/N) |
|---|---|---|---|---|---|
| ≦2.0% | ≦2.0% | Title compound: 12.5 to 13.5 min other enantiomer: 15.4 to 16.4 min | $0.7 \leq A_s \leq 2.0$ | $N_{USP} \geq 1600$ | ≧10 |

Alternative Synthesis B

Synthesis B provides alternatives for the preparation of (±)-4-{5-[1-(1-Hydroxy-ethyl)-cyclopropyl]-4-phenyl-isoxazol-3-yl}-phenol

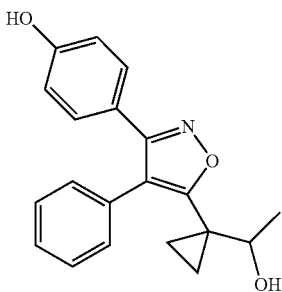

Step A)

Preparation of synthetic intermediate 1-{3-[4-(tert-Butyl-dimethyl-silanyloxy)-phenyl]-5-hydroxy-4-phenyl-4,5-dihydro-isoxazol-5-yl}-cyclopropanecarboxylic acid ethyl ester This synthetic intermediate (230.8 g) is prepared according to the general procedure described in Example 1, Step C, except cyclopropane-1,1-dicarboxylic acid diethyl ester is substituted for cyclopropane-1,1-dicarboxylic acid dimethyl ester.

Step B)

Preparation of the synthetic intermediate 1-{3-[4-(tert-butyl-dimethyl-silanyloxy)-phenyl]-4-phenyl-isoxazol -5-yl}-cyclopropanecarboxylic acid ethyl ester This synthetic intermediate (277.2 g) is prepared according to the general procedure described in Example 1, Step D, except the synthetic intermediate of Step A of this example is substituted for 1-{3-[4-(tert-butyl-dimethyl-silanyloxy)-phenyl]-5-hydroxy-4-phenyl-4,5-dihydro-isoxazol-5-yl}-cyclopropanecarboxylic acid methyl ester (alternatively called methyl 1-[3-(4-{[tert-butyl(dimethyl)silyl]oxy}phenyl)-5-hydroxy-4-phenyl-4,5-dihydroisoxazol-5-yl]cyclopropanecarboxylate.)

Step C)

In Step C, two alternative preparations for Compound E, from Example 1, (1-{3-[4-(tert-butyl-dimethyl-silanyloxy)-phenyl]-4-phenyl-isoxazol-5-yl}-cyclopropyl)-methanol are described. Regardless of how Compound E is prepared, it may be used in Step D described immediately below:

Alternative 1

This synthetic intermediate (18.0 g) is prepared according to the general procedure described in Example 1, Step E, except the synthetic intermediate prepared in Step B of this example is substituted for 1-{3-[4-(tert-butyl-dimethyl-silanyloxy)-phenyl]-4-phenyl-isoxazol-5-yl}-cyclopropanecarboxylic acid methyl ester (alternatively called methyl 1-[3-(4-{[tert-butyl(dimethyl)silyl]oxy}phenyl)-4-phenylisoxazol-5-yl]cyclopropanecarboxylate.)

Alternative 2

To a stirring mixture of the synthetic intermediate from Step B of this example (23 g) in THF (300 mL) at −15° C. under a nitrogen atmosphere is added dropwise a solution consisting of 1 M lithium aluminum hydride in THF (100 mL) over 25 minutes, maintaining the reaction mixture temperature below −5° C. The mixture is stirred at −10° C. for 1.5 hours and is subsequently treated with saturated aqueous ammonium chloride (50 mL) by dropwise addition. Additional THF (200 mL) is added. To the stirring mixture is subsequently added water (50 mL) and by ethyl acetate (150 mL.) The reaction mixture is filtered to remove solids and the filtrate is washed with brine solution (100 mL.) The layers are separated and the aqueous layer is extracted with a fresh portion of ethyl acetate. The combined organic layers are concentrated under reduced pressure and the concentrate is dissolved again in ethyl acetate (200 mL.) The mixture is washed sequentially with water and brine solution, is dried over anhydrous sodium sulfate, and is concentrated under reduced pressure. Subjection to high vacuum affords (1-{3-[4-(tert-butyl-dimethyl-silanyloxy)-phenyl]-4-phenyl-isoxazol-5-yl}-cyclopropyl)-methanol (21 g.)

Step D)

In Step D, two alternative preparations for 1-{3-[4-(tert-butyl-dimethyl-silanyloxy)-phenyl]-4-phenyl-isoxazol-5-yl}-cyclopropanecarbaldehyde are described. Regardless of how the compound is prepared, it may be used in Step E described immediately below:

Alternative 1

To a stirring mixture consisting of the synthetic intermediate prepared according to either method of the methods described in Step C immediately above (0.5 g), 4-methylmorpholine 4-oxide (0.18 g), and powdered 4 Angstrom molecular sieves (0.2 g) in dichloromethane (20 mL) at 0° C. is added tetrapropylammonium perruthenate (0.07 g.) The mixture is stirred at 0° C. for four hours and is evaporated onto flash silica gel (4 g.) Elution with hexanes-ethyl acetate (4:1 v/v) affords the desired synthetic intermediate (0.343 g.)

Alternative 2

To a stirring solution of oxalyl chloride (8.4 g) in dichloromethane (145 mL) at −78° C. under a nitrogen atmosphere is added dropwise a solution consisting of dimethyl sulfoxide (10.3 g) in dichloromethane (32 mL.) The mixture is stirred for one hour at −78° C. To this mixture is subsequently added dropwise a mixture consisting of the synthetic intermediate prepared in Step C (immediately above, either method, 23.2 g) in dichloromethane (180 mL) over 1.5 hours. The mixture is stirred for one additional hour at −78° C., and triethylamine (27.9 g) is added over ten minutes. The resulting reaction mixture is stirred at −78° C. for ten minutes and the cold bath is removed. The reaction mixture is stirred over one hour as the reaction mixture is brought to room temperature. The mixture is treated with water and the layers are separated. The aqueous layer is extracted with a fresh portion of dichloromethane and the combined organic extracts are washed with brine solution. The layers are separated and the organic layer is dried over anhydrous magnesium sulfate, filtered, and concentrated under reduced pressure. The concentrate is purified by flash silica gel column chromatography. Elution with a gradient (0-15% ethyl acetate in hexanes) followed by a constant 15% ethyl acetate in hexanes solution affords the desired synthetic intermediate (17.3 g.)

Step E)

Preparation of the synthetic intermediate (±)-1-(1-{3-[4-(tert-butyl-dimethyl-silanyloxy)-phenyl]-4-phenyl-isoxazol-5-yl}-cyclopropyl)-ethanol To a stirring solution consisting of the synthetic intermediate prepared according to either method of Step D immediately above, (15.5 g) in THF (300 mL) at 0° C. under a nitrogen atmosphere is added a mixture of 1.4 M methylmagnesium bromide in toluene-THF (39 mL, 3:1 v/v) over fifteen minutes. The stirring reaction mixture is brought gradually to room temperature overnight. The mixture is treated with saturated aqueous ammonium chloride and is twice extracted into ethyl acetate. The combined organic extracts are washed with brine solution, dried over anhydrous magnesium sulfate, filtered, and concentrated under reduced pressure to afford the desired synthetic intermediate (17.9 g.)

Step F)

Preparation of the Title Compound

To a stirring solution consisting of the synthetic intermediate prepared in Step E of this example (2.2 g) in anhydrous THF (60 mL) at room temperature under a nitrogen atmosphere is added tetrabutylammonium fluoride hydrate (2.6 g.) The reaction mixture is stirred at room temperature for four hours and is subsequently treated with saturated aqueous ammonium chloride (50 mL) and ethyl acetate (300 mL.) The organic layer is separated and washed with fresh portions of saturated aqueous ammonium chloride (2×50 mL) and with brine solution (50 mL.) The organic layer is dried over anhydrous sodium sulfate, filtered, and concentrated under reduced pressure. The concentrate is purified by flash silica gel column chromatography. Elution with hexanes-ethyl acetate (3:2 v/v) affords the title compound (1.42 g); MS (APCI$^+$) m/z 322 (MH$^+$.)

Alternative Synthesis C

Preparation of (R)-(−)-4-{5-[1-(1-Hydroxy-ethyl)-cyclopropyl]-4-phenyl-isoxazol-3-yl}-phenol The title compound of alternative synthesis B, which may be produced as described immediately above (1.31 g) is separated into its enantiomers by way of preparatory chiral HPLC (stationary phase: SCF Chiralcel AD-H; mobile phase: 30% cosolvent (isopropanol-methanol 9:1 v/v), 70% carbon dioxide) to afford the title compound (0.3 g); melting point 219-221° C.; specific rotation (Rudolph Research Analytical Model AutoPol IV): [α]=−30.7° (methanol, temperature=24° C.)

Alternative Synthesis D

Preparation of (S)-(+)-4-{5-[1-(1-Hydroxy-ethyl)-cyclopropyl]-4-phenyl-isoxazol-3-yl}-phen The title compound of alternative synthesis B, which may be produced as described therein (1.31 g) is separated into its enantiomers by way of preparatory chiral HPLC (stationary phase: SCF Chiralcel AD-H; mobile phase: 30% cosolvent (isopropanol-methanol 9:1 v/v), 70% carbon dioxide) to afford the title compound (0.3 g); melting point 220-221° C.; specific rotation (Rudolph Research Analytical Model AutoPol IV): [α]=+24.6° (methanol, temperature=24° C.)

Alternative Synthesis E

Preparation of (R)-(−)-4-{5-[1-(1-Hydroxy-propyl)-cyclopropyl]-4-phenyl-isoxazol-3-yl}-phe The title compound of Example 47 (1.38 g) is separated into its enantiomers by way of preparatory chiral HPLC (stationary phase: SCF Chiralcel AD-H; mobile phase: 30% cosolvent (isopropanol-methanol 9:1 v/v), 70% carbon dioxide) to afford the title compound (0.558 g); melting point 163-165° C.; specific rotation (Rudolph Research Analytical Model AutoPol IV): [α]=−37.4° (methanol, temperature=24° C.)

Alternative Synthesis F

Preparation of (S)-(+)-4-{5-[1-(1-Hydroxy-propyl)-cyclopropyl]-4-phenyl-isoxazol-3-yl}-phe The title compound of Example 47 (1.38 g) is separated into its enantiomers by way of preparatory chiral HPLC (stationary phase: SCF Chiralcel AD-H; mobile phase: 30% cosolvent (isopropanol-methanol 9:1 v/v), 70% carbon dioxide) to afford the title compound (0.476 g); melting point 165-166° C.; specific rotation (Rudolph Research Analytical Model AutoPol IV): [α]=+40.5° (methanol, temperature=24° C.)

Example 101

1-{1-[3-(4-Hydroxy-phenyl)-4-phenyl-isoxazol-5-yl]-cyclopropyl}-ethanone

Step A)

To a mixture consisting of Example 87 (3.4 g) in anhydrous dichloromethane (110 mL) is added sequentially anhydrous N,N-dimethylformamide (4 drops) and oxalyl chloride (1.9 g.) The mixture is stirred at room temperature for 18 hours and subsequently filtered. The filtrate is concentrated under reduced pressure to afford the synthetic intermediate 1-[3-(4-hydroxy-phenyl)-4-phenyl-isoxazol-5-yl]-cyclopropanecarbonyl chloride (2.98 g.)

Step B)

To a mixture consisting of ethyl acetate (16 mL) and water (8 mL) is added sequentially sodium carbonate (2.0 g) and morpholine (0.84 g.) The reaction mixture is cooled to 0° C. and a solution consisting of the synthetic intermediate prepared in Step A (3.0 g) in a mixture of ethyl acetate (16 mL) and dichloromethane (16 mL) is subsequently added. The reaction mixture is stirred at 0° C. for two hours and then at room temperature for 18 hours. A precipitate formed. The reaction mixture is filtered to remove the solid. The filtrate is diluted with ethyl acetate (250 mL) and the organic layer is washed with saturated aqueous ammonium chloride (3×50 mL) and brine (50 mL.) The organic layer is separated, dried over anhydrous sodium sulfate, filtered, and concentrated under reduced pressure. Purification by flash chromatography (silica gel, 60-80% ethyl acetate in hexane) afforded the synthetic intermediate {1-[3-(4-hydroxy-phenyl)-4-phenyl-isoxazol-5-yl]-cyclopropyl}-morpholin-4-yl-methanone (2.25 g); melting point 195-196° C.; MS (APCI$^+$) m/z 391 (MH$^+$.)

Step C)

To a stirring solution consisting of the synthetic intermediate prepared in Step B (0.50 g) in anhydrous tetrahydrofuran (5 mL) is added a solution consisting of 1.0 $\underline{M}$ ethylmagnesium bromide in toluene-tetrahydrofuran (7:3 v/v, 2.6 mL.) The reaction mixture is stirred at 0° C. for two hours and then at room temperature for 18 hours. Saturated aqueous ammonium chloride (50 mL) is added and the reaction mixture is diluted with ethyl acetate (200 mL.) The aqueous layer is removed and the organic layer is subsequently washed with additional saturated aqueous ammonium chloride (50 mL) and brine (50 mL.) The organic layer is dried over anhydrous sodium sulfate, filtered, and concentrated under reduced pressure. The concentrate is purified by flash silica gel column chromatography. Elution with hexanes-ethyl acetate (4:1 v/v) afforded, after drying, the title compound (0.071 g); MS (APCI$^+$) m/z 320 (MH$^+$); elemental microanalysis for $C_{20}H_{17}NO_3 \cdot 0.18 H_2O$: % C(calculated/found) 74.46/74.43, % H, 5.42/5.27; % N, 4.34/4.20.

Example 102

Alternative Synthesis of 1-(1-{3-[4-(tert-Butyl-dimethyl-silanyloxy)-phenyl]-4-phenyl-isoxazol-5-yl}-cyclopropyl)-ethanone Step A)

A solution consisting of boron tribromide (114 mL of a 1 $\underline{M}$ solution in dichloromethane) and dichloromethane (100 mL) is cooled in an ice/salt/methanol bath to −10° C. and a solution consisting of 1-[3-(4-methoxy-phenyl)-4-phenyl-isoxazol-5-yl]-cyclopropanecarboxylic acid methyl ester (10 g) dichloromethane (150 mL) is added dropwise while the temperature is maintained at −10° C. over 1 hour. The reaction mixture is allowed to warm to 0° C. and stirred for 4 hours until all starting material is consumed. The solution is cooled to −10° C. and 5% sodium bicarbonate solution (250 mL) is added slowly by addition funnel while maintaining the temperature below 0° C. The reaction flask is removed from the cold bath and water added, the organic layer is separated, dried, and concentrated to give 1-[3-(4-hydroxy-phenyl)-4-phenyl-isoxazol-5-yl]-cyclopropanecarboxylic acid methyl ester (9.6 g.)

Step B)

Imidazole (2.1 g) is added to a solution consisting of the 1-[3-(4-hydroxy-phenyl)-4-phenyl-isoxazol-5-yl]-cyclopropanecarboxylic acid methyl ester (9.6 g) and tert-butyldimethylsilyl chloride (4.7 g) in THF (100 mL). The reaction mixture is stirred at room temperature overnight. Brine solution is added and the reaction mixture is twice extracted with ethyl acetate. The combined extracts are dried and concentrated. Repeated concentration from hexane and then pentane gave 1-{3-[4-(tert-butyl-dimethyl-silanyloxy)-phenyl]-4-phenyl-isoxazol-5-yl}-cyclopropanecarboxylic acid methyl ester (12.8 g.)

Step C)

A solution consisting of morpholine (7.5 mL) in THF (100 mL) is cooled to 0° C. (ice/salt bath) and a solution of methylmagnesium bromide (55 mL of a 1.4 $\underline{M}$ solution in toluene/THF 3:1 v/v) is added by addition funnel while the temperature is maintained between 0 and 5° C. (over 15 minutes.) The orange reaction mixture is stirred at 0° C. for 30 minutes and subsequently a mixture consisting of 1-{3-[4-(tert-butyl-dimethyl-silanyloxy)-phenyl]-4-phenyl-isoxazol-5-yl}-cyclopropanecarboxylic acid methyl ester (12.8 g) in THF (50 mL) is added by addition funnel over 5 minutes. The flask is removed from the ice bath. The reaction mixture is cooled to 0° C. and a solution consisting of methylmagnesium bromide (55 mL of a 1.4 $\underline{M}$ solution in toluene/THF 3:1 v/v) is added over 10 minutes. After 20 min further methylmagnesium bromide (55 mL of a 1.4 $\underline{M}$ solution in toluene/THF 3:1 v/v) is added over 10 minutes. The ice bath is removed and the reaction mixture is allowed to warm to room temperature overnight. The reaction mixture is poured into an ice/ammonium chloride solution. The mixture is twice extracted with ethyl acetate and the combined extracts are dried and concentrated under reduced pressure. The concentrate is purified by flash silica gel column chromatography. Elution with a gradient (1% to 5% ethyl acetate in hexanes) afforded 1-(1-{3-[4-(tert-butyl-dimethyl-silanyloxy)-phenyl]-4-phenyl-isoxazol-5-yl}-cyclopropyl)-ethanone (4.8 g); MS (APCI$^+$) m/z 434 (MH$^+$.)

Example 103

4-[5-(1-methylaminomethyl-cyclopropyl)-4-phenyl-isoxazol-3-yl]-phenol

A mixture consisting of the synthetic intermediate prepared in Example 32, Step A (8.96 g) in methanol (10 mL) is transferred to a sealed tube and cooled to 0° C. Methylamine (7.9 g) is subsequently added and the tube is sealed, stirred and heated to 60° C. for 16 hours. The reaction mixture is cooled to room temperature and concentrated under reduced pressure. The concentrate is partitioned between diethyl ether and water. The biphasic mixture is filtered to remove insoluble material and the insolubles are rinsed with diethyl ether. The solids are suctioned and subsequently dried in a vacuum oven (60° C.) to afford the title compound (3.81 g); $^{13}$C-NMR (100 MHz; DMSO-d$_6$) δ 170.8, 161.5, 159.2, 131.0, 130.9, 130.0, 129.1, 128.5, 120.1, 116.2, 116.0, 57.8, 36.5, 18.8, 11.8; MS (APCI$^+$) m/z 321.1 (MH$^+$.)

Example 104

4-[5-(1-{[(2-hydroxyethyl)amino]methyl}cyclopropyl)-4-phenylisoxazol-3-yl]phenol

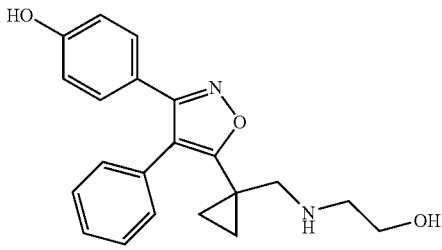

A solution consisting of the synthetic intermediate prepared in Example 32, Step A (8.96 g) and ethanolamine (2 mL) in THF (150 mL) is allowed to stand at room temperature overnight. The mixture is concentrated under reduced pressure at 60° C. and the concentrate is dissolved in fresh ethanolamine (17 mL.) The mixture is allowed to stand at room temperature for 30 minutes and is subsequently warmed over a steam bath for five minutes and is allowed to cool to room temperature while standing overnight. The mixture is partitioned between diethyl ether (250 mL) and water (250 mL) and the layers are separated. The organic layer is dried over anhydrous magnesium sulfate and is concentrated under reduced pressure to afford the title compound; MS (APCI$^+$) m/z 351 (MH$^+$.)

Example 105

4-{5-[1-(Aminomethyl)cyclopropyl]-4-phenylisoxazol-3-yl}phenol

Step A)

A mixture consisting of the synthetic intermediate prepared in Example 32, Step A (10.04 g) and sodium azide (3.3 g) in anhydrous dimethyl sulfoxide (100 mL) is stirred at room temperature overnight. The reaction mixture is diluted with water (200 mL) and extracted with diethyl ether (400 mL.) The layers are separated and the organic layer is washed successively with saturated aqueous sodium bicarbonate solution (200 mL) and brine solution (100 mL.) The organic layer is dried over anhydrous magnesium sulfate, filtered and concentrated under reduced pressure. The concentrate is purified by flash silica gel column chromatography. Elution with dichloromethane afforded the synthetic intermediate 4-[5-(1-azidomethyl-cyclopropyl)-4-phenyl-isoxazol-3-yl]-phenol (2.96 g.)

Step B)

A mixture consisting of the synthetic intermediate prepared in Step A (4.5 g) in methanol (100 mL) is hydrogenated with 5% palladium on carbon over 2.2 hours. The catalyst is removed by filtration. The filtrate is partially concentrated under reduced pressure to give a precipitate. The precipitate is collected by vacuum filtration in two crops affording the title compound (3.0 g); melting point 220-225° C.; MS (APCI$^+$) m/z 307 (MH$^+$.)

Examples 106-129

Examples 106-129 are prepared by a variety of combinatorial chemistry methods. The specifics of each are described below. The letter identifying each method is used in the examples below to explain how the compounds are made, purified, and characterized.

All of the combinatorial methods are based upon Reaction Scheme IV shown below in which R represents the substituent bonded to the 2-position of the 1,3 oxadiazole ring.

Reaction Scheme IV

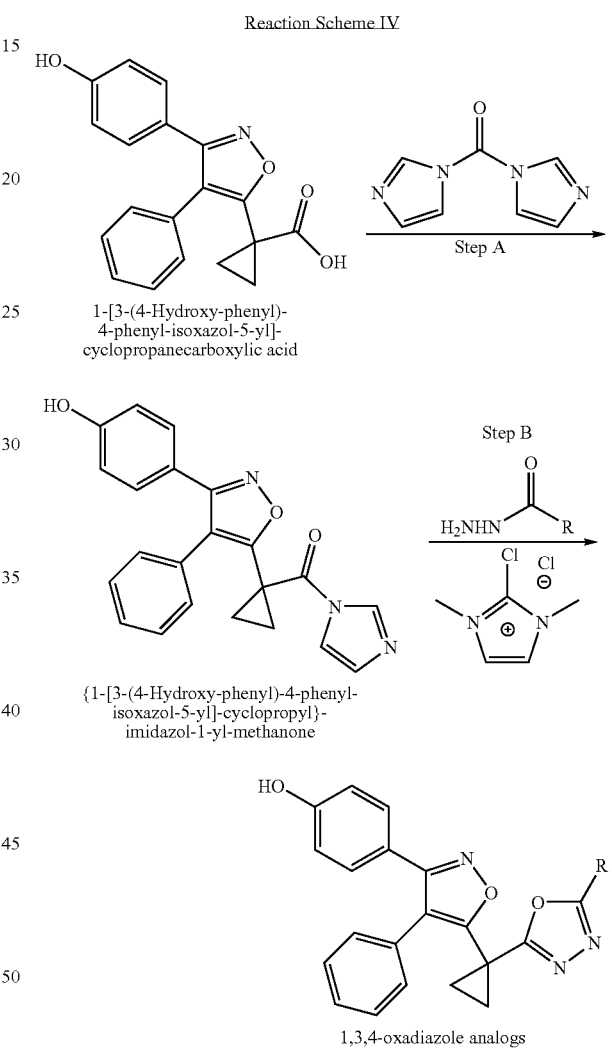

1-[3-(4-Hydroxy-phenyl)-4-phenyl-isoxazol-5-yl]-cyclopropanecarboxylic acid

{1-[3-(4-Hydroxy-phenyl)-4-phenyl-isoxazol-5-yl]-cyclopropyl}-imidazol-1-yl-methanone 1,3,4-oxadiazole analogs Step A)

Preparation of common intermediate {1-[3-(4-hydroxy-phenyl)-4-phenyl-isoxazol-5-yl]-cyclopropyl}-imidazol-1-yl-methanone 1-[3-(4-Hydroxy-phenyl)-4-phenyl-isoxazol-5-yl]-cyclopropanecarboxylic acid (Example 87, 2.41 g) is dissolved in acetonitrile (50 mL.) 1,1-Carbonyldiimidazole (2.42 g) is added and the mixture is stirred at reflux for one hour. After cooling to room temperature the mixture is carried onto the next reaction.

Step B)

Preparation of 1,3,4-Oxadiazole analogs

Method A

To the each acylhydrazide (150 μmol, see structures on table) is added {1-[3-(4-hydroxy-phenyl)-4-phenyl-isoxazol-5-yl]-cyclopropyl}-imidazol-1-yl-methanone (150 μmol) in acetonitrile (2.5 mL). The mixtures are heated in the cavity of a microwave to 140° C. for 600 seconds. 2-Chloro-1,3-dimethylimidazolinium chloride (450 μmoles) and triethylamine (900 μmoles) is added and the reactions are heated in the cavity of a microwave to 140° C. for 600 seconds. The solvent is removed in vacuo using a Genevac EZ-2. To each reaction mixture is added methylene chloride (2 mL) and water (2 mL). The layers are separated by filtering through Phase Separator SPE (solid phase extraction) Columns. Each organic layer is filtered through a Silica (500 mg) SPE column and eluted with methylene chloride (6 mL). The solvent is removed in vacuo using a Genevac EZ-2 to obtain a sample that is then purified by reverse phase HPLC.

Method B

To the each acylhydrazide (600 μmol, see structures on table) is added {1-[3-(4-hydroxy-phenyl)-4-phenyl-isoxazol-5-yl]-cyclopropyl}-imidazol-1-yl-methanone (300 μmol) in acetonitrile (2 mL). The reaction mixtures are heated to reflux for 18 hours. A solution of 2-Chloro-1,3-dimethylimidazolinium chloride (900 μmoles) in acetonitrile (1 mL) and triethylamine (0.250 mL, 1800 μmoles) is added and the mixtures are heated to reflux for 18 hours. The solvent is removed in vacuo using a Genevac EZ-2. To each reaction mixture is added methylene chloride (2 mL) and water (2 mL). The layers are separated by filtering through Phase Separator SPE (solid phase extraction) Columns. The organic layers are evaporated in vacuo using a Genevac EZ-2 to obtain a sample that is then purified by reverse phase HPLC.

Purification Methods

II) Preparative HPLC Methods (High Performance Liquid Chromatography)

Method A:

Column: Xterra C18 5 μm 19×100 mm

Flow rate: 30 mL/min

Solvent: A=Acetonitrile w/3% 1-Propanol; B=Water w/3% 1-Propanol

Method: 0-1 min: 30% A, 70% B; 1-6.5 min: 100% A, 0% B; 6-10 min 100% A

Method B:

Column: Xterra MS C18 5 μm 19×150 mm

Flow rate: 28 mL/min

Solvent: A=Water w/0.1% Formic acid c; B=Acetonitrile w/0.1% Formic acid

Method: Autopurification gradient determined by instrument

Characterization Methods

I) LCMS (Liquid Chromatography Mass Spectrum) Methods

Method A:

Column: Atlantis dC18, 5 cm×4.6 mm, 3μ

Flow rate: 1 mL/min

Solvent: A=Water w/0.005M Formic acid c; B=Acetonitrile w/0.005M Formic acid, Method: 0-3.5 min: 90% A, 10% B; 3.5-5 min: 2% A, 98% B; 5.1-7 min: 90% A, 10% B Method B:

Column: Xterra MS C18 5 μm 4.6×150 mm

Flow rate: 1.5 mL/min

Solvent: A=Water w/0.1% Formic acid c; B=Acetonitrile w/0.1% Formic acid

Method: 90% A to 10% A in 8 min, hold at 90% A for 1.5 min.

| Example | Structure | Name | Acylhydrazine Starting Material | Synthetic Method | HPLC Method | LCMS Method | Mass Spectrometry |
|---|---|---|---|---|---|---|---|
| 106 | 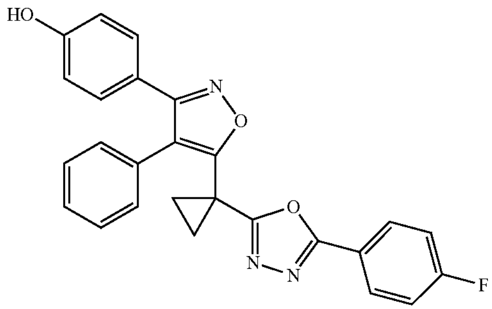 | 4-(5-{1-[5-(4-fluorophenyl)-1,3,4-oxadiazol-2-yl]cyclopropyl}-4-phenylisoxazol-3-yl)phenol | 4-fluorobenzoyl hydrazide | A | A | A | MS: 439.1 (M + 1 for $C_{26}H_{18}N_3O_3F$), Ret. Time: 3.54 Purity: 100% |
| 107 | 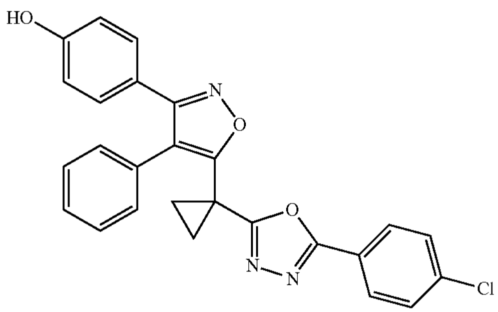 | 4-(5-{1-[5-(4-chlorophenyl)-1,3,4-oxadiazol-2-yl]cyclopropyl}-4-phenylisoxazol-3-yl)phenol | 4-chlorobenzoyl hydrazide | A | A | A | MS: 455.1 (M + 1 for $C_{26}H_{18}N_3O_3Cl$), Ret. Time: 3.75 Purity: 100% |
| 108 | 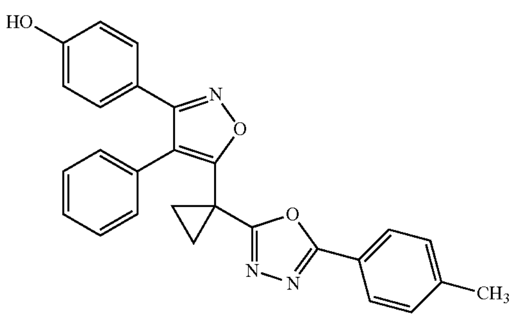 | 4-(5-{1-[5-(4-methylphenyl)-1,3,4-oxadiazol-2-yl]cyclopropyl}-4-phenylisoxazol-3-yl)phenol | 4-methylbenzoyl hydrazide | A | A | A | MS: 435.1 (M + 1 for $C_{27}H_{21}N_3O_3$), Ret. Time: 3.66 Purity: 100% |

| Example | Structure | Name | Acylhydrazine Starting Material | Synthetic Method | HPLC Method | LCMS Method | Mass Spectrometry |
|---|---|---|---|---|---|---|---|
| 109 | 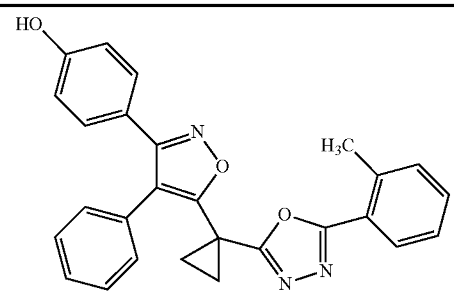 | 4-(5-{1-[5-(2-methylphenyl)-1,3,4-oxadiazol-2-yl]cyclopropyl}-4-phenylisoxazol-3-yl)phenol | | A | A | A | MS: 435.1 (M + 1 for $C_{27}H_{21}N_3O_3$), Ret. Time: 3.69 Purity: 100% |
| 110 | 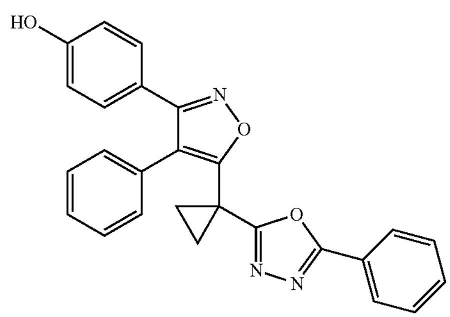 | 4-{4-phenyl-5-[1-(5-phenyl)-1,3,4-oxadiazol-2-yl]cyclopropyl]isoxazol-3-yl}phenol | | A | A | A | MS: 421.1 (M + 1 for $C_{26}H_{19}N_3O_3$), Ret. Time: 3.50 Purity: 96.1% |
| 111 | 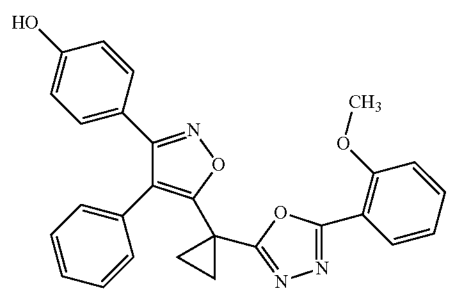 | 4-(5-{1-[5-(2-methylphenyl)-1,3,4-oxadiazol-2-yl]cyclopropyl}-4-phenylisoxazol-3-yl)phenol | | A | A | A | MS: 451.1 (M + 1 for $C_{27}H_{21}N_3O_4$), Ret. Time: 3.37 Purity: 99.3% |

| Example | Structure | Name | Acylhydrazine Starting Material | Synthetic Method | HPLC Method | LCMS Method | Mass Spectrometry |
|---|---|---|---|---|---|---|---|
| 112 | 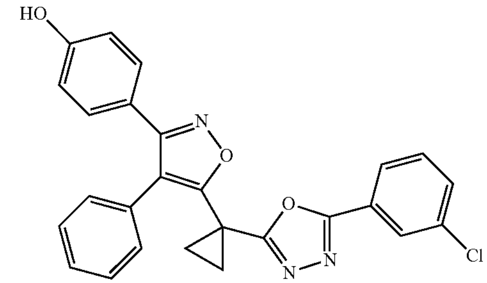 | 4-(5-{1-[5-(3-chlorophenyl)-1,3,4-oxadiazol-2-yl]cyclopropyl}-4-phenylisoxazol-3-yl)phenol | | A | A | A | MS: 455.1 (M + 1 for $C_{26}H_{18}N_3O_3Cl$), Ret. Time: 3.76 Purity: 96.5% |
| 113 | 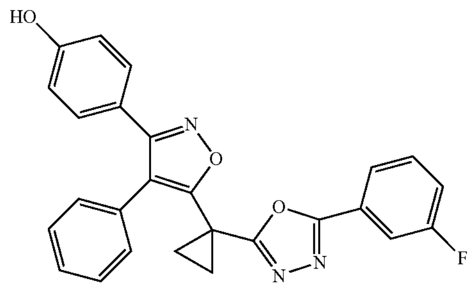 | 4-(5-{1-[5-(3-fluorophenyl)-1,3,4-oxadiazol-2-yl]cyclopropyl}-4-phenylisoxazol-3-yl)phenol | | A | A | A | MS: 439.1 (M + 1 for $C_{26}H_{18}N_3O_3F$), Ret. Time: 3.57 Purity: 93.3% |
| 114 | 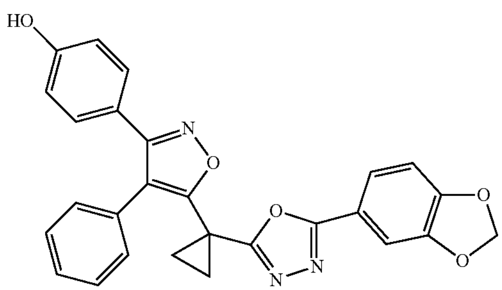 | 4-(5-{1-[5-(1,3-benzodioxol-5-yl)-1,3,4-oxadiazol-2-yl]cyclopropyl}-4-phenylisoxazol-3-yl)phenol | | A | A | A | MS: 465.1 (M + 1 for $C_{27}H_{19}N_3O_5$), Ret. Time: 3.43 Purity: 100% |

-continued

| Example | Structure | Name | Acylhydrazine Starting Material | Synthetic Method | HPLC Method | LCMS Method | Mass Spectrometry |
|---|---|---|---|---|---|---|---|
| 115 | 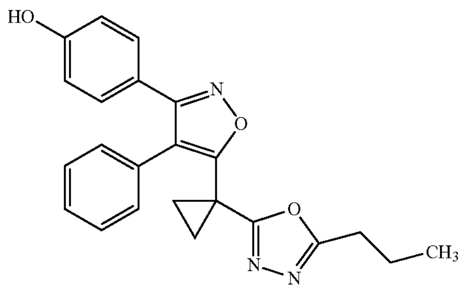 | 4-{4-phenyl-5-[1-(5-propyl-1,3,4-oxadiazol-2-yl)cyclopropyl]isoxazol-3-yl}phenol | | A | A | A | MS: 387.1 (M + 1) for $C_{23}H_{21}N_3O_3$, Ret. Time: 3.29 Purity: 97.1% |
| 116 | 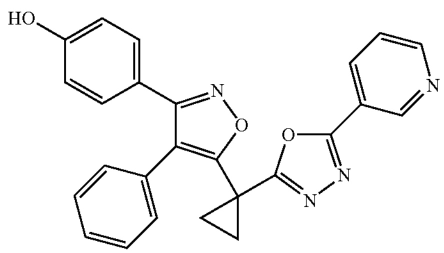 | 4-{4-phenyl-5-[1-(5-pyridin-3-yl-1,3,4-oxadiazol-2-yl)cyclopropyl]isoxazol-3-yl}phenol | | B | B | B | MS: 442.45 (M + 1) for $C_{25}H_{18}N_4O_3$, Ret. Time: 6.83 Purity: 90% |
| 117 | 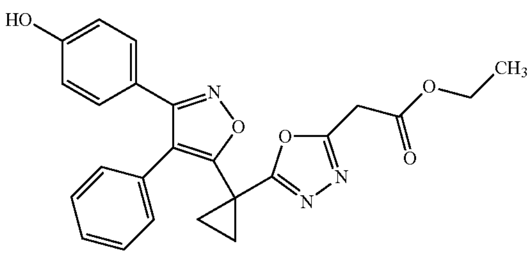 | ethyl (5-{1-[3-(4-hydroxyphenyl)-4-phenylisoxazol-5-yl]cyclopropyl}-1,3,4-oxadiazol-2-yl)acetate | | B | B | B | MS: 431.45 (M + 1) for $C_{24}H_{21}N_3O_3$, Ret. Time: 4.00 Purity: 95% |

| Example | Structure | Name | Acylhydrazine Starting Material | Synthetic Method | HPLC Method | LCMS Method | Mass Spectrometry |
|---|---|---|---|---|---|---|---|
| 118 | 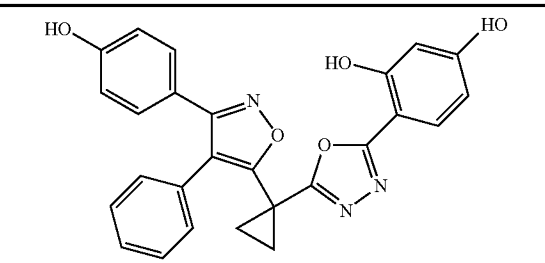 | 4-(5-{1-[3-(4-hydroxyphenyl)-4-phenylisoxazol-5-yl]cyclopropyl}-1,3,4-oxadiazol-2-yl)benzene-1,3-diol | | B | B | B | MS: 453.46 (M + 1 for $C_{26}H_{19}N_3O_5$), Ret. Time: 4.00 Purity: 90% |
| 119 | 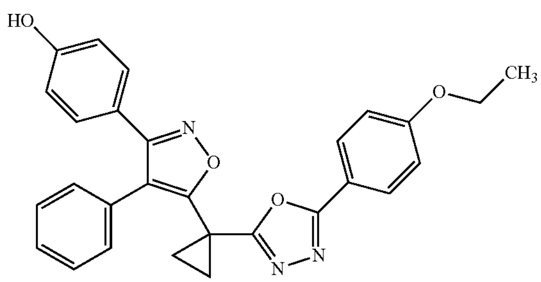 | 4-(5-{1-[5-(4-ethoxyphenyl)-1,3,4-oxadiazol-2-yl]cyclopropyl}-4-phenylisoxazol-3-yl)phenol | | B | B | B | MS: 465.51 (M + 1 for $C_{28}H_{23}N_3O_4$), Ret. Time: 7.83 Purity: 90% |
| 120 | 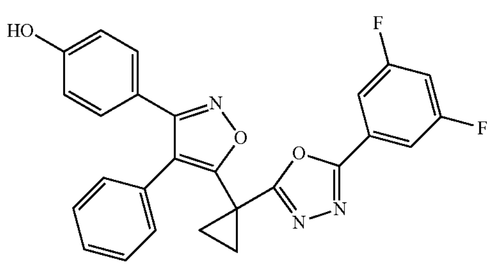 | 4-(5-{1-[5-(3,5-difluorophenyl)-1,3,4-oxadiazol-2-yl]cyclopropyl}-4-phenylisoxazol-3-yl)phenyl | | B | B | B | MS: 457.44 (M + 1 for $C_{26}H_{17}N_3O_3F_2$), Ret. Time: 6.60 Purity: 90% |

| Example | Structure | Name | Acylhydrazine Starting Material | Synthetic Method | HPLC Method | LCMS Method | Mass Spectrometry |
|---|---|---|---|---|---|---|---|
| 121 | 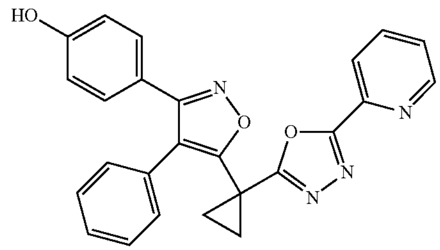 | 4-{4-phenyl-5-[1-(5-pyridin-2-yl-1,3,4-oxadiazol-2-yl]cyclopropyl]isoxazol-3-yl}phenol | | B | B | B | MS: 422.45 (M + 1) for $C_{25}H_{18}N_4O_3$, Ret. Time: 6.25 Purity: 0% |
| 122 | 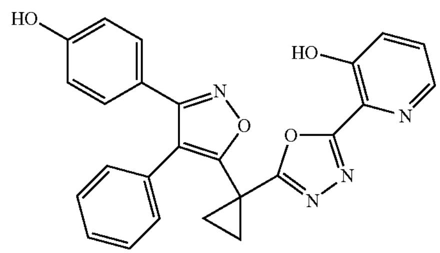 | 2-(5-{1-[3-(4-hydroxyphenyl)-4-phenylisoxazol-5-yl]cyclopropyl}-1,3,4-oxadiazol-2-yl)phenol | | B | B | B | MS: 437.46 (M + 1) for $C_{26}H_{19}N_3O_4$, Ret. Time: 7.90 Purity: 90% |
| 123 | 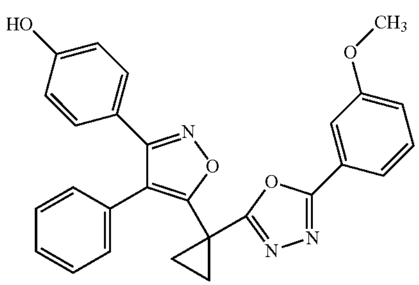 | 4-(5-{1-[5-(3-methoxyphenyl)-1,3,4-oxadiazol-2-yl]cyclopropyl}-4-phenylisoxazol-3-yl)phenol | | B | B | B | MS: 451.49 (M + 1) for $C_{27}H_{21}N_3O_4$, Ret. Time: 7.45 Purity: 90% |

| Example | Structure | Name | Acylhydrazine Starting Material | Synthetic Method | HPLC Method | LCMS Method | Mass Spectrometry |
|---|---|---|---|---|---|---|---|
| 124 | 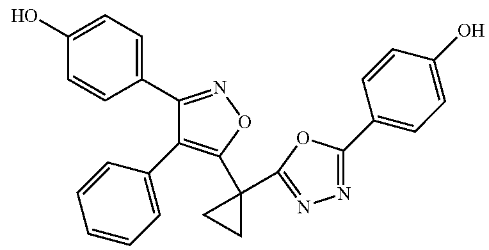 | 4-(5-{1-[5-(4-hydroxyphenyl)-1,3,4-oxadiazol-2-yl]cyclopropyl}-4-phenylisoxazol-3-yl)phenol | | B | B | B | MS: 437.46 (M + 1 for $C_{26}H_{19}N_3O_4$), Ret. Time: 6.27 Purity: 90% |
| 125 | 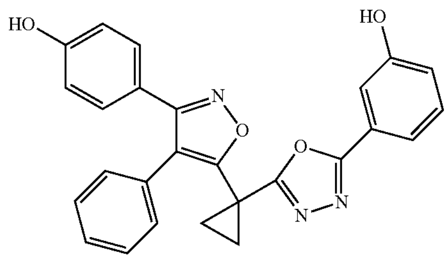 | 3-(5-{1-[3-(4-hydroxyphenyl)-4-phenylisoxazol-5-yl]cyclopropyl}-1,3,4-oxadiazol-2-yl)phenol | | B | B | B | MS: 437.46 (M + 1 for $C_{26}H_{19}N_3O_4$), Ret. Time: 6.45 Purity: 90% |
| 126 | 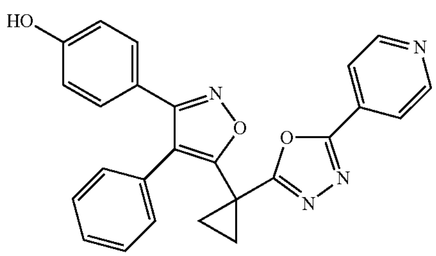 | 4-{4-phenyl-5-[1-(5-pyridin-4-yl-1,3,4-oxadiazol-2-yl)cyclopropyl]isoxazol-3-yl}phenol | | B | B | B | MS: 422.45 (M + 1 for $C_{25}H_{18}N_4O_3$), Ret. Time: 5.98 Purity: 90% |

| Example | Structure | Name | Acylhydrazine Starting Material | Synthetic Method | HPLC Method | LCMS Method | Mass Spectrometry |
|---|---|---|---|---|---|---|---|
| 127 | 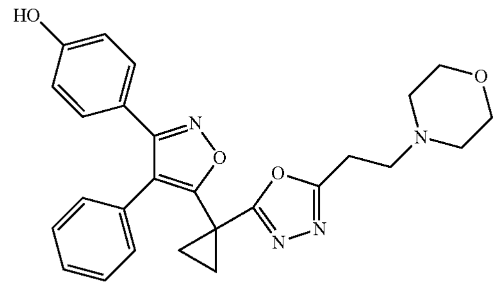 | 4-(5-{1-[5-(2-morpholin-4-ylethyl)-1,3,4-oxadiazol-2-yl]cyclopropyl}-4-phenylisoxazol-3-yl)phenol | | B | B | B | MS: 458.52 (M + 1 for $C_{26}H_{26}N_4O_4$), Ret. Time: 4.02 Purity: 90% |
| 128 | 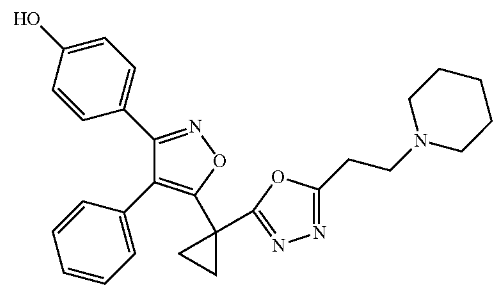 | 4-(4-phenyl-5-{1-[5-(2-piperidin-1-ylethyl)-1,3,4-oxadiazol-2-yl]cyclopropyl}isoxazol-3-yl)phenol | | B | B | B | MS: 456.55 (M + 1 for $C_{27}H_{28}N_4O_3$), Ret. Time: 3.92 Purity: 90% |
| 129 | 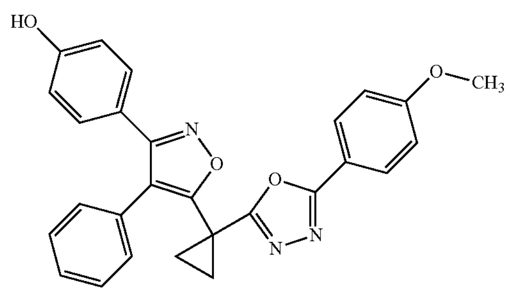 | 4-(5-{1-[5-(4-methoxyphenyl)-1,3,4-oxadiazol-2-yl]cyclopropyl}-4-phenylisoxazol-3-yl)phenol | | B | B | B | MS: 451.49 (M + 1 for $C_{27}H_{21}N_3O_4$), Ret. Time: 7.30 Purity: 90% |

Example 130

Animal Model for Reversal of Wrinkles

Uzuka et al. describes an increase in mouse back skin water content, hyaluronic acid (HA) content, and hyaluronic acid synthetase activity following topical application or subcutaneous injection of estradiol (Biochimica et Biophysica Acta, 627, 199-206, 1980; Biochimica et Biophysica Acta 673, 387-393, 1981). Gendimenico et al. extended these findings to demonstrate an increase in back skin thickness following topical application of estradiol (Arch. Derm. Res. 294, 231-236, 2002). Thus, this model may be used to as a preliminary screen to assess the potential for estrogen modulators to alleviate wrinkles in human skin.

The skin thickness model uses hairless female SKH, 1-hr mice. Mice aged to approximately 11 weeks are introduced into the laboratory environment and acclimated for at least 1 week prior to use in the study may be used. Each group typically consisted of 7 animals that may be run in parallel with vehicle and the positive control estradiol. Based on binding and/or cellular assay data, compounds are chosen for screening in this model. Those compounds include the products of Examples, 2, 9, 15, 46, 47, 48, 51, 52, 61, 135, and 137. Prior to topical application to mouse dorsal skin, a sufficient quantity of each compound is dissolved in a solvent generally consisting of ethanol and propylene glycol (70/30% v/v) (vehicle) to achieve the final concentration specified in Table C below. Animals are dosed topically QD or BID, for three days. Each dose consisted of 100 microliters of vehicle or drug applied uniformly to the entire dorsal surface (~18 cm$^2$). All animals are sacrificed approximately 18-24 hours after the final dose. Skin thickness (ST) is measured using a caliper. HA is extracted from the skin and quantitated using commercially-available enzyme-linked immunosorbent assays (ELISAs)(HA).

Data are presented as percent of the estradiol response after subtracting out the ST for vehicle-treated mouse skin. The estradiol response is set to 100% and the vehicle resoibse becines 0%. For example, the compound of Example 2 had an increase in ST that is 19% of the estradiol response and an increase in HA that is 15% of the estradiol response.

TABLE C

| Example # | Conc | Dose | ST | HA |
|---|---|---|---|---|
| 100, Alt. D | 1% | BID | 0% | 19% |
| 100, Alt. F | 1.5% | BID | 23% | 37% |
| 2 | 1% | QD | 19% | 15% |
| 9 | 3% | QD | 49% | 58% |
| 15 | 3% | QD | 41% | 47% |
| 46 | 1% | QD | 36% | 48% |
| 46 | 0.5% | BID | 53% | 39% |
| 46 | 0.015% | BID | 20% | 11% |
|  | 0.05% |  | 47% | 52% |
|  | 0.15% |  | 65% | 55% |
|  | 0.5% |  | 71% | 68% |
| 46 | 0.5% | BID | 73% | 76% |
| 47 | 1% | BID | 53% | 59% |
| 48 | 1% | QD | 64% | 47% |
| 48 | 1% | BID | 72% | 34% |
| 48 | 0.03% | QD | 13% | 18% |
|  | 0.1% |  | 29% | 32% |
|  | 0.3% |  | 57% | 41% |
|  | 1% |  | 41% | 42% |
| 48 | 0.03% | BID | 33% | 26% |
|  | 0.1% |  | 58% | 63% |
|  | 0.3% |  | 80% | 96% |
|  | 1% |  | 89% | 85% |
| 48 | 0.5% | BID | 78% | 84% |
| 51 | 1% | QD | 19% | 35% |
| 52 | 3% | QD | 21% | 34% |
| 61 | 3% | QD | 32% | 38% |

Example 131

The following Example illustrates the preparation of a number of topical formulations, suitable for use with human subjects. All amounts below are expressed as gm/100 ml.

TABLE D

| Ingredient | 1 | 2 | 3 | 4 | 5 | 6 |
|---|---|---|---|---|---|---|
| Active* | 0.5 | 0.5 | 0.5 | 0.5 | 0.5 | 0.5 |
| Ethanol | 70 | 54.5 | 54.5 | 54.3 | 34.5 | 54.8 |
| Distilled Water | — | 20 | 20 | 20 | 30 | 20 |
| PEG 400 |  | 10 |  | 10 | 15 | 10 |
| Propylene Glycol | 30 | 15 | 10 | 10 | 10 | 10 |
| Glycerin |  |  | 5 | 5 | 5 | 5 |
| Benzyl Alcohol |  |  |  |  | 5 |  |
| Hexylene Glycol |  |  | 10 |  |  |  |
| Klucel |  | 0.5 | 0.5 | 0.5 | 0.5 |  |
| Methylparaben |  |  |  | 0.2 |  | 0.2 |

*Active is (R)-(-)-4-{5-[1-(1-Hydroxy-ethyl)-cyclopropyl]-4-phenyl-isoxazol-3-yl}-phenol, which may be produced as in Example 46

The far left column identifies the components that are present in the formulation. The subsequent 6 columns indicate the amount of each individual component that is in the formulation. A blank indicates that the formulation did not incorporate that component.

Formulations #1 and #6 are made by weighing the appropriate weight of the specified component and the active. These materials are then added to a 100 ml volumetric flask. Ethanol is then added to reach the target volume of the formulation, which is 100 ml. The mixture is stirred as required to dissolve the components.

Formulations #2, #3, #4, and #5 are made by weighing the appropriate weight of the specified component and the active. All of these materials, except the Klucel, are added to a 100 ml volumetric flask. Ethanol is then added to reach the target volume of the formulation, which is 100 ml. The mixture is then stirred and the Klucel is added while the stirring continues until a uniform mixture is obtained.

Example 132

The compounds ability to mimic the effects of estrogen on the estrogen receptor were determined in a whole cell assay as described immediately below.

Experimental Procedure for ER Agonist Cell Assay

Cell line and plasmids: The human hepatoma cell line Huh-7 was used for co-transfections. Cells were maintained in culture medium and split when they reached 80-90% confluency. Three plasmids were routinely used in the assay. pG5luc contained the firefly luciferase gene and was obtained from Promega. The ligand binding domain of the estrogen receptor alpha chain (ERαLBD) was cloned into the pBIND vector as was the ligand binding domain of the estrogen receptor beta chain (ERβLBD) that contained a point mutation at amino acid residue 418 (pm418).

Cell Culture Media and Reagents:
Culture medium: DMEM (phenol red free), 10% charcoal treated HyClone serum, 1% L-glutamine, and 1% penicillin/streptomycin
Transfection medium: DMEM (phenol red free) and 10% charcoal treated HyClone serum
Luciferase reagents: Dual-Glo Luciferase Kit (Promega cat #E2980) was used for determination of luciferase activity.

Transfection Procedure:
Transient transfections were preformed using the lipophilic reagent FuGENE 6 (Roche). Cells were split and seeded at $7.2 \times 10^6/150$ cm$^2$ flask in 20 mL of transfection medium. 5-6 hrs later cells were co-transfected with either pG5luc and ERαLBD or pG5luc and ERβLBD(pm418). Transfected cells grew overnight and were then used the next day.

Assay Procedure:
Opaque 96 well culture plates had 10 ul of compound added to each well. Cells transfected 24 hrs earlier were harvested, counted, and seeded in wells containing compound at a density of $1 \times 10^4$ cells/well. Final DMSO conc. was 0.5% and final conc. of compound was 10,000 nM, 2000 nM, 400 nM, 80 nM, 16 nM, 3.2 nM, and 0.64 nM. Cells were incubated overnight at 37° C. and 5% $CO_2$ in the presence of compound. The following day medium was aspirated from the wells and 100 ul of Dual-Glo™ Luciferase Reagent were added to each well. Plates were incubated at room temperature for 20 minutes and firefly luminescence was measured on a luminometer. Next, 50 ul of Dual-Gbo™ Stop & Glo® Reagent were added to each well and after 20 minutes at room temperature the *Renilla* luminescence was measured on a luminometer. Values from each well were normalized by dividing the firefly luminescence by the *Renilla* luminescence. Estradiol was used as the standard and run in each assay. The fold induction over background for each compound was compared to the maximum fold induction for estradiol in each assay. Results were expressed using two parameters: Percent of the maximum estradiol fold change (% of Max E2 Response) and as the concentration of test compound which produced half maximal fold change for each compound (Effective concentration 50%, or $EC_{50}$). Those compounds that were not tested, or the data was unavailable are marked as NT.

| Ex. # | EC50 (ERα) (μM) | ERα % of Max E2 Response | EC50 (ERβ) (μM) | ERβ % of Max E2 Response |
|---|---|---|---|---|
| 1 | NT | NT | NT | NT |
| 2 | 0.0276 | 55.7 | 0.025 | 56.7 |
| 3 | 0.0971 | 32.2 | 0.568 | 1.32 |
| 4 | 0.141 | 14.7 | >10.0 | >0.727 |
| 5 | 0.0459 | 19.3 | >10.0 | >4.51 |
| 6 | 0.237 | 9.48 | >10.0 | >3.19 |
| 7 | 0.208 | 17.2 | >10.0 | >0.485 |
| 8 | 0.0258 | 40.4 | 0.0688 | 3.65 |
| 9 | 0.177 | 40.2 | 0.0413 | 2.63 |
| 10 | 0.0177 | 15.1 | 0.197 | 1.18 |
| 11 | 0.171 | 23.4 | 0.0147 | 1.98 |
| 12 | 0.354 | 26.2 | NT | 0.577 |
| 13 | NT | 19 | NT | 0.552 |
| 14 | 0.043 | 45.4 | 0.136 | 17.7 |
| 15 | 0.0243 | 43.8 | 0.15 | 15.6 |
| 16 | 0.0443 | 63.2 | NT | 2.37 |
| 17 | 0.0344 | 56.8 | 0.126 | 3.82 |
| 18 | NT | NT | NT | NT |
| 19 | NT | NT | NT | NT |
| 20 | NT | NT | NT | NT |
| 21 | NT | NT | NT | NT |
| 22 | NT | NT | NT | NT |
| 23 | 0.559 | 21 | 3.86 | 5.5 |
| 24 | 0.0126 | 30.9 | >10.0 | >0.860 |
| 25 | 0.0265 | 18.2 | >10.0 | >0.571 |
| 26 | 0.066 | 20.9 | NT | 1.03 |
| 27 | NT | NT | NT | NT |
| 28 | NT | NT | NT | NT |
| 29 | NT | 11.4 | NT | 0.601 |
| 30 | NT | NT | NT | NT |
| 31 | 0.0269 | 30 | 0.151 | 1.35 |
| 32 | 0.0229 | 38.5 | 0.0195 | 0.999 |
| 33 | NT | NT | NT | NT |
| 34 | NT | NT | NT | NT |
| 35 | 0.171 | 25 | 0.13 | 5.78 |
| 36 | NT | NT | NT | NT |
| 37 | 0.202 | 30.7 | 0.302 | 4.3 |
| 38 | 1.13 | 11.4 | 0.749 | 6.6 |
| 39 | NT | NT | NT | NT |
| 40 | 0.107 | 39.5 | 0.139 | 1.12 |
| 41 | NT | NT | NT | NT |
| 42 | 0.0377 | 51.7 | 0.198 | 6.17 |
| 43 | NT | NT | NT | NT |
| 44 | NT | NT | NT | NT |
| 45 | 0.0475 | 79.3 | 0.0467 | 81.2 |
| 46 | 0.0331 | 106 | 0.0432 | 99.7 |
| 47 | 0.0224 | 92 | 0.144 | 87.4 |
| 48 | 0.0313 | 88.8 | 0.0847 | 71.8 |
| 49 | 0.159 | 94.6 | 0.0236 | 36.7 |
| 50 | 0.124 | 80.2 | NT | 1 |
| 51 | 0.152 | 63.8 | 0.0842 | 75.2 |
| 52 | 0.138 | 66 | 0.117 | 121 |
| 53 | 0.0456 | 85.4 | 0.0711 | 79 |
| 54 | 0.0388 | 60.4 | 0.108 | 65.8 |
| 55 | 0.0057 | 55.8 | 0.0236 | 32.6 |
| 56 | 0.0111 | 42.1 | 0.0306 | 3 |
| 57 | 0.245 | 71.9 | 0.137 | 112 |
| 58 | 0.137 | 59.9 | 0.0979 | 92 |
| 59 | NT | NT | NT | NT |
| 60 | 0.0129 | 23.3 | >10.0 | >3.71 |
| 61 | 0.075 | 21.1 | >10.0 | >1.83 |
| 62 | NT | NT | NT | NT |
| 63 | NT | NT | NT | NT |
| 64 | NT | NT | NT | NT |
| 65 | NT | NT | NT | NT |
| 66 | NT | NT | NT | NT |
| 67 | NT | NT | NT | NT |
| 68 | NT | NT | NT | NT |
| 69 | NT | NT | NT | NT |
| 70 | NT | NT | NT | NT |
| 71 | NT | NT | NT | NT |
| 72 | NT | NT | NT | NT |
| 73 | NT | NT | NT | NT |
| 74 | NT | NT | NT | NT |
| 75 | NT | NT | NT | NT |
| 76 | NT | NT | NT | NT |
| 77 | NT | NT | NT | NT |
| 78 | NT | NT | NT | NT |
| 79 | NT | NT | NT | NT |
| 80 | NT | NT | NT | NT |
| 81 | NT | NT | NT | NT |
| 82 | NT | NT | NT | NT |
| 83 | NT | NT | NT | NT |
| 84 | NT | NT | NT | NT |
| 85 | NT | NT | NT | NT |
| 86 | NT | NT | NT | NT |
| 87 | NT | NT | NT | NT |
| 88 | 0.0294 | 29.2 | >10.0 | >3.41 |
| 89 | 0.0305 | 26 | >10.0 | >2.93 |
| 90 | NT | NT | NT | NT |
| 91 | NT | NT | NT | NT |
| 92 | 0.0572 | 19.7 | >10.0 | >1.04 |
| 93 | 0.0338 | 20.4 | >10.0 | >0.813 |
| 94 | 0.0293 | 24.3 | >10.0 | >0.800 |
| 95 | 0.0136 | 21.5 | >10.0 | >0.728 |

-continued

| Ex. # | EC50 (ERα) (μM) | ERα % of Max E2 Response | EC50 (ERβ) (μM) | ERβ % of Max E2 Response |
|---|---|---|---|---|
| 96 | NT | NT | NT | NT |
| 97 | NT | 19.7 | NT | 1.08 |
| 98 | 0.985 | 46 | 0.799 | 36.8 |
| 99 | 0.0384 | 45.3 | NT | 0.679 |
| 100 | NT | NT | NT | NT |
| 101 | 0.122 | 58.3 | NT | 13.6 |
| 102 | NT | NT | NT | NT |
| 103 | NT | 10.2 | NT | 1.21 |
| 104 | NT | NT | NT | NT |
| 105 | NT | NT | NT | NT |
| 106 | NT | NT | NT | NT |
| 107 | NT | NT | NT | NT |
| 108 | NT | NT | NT | NT |
| 109 | NT | NT | NT | NT |
| 110 | NT | NT | NT | NT |
| 111 | NT | NT | NT | NT |
| 112 | NT | NT | NT | NT |
| 113 | NT | NT | NT | NT |
| 114 | NT | NT | NT | NT |
| 115 | NT | NT | NT | NT |
| 116 | NT | NT | NT | NT |
| 117 | NT | NT | NT | NT |
| 118 | 0.0251 | 15 | >10.0 | >0.789 |
| 119 | 0.469 | 22.3 | >10.0 | >3.74 |
| 120 | NT | NT | NT | NT |
| 121 | NT | NT | NT | NT |
| 122 | 0.0715 | 21.9 | >10.0 | >0.756 |
| 123 | 0.0469 | 35.9 | >10.0 | >0.658 |
| 124 | 0.152 | 24.4 | >10.0 | >0.539 |
| 125 | 0.419 | 22.1 | >10.0 | >0.535 |
| 126 | NT | NT | NT | NT |
| 127 | NT | NT | NT | NT |
| 128 | NT | NT | NT | NT |
| 129 | 10 | 19.1 | >10.0 | 0.625 |

Example 133-206

Examples 133-206 discloses alternative processes for making 4-{5-[1-(1-hydroxy-ethyl)-cyclopropyl]-4-phenyl-isoxazol-3-yl]-phenol, 4-{5-[1-(1-(1-hydroxy-propyl)-cyclopropyl]-4-phenyl-isoxazol-3-yl}-phenol, the individual enantiomers of each compound, and various intermediates useful in the preparation of these compounds.

Preparation of Protected Ketones as Described by Structure 2, in Scheme I on Page 9, General Preparation of Isoxazoles Example 133

This example illustrates alternative preparations of 1-(4-methoxy-phenyl)-2-phenyl-ethanone Example 133A An oven-dried 1 L three-neck flask equipped with mechanical stirrer, constant addition funnel, and digital thermometer probe is purged with nitrogen and is charged with anisole (190 mL.) The liquid is stirred and cooled to −5.0° C. with a methanol-ice bath. A total of 102 g of aluminum trichloride is added in four portions over 25 minutes keeping the internal mixture temperature at or below +1.2° C. A yellow slurry is formed, and the internal mixture is cooled to −4.1° C. The phenylacetyl chloride (92 mL) is added dropwise from the addition funnel over 85 minutes keeping the internal temperature below +6.8° C. The reaction mixture is allowed to warm slowly to room temperature as it is stirred for 20 hours. A 2 L three-neck flask equipped with mechanical stirrer, constant addition funnel, and digital thermometer probe is charged with toluene (500 mL) and ice-cooled water (800 mL.) The flask is submerged into an ice-water bath for additional cooling. The biphasic mixture is stirred vigorously, and the dark red reaction mixture that had been transferred to the additional funnel is added slowly over 15 minutes keeping the internal temperature below +25.5° C. The reaction flask is rinsed with toluene and the rinse is likewise added to the stirring biphasic mixture. The phases (both layers are cloudy tan oily suspensions) are separated using a 2 L separatory funnel and the organic phase is washed with ~20% aqueous potassium carbonate (500 mL) and a portion of fresh water (500 mL), is dried over anhydrous potassium carbonate, and is concentrated in vacuo (water bath temperature=75° C., 200 mbar vacuum), until no further toluene is removed, to a clear yellow oil. With the oil still warm, hexanes are added with swirling to form an oily suspension that is allowed to stand open at room temperature in the fume hood for several hours as a white crystalline solid precipitates. The crystals are collected by vacuum filtration. After rinsing with hexanes, the product is suction dried to afford the white crystalline solid title compound (114.65 g); $^1$H-NMR (400 MHz, CDCl$_3$) δ 8.00 (m, 2H), 7.34-7.22 (m, 5H), 6.92 (m, 2H), 4.23 (s, 2H), 3.85 (s, 3H); $^{13}$C-NMR (100 MHz, CDCl$_3$) δ 196.4, 163.7, 135.2, 131.2, 129.9, 129.6, 128.9, 127.0, 114.0, 55.7, 45.5; MS (APCI+) 227 (MH$^+$.)

Isolation of Second Crop of Crystals:

The mother liquor yielded a white crystalline precipitate upon standing over the weekend. These crystals are collected by vacuum filtration and are suction dried to afford the white crystalline solid title compound (9.18 g.)

Alternatively, A two liter, three neck round bottom flask fitted with a thermocouple is charged with anisole (985 mL, Sigma-Aldrich Chemical, catalog #12,322-6, lot #05107AV.) The reaction vessel is cooled to near 0° C. and aluminum trichloride (477 gram, Sigma-Aldrich Chemical, catalog #195352, lot #17019MO) is added in 50 gram shots while keeping the temperature below 5° C. While maintaining the temperature between 5° C. and 10° C., phenylacetyl chloride (503 grams, Sigma-Aldrich Chemical, catalog #P16753, lot #03618HA) is added. The addition is done over a two and one half hour period. During the addition, the mixture went from a dilute pale yellow slurry to a very deep red colored solution. The reaction is left to warm to room temperature. After stirring overnight, the reaction is quenched by slowly pumping (via syringe pump, J-KEM) to 2.25 liters of cold (−5° C.) water. The temperature is maintained between 5° C. and 10° C. during the addition. The addition is done over a ten-hour period due to the slow output of the pump. After the addition is complete, toluene (1 liter) is added. The mixture is stirred for one hour. The stirrer is stopped and the phases are left to separate overnight. The material is transferred to a six liter separatory and toluene is added until all the solids went into solution (1.25 liters). The phases are separated and the aqueous is washed with toluene (500 mL). The aqueous phase is sampled and checked for product via HPLC. None found. The organics are combined and concentrated via vacuum (40 mm Hg) roto-evaporation (bath at 50° C.) The valve to the receiver is closed and heptane (two liters) is added by way of the feed line. The heptane started to reflux as it is being added and this cooled the liquid in the flask. After cooling to room temperature, the solids are filtered, washed with heptane (2×300 mL) and left to air dry to afford the dry solid title compound (662.6 g.)

Example 133 B

A 100 mL round-bottomed flask containing a stir bar is purged with nitrogen and charged with 10.27 g of phenylacetic acid and 50 mL of Eaton's reagent. The mixture is stirred and 8.2 mL of anisole is added. The solution is stirred overnight and then poured into a mixture of 100 mL of toluene and 100 mL of water. The mixture is stirred 30 min and then the layers are separated. The organic layer is washed with 100 mL of water, 100 mL of 5% potassium carbonate and 100 mL of water. The organic layer is dried over magnesium sulfate, filtered and concentrated at the Rotavap. The oil is triturated with 100 mL of heptane. The slurry is stirred for one hour and then filtered. The solids are washed with petroleum ether and then air dried overnight giving 13.26 g.

Example 133 C

To a stirring suspension comprised of benzyl 4-hydroxyphenyl ketone (1.0 g) and cesium carbonate (1.5 g) in tetrahydrofuran (100 mL) under a nitrogen atmosphere at ambient temperature is added the 2.0 M iodomethane in MTBE solution (2.2 mL) via syringe. The reaction mixture is allowed to stir for 16 hours. A second equivalent of iodomethane is added (2.2 mL of the 2.0 M iodomethane solution in MTBE) and the reaction mixture is stirred for three hours. Two additional equivalents of iodomethane (as the 2.0 M MTBE solution) are added and the reaction mixture is stirred overnight (another 15 hours.) The reaction mixture is combined with the workup of the following experiment:

To a stirring suspension comprised of benzyl 4-hydroxyphenyl ketone (22.2 g) and cesium carbonate (35 g) in tetrahydrofuran (300 mL) under a nitrogen atmosphere at ambient temperature is added the iodomethane (20 mL.) The reaction mixture is allowed to stir for 3.5 hours and is analyzed by thin layer chromatography. An additional 10 mL of iodomethane is added to the reaction mixture, which is stirred for 2.5 hours more. The reaction mixture is analyzed by mass spectrometry, LC/MS, and thin layer chromatography. Another 12 mL of iodomethane is added to the reaction mixture and the mixture is stirred for an additional 15 minutes. Thin layer chromatography analysis still showed the presence of some material that coeluted with the starting material. An additional 20 mL of iodomethane is added to the reaction mixture and the reaction mixture is stirred overnight. The reaction mixture is combined with the reaction mixture for the first experiment described above and the combined mixture is partitioned between saturated aqueous potassium carbonate (300 mL) and diethyl ether (300 mL.) The layers are separated and the organic phase is washed with water (300 mL) and brine (200 mL), and is dried over anhydrous magnesium sulfate. Vacuum filtration to remove the magnesium sulfate followed by concentration of the filtrate under reduced pressure affords a clear oil (25.38 g.) The oil slowly solidified to a yellow solid on standing. The product is purified by flash silica chromatography. The 25 g of material is dissolved in dichloromethane and the solution is split into two portions. The portions are chromatographed separately. The portions are loaded onto their respective columns and the columns are eluted with hexanes to remove the dichloromethane. Elution with 0-5% ethyl acetate in hexanes afforded separation of the desired material from the starting material. The clean fractions containing product from the first column are combined and concentrated under reduced pressure to afford the pale yellow solid (8.31 g.) The clean fractions containing product from the second column are combined and concentrated under reduced pressure (with chloroform chase) to obtain the pale yellow solid (upon standing, 10.25 g); MS (APCI+) 227 (MH+.)

Example 134

This example illustrates alternative preparations of 1-[4-(tert-butyl-dimethyl-silanyloxy)-phenyl]-2-phenyl-ethanone.

To a 5 L four-neck round bottom flask equipped with a mechanical stirrer, a thermometer and a nitrogen inlet is added 1-(4-hydroxy-phenyl)-2-phenyl-ethanone (Aldrich, 185.77 g) and 2325 mL THF. The 145 g of tert-butyldimethylsilyl chloride is added, no temperature change is observed. Imidazole (65.5 grams) is added in portions over 30 minutes, temperature rose to 22° C. Water/ice bath cooled to maintain temperature below 25° C. Stir at room temperature under nitrogen overnight. Combine with the reaction mixture from the following experiment for workup:

To a gently stirring clear yellow solution comprised of 1-(4-hydroxy-phenyl)-2-phenyl-ethanone (75.0 g) and tert-butyldimethylsilyl chloride (58.6 g) in tetrahydrofuran (950 mL) under a nitrogen stream in a three-neck 2 L flask equipped with mechanical stirrer and digital thermometer cooled with an ice-water bath (internal temperature 15° C.) is added solid imidazole (25.9 g) directly. No exotherm is observed. The slurry is stirred overnight as the reaction temperature slowly increases to room temperature. The resulting reaction mixture is combined with the preceding reaction mixture and the combined mixtures are worked up as follows:

Added 1.5 L of brine and 250 mL water to the combined mixture and separated layers. Evaporate organic layer under reduced pressure. Add 1.5 L of ethyl acetate to residue and wash with 600 mL water. Evaporate organic layer. Solid obtained is triturated with hexanes, filtered and dried in a 40° C. vacuum oven to afford the title compound (358.5 g.)

Alternatively, set up a 500 mL 4-neck flask with a stir bar, nitrogen line and temperature probe. Purge with nitrogen. Add 23.71 g of 1-(4-hydroxy-phenyl)-2-phenyl-ethanone, 18.41 g of tert-butyldimethylsilyl chloride and 250 mL of dichloromethane. Stir. Add 10.0 mL of 1-methylimidazole over about one minute. Temperature increases from +16.0° C. to +23.5° C. and the mixture is stirred for two days. Concentrate the mixture under reduced pressure. Partition between 300 mL of MTBE and 250 mL of water. Separate layers. Wash organic layer with 250 mL of water. Separate layers. Dry organic over anhydrous magnesium sulfate, filtered through Celite, and then concentrate under reduced pressure to afford the title compound (36.82 g.)

Example 135

This example illustrates alternative preparations of, 1-(4-benzyloxy-phenyl)-2-phenyl-ethanone.

Example 135A

Set up a 2 L 4N flask with a mechanical stirrer, heating mantle and reflux condenser. Add 49.91 g of 1-(4-hydroxy-phenyl)-2-phenyl-ethanone, 36.98 g of powdered potassium carbonate and 500 mL acetone and stir. Add 31 mL of benzyl bromide using a syringe. Yellowish slurry. Heat mixture to reflux (57 C) for 2 hours. Dilute reaction mixture with 500 mL of water and stir overnight. Filter solids. Wash with 500 mL of 1:1 acetone:water and then 500 mL of water. White solids are put on nitrogen press. Net=69.04 g Alternative 1: To a 250-mL round-bottomed flask is added benzyl 4-hydroxyphenyl-ethanone (10.0 g) and acetone (100 mL) and the mixture is stirred until completely dissolved. Benzylbromide (8.4 mL), potassium carbonate (7.82 g), and TBAl (350 mg) are added and the mixture is stirred at r.t. under $N_2$. Initial solution is a clear and colorless w/$K_2CO_3$ stirring at the bottom of the flask. The reaction is stirred overnight. Reaction mixture had solidified as a white ppt., EtOAc (300 mL) is added and used to transfer crude reaction mixture to a seperatory funnel. Flask is also rinsed w/water. Water (200 mL) is added and the layers separated; insolubility of white ppt caused emulsions. Organics are subsequently washed with sat'd $NH_4Cl$ (200 mL), sat'd $NaHCO_3$ (200 mL), water (200 mL), and sat'd brine (200 mL). Resultant organics are concentrated under rotary evaporation, slurried with 100 mL of acetone, filtered and rinsed with acetone, and dried under vacuum. Product is a white, chalky, ppt; obtained 11.96 g.

Alternative 2: 1-(4-Hydroxy-phenyl)-2-phenyl-ethanone and potassium carbonate are suspended in 100 mL ethanol. Benzyl bromide is added. The mixture is stirred at reflux.

Alternative 3: Set up a 25 mL rb with a stir bar. Add 1005 mg of 1-(4-Hydroxy-phenyl)-2-phenyl-ethanone, 7.5 mL of MeOH and 0.56 mL of BnBr. Stir. Add 2×0.54 mL of 25 wt % NaOMe. Stir overnight.

Example 135 B

Benzyl phenyl ether is stirred in 75 ml dichloromethane at 0° C. under nitrogen. To the mixture is added the $AlCl_3$ in 2 portions. After cooling to 0° C. the phenacetyl chloride is added in 4 portions. The ice bath is removed and the reaction mixture is allowed to warm to room temperature. HPLC showed that neither starting material remained. The reaction mixture is cooled to 0° C. and quenched with the addition of ice chunks. The reaction mixture is poured into a sep funnel, brine is added. The layers are separated, the organic layer is concentrated under reduced pressure, taken up in toluene and again concentrated under reduced pressure to give 9 g of an oil. HPLC and TLC of product showed many different entities present. Product peak is the main peak in the MS, HPLC has 53 peaks, the largest integrates for 15%.

Example 135 C

Benzyl phenyl ether and phenylacetic acid are stirred in 25 ml Eaton's reagent at 60° C. for 4 hours. TLC and HPLC indicated no product but showed that the benzyl phenyl ether is gone. The reaction mixture is discarded.

Preparation of Protected Oximes as Described by Structure 3, in Scheme I on Page 9, General Preparation of Isoxazoles Example 136

This example illustrate the preparation of, 1-[4-(tert-butyl-dimethyl-silanyloxy)-phenyl]-2-phenyl-ethanone oxime.

A solution of 1-[4-(tert-butyl-dimethyl-silanyloxy)-phenyl]-2-phenyl-ethanone, which may be produced as in Example 134 (1.01 Kg) is suspended in 3.8 L of ethanol. Hydroxylamine hydrochloride (255 g) is added followed by the addition of sodium acetate (303 g.) After the addition is complete, the reaction mixture is stirred at room temperature overnight. Water (3.0 L) is added over 1 hour, and the mixture is stirred for an additional 30 minutes. The solid is collected on the filter and dried in a vacuum oven at 50° C. overnight to give 872 g of the title compound, which is used without further purification. This reaction can also be carried out at 50° C. instead of room temperature.

Example 137

This example illustrates alternative preparations of, 1-(4-methoxy-phenyl)-2-phenyl-ethanone oxime.

A one-neck 250 mL round-bottomed flask is charged with 1-(4-methoxy-phenyl)-2-phenyl-ethanone, which may be produced by any of the methods described Example 133 (limiting reagent, 9.5 g) and absolute ethanol (80 mL). To the slurry is added hydroxylamine hydrochloride (3.47 g) followed by sodium acetate (4.1 g). The reaction is stirred for 24 h at room temperature. Water (150 mL) is added to the slurry. After stirring for 15 minutes, the solids are isolated by filtration and washed with a 10% citric acid solution (100 mL), water (100 mL), and acetonitrile (50 mL). The solids are placed in a vacuum oven for 2 hours, providing the title compound (8.9 g) as a mixture of geometric isomers.

Alternatively, the following solvent/base combinations may be used as a substitute for ethanol/sodium acetate: tetrahydrofuran/sodium acetate; methanol/sodium acetate; isopropyl alcohol/sodium acetate; acetonitrile/sodium acetate; isopropyl alcohol/potassium carbonate; isopropyl alcohol/triethylamine; tetrahydrofuran/pyridine; ethanol/triethylamine; or ethanol/sodium pentoxide.

Example 138

This example illustrates the preparation of 1-(4-benzyloxy-phenyl)-2-phenyl-ethanone oxime.

To a single-necked 250 mL round-bottomed flask charged with 1-(4-benzyloxy-phenyl)-2-phenyl-ethanone, which may be produced by any of the alternative methods described in Example 135, (11.96 g) is added absolute EtOH (100 mL). Note that the ketone is only slightly soluble in EtOH. To this mixture is added hydroxylamine HCl in one portion as a solid (3.3 g) followed by NaOAc (anhydrous; powdered; 3.89 g). The reaction mixture is heated to 50° C. and stirred overnight. TLC of the crude reaction mixture using 4:1 Hexanes:EtOAc shows complete conversion to oxime. The Reaction is cooled to rt and concentrated via rotary-evaporation. To the resultant white solid is added EtOAc (250 mL) to transfer to a seperatory funnel; most of the material is soluble. This organic layer is washed with sat'd NaHCO3 (150 mL), sat'd NH4Cl (150 mL), water (150 mL), and brine (200 mL); and the organics are dried over MgSO4, filtered, and concentrated. Crude white solid is dried further in vacuo overnight. m=10.22 g of white solid. Alternatively, the product may be isolated by cooling the reaction mixture to room temperature, diluting with water and filtering the resulting slurry.

Preparation of 5-Hydroxyisoxazole as Described by Structure 5, in Scheme I on Page 9, General Preparation of Isoxazoles Example 139

This example illustrates the preparation of 1-[3-(4-benzyloxy-phenyl)-5-hydroxy-4-phenyl-4,5-dihydro-isoxazol-5-yl]-cyclopropanecarboxylic acid methyl ester.

Tetrahydrofuran (70 mL) is added to 1-(4-benzyloxy-phenyl)-2-phenyl-ethanone oxime, which may be produced as in Example 138, (10 g) and the mixture is stirred until all solids had dissolved. The solution is degassed with nitrogen and cooled to −10° C. at which point a suspension forms. A solution of n-butyllithium (25 mL, 2.5 M in hexanes) is added to the stirring suspension while the temperature is maintained below 0° C. After the addition is complete the mixture is stirred for 15 minutes while the temperature is maintained between −15° C. and −20° C. Dimethyl 1,1-cyclopropane dicarboxylate (10.4 mL) is added while the temperature is kept below 0° C. The reaction mixture is stirred 2 hours and then cooled to 0° C. and quenched with saturated aqueous ammonium chloride solution. The mixture is extracted with ethyl acetate. The organic extracts are washed with saturated ammonium chloride solution, dried, filtered through a plug of silica, and then concentrated to give a yellow oil. Ethyl acetate/hexanes (4:1) is added to the yellow residue and the resulting white solid is collected by filtration and dried to give 1-[3-(4-benzyloxy-phenyl)-5-hydroxy-4-phenyl-4,5-dihydro-isoxazol-5-yl]-cyclopropanecarboxylic acid methyl ester (5.98 g). The mother liquor is concentrated and purified on a Biotage Horizon system using a 0% to 100% ethyl acetate/hexane gradient to afford further 1-[3-(4-benzyloxy-phenyl)-5-hydroxy-4-phenyl-4,5-dihydro-isoxazol-5-yl]-cyclopropanecarboxylic acid methyl ester (1.53 g).

Example 140

This example illustrates the preparation of, 1-[5-hydroxy-3-(4-hydroxy-phenyl)-4-phenyl-4,5-dihydro-isoxazol-5-yl]-cyclopropanecarboxylic acid ethyl ester.

A solution of 1-[4-(tert-butyl-dimethyl-silanyloxy)-phenyl]-2-phenyl-ethanone oxime, which may be produced as in Example 136 (25.0 g) is dissolved in 300 mL THF, purged with N₂, and cooled to −15° C. n-butyllithium (1.6 M in hexanes, 96.08 mL) is added over 15 minutes keeping the internal temperature below −8.8° C. After 30 minutes, cyclopropane-1,1-dicarboxylic acid diethyl ester (14.12 mL) is added over about 5 minutes. The reaction is allowed to warm to room temperature overnight. The reaction is diluted with 300 mL of ethyl acetate, washed with water and brine, dried over Na₂SO₄, and evaporated to afford the title compound as a thick gum which is used without further purification.

Example 141

This example illustrates alternative preparations of 1-{3-[4-(tert-butyl-dimethyl-silanyloxy)-phenyl]-5-hydroxy-4-phenyl-4,5-dihydro-isoxazol-5-yl}-cyclopropanecarboxylic acid methyl ester.

An oven-dried 1 L three-neck flask equipped with magnetic stir bar, nitrogen gas inlet valve, and digital thermometer probe, and addition funnel is charged with 1-[4-(tert-butyl-dimethyl-silanyloxy)-phenyl]-2-phenyl-ethanone oxime, which may be produced as in Example 136 (26.59 g) and anhydrous tetrahydrofuran (140 mL.) The reaction vessel is submerged in an ice-methanol bath equipped with a thermometer reading −18° C. The internal solution temperature is cooled to −9.0° C. A solution comprised of 2.5 M n-butyllithium in hexane (31 mL) is added dropwise over 25 minutes (bath temperature −18 to −16° C., internal mixture temperature −9.0 to −0.6° C.), over which time the solution color turns from yellow after addition of the first few drops to orange at the first endpoint. The reaction mixture is stirred for three minutes as the internal mixture temperature cooled to −3.3° C. (bath temperature −14° C.) Another 31 mL of 2.5 M n-butyllithium in hexane is added over 11 minutes (bath temperature −14 to −16° C., internal mixture temperature −3.3 to −0.3° C. with a peak temperature in that time period of +0.2° C.) The reaction mixture is stirred for 31 minutes as the internal mixture temperature cooled to −10.1° C. (bath temperature −14° C.) Dimethyl cyclopropanedicarboxylate (26.0 mL) is added over less than one minute to give an internal mixture temperature of +4.6° C. (bath temperature −13° C.) The reaction mixture is stirred for one hour and is quenched with the addition of brine solution (100 mL.) The layers are separated and the organic phase is dried over anhydrous magnesium sulfate and is concentrated under reduced pressure to afford a clear yellow-orange liquid (59.9 g crude) This material is combined with another batch of crude product prepared using the same method (100 g crude) and is purified by filtration through a 1 Kg silica plug (gradual enrichment of ethyl acetate in hexanes) giving a viscous residue (60 g.) This material is divided into two portions and each portion is subsequently purified by flash silica gel chromatography. Elution with a gradient (100% hexanes to 100% ethyl acetate over 4200 mL, or seven column volumes) affords the title compound as a foam (42 g.) Alternatively, the reaction mixture may be quenched with acetic acid instead of brine solution.

Alternatively, THF is added to 1-[4-(tert-butyl-dimethyl-silanyloxy)-phenyl]-2-phenyl-ethanone oxime (5.0 g) with stirring until it completely dissolves. The solution is degassed with nitrogen and cooled to −15° C. N-butyllithium is added while keeping the temperature below 0° C. Reaction mixture turns from light yellow to orange upon addition of the second equivalent of n-butyllithium. After addition is complete, the mixture is stirred for 15 minutes between −15 to −10° C. Dimethyl 1,1-cyclopropane dicarboxylate is added keeping the temperature below 0° C. Upon addition, the reaction mixture turned yellow. Allow reaction to stir over 20 minutes. The reaction is brought up to 0° C. and quenched with brine (25 mL.) To the resulting cloudy solution is added ethyl acetate (25 mL) then 1 M HCl until a clear solution is obtained. The layers are separated and the organics washed with additional brine. The organic layer is dried (anhydrous magnesium sulfate), filtered and concentrated under reduced pressure. Purify resulting yellow residue by flash chromatography (0% to 50% ethyl acetate-hexanes). Isolate 5.7 g of the title compound as a white foamy solid; TLC $R_f$=0.08 (4:1 hexanes-ethyl acetate); MS (APCI⁺ 10V)=450 (MH⁺-18.)

The amorphous product is crystallized from methanol.

Example 142

This example illustrates the preparation of 1-[5-hydroxy-3-(4-methoxy-phenyl)-4-phenyl-4,5-dihydro-isoxazol-5-yl]-cyclopropanecarboxylic acid methyl ester.

1-(4-Methoxy-phenyl)-2-phenyl-ethanone oxime, which may be produced as in Example 137 (110 g, 456 mmol, 1 equiv) is dissolved in tetrahydrofuran (825 mL), and the solution is cooled to about 0 □C in an ice/isopropyl alcohol bath. Butyllithium (2.5 M in hexane, 383 mL, 957 mmol, 2.1 equiv) is added at a rate to keep the temperature below 10 □C (about 1 hour addition time). The solution is allowed to stir for about 15 minutes. Cyclopropane-1,1-dicarboxylic acid dimethyl ester (86.5 g, 547 mmol, 1.2 equiv.) is added rapidly, and the reaction is allowed to stir for about 15 minutes. The reaction is quenched by the addition of acetic acid (65.3 mL, 1140 mmol, 2.5 equiv), and water (200 mL) is added. The mixture is allowed to sit overnight. The water layer is removed, and the organic layer is washed with water (300 mL). Toluene (100 mL) is added, and the organic layer is concentrated to give crude title compound, 1-[5-hydroxy-3-(4-methoxy-phenyl)-4-phenyl-4,5-dihydro-isoxazol-5-yl]-cyclopropanecarboxylic acid methyl ester, which may be used without purification.

Illustration of the Dehydration of the 5-Hydroxyisoxazole as Described by Structure 5, into the Corresponding Protected Isoxazole of Structure 6 in Scheme I on page 9, General Preparation of Isoxazoles Example 143

This example illustrates the preparation of (1-{3-[4-(tert-Butyl-dimethyl-silanyloxy)-phenyl]-4-phenyl-isoxazol-5-yl}-cyclopropanecarboxylic acid methyl ester, one of the protected isoxazoles of structure 6.

A solution consisting of 1-{3-[4-(tert-butyl-dimethyl-silanyloxy)-phenyl]-5-hydroxy-4-phenyl-4,5-5-yl}-cyclopropanecarboxylic acid methyl ester, which may be produced as in Example 141 (103.4 g) in toluene (300 mL) is warmed over a steam bath. A suspension consisting of p-toluenesulfonic acid hydrate (4.21 g) in toluene (100 mL) is warmed over a steam bath and is subsequently added to the warm ester solution with swirling. The mixture is heated over a steam bath until the internal mixture temperature is raised to 80° C. The mixture is then removed from the steam bath and is treated with water (100 mL.) The layers are stirred vigorously and separated and the toluene phase is dried over anhydrous magnesium sulfate and is concentrated under reduced pressure to afford a yellow oil that is purified by flash chromatography. Elution through a 400 g Analogix silica cartridge with a gradient (100% hexanes to 35% ethyl acetate over 1800 mL, or three column volumes) affords a concentrate that is redissolved in chloroform. The mixture is concentrated under reduced pressure to afford the clear viscous residue, which solidifies overnight under high vacuum to the off-white solid title compound (84.95 g.)

Alternatively, 1-{3-[4-(tert-butyl-dimethyl-silanyloxy)-phenyl]-5-hydroxy-4-phenyl-4,5-dihydro-isoxazol-5-yl}-cyclopropanecarboxylic acid methyl ester (57.23 g) is dissolved in toluene (500 mL) and p-toluenesulfonic acid hydrate (1.16 g) added in one portion. Warm reaction to 80° C. and stir for 30 minutes. Cool reaction mixture to room temperature. Concentrate under reduced pressure and dissolve yellow residue in ethyl acetate. Wash organics with aqueous sodium bicarbonate and brine. Dry organic layer (anhydrous magnesium sulfate), filter, and concentrate. Divide material into four equal portions (approximately 13.7 grams each). Purify each, by flash chromatography (0% to 30% ethyl acetate-hexanes.) Isolate 49.5 g of the title compound as a white solid; TLC $R_f$=0.34 (4:1 hexanes-ethyl acetate); MS (APCI$^+$)=450 (MH$^+$.)

Example 144

This example illustrates the preparation of (1-{3-[4-(tert-butyl-dimethyl-silanyloxy)-phenyl]-4-phenyl-isoxazol-5-yl}-cyclopropanecarboxylic acid methyl ester, one of the protected isoxazoles of structure 6.

Set up a 250 mL 3N flask with a stir bar, cold bath, nitrogen line and temperature probe. Purge flask with nitrogen. Add 5.09 g of the oxime 1-[4-(tert-butyl-dimethyl-silanyloxy)-phenyl]-2-phenyl-ethanone oxime, which may be produced as in Example 136, and 50 mL of THF. Stir clear, colorless solution and cool to −24.0° C. Add 19.0 mL of 1.6 $\underline{M}$ n-butyllithium (hexanes) over seven minutes. Stir cold for 25 minutes. Cool to −25.0° C. and then add 2.50 mL of cyclopropane-1,1-dicarboxylic acid dimethyl ester all at once. Stir for 50 minutes. Quench mixture by adding 2.10 mL of acetic acid. Add 50 mL of water. Transfer to a separatory funnel with 100 mL of MTBE. Mix well and then let stand. Separate layers. Wash organic layer with 50 mL of water. Concentrate organic layer under reduced pressure to give a yellow oil. Take up in 50 mL of toluene and add 157 mg of p-toluenesulfonic acid monohydrate. Heat to reflux for 1.5 hours and allow to cool to room temperature. Add 25 mL of 1 $\underline{M}$ sodium carbonate and mix well. Filter through Celite, wash with toluene. Transfer to a separatory funnel. Let stand. Dilute with 2×25 mL of ethyl acetate and mix well. Dilute with 2×25 mL of THF and mix well. Heat. Concentrate under reduced pressure. Dilute with 50 mL of ethyl acetate and transfer to a separatory funnel. Rinse and dilute with another 50 mL of ethyl acetate and add 50 mL of water. Mix well. Add 50 mL of brine and mix well. Separate layers. Wash organic layer with 50 mL of water. Add 50 mL of brine and mix well. Separate layers. Back-extract aqueous layers with 60 mL of ethyl acetate. Combine organic layers, dry over anhydrous magnesium sulfate, filter through Celite and concentrate under reduced pressure to give an orange oil.

Example 145

This example illustrates the preparation of (1-{3-[4-(tert-butyl-dimethyl-silanyloxy)-phenyl]-4-phenyl-isoxazol-5-yl}-cyclopropanecarboxylic acid ethyl ester, one of the protected isoxazoles of structure 6.

n-Butyllithium (2.5 $\underline{M}$ in hexane, 983.8 mL) is added to a solution of 1-[4-(tert-butyl-dimethyl-silanyloxy)-phenyl]-2-phenyl-ethanone oxime, which may be produced as in Example 136 (400 g) in THF (4 L) at 0° C. and the reaction solution is stirred for one hour at this temperature. Diethyl 1,1-cyclopropanedicarboxylate (227 mL) is added to the reaction solution, stirred for one hour at 0° C. and then the reaction is quenched with saturated ammonium chloride, diluted with ethyl acetate, washed with water, brine, dried over anhydrous sodium sulfate, filtered, and the filtrate evaporated under reduced pressure. The crude product is purified by column chromatography with 5-10% ethyl acetate in hexane to give a light yellow solid, which is triturated with pentane and filtered to give 1-{3-[4-(tert-butyl-dimethyl-silanyloxy)-phenyl]-5-hydroxy-4-phenyl-4,5-dihydro-isoxazol-5-yl}-cyclopropanecarboxylic acid ethyl ester (230.8 g.)

p-Toluenesulfonic acid monohydrate (12.47 g) is added to the solution of 1-{3-[4-(tert-butyl-dimethyl-silanyloxy)-phenyl]-5-hydroxy-4-phenyl-4,5-dihydro-isoxazol-5-yl}-cyclopropanecarboxylic acid ethyl ester (288 g) in toluene (3 L) and heated at 80° C. for two hours. The reaction solution is cooled, taken in ethyl acetate, washed with saturated sodium bicarbonate, brine, dried over anhydrous sodium sulfate, filtered, and the filtrate evaporated under reduced pressure to give the title compound (277.2 g.)

Example 146

This example illustrates alternative preparations of 1-[3-(4-benzyloxy-phenyl)-4-phenyl-isoxazol-5-yl]-cyclopropanecarboxylic acid methyl ester one of the protected isoxazoles of structure 6.

Example 146 A

A mixture of 1-[3-(4-benzyloxy-phenyl)-3-hydroxyimino-2-phenyl-propionyl]-cyclopropanecarboxylic acid methyl ester, which may be produced as in Example 139, (7.0 g) and tosic acid monohydrate (0.3 g) in toluene (100 mL) is heated at reflux for 3 h until TLC and LCMS showed no starting material remained. Heating is stopped and as the reaction mixture cools, a white solid forms. LCMS showed the solid to be a mixture containing the oxime starting material and product. Solvent is removed under reduced pressure. Recrystallization from isopropanol-hexane gave a mixture containing the starting oxime and product. Attempted recrystallization from ethanol/water caused the material to oil out.

Dichloromethane is added to the crude oil and a small amount of a white solid is formed, this was collected by filtration. The remaining oil is chromatographed. Elution with a 5% to 35% ethyl acetate-hexane gradient, the starting oxime and product co-eluted. The mixture is triturated with isopropanol and left over the weekend. The white solid is collected by filtration and washed with isopropanol to give the title compound. Further material is obtained from the mother liquor to give a total of 3.1 g of the title compound (two batches.)

Alternatively, 1-[3-(4-benzyloxy-phenyl)-3-hydroxy-imino-2-phenyl-propionyl]-cyclopropanecarboxylic acid methyl ester (5.0 g) and tosic acid monohydrate (0.1 g) in toluene (50 mL) is heated at reflux overnight. The mixture is cooled to room temperature and the product is collected by filtration.

Example 146B

To a mixture of 1-[3-(4-benzyloxy-phenyl)-5-hydroxy-4-phenyl-4,5-dihydro-isoxazol-5-yl]-cyclopropanecarboxylic acid methyl ester, which may be produced as in Example 139 (21.2 g) in toluene (220 mL) at room temperature is added concentrated HCl (37.8% aqueous, 8.0 mL) dropwise. The resulting solution is warmed to 70° C. for 10 minutes, during which time a clear light yellow solution forms. The reaction mixture is cooled to room temperature and diluted with 300 mL water/ethyl acetate (1:1). The layers are partitioned and the organic layer washed with additional brine. The organic layer is dried (MgSO$_4$), filtered, and concentrated under reduced pressure to afford a foamy white solid. The residue is dissolved in a minimum amount of ethyl acetate and isopropanol added. A white solid immediately precipitates out of solution. The resulting white solids are collected by filtration and dried. MS (APCI+) 426 (MH+.)

Example 147A

This example illustrates alternative preparations of 1-[3-(4-benzyloxy-phenyl)-4-phenyl-isoxazol-5-yl]-cyclopropanecarboxylic acid methyl ester one of the protected isoxazoles of structure 6.

Set up a 50 mL cone-bottom flask with a triangular stir bar. Purge well with nitrogen and then add 21 mL of 1.6 M nBuLi/hexanes. Cool in ice-water bath with stirring and add 4.70 mL of diisopropylamine over 15 min. Additional 10 mL of THF is added. Stir turbid solution cold for 30 min. and then remove from bath. Set up a 250 mL 3N flask with a stir bar, nitrogen line and temperature probe. Purge with nitrogen. Add 5.01 g of 1-(4-benzyloxy-phenyl)-2-phenyl-ethanone oxime, which may be produced as in Example 147, and 40 mL of fresh THF. Cool to −10.7 C and add lithium diisopropylamide solution over 5 minutes. Add 2.750 mL of cyclopropane-1,1-dicarboxylic acid dimethylester. Quench after 10 minutes with 50 mL of sat. NH$_4$Cl. Stir 5 min. and then let stand. Transfer mixture to a separatory funnel, with 100 mL of EtOAc. Mix well and separate layers. Wash organic layer with 50 mL of water. Concentrate organic layer at the Rotavap. Take residue up in 50 mL of toluene and add 175 mg of TsOH:H2O. Heat to reflux overnight. Let cool to rt. Transfer to a separatory funnel with 50 mL of EtOAc. Wash with 25 mL of water+25 mL of brine. Separate layers. Back-extract aqueous layer with 50 mL of EtOAc. Combine organic layers. Dry over MgSO4. Filter through Celite. Concentrate at the Rotavap to a dark, orange oil. Net=8.22 g. Take up in 30 mL of IPA. Stir. Dilute with 30 mL of heptane. Heat to reflux. Let cool. Stir for 2 hours and then cool in ice water for 30 min. Filter solids. Wash with 2×30 mL of 1:1 IPA:heptane and then 200 mL of petroleum ether. Put on nitrogen press overnight. Light-brown, powdery solids. Net=3.95 g.

Alternative 2: Flask 1: Set up a 250 mL 3N flask with a stir bar, nitrogen line, temperature probe and cooling bath. Purge with nitrogen and add 35.0 mL of diisopropylamine and 70 mL of THF. Stir and cool to +5.3 C using an ice-water bath. Add 100 mL of nBuLi (2.5 M in hex) over 30 minutes. Remove cold bath and stir mixture.

Flask 2: Set up a 1 L 4N flask with a mechanical stirrer, nitrogen line, cooling bath and temperature probe. Purge with nitrogen and then add 36.91 g of 1-(4-benzyloxy-phenyl)-2-phenyl-ethanone oxime and 300 mL of THF. Stir. Cool to −8.8 C using a dry-ice acetone bath and add the LDA solution prepared above (flask 1) over 7 minutes.

Flask 3: Set up a 1 L 4N flask with a mechanical stirrer, nitrogen line, cooling bath and temperature probe. Purge with nitrogen and then add 20.0 mL of cyclopropane-1,1-dicarboxylic acid dimethylester and 80 mL of THF. Stir. Transfer the cold solution from flask 2 into flask 3 over 8 minutes. Rinse flask 2 with 25 mL of THF.

Flask 2: Add 100 mL of water and 100 mL of sat. aq. NH$_4$Cl to empty 1 L 4N flask. Stir. Transfer reaction mixture into quench solution. Rinse reaction flask with 25 mL of THF. Cloudy two-phase mixture. Acidify to pH 5 with 31.2 mL of MsOH. Exothermic. Transfer mixture to a separatory funnel with 2×100 mL of EtOAc. Mix well and then let stand. Separate aqueous layer. Wash organic layer with 2×200 mL of water. Transfer organic layer into a 2 L 4N flask and rinse with 50 mL of EtOAc. Fit flask with a mechanical stirrer, heating mantle, J-KEM temperature controller, still take-off and reflux condenser. Heat mixture with stirring. Collect a total of about 485 mL of distillate. Dilute mixture with 500 mL of EtOAc and let cool to rt. Let mixture stand overnight. Some material crystallizes on flask walls. Stir and begin heating. Added 0.75 mL of MsOH. Heat mixture to 75° C. Reflux. Heat for 1 hour 30 minutes. Stop heating and cool to 25° C. Transfer to a separatory funnel. Rinse flask with 50 mL of EtOAc and then 200 mL of water. Transfer both rinses to the separatory funnel. Mix well and let stand. Add 6.12 g of solid Na$_2$CO$_3$ and shake a few times until dissolved—carefully vent $CO_2$. Remove aqueous layer and then add another 200 mL of water to organic layer. Mix well and then let stand. Add 6.18 g of $Na_2CO_3$ and shake until dissolved (some off-gasing). Let stand. Remove aqueous. Filter organic layer through Celite. Rinse separatory funnel with 50 mL of EtOAc and put rinse through filter. Wash Celite cake with another of 50 mL of EtOAc. Combine filtrates. Transfer back into 2 L 4N flask. Rinse with 50 mL of EtOAc. Stir solution and heat to reflux. Distill and collect about 650 mL of distillate. Add 230 mL of IPA to the pot and begin distilling again. Collect about 150 mL of distillate. Distill about another 150 mL of distillate. Dilute pot with 250 mL of IPA. Add 250 mL of heptane to the pot over 5 min. using an addition funnel. Clear, orange solution. Let cool to room temperature with stirring. Add ~10 mg of seeds crystals. Solids precipitate. Stir 20 min. and then let stand for 2 days. Filter solid. Wash solids with 300 mL of 1:1 IPA:heptane and then 300 mL of heptane. Put solids into a glass dish. Light-orange solids. Put solids in vacuum oven at 45° C. Net=37.73 g.

Example 147B

This example illustrates the preparation of 1-[3-(4-methoxy-phenyl)-4-phenyl-isoxazol-5-yl]-cyclopropanecarboxylic acid methyl ester, one of the protected isoxazoles of structure 6.

1-[5-Hydroxy-3-(4-methoxy-phenyl)-4-phenyl-4,5-dihydro-isoxazol-5-yl]-cyclopropanecarboxylic acid methyl ester, which may be produced as in Example 142, is dissolved in toluene (1000 mL) and para-toluenesulfonic acid (1.10 g, 6.38 mmol, 0.014 equiv) is added. The reaction is heated to reflux for about 1.5 h using a Dean-Stark trap to remove water. After cooling to room temperature, the reaction is filtered and concentrated to give a yellow solid. The residue is slurried in isopropyl alcohol (405 mL), and the slurry is heated to 75° C. to give a clear solution. Heptane (270 mL) is added while keeping the temperature at about 76° C. The solution is allowed to cool to 25° C. at 10° C./hour and stir over the weekend. The slurry is filtered, and the filter cake is washed with heptanes and dried by pulling air through it to give the title compound 1-[3-(4-methoxy-phenyl)-4-phenyl-isoxazol-5-yl]-cyclopropanecarboxylic acid methyl ester; Micro Anal Found: C, 71.97%; H, 5.33%; N, 4.05%. Theory: C, 72.19%; H, 5.48%; N, 4.01%.

Example 147C

1-[3-(4-Methoxy-phenyl)-4-phenyl-isoxazol-5-yl]-cyclopropanecarboxylic acid ethyl ester The title compound is prepared using the experimental procedure described in Example 147B except cyclopropane-1,1-dicarboxylic acid diethyl ester is used instead of cyclopropane-1,1-dicarboxylic acid dimethyl ester in Example 147A. The intermediate serving as the starting material for Example 147B is therefore 1-[5-hydroxy-3-(4-methoxy-phenyl)-4-phenyl-4,5-dihydro-isoxazol-5-yl]-cyclopropanecarboxylic acid ethyl ester instead of 1-[5-hydroxy-3-(4-methoxy-phenyl)-4-phenyl-4,5-dihydro-isoxazol-5-yl]-cyclopropanecarboxylic acid methyl ester.

Illustration of the Dehydration of the 5-Hydroxyisoxazole as Described by Structure 5, into an Isoxazole of Formula I, (i.e. a Final Product)

Example 148

This example illustrates the preparation of 1-[3-(4-Hydroxy-phenyl)-4-phenyl-isoxazol-5-yl]-cyclopropanecarboxylic acid ethyl ester, one of the final products of Formula I.

A solution of 1-[5-hydroxy-3-(4-hydroxy-phenyl)-4-phenyl-4,5-dihydro-isoxazol-5-yl]-cyclopropanecarboxylic acid ethyl ester, which may be produced as in Example 140, (26.89 g) in toluene (200 mL) is treated with tosic acid (13.92 g) and heated at 100° C. overnight. The reaction is cooled to room temperature, washed with water and brine, dried over $Na_2SO_4$, and evaporated. Flash silica gel chromatography (300 g RediSep column eluting with a gradient of 0 to 50% ethyl acetate in hexanes) provides the title compound.

Illustration of the Optional Deprotection and Functionalization Reactions of Step E, From Reaction Scheme I Examples 133 thru 147 illustrate the preparation of one of the isoxazoles as described by Structure 6 in Scheme I, in which A is represented by an ester. As shown in Scheme IV below, this ester may be converted into a lower alkyl group substituted with a hydroxyl function by a number of alternative pathways. Examples 149-178 describe how such reactions may be carried out.

Scheme IV. General Pathway of Ester Intermediates to Alcohol Compounds (Examples 149-178)

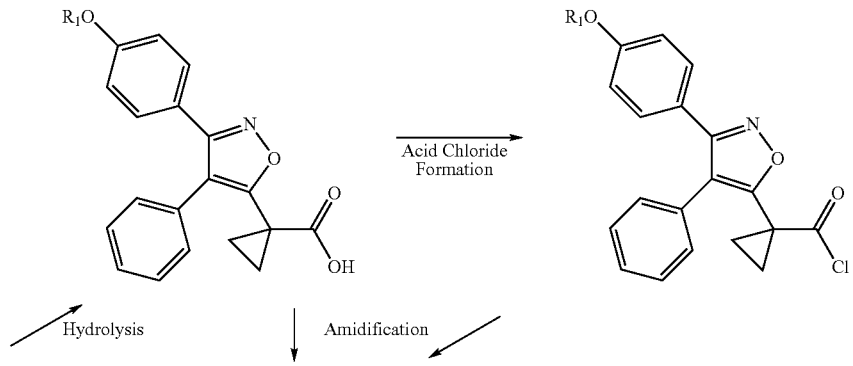

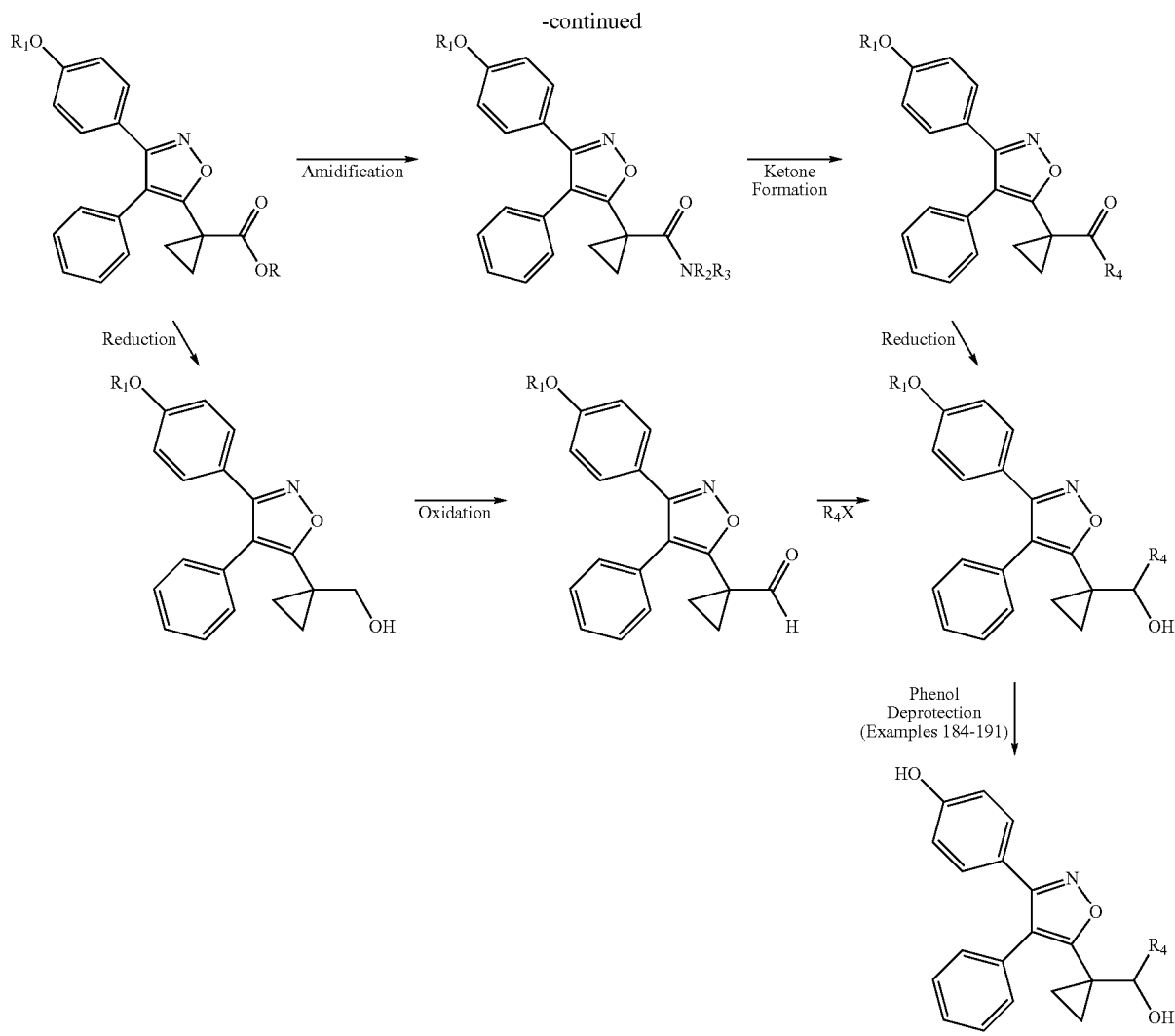

R = Me, Et
R₁ = H, Me, Bn, TBDMS
NR₂R₃ = N(Me)OMe, N(CH₂CH₂)₂O
R₄ = Me, Et
X = MgBr, Li

A) Conversion of the Cyclopropyl Ester or Free Acid Moiety (A') into an Alcohol, Acid Chloride, Amides Free Acid, etc.

Example 149

This Example illustrates the conversion of 1-[3-(4-benzyloxy-phenyl)-4-phenyl-isoxazol-5-yl]-cyclopropanecarboxylic acid methyl ester into 1-[3-(4-benzyloxy-phenyl)-4-phenyl-isoxazol-5-yl]-cyclopropanecarboxylic acid (i.e. A' of Structure 6, Scheme I is converted from an ester to an acid)

Example 149A

Set up a 250 mL round-bottomed flask with a stir bar and add 10.04 g of 1-[3-(4-benzyloxy-phenyl)-4-phenyl-isoxazol-5-yl]-cyclopropanecarboxylic acid methyl ester, which may be produced as described in Example 146, and 50 mL of THF. The reaction is stirred. Add 3.02 g of LiOH:H₂O and then 50 mL of water to provide a cloudy solution. The reaction is heated to 64° C. and stirred for 1 hour and 50 minutes. The cooled reaction mixture is acidified with 24 mL of 3N HCl. The solution is transferred to a separatory funnel with 100 mL of EtOAc and the layers separated. The organic layer is washed with 2×25 mL of water, dried over MgSO₄., filtered through Celite and concentrated under rotary evaporation to provide an off-white solid. Alternatively, this chemical transformation can be carried out using sodium hydroxide in place of lithium hydroxide monohydrate.

Example 150

This Example illustrates the conversion of 1-[3-(4-benzyloxy-phenyl)-4-phenyl-isoxazol-5-yl]-cyclopropanecarboxylic acid methyl ester into {1-[3-(4-benzyloxy-phenyl)-4-phenyl-isoxazol-5-yl]-cyclopropyl}-morpholin-4-yl-methanone (i.e. A' of Structure 6, Scheme I is converted from an ester to an amide).

A solution of morpholine (0.615 mL) in THF (8.5 mL) is cooled to 0° C. in a 3-necked rounded-bottomed flask under nitrogen. To this solution is added MeMgBr (2.1 mL, 3.0M in ether). Upon completion of addition, the mixture is stirred for 15 minutes. Mixture is yellow and gummy. A solution of 1-[3-(4-benzyloxy-phenyl)-4-phenyl-isoxazol-5-yl]-cyclopropanecarboxylic acid methylester, which may be produced as in Example 146, (1 g) in THF (4.5 mL) is added via addition funnel. Mixture begins to clear and turns orange upon ester addition. Allow to warm on its own (over 35 minutes). Cool reaction mixture back down to 0° C. and quench with saturated aqueous NH₄Cl. Dilute with EtOAC and separate layers. Wash organics with additional NH₄Cl, then brine. Dry organic layer (MgSO₄), filter through a pad of silica gel and concentrate in vacuo. Isolate desired amide as a white foam.

Example 151

This Example illustrates the conversion of 1-[3-(4-benzyloxy-phenyl)-4-phenyl-isoxazol-5-yl]-cyclopropanecarboxylic acid methyl ester, or the free acid, into 1-[3-(4-benzyloxy-phenyl)-4-phenyl-isoxazol-5-yl]-cyclopropanecarboxylic acid methoxy-methyl-amide (i.e. A' of Structure 6, Scheme I is converted from an ester to an amide).

Example 151A

Set up a 25 mL oven-dried reaction tube with a stir bar and purged well with nitrogen. Add 247 mg of N,O-dimethylhydroxylamine hydrochloride and 2.5 mL of THF. Stir white suspension and cool in a −40° C. bath. Add 2.55 mL of PhMgCl solution (2.0 M in THF) over 10 min. Off-white suspension. Stir cold 25 min. and then add 503 mg of 1-[3-(4-benzyloxy-phenyl)-4-phenyl-isoxazol-5-yl]-cyclopropanecarboxylic acid methylester (which may be produced as in Example 146) dissolved in 2.0 mL of THF. Some gas evolution. Clear, light orange solution forms within 2 min. Stir and let warm to rt. After 1 hour and 20 minutes, quench with 3 mL of NH₄Cl+3 mL of water. Transfer to a separatory funnel with 20 mL of EtOAC. Separate layers. Wash organic layer with 10 mL of water. Dry organic layer over MgSO4. Filter and then concentrate to orange oil. Pump on mechanical pump for one hour.

Alternatively, methyl magnesium bromide (3M in diethyl ether) can be used instead of PhMgCl solution.

Example 151B

Charge a 20 mL vial with a stir bar, 241 mg of 1-[3-(4-benzyloxy-phenyl)-4-phenyl-isoxazol-5-yl]-cyclopropanecarboxylic acid (which may be produced as in Example 149), 66 mg of N,O-dimethylhydroxylamine hydrochloride and 3.5 mL of EtOAc. Stir. Off-white suspension. Add 204 uL of NEt₃. Cloudy solution. Add 0.770 mL of 2-propanephosphonic acid anhydride (50 wt % in EtOAc). Stir overnight. Transfer to a separatory funnel with 10 mL of EtOAc and add 10 mL of water. Mix well and then separate layers. Wash organic layer with 2×10 mL of water. Dry organic layer over MgSO₄, filter and then concentrate at the Rotavap to a cloudy, yellowish oil. Alternatively, this transformation may be carried out in dichloromethane in place of ethyl acetate.

Example 152

This Example illustrates the conversion of 1-[3-(4-hydroxy-phenyl)-4-phenyl-isoxazol-5-yl]-cyclopropanecarboxylic acid into 1-[3-(4-hydroxy-phenyl)-4-phenyl-isoxazol-5-yl]-cyclopropanecarbonyl chloride (i.e. A' of Structure 6, Scheme I is converted from an ester to an acid chloride).

To a mixture of 1-[3-(4-hydroxy-phenyl)-4-phenyl-isoxazol-5-yl]-cyclopropanecarboxylic acid, which may be produced as in Example 190 or 191, (1.2 g, 3.6 mmoles) in 40 mL of anhydrous dichloromethane is added anhydrous DMF (4 drops, cat), followed by 0.38 mL of oxalyl chloride (0.55 g, 4.3 mmoles). The reaction mixture is stirred at room temperature for 18 hrs and then evaporated to afford a yellow foamy solid, which is dried to provide the title compound.

Example 153

This Example illustrates the conversion of 1-[3-(4-methoxy-phenyl)-4-phenyl-isoxazol-5-yl]-cyclopropanecarboxylic acid methyl ester into {1-[3-(4-methoxy-phenyl)-4-phenyl-isoxazol-5-yl]-cyclopropyl}-morpholin-4-yl-methanone (i.e. A' of Structure 6, Scheme I is converted from an ester to an amide).

Example 153 A

To a stirring solution comprised of morpholine (22 g, 249 mmoles) in 710 mL of tetrahydrofuran at 0° C. under a nitrogen stream is added 160 mL of a 1.4M solution of methylmagnesium bromide (27 g, 224 mmoles) 75% toluene in THF. The pale yellow cloudy mixture is stirred for 20 minutes at 0° C. and a solution of 1-[3-(4-methoxy-phenyl)-4-phenyl-isoxazol-5-yl]-cyclopropanecarboxylic acid methyl ester, which may be produced as in Example 147B (29 g, 83 mmoles) in tetrahydrofuran (180 mL) is added affording a clear yellow solution. The ice-water bath is removed and the reaction mixture is allowed to warm to room temperature over one hour. The reaction mixture is quenched with saturated aqueous ammonium chloride (150 mL) and the biphasic mixture is stirred overnight. The stirring biphasic mixture is diluted with ethyl acetate (300 mL) and the layers are separated. The aqueous phase is extracted with fresh ethyl acetate (300 mL) and the combined organic phases are washed with saturated aqueous ammonium chloride (200 mL), water (200 mL), and brine solution (200 mL), are dried over anhydrous sodium sulfate and filtered through a silica plug. The filtrate is concentrated in vacuo and the concentrate is redissolved in dichloromethane and reconcentrated in vacuo to afford yellow foam as the title compound.

The following conditions are optionally substituted into the preceding procedure:
1) at 0° C. for 2 hrs and then at room temperature for 18 hrs with 6 eq morpholine and 5.5 molar equivalents of methylmagnesium bromide. The title compound can be purified by flash chromatography (silica gel, 60% ethyl acetate in hexane.)
2) at 0° C. for 15 min and then at room temperature for 18 hrs with 5 molar equivalents of morpholine and 4.5 molar equivalents of methylmagnesium bromide.
3.) at 0-5° C. for 15 min and then at room temperature for 1 hr
4.) at 0° C. for 15 min and then at room temperature for 2.25 hrs
5.) 4.) at 0° C. for 15 min and then at room temperature for 45 min.

Example 153B

To solution of 1-[3-(4-methoxy-phenyl)-4-phenyl-isoxazol-5-yl]-cyclopropanecarboxylic acid methyl ester, which may be produced as in Example 147B (1.0 g, 2.9 mmoles) in 20 mL of anhydrous toluene is added 0.27 mL of morpholine (0.27 g, 1.1 mmole). The reaction mixture is heated at reflux for 18 hrs. Analyses by TLC indicated that no reaction occurred with no evidence of cleavage of the cyclopropane ring. An additional 0.97 mL of morpholine (0.97 g, 3.9 mmoles) is added, followed by potassium carbonate (2.0 g, 14 mmoles) and then the reaction mixture is heated at reflux for 3 days. Analyses by TLC indicated that the title compound had formed. Starting material, however, is mostly present.

Example 154

This Example illustrates the conversion of 1-[3-(4-hydroxy-phenyl)-4-phenyl-isoxazol-5-yl]-cyclopropanecarbonyl chloride to {1-[3-(4-hydroxy-phenyl)-4-phenyl-isoxazol-5-yl]-cyclopropyl}-morpholin-4-yl-methanone (i.e. A' of Structure 6, Scheme I is converted from an acid chloride into an amide).

To a mixture of 16 mL of ethyl acetate and 8 mL of water is added sodium carbonate (2.0 g, 18 mmoles), followed by morpholine (0.84 g, 9.6 mmoles). The reaction mixture is cooled to 0° C. and then a solution of 1-[3-(4-hydroxy-phenyl)-4-phenyl-isoxazole-5-yl]-cyclopropanecarbonyl chloride, which may be produced as in Example 152, (3.0 g, 8.8 mmoles) in a mixture of 16 mL of ethyl acetate and 16 mL of dichloromethane (to enhance solubility) is added to the reaction mixture. The reaction mixture is stirred as 0° C. for 2 hrs and then at room temperature for 18 hrs. A white precipitate forms. The reaction mixture is filtered to remove the solid. The filtrate is diluted with 250 mL of ethyl acetate and then the organic layer is washed with saturated ammonium chloride (3×50 mL), followed with brine (50 mL.) The organic layer is separated, dried (sodium sulfate), filtered, and then the filtrate is evaporated to give a crude off-white solid. Purification by flash chromatography (silica gel, 60-80% ethyl acetate in hexane) affords the title compound as a white solid.

Example 155

This Example illustrates the conversion of 1-{3-[4-(tert-butyl-dimethyl-silanyloxy)-phenyl]-4-phenyl-isoxazol -5-yl}-cyclopropanecarboxylic acid methyl ester to (1-{3-[4-(tert-butyl-dimethyl-silanyloxy)-phenyl]-4-phenyl-isoxazol-5-yl}-cyclopropyl)-methanol (i.e. A' of Structure 6, Scheme I is transformed from an ester into an alcohol).

To a stirring solution comprised of 1-{3-[4-(tert-butyl-dimethyl-silanyloxy)-phenyl]-4-phenyl-isoxazol-5-yl}-cyclopropanecarboxylic acid methyl ester, which may be produced in either Example 143 or 144, (29.92 g) in dichloromethane (200 mL) at −78° C. under an argon atmosphere is added the diisobutyl aluminum hydride solution (1.0 M in hexanes) via syringe. The reaction mixture is stirred as it gradually warmed to 10° C. overnight. The stirring reaction mixture is cooled with an ice-water bath and is quenched cautiously with the slow addition of methanol (~50 mL.) Within five minutes of methanol addition, a thick white precipitate forms. The reaction mixture is then poured into a saturated aqueous sodium bicarbonate solution (250 mL.) Dichloromethane is added to dilute the biphasic mixture, and the insolubles are removed by vacuum filtration. The layers are separated and the dichloromethane layer is dried over anhydrous magnesium sulfate. The dried, filtered solution is concentrated under reduced pressure to an oil that solidified under high vacuum to give the title compound; MS (APCI+) 422 (MH+.)

Example 156

This Example illustrates the conversion of 1-{3-[4-(tert-butyl-dimethyl-silanyloxy)-phenyl]-4-phenyl-isoxazol -5-yl}-cyclopropanecarboxylic acid ethyl ester to 1-{3-[4-(tert-butyl-dimethyl-silanyloxy)-phenyl]-4-phenyl-isoxazol-5-yl}-cyclopropyl)-methanol (i.e. A' of Structure 6, Scheme I is transformed from an ester into an alcohol).

Example 156A

To a cold (−78° C.) solution of 1-{3-[4-(tert-butyl-dimethyl-silanyloxy)-phenyl]-4-phenyl-isoxazol-5-yl}-cyclopropane carboxylic acid ethyl ester, which may be produced as in Example 145, 20 g, 43 mmoles) in 200 mL of anhydrous dichloromethane is added 91 mL of 1 M solution of diisobutylaluminum hydride (DIBAL-H) (13 g, 91 mmoles) in hexanes. Upon completion of addition, the reaction mixture is warmed up to room temperature on its own and then stirred at room temperature for 18 hrs. Methanol (50 mL) is added to the ice cold (0° C.) reaction mixture. Saturated sodium bicarbonate (200 mL) is added, followed by addition of 1 M Rochelle's salt (potassium sodium tartrate tetrahydrate) and dichloromethane. The organic layer is separated, dried (magnesium sulfate), filtered, and then the filtrate is concentrated to provide 18.01 g of a yellow oil, which solidified to a waxy solid as the title compound.

Alternatively, the reaction is run at −60° C. employing the reaction conditions above or in THF at −60° C. using a 1 M solution of DIBAL-H in THF. Also, the title compound may be purified by flash chromatography on silica gel with 20-30% ethyl acetate in hexane as eluent.

Example 156B

To a −5° C., $N_2$ purged solution of 1-{3-[4-(tert-butyl-dimethyl-silanyloxy)-phenyl]-4-phenyl-isoxazol-5-yl}-cyclopropanecarboxylic acid ethyl ester, which may be produced as in Example 145, (20.0 g) in 300 mL THF is added lithium aluminum hydride (1.0 M in THF, 86.3 mL) over 15 minutes. After 1 hour, 0 mL sat. $NH_4Cl$ is added dropwise followed by 50 mL water and 100 mL of ethyl acetate. After stirring for 30 minutes, the solids are filtered off, and the resultant solution is washed with water and brine, dried over $Na_2SO_4$, and evaporated to give the title compound in nearly quantitative yield without further purification.

Example 157

This Example illustrates the conversion of 1-{3-[4-(tert-butyl-dimethyl-silanyloxy)-phenyl]-4-phenyl-isoxazol -yl}-cyclopropanecarboxylic acid methyl ester to (1-{3-[4-(tert-butyl-dimethyl-silanyloxy)-phenyl]-4-phenyl-isoxazol-5-yl}-cyclopropyl)-morpholin-4-yl-methanone (i.e. A' of Structure 6, Scheme I is transformed from an ester into amide).

Example 157 A

A solution of morpholine (6.36 g) is purged with $N_2$ and cooled to an internal temperature of 0° C. Methylmagnesium bromide (1.4 M in 75% toluene in THF, 46.9 mL) is added. After 15 minutes, a solution of 1-{3-[4-(tert-butyl-dimethyl-silanyloxy)-phenyl]-4-phenyl-isoxazol-5-yl}-cyclopropanecarboxylic acid methyl ester, which may be produced as described in either Example 143 or 144, (10.94 g) in 50 mL THF is added. After stirring 1 hour, the reaction is quenched with sat. NH$_4$Cl. The reaction mixture is extracted with ethyl acetate. The combined organic extracts are washed with water and brine, dried over Na$_2$SO$_4$, and evaporated to give the title compound as an orange gum.

Example 157 B

A solution of morpholine (1.16 g) is purged with N$_2$ and cooled to an internal temperature of 0° C. Ethylmagnesium bromide (1.0 M in MTBE, 12.0 mL) is added over 2 minutes. After 15 minutes, a solution of 1-{3-[4-(tert-butyl-dimethyl-silanyloxy)-phenyl]-4-phenyl-isoxazol-5-yl}-cyclopropan-ecarboxylic acid methyl ester, which may be produced as in either Example 143 or 144, (2.0 g) in 10 mL THF is added over 5 minutes. After stirring 1.5 hours at 0° C., the reaction is deemed complete by LC/MS and used directly without isolation.

Example 158

This Example illustrates the conversion of 1-{3-[4-(tert-butyl-dimethyl-silanyloxy)-phenyl]-4-phenyl-isoxazol-5-yl}-cyclopropanecarboxylic acid methyl ester to 1-{3-[4-(tert-butyl-dimethyl-silanyloxy)-phenyl]-4-phenyl-isoxazol-5-yl}-cyclopropanecarboxylic acid methoxy-methyl-amide (i.e. A' of Structure 6, Scheme I is transformed from an ester into amide).

Example 158A

To a slurry of the 1-{3-[4-(tert-butyl-dimethyl-silanyloxy)-phenyl]-4-phenyl-isoxazol-5-yl}-cyclopropanecarboxylic acid methyl ester, which may be produced a in either Example 143 or 144, (0.1 g) and N,O-dimethylhydroxylamine hydrochloride (43 mg) in tetrahydrofuran (1 mL) at room temperature is added a solution of ethyl magnesium bromide (0.9 mL of a 1 M solution in tetrahydrofuran). The reaction mixture is heated at 40° C. overnight. LCMS shows conversion to the title compound.

Example 158B

The reaction vessel is purged with N$_2$ before charging with hydroxylamine hydrochloride (43.4 g) and 435 mL THF. The suspension is cooled to −24.9° C. before adding n-butyl-lithium (1.6 M in hexanes, 356 mL) over 50 minutes. The reaction mixture is stirred for 35 minutes before adding a solution of 1-{3-[4-(tert-butyl-dimethyl-silanyloxy)-phenyl]-4-phenyl-isoxazol-5-yl}-cyclopropanecarboxylic acid methyl ester, which may be produced as in either Example 143 or 144, (100 g) in 136 g THF over about a minute. Quench reaction after 50 minutes with 250 mL of sat. NH$_4$Cl and 250 mL water. After 10 minutes of stirring, the mixture is transferred to a separatory funnel with 1 L MTBE. Separate layers, wash organic phase with 2×250 mL water, and dry over MgSO$_4$. Filter through Celite and concentrate to give the title compound as oil.

Example 159

This Example illustrates the conversion of 1-{3-[4-(tert-butyl-dimethyl-silanyloxy)-phenyl]-4-phenyl-isoxazol-5-yl}-cyclopropanecarboxylic acid ethyl ester to 1-{3-[4-(tert-butyl-dimethyl-silanyloxy)-phenyl]-4-phenyl-isoxazol-5-yl}-cyclopropanecarboxylic acid methoxy-methyl-amide (i.e. A' of Structure 6, Scheme I is transformed from an ester into amide).

To a cold (−60° C.) mixture of N,O-dimethylhydroxylamine hydrochloride (0.93 g, 9.5 mmoles) in 5 mL of THF is added 7.60 mL of a 2.5 M solution of n-butyllithium (1.2 g, 20 mmoles) in hexanes. The reaction mixture becomes one phase. The reaction mixture is stirred for 30 minutes, followed by addition of a solution of 1-{3-[4-(tert-butyl-dimethyl-silanyloxy)-phenyl]-4-phenyl-isoxazol-5-yl}-cyclopropanecarboxylic acid ethyl ester, which may be produced as in Example 145, (0.88 g, 1.9 mmoles) in 5 mL of THF. The reaction mixture is stirred at −60° C. for 2 hrs and then at room temperature for 18 hrs. The reaction mixture is cooled to −78° C. and then quenched with saturated ammonium chloride (25 mL.) The reaction mixture is warmed to room temperature and then diluted with 250 mL of ethyl acetate. The aqueous layer is removed and then the organic layer is washed with additional ammonium chloride, followed with brine (25 mL). The organic layer is separated, dried (sodium sulfate), filtered, and then the filtrate is evaporated to afford an oil, which is flash chromatographed (silica gel, 20% ethyl acetate in hexane) to give 214 mg of a colorless tacky solid as a mixture. No desired product is isolated.

Example 160

This Example illustrates the conversion of 1-[3-(4-methoxy-phenyl)-4-phenyl-isoxazol-5-yl]-cyclopropanecarboxylic acid methyl ester to {1-[3-(4-methoxy-phenyl)-4-phenyl-isoxazol-5-yl]-cyclopropyl}-methanol (i.e. A' of Structure 6, Scheme I is transformed from an ester into alcohol).

Example 160A

The reaction is run in two batches of 25 g of starting material each. A solution of 1-[3-(4-methoxy-phenyl)-4-phenyl-isoxazol-5-yl]-cyclopropanecarboxylic acid methyl ester, which may be produced as in Example 147B, (25 g) in 200 mL dichloromethane under N$_2$ atmosphere is cooled to −78° C. (dry ice/acetone.) Diisobutyl aluminum hydride (150 mL, 1.0 M/hexanes) is added and allowed to gradually warm to room temperature overnight stirring for 18 hours. The reaction is cooled to 0° C. and quenched carefully with 55 mL of methanol. The reaction is stirred for approximately 30 minutes resulting in the reaction mixture becoming cloudy. The reaction is diluted with saturated sodium bicarbonate. To the reaction mixture is added sodium potassium tartrate, water, and more dichloromethane. The layers are separated and the organic layer is dried over anhydrous magnesium sulfate, filtered, and concentrated. The two batches are combined. The resulting pale yellow solid is precipitated from ethanol-hexane. The filtrate is concentrated and purified by column chromatography (0-25% ethyl acetate/hexanes) to give an additional title compound.

Example 160B

To a stirring solution comprised of 1-[3-(4-methoxy-phenyl)-4-phenyl-isoxazol-5-yl]-cyclopropanecarboxylic acid methyl ester, which may be produced as in Example 147B, (17.5 g) in tetrahydrofuran (300 mL) cooled to −10° C. with a methanol-ice bath is added a solution comprised of 1.0 M lithium aluminum hydride in tetrahydrofuran (100 mL) over five minutes. The clear solution turned to a clear pale yellow. The reaction mixture is stirred cold for 30 minutes. The methanol-ice bath is cooled to −25° C. with the addition of some dry ice, and the stirring reaction mixture is slowly quenched by the sequential addition of saturated aqueous ammonium chloride (50 mL, after which time the methanolice-dry ice bath is replaced with an ice-water bath to melt the freezing reaction mixture), water (50 mL), and ethyl acetate (100 mL.) The stirring mixture is allowed to warm to room temperature overnight. The reaction mixture is diluted with ethyl acetate (100 mL) and is vacuum filtered to remove the aluminum salts. The layers are separated and the aqueous phase is extracted with a fresh portion of ethyl acetate. The organic phases are combined and are washed with brine solution, are dried over anhydrous magnesium sulfate, and are concentrated under reduced pressure to afford viscous yellow oil. The product is reconstituted in chloroform and is reconcentrated under reduced pressure and subjected to the house high vacuum to afford the title compound MS (APCI+) 322 (MH+.)

Alternatively, the internal temperature of the reaction mixture is monitored in the lithium aluminum hydride addition stage and is maintained below −1.5° C. In addition, anhydrous sodium sulfate is used as a drying agent instead of anhydrous magnesium sulfate.

Example 161

This Example illustrates the conversion of 1-[3-(4-methoxy-phenyl)-4-phenyl-isoxazol-5-yl]-cyclopropanecarboxylic acid ethyl ester to {1-[3-(4-methoxy-phenyl)-4-phenyl-isoxazol-5-yl]-cyclopropyl}-methanol (i.e. A' of Structure 6, Scheme I is transformed from an ester into alcohol).

A solution of 1-[3-(4-methoxy-phenyl)-4-phenyl-isoxazol-5-yl]-cyclopropanecarboxylic acid ethyl ester, which may be produced as in Example 147C (20.0 g) in 300 mL THF is purged with $N_2$ and cooled to −5° C. Lithium aluminum hydride (1.0 M in THF, 110.1 mL) is added over 15 minutes. After 1 hour, sat. $NH_4Cl$ (total 50 mL) is carefully added followed by 50 mL water and 100 mL ethyl acetate. Allow to stir at room temperature overnight at which time the solid is filtered and washed with 100 mL water and 100 mL of ethyl acetate. The layers are separated and the organic phase is washed with brine and dried over $Na_2SO_4$. The solution is concentrated and purified by flash silica gel chromatography (300 g Redi-Sep column, 0 to 75% ethyl acetate in hexanes) to provide the solid title compound after trituration with hexanes.

B) Conversion of Cyclopropyl Amide Moiety (A') into a Ketone

Example 162

This Example illustrates conversion of 1-{3-[4-(tert-butyl-dimethyl-silanyloxy)-phenyl]-4-phenyl-isoxazol-5-yl}-cyclopropanecarboxylic acid methoxy-methyl-amide into 1-(1-{3-[4-(tert-Butyl-dimethyl-silanyloxy)-phenyl]-4-phenyl-isoxazol-5-yl}-cyclopropyl)-ethanone (i.e. A' of Structure 6, Scheme I is transformed from an amide into a ketone).

A solution of 1-{3-[4-(tert-butyl-dimethyl-silanyloxy)-phenyl]-4-phenyl-isoxazol-5-yl}-cyclopropanecarboxylic acid methoxy-methyl-amide, which may be produced as in Example 159, (100.75 g) in tetrahydrofuran (800 mL) is cooled to 0° C. and a solution of methyl magnesium bromide (448 mL of a 1.4 M solution in toluene/tetrahydrofuran) is added while the temperature is maintained below 10° C., the addition took 55 min to complete. The reaction mixture is stirred at room temperature overnight. The next day the reaction mixture is cooled to 0° C. and saturated ammonium chloride is added slowly until bubbling ceased (approx 60 mL), a sticky white solid forms, water (approximately 20 mL) is added and further white solid forms. The solution is decanted away from the sticky solid, the solid is washed well with ethyl acetate. The organics are combined, dried, and concentrated to give a white solid. The solid is purified by flash chromatography on a Biotage Horizon System using a 0 to 25% ethyl acetate/hexane gradient to afford the title compound.

Alternatively, a solution of 3 M methyl magnesium bromide in ether is used instead of the 1.4 M solution of methyl magnesium bromide in toluene/tetrahydrofuran.

Example 163

This Example illustrates conversion of (1-{3-[4-(tert-butyl-dimethyl-silanyloxy)-phenyl]-4-phenyl-isoxazol-5-yl}-cyclopropyl)-morpholin-4-yl-methanone into 1-(1-{3-[4-(tert-butyl-dimethyl-silanyloxy)-phenyl]-4-phenyl-isoxazol-5-yl}-cyclopropyl)-ethanone (i.e. A' of Structure 6, Scheme I is transformed from an amide into a ketone).

Example 163A

To a cold (−10° C.) solution of (1-{3-[4-(tert-butyl-dimethyl-silanyloxy)-phenyl]-4-phenyl-isoxazol-5-yl}-cyclopropyl)-morpholin-4-yl-methanone, which may be produced as in Example 157 (21 g, 42 mmoles) in 200 mL of anhydrous THF is added 200 mL of a 1.40 M solution of methylmagnesium bromide (33 g, 280 mmoles) in 75:25 toluene:THF over 30 minutes. The reaction mixture is allowed to warm up on its own and then stir for 18 hrs. The reaction mixture is quenched with saturated ammonium chloride (100 mL). The reaction mixture is diluted with ethyl acetate (500 mL) and then the aqueous layer is removed. The organic layer is washed with another portion of saturated ammonium chloride (100 mL), followed with brine (100 ml). The organic layer is separated, dried (sodium sulfate), filtered, and then the filtrate is evaporated to give an oil. Purification by column chromatography (silica gel, 70-230 mesh; 20% ethyl acetate in hexane) provides, after drying, a light green oil, which is solidified to a white solid upon standing at room temperature. Impure fractions are combined and rechromatographed as above to give additional product as a white solid.

Alternatively the reaction is either heated at reflux for three days with 6.0 molar equivalents of methylmagnesium bromide (Grignard reagent), at room temperature with 8.0 molar equivalents of Grignard reagent, or at 0° C. with 3.0 molar equivalents of Grignard reagent. The title compound is purified by either flash or gravity chromatography on silica gel using either 5% ethyl acetate in hexane or 5-15% ethyl acetate in hexane as eluents. Also, the title compound is purified by triturating the reaction mixture with a mixture of ether and hexane, filtering off an insoluble impurity, followed by flash chromatography on silica gel using 1-15% ethyl acetate in hexane as eluent. Furthermore, the reaction mixture may be quenched with 1 M HCl and then washed with saturated sodium bicarbonate. The organic layer is removed, dried (sodium sulfate), filtered, and then the filtrate is evaporated to provide a residue, which is purified by flash chromatography on silica gel using 0-100% ethyl acetate in hexane as eluent.

Example 163B

To a cold (−10° C.) solution of (1-{3-[4-(tert-butyl-dimethyl-silanyloxy)-phenyl]-4-phenyl-isoxazol-5yl}-cyclopropyl)-morpholin-4-yl-methanone, which may be produced as in Example 157, (0.50 g, 0.99 mmoles) in 3 mL of anhydrous THF is added a 3.8 mL of a 1.60 molar solution of methyllithium (0.13 g, 6.0 mmoles) in diethyl ether. The reaction mixture is stirred at −10° C. for 2 hrs and then at room temperature for 18 hrs. The reaction mixture is cooled to 10° C. and then quenched with saturated ammonium chloride (30 mL.) The reaction mixture is diluted with ethyl acetate (250 mL) and then the aqueous layer is removed. A precipitate forms in the organic layer and is filtered to give 159 mg of an unknown yellow solid. The organic filtrate is washed with another portion of saturated ammonium chloride (50 mL), followed with brine (100 ml). The organic layer is separated, dried (sodium sulfate), filtered, and then the filtrate is removed to give a crude dark tan oil as the title compound.

Example 164

This Example illustrates conversion of {1-[3-(4-hydroxy-phenyl)-4-phenyl-isoxazol-5-yl]-cyclopropyl}-morpholin-4yl-methanone into 1-{1-[3-(4-hydroxy-phenyl)-4-phenyl-isoxazol-5-yl]-cyclopropyl}-ethanone (i.e. A' of Structure 6, Scheme I is transformed from an amide into a ketone).

To a cold (0° C.) solution of {1-[3-(4-hydroxy-phenyl)-4-phenyl-isoxazol-5-yl]-cyclopropyl}-morpholin-4yl-methanone, which may be produced as in either Example 154 or 186, (0.50 g, 1.3 mmoles) in 5 mL of anhydrous THF, is added 2.6 mL of ethyl magnesium bromide (0.32 g, 2.7 mmoles, 1.0 M in 70:30 Toluene-THF). The reaction mixture is stirred at 0° C. for 2 hrs and then at room temperature for 18 hrs. Saturated ammonium chloride (50 mL) is added and then the reaction mixture is diluted with 200 mL of ethyl acetate. The aqueous layer is removed and then the organic layer is washed with additional ammonium chloride (50 mL), followed with brine (50 mL). The organic layer is dried (sodium sulfate), filtered, and then the filtrate is evaporated to provide an oil, which is flash chromatographed (silica gel, 20% ethyl acetate in hexane) to afford, after drying, a white foamy solid as the title compound.

Alternatively, the preceding procedure employs 4.3 molar equivalents of methyllithium or is heated at reflux for 3 hrs.

Example 165

This Example illustrates conversion of 1-{3-[4-(tert-butyl-dimethyl-silanyloxy)-phenyl]-4-phenyl-isoxazol-5-yl}-cyclopropanecarboxylic acid methoxy-methyl-amide into 1-(1-{3-[4-(tert-butyl-dimethyl-silanyloxy)-phenyl]-4-phenyl-isoxazol-5-yl}-cyclopropyl)-propan-1-one (i.e. A' of Structure 6, Scheme I is transformed from an amide into a ketone).

A solution of 1-{3-[4-(tert-butyl-dimethyl-silanyloxy)-phenyl]-4-phenyl-isoxazol-5-yl}-cyclopropanecarboxylic acid methoxy-methyl-amide, which may be produced as in Example 159, (53 g) in tetrahydrofuran (700 mL) is cooled to 0° C. and then a solution of ethyl magnesium bromide (111 mL of a 3 M solution in diethyl ether) is added while the temperature is maintained below 5° C., the addition took 25 min to complete. The reaction mixture is allowed to warm to room temperature overnight. The next day the reaction mixture is cooled to 0° C. and quenched by addition of saturated aqueous ammonium chloride. The organic layer is separated and the aqueous is re-extracted with further ethyl acetate. The combined extracts are dried and concentrated to give a yellow oil that is solidified to give a cream colored solid by concentration from ether/hexane and then pentane. Quick filtration chromatography through a plug of silica gave the title compound as a white solid.

Example 166

This Example illustrates conversion of (1-{3-[4-(tert-butyl-dimethyl-silanyloxy)-phenyl]-4-phenyl-isoxazol-5-yl}-cyclopropyl)-morpholin-4-yl-methanone into 1-(1-{3-[4-(tert-butyl-dimethyl-silanyloxy)-phenyl]-4-phenyl-isoxazol-5-yl}-cyclopropyl)-propan-1-one (i.e. A' of Structure 6, Scheme I is transformed from an amide into a ketone).

Example 166A

To a solution of (1-{3-[4-(tert-butyl-dimethyl-silanyloxy)-phenyl]-4-phenyl-isoxazol-5-yl}-cyclopropyl)-4-yl-methanone, which may be produced as in Example 157, (18.0 g) in 25 mL THF at −10° C. under a stream of nitrogen is added ethylmagnesium bromide (1.0 M in THF, 259 mL.) The reaction mixture is allowed to warm to ambient temperature and stir for 12 days. The reaction mixture is cooled in an ice bath and quenched with sat. NH$_4$Cl. The layers are separated and the organic phase is dried over Na$_2$SO$_4$. Evaporation and flash silica gel chromatography (400 g Analogix cartridge, 100% hexanes to 30% ethyl acetate in hexanes over 1800 mL) provides the title compound as a yellow oil.

Alternatively, lithium chloride (1 molar equivalent) is added to the reaction mixture.

Example 166B

A solution of (1-{3-[4-(tert-butyl-dimethyl-silanyloxy)-phenyl]-4-phenyl-isoxazol-5-yl}-cyclopropyl)-morpholin-4-yl-methanone, which may be produced as in Example 157, (400 mg) in 10 mL THF is purged with N$_2$ and cooled to −78° C. Ethyllithium (0.5 M in 90:10 benzene:cyclohexane, 2.38 mL) is added. After 6 hours at −78° C., the reaction is allowed to warm to room temperature overnight.

Example 167

This Example illustrates conversion of 1-[3-(4-benzyloxy-phenyl)-4-phenyl-isoxazol-5-yl]-cyclopropyl)-morpholin-4-yl-methanone into 1-{1-[3-(4-benzyloxy-phenyl)-4-phenyl-isoxazol-5-yl]-cyclopropyl}-ethanone (i.e. A' of Structure 6, Scheme I is transformed from an amide into a ketone).

Example 167A

A 500 mL 3-neck round bottom flask is equipped with a reflux condenser and an addition funnel. To a solution of {1-[3-(4-benzyloxy-phenyl)-4-phenyl-isoxazol-5-yl]-cyclopropyl}-morpholin-4-yl-methanone, which may be produced as in Example 150, (19.7 g) in THF (205 mL) at room temperature is added methyl magnesium bromide (55 mL, 3.0 M solution in diethyl ether) slowly via addition funnel. The resulting orange solution is warmed to 40° C. over 18 hours. The reaction mixture is cooled to 0° C. and saturated aqueous NH$_4$Cl (100 mL) is slowly added via addition funnel. (Note: observed gas evolution and temperature rise to 22° C.) The resulting yellow suspension is allowed to stir over 2 hours. The layers are separated and the aqueous layer extracted with additional ethyl acetate. The combined organic layers are washed with brine, dried (MgSO$_4$), filtered through a pad of silica and concentrated under reduced pressure. The title compound is isolated as a light yellow foam without further purification; MS (APCI+) 410 m/z (MH+.)

Example 167B

A solution of {1-[3-(4-benzyloxy-phenyl)-4-phenyl-isoxazol-5-yl]-cyclopropyl}-morpholin-4-yl-methanone, which may be produced as in Example 150, (105 mg) in THF (1.2 mL) is cooled to −78° C. and treated with methyllithium (0.59 mL, 1.6 M in diethyl ether.) Allow reaction mixture to warm to room temperature over 18 hours. The reaction mixture is cooled to 0° C. and quenched with saturated aqueous NH$_4$Cl. The aqueous layer is extracted with ethyl acetate (3×) and combined organics washed with brine. The organic layer is dried (MgSO$_4$), filtered and concentrated. The resulting residue is purified by flash chromatography (0% to 40% ethyl acetate-hexanes.) The title compound is isolated as a light yellow oil; MS (APCI+) m/z 410 (MH+.)

Example 168

This Example illustrates conversion of 1-[3-(4-benzyloxy-phenyl)-4-phenyl-isoxazol-5-yl]-cyclopropanecarboxylic acid methoxy-methyl-amide into 1-{1-[3-(4-benzyloxy-phenyl)-4-phenyl-isoxazol-5-yl]-cyclopropyl}-ethanone (i.e. A' of Structure 6, Scheme I is transformed from an amide into a ketone).

1-[3-(4-Benzyloxy-phenyl)-4-phenyl-isoxazol-5-yl]-cyclopropanecarboxylic acid methoxy-methyl-amide, which may be produced as in Example 151 dissolved in THF is stirred and 11.6 mL of 3M MeMgBr ("methyl magnesium bromide") (in Et$_2$O) is added over 10 minutes. The clear, light-orange solution is stirred for 30 minutes. Add 1.0 mL of sat. aq. NH$_4$Cl dropwise over 10 minutes. Add 4 mL of NH$_4$Cl+5 mL of water. Stir vigorously. Dilute with 5.0 mL of water and 5.0 mL of NH$_4$Cl. Transfer mixture to a separatory funnel with 100 mL of methyl tert-butyl ether. Add 20 mL of water and mix well. Separate layers. Wash organic layer with 50 mL of water. Dry over MgSO4, filter through Celite, concentrate at the Rotavap. Thick, yellowish, clear oil. Put under high vacuum for one hour. Remove from vacuum. Let stand overnight. Yellowish, waxy solids.

Alternatively, 3.0 M solution of methyl magnesium bromide in diethyl ether can be replaced with a 3.0 M solution of methyl magnesium chloride in THF.

C) Conversion of Cyclopropyl Alcohol Moiety (A') into a Ketone or Aldehyde

Example 169

This Example illustrates conversion of 1-(1-{3-[4-(tert-butyl-dimethyl-silanyloxy)-phenyl]-4-phenyl-isoxazol-5-yl}-cyclopropyl)-ethanol into 1-(1-{3-[4-(tert-butyl-dimethyl-silanyloxy)-phenyl]-4-phenyl-isoxazol-5-yl}-cyclopropyl)-ethanone (i.e. A' of Structure 6, Scheme I is transformed from an alcohol into a ketone).

A solution of oxalyl chloride (0.24 mL) in CH$_2$Cl$_2$ (10 mL) is cooled to −78° C. DMSO (0.39 mL) is added slowly and the resulting mixture kept at −78° C. over 15 minutes. A solution of 1-(1-{3-[4-(tert-butyl-dimethyl-silanyloxy)-phenyl]-4-phenyl-isoxazol-5-yl}-cyclopropyl)-ethanol, which may be produced as in Example 178 (990 mg) in CH$_2$Cl$_2$ (12 mL) is then added. After 15 minutes, triethylamine (1.58 mL) is added. The cold bath is removed and the solution warmed to ambient temperature over 2 hours. Brine is added and the layers separated. The aqueous layer is further extracted with CH$_2$Cl$_2$. The combined organics are dried (MgSO$_4$), filtered, and concentrated. The resulting colorless residue is purified by flash chromatography (0% to 40% ethyl acetate-hexanes) and affords the title compound as a colorless tacky oil; MS (APCI+) m/z 434 (MH+.)

Example 170

This Example illustrates conversion of {1-[3-(4-methoxy-phenyl)-4-phenyl-isoxazol-5-yl]-cyclopropyl}-methanol into 1-[3-(4-methoxy-phenyl)-4-phenyl-isoxazol-5-yl]-cyclopropanecarbaldehyde (i.e. A' of Structure 6, Scheme I is transformed from an alcohol into an aldehyde).

Example 170A

To a stirring solution comprised of oxalyl chloride (15.5 mL) in dichloromethane (320 mL) at −78° C. under a stream of argon is added dropwise a solution comprised of dimethylsulfoxide (25 mL) in dichloromethane (70 mL) over 1 hour 47 minutes in an oven-dried 1 L round bottom flask equipped with a magnetic stir bar and a 500 mL addition funnel. The reaction mixture is stirred at −78° C. for 30 minutes. A clear yellow solution comprised of the substrate, {1-[3-(4-methoxy-phenyl)-4-phenyl-isoxazol-5-yl]-cyclopropyl}-methanol, which may be produced as in Example 160, (50.07 g) in dichloromethane (390 mL) is added dropwise from the addition funnel over 50 minutes. The reaction mixture is stirred at −78° C. for two hours, and triethylamine (103 mL) is added dropwise over ten minutes. The stirring reaction mixture under an argon stream is allowed to warm to room temperature overnight. The reaction mixture is treated with water (250 mL) and the layers are separated. The aqueous phase is extracted with dichloromethane (250 mL) and the combined organic phases are dried over anhydrous magnesium sulfate and are concentrated under reduced pressure to afford an orange-yellow semisolid (60 g.) The crude product is precipitated from ethanol-hexanes. The mother liquor is decanted from the resulting solid. The solids are washed with hexanes (400 mL) following collection by filtration. The solids are dried in a vacuum oven at ambient temperature for about an hour to afford the title compound; ($^1$H NMR (400 MHz, DMSO-d6) δ61.41 (7 H, d, J=3.3 Hz), 1.42 (2 H, s), 1.59-1.66 (8 H, m), 2.48 (11 H, dt, J=3.7, 1.9 Hz), 3.30 (19 H, s), 3.73 (13 H, s), 6.87-6.94 (8 H, m), 7.13-7.20 (8 H, m), 7.22-7.29 (8 H, m), 7.34-7.38 (9 H, m), 7.38 (3 H, s), 8.82 (4 H, s.)

Isolation of Second Crop of Title Compound:

The mother liquor decantate and the hexanes wash are combined and concentrated under reduced pressure to an orange oil that is dissolved in dichloromethane (20 mL) and purified by flash silica gel chromatography. Application of the dichloromethane solution of the crude oil to and elution through a 330 g Analogix flash silica cartridge with a gradient (100% hexanes to 35% ethyl acetate over 2001 mL, then to 60% ethyl acetate over another 2001 mL, then to 80% ethyl acetate over 501 mL with continued elution with 80% ethyl acetate for another 501 mL) affords separation of the desired material from major impurities (by TLC.) The fractions containing desired material are combined and concentrated under reduced pressure to an oil that is precipitated from ethanol-hexanes to afford a solid.

Isolation of Third Crop of Title Compound:

A third crop of title compound is obtained by vacuum filtration of the mother liquor left over from the isolation of the second crop.

Example 170B

To a suspension of 1,1,1-tris(acetyloxy)-1,1-dihydro-1,2-benziodoxol-3-(1H)-one (44.75 g) in 500 mL CH$_2$Cl$_2$ is added {1-[3-(4-methoxy-phenyl)-4-phenyl-isoxazol-5-yl]-cyclopropyl}-methanol, which may be produced as in Example 160, (21.2 g.) After stirring at room temperature for 18 hours, a 5% solution of NaHCO$_3$ is added. Additional solid NaHCO$_3$ is added to pH 9. The mixture is extracted with CH$_2$Cl$_2$. The combined extracts are washed with sat. Na$_2$SO$_3$, water, and brine, dried over Na$_2$SO$_4$, and evaporated to give the title compound as an off-white solid.

Purification

Crude 1-[3-(4-methoxy-phenyl)-4-phenyl-isoxazol-5-yl]-cyclopropanecarbaldehyde which may be produced as in Example 170A or B (approx. 47 g) is precipitated from ethanol-hexanes. The mother liquor is decanted and the solid is washed with 400 mL hexanes. The solid is dried under vacuum at ambient temperature to constant weight. Collect the title compound as a light-yellow solid.

Example 171

This Example illustrates conversion of 4-[5-(1-hydroxymethyl-cyclopropyl)-4-phenyl-isoxazol-3-yl]-phenol into 1-[3-(4-Hydroxy-phenyl)-4-phenyl-isoxazol-5-yl]-cyclopropanecarbaldehyde (i.e. A' of Structure 6, Scheme I is transformed from an alcohol into an aldehyde).

To a suspension of 1,1,1-tris(acetyloxy)-1,1-dihydro-1,2-benziodoxol-3-(1H)-one (33.89 g, 79.91 mmol) in 400 mL CH$_2$Cl$_2$ under a nitrogen atmosphere at room temperature is added 4-[5-(1-hydroxymethyl-cyclopropyl)-4-phenyl-isoxazol-3-yl]-phenol, which may be produced as in Examples 184, 185, or 206 (15.4 g, 49.94 mmol). After stirring at room temperature for 5 hours, an additional 7 g (16.5 mmol) is added, and the reaction is stirred overnight. About 200 mL of a 5% solution of NaHCO$_3$ is added, and the mixture is extracted with CH$_2$Cl$_2$. The combined extracts are washed with sat. Na$_2$SO$_3$, water, and brine, dried over Na$_2$SO$_4$, evaporated, and flashed (40 g silica gel column eluting with a gradient of 100% hexanes to 100% ethyl acetate) to give the title compound.

Example 172

This Example illustrates conversion of (1-{3-[4-(tert-butyl-dimethyl-silanyloxy)-phenyl]-4-phenyl-isoxazol-5-yl}-cyclopropyl)-methanol into 1-{3-[4-(tert-butyl-dimethyl-silanyloxy)-phenyl]-4-phenyl-isoxazol-5-yl}-cyclopropanecarbaldehyde (i.e. A' of Structure 6, Scheme I is transformed from an alcohol into an aldehyde).

Example 172A

In a 3 neck round bottom flask is added oxalyl chloride in 115 mL CH$_2$Cl$_2$. Cool to −78° C. Add DMSO in 25 mL CH$_2$Cl$_2$ dropwise via an addition funnel over 15 minutes. Stir at −78° C. for 30 minutes. Add a solution (cloudy) of (1-{3-[4-(tert-butyl-dimethyl-silanyloxy)-phenyl]-4-phenyl-isoxazol-5-yl}-cyclopropyl)-methanol, which may be produced as in Example 155, in 140 mL CH$_2$Cl$_2$ via an addition funnel over 50 minutes. Stir ~20 minutes and add triethylamine over 10 min. Allow to gradually warm to room temperature overnight. TLC indicates complete consumption of starting material. (25% EtOAc/hex). Dilute cloudy reaction with water. Separate layers. Extract again into CH$_2$Cl$_2$. Wash combined organic extracts (cloudy) with brine which clear up organic layer. Dry over MgSO$_4$. Filter and concentrate to an orange oil. Add hexanes. Stripping to dryness results in an oil. Run a short column to remove orange color. (Biotage Horizon system, 120 g Analogix column, equilibrated with 100% hexanes, eluted with 15% EtOAc/hex.)

Fractions 1-3 contain a minor nonpolar impurity. Combine and concentrate to a pale yellow oil that is diluted with hexanes. A white solid forms. Collect by filtration to yield the title compound.

Product is soluble in hexanes. Concentrate filtrate to dryness and precipitate from hexanes. Collect by filtration rinsing with minimal, cold hexanes to afford another batch of title compound.

Fractions 4-19 are combined and concentrated to an oil that is diluted with hexanes and once the white solid started to form, it is put in the fridge. Collected white solid, rinsing with minimal, cold hexanes to afford another batch of the title compound.

Combine all filtrates, rinses and concentrate to dryness. Triturate with minimal, cold hexanes to afford another batch of the title compound upon filtration.

Concentrate filtrate to obtain a sticky yellow solid.

Example 172B

To a cold (0° C.) solution of (1-{3-[4-(tert-butyl-dimethyl-silanyloxy)-phenyl]-4-phenyl-isoxazol-5-yl}-cyclopropyl)-methanol, which may be produced as in Example 155, (0.50 g, 1.2 mmoles) in 20 mL of anhydrous dichloromethane is added 200 mg of crushed molecular sieves (4 Angstroms), 4-methylmorpholine-N-oxide (0.18 g, 1.5 mmoles), followed with tetrapropylammonium perruthenate (TPAP) (0.07 g, 0.20 mmoles). The reaction mixture is stirred at 0° C. for 4 hrs after which time starting material is completely consumed in the reaction as indicated by TLC. The reaction mixture is evaporated onto 4 g of silica gel and then flash chromatographed (silica gel, 20% ethyl acetate in hexane) to provide a colorless oil as the title compound. The oil solidifies to a white solid upon standing at room temperature for 3 days.

Alternatively, the reaction is run either at 0-10° C. for 4 hrs, at 0° C. for 1 or 2 hrs or at 24° C. for 2 hr. The product is alternatively purified by filtering the reaction mixture through a bed of silica gel, followed by flash chromatography on silica gel with 0-25% ethyl acetate in hexane as eluent. Also, the product may be purified by filtering the reaction mixture through a pad of silica gel, followed by flash chromatography on silica gel with dichloromethane as eluent.

Example 172C

Based on: Krishnaveni, N. S.; Surendra, K.; Rao, K. R. Adv. Synth. Catal. 2004, 346, 346-350

To a solution comprised of β-cyclodextrin (2.5 g) in water (30 mL) at 60° C. (over steam bath) under air is added a solution comprised of (1-{3-[4-(tert-butyl-dimethyl-silanyloxy)-phenyl]-4-phenyl-isoxazol-5-yl}-cyclopropyl)-methanol, which may be produced as in Example 155, (0.9 g) in methanol/acetone 1:1 v/v (2 mL.) The suspension is cooled to 30° C. and N-bromosuccinimide (0.4 g) is added. Additional methanol is added and the mixture remains a suspension. The reaction mixture is stirred for one hour at room temperature and is extracted with ethyl acetate.

Example 172D

A solution of (1-{3-[4-(tert-butyl-dimethyl-silanyloxy)-phenyl]-4-phenyl-isoxazol-5-yl}-cyclopropyl)-methanol (0.5 g), which may be produced as in Example 155, in 5 mL $CH_2Cl_2$ is added via syringe to a suspension of Dess-Martin reagent (0.8 g) in 5 mL $CH_2Cl_2$ under $N_2$ atmosphere. Reaction mixture slowly becomes a solution. Stir at room temperature for 5 hours, 45 minutes. TLC indicates starting material is consumed (25% EtOAC/hex). Add saturated $NaHCO_3$. Stir ~5 minutes and separate layers. Wash organic layer with sat'd $Na_2SO_3$ and brine. Dry over $MgSO_4$.

Concentrate and column (Biotage Horizon system, 40 g Redi-Sep column, equilibrate with 100% hexanes, elute with 20% EtOAc/hex).

Isolate an oil that is chased 2× with $CHCl_3$.

Afford the title compound as a pale yellow oil.

Example 172

Purification

A black solution of crude 1-{3-[4-(tert-butyl-dimethyl-silanyloxy)-phenyl]-4-phenyl-isoxazol-5-yl}-cyclopropanecarbaldehyde, which may be produced by any method above, is concentrated in vacuo to a dark oil. This oil is loaded onto a 120-g RediSep flash silica cartridge. The exit connector is broken off during loading, thus the column could not be run on the Biotage fraction collector. The column is flushed with ethyl acetate and the eluent is received in a large beaker. Most of the dark color is removed from the product with this silica filtration. The collected eluent is concentrated in vacuo to afford 3.0 g of a tan-colored oil. This oil is purified by flash silica chromatography (Biotage Horizon Chromatography station.) The oil, dissolved in dichloromethane (40 mL), is loaded onto a 120-g RediSep flash silica cartridge. The column is eluted with a gradient (0-5% ethyl acetate in hexanes over 1251 mL, followed by a 5-25% linear increase in ethyl acetate over an additional 1251 mL) to give a set of fractions containing a single spot (TLC; solvent system=4:1 v/v hexanes-ethyl acetate, Rf=0.46.) The fractions are combined and concentrated in vacuo to afford a clear colorless viscous oil. The product is redissolved in chloroform to chase any residual ethyl acetate. Concentration in vacuo affords the title compound clear colorless viscous residue.

Example 173

This Example illustrates conversion of 1-{1-[3-(4-methoxy-phenyl]-4-phenyl-isoxazol-5-yl}-cyclopropyl)-methanol into 1-{1-[3-(4-methoxy-phenyl)-4-phenyl-isoxazol-5-yl]-cyclopropyl}-ethanone (i.e. A' of Structure 6, Scheme I is transformed from an alcohol into a ketone).

To a stirring solution comprised of oxalyl chloride (7.5 mL) in dichloromethane (200 mL) at -78° C. under a stream of nitrogen is added dropwise a solution comprised of dimethylsulfoxide (12 mL) in dichloromethane (70 mL) over 1 hour 47 minutes in an oven-dried 1 L round bottom flask equipped with a magnetic stir bar and a 500 mL addition funnel. The reaction mixture is stirred at -78° C. for 45 minutes. A clear yellow solution comprised of 1-{1-[3-(4-methoxy-phenyl]-4-phenyl-isoxazol-5-yl}-cyclopropyl)-methanol, which may be produced as in Example 160 or 161, in dichloromethane (250 mL) is added dropwise from the addition funnel over 90 minutes. The reaction mixture is stirred at -78° C. for two hours, and triethylamine (50 mL) is added dropwise over ten minutes. The stirring reaction mixture under a nitrogen stream is allowed to warm to room temperature overnight. The reaction mixture is treated with water (250 mL.) The resulting biphasic solution is treated with brine solution (100 mL) and the layers are separated. The aqueous phase is extracted with fresh dichloromethane (150 mL) and the combined organic layers are dried over anhydrous magnesium sulfate and are concentrated under reduced pressure. The concentrate (approximately 23 g) is dissolved in hot ethyl acetate (approximately 125 mL.) Hot hexanes are subsequently added slowly until the solution turned cloudy.

The mixture is allowed to cool to room temperature and a solid precipitates from solution. The solid is collected by vacuum filtration. The solid and the filtrate are combined and the solvent is removed under reduced pressure. The concentrate is dissolved in ethyl acetate (approximately 50 mL) and the mixture is brought to reflux. Hot hexanes (approximately 50 mL) are added and some precipitate is observed. Hot ethyl acetate (approximately 50 mL) is added until the cloudiness disappeared; however, some solids remain undissolved. The hot mixture is filtered and the filtrate is concentrated under reduced pressure to obtain a solid. The solid is dried in the vacuum oven overnight to afford the title compound.

Example 174

This Example illustrates conversion of 1-(1-{3-[4-(tert-butyl-dimethyl-silanyloxy)-phenyl]-4-phenyl-isoxazol-5-yl}-cyclopropyl)-propan-1-ol into 1-(1-{3-[4-(tert-butyl-dimethyl-silanyloxy)-phenyl]-4-phenyl-isoxazol-5-yl}-cyclopropyl)-propan-1-one (i.e. A' of Structure 6, Scheme I is transformed from an alcohol into a ketone).

To a cold (10° C.) solution of 1-(1-{3-[4-(tert-butyl-dimethyl-silanyloxy)-phenyl]-4-phenyl-isoxazol-5-yl}-cyclopropyl)-propan-1-ol, which may be produced as in Example 178B, (0.84 g, 1.9 mmoles) in 30 mL of anhydrous dichloromethane is added 0.50 g of crushed molecular sieves (4 Angstroms), 4-methylmorpholine-N-oxide (0.28 g, 2.4 mmoles), followed with tetrapropylammonium perruthenate (TPAP) (0.11 g, 0.31 mmoles.) The reaction mixture is stirred at 10° C. for 30 min and then at room temperature for 4 hrs. The reaction mixture is evaporated to give a black solid. Purification by flash chromatography (silica gel, 20% ethyl acetate in hexane) provides a light-yellow solid as the title compound.

D) Conversion of Cyclopropyl Ester Moiety A into a Ketone

Example 175

This Example illustrates conversion of 1-[3-(4-methoxy-phenyl)-4-phenyl-isoxazol-5-yl]-cyclopropanecarboxylic acid methyl ester into 1-{1-[3-(4-methoxy-phenyl)-4-phenyl-isoxazol-5-yl]-cyclopropyl}-ethanone (i.e. A' of Structure 6, Scheme I is transformed from an ester into a ketone).

To a cold (0° C.) solution of morpholine (0.78 g, 8.9 mmoles) in 15 mL of anhydrous THF is added 5.7 mL of a 1.4 M solution of methylmagnesium bromide (0.96 g, 8.0 mmoles) in 75% toluene in THF. The reaction mixture is stirred at 0° C. for 15 minutes. 1-[3-(4-Methoxy-phenyl)-4-phenyl-isoxazol-5-yl]-cyclopropanecarboxylic acid methyl ester, which may be produced as in Example 160, (1.0 g, 3.0 mmoles) is added (neat) and the reaction mixture is allowed to warm up on its own to room temperature and stir for 18 hrs.

Analysis by TLC shows a single spot suggesting a complete and clean conversion to the amide intermediate. The reaction mixture is cooled (0° C.) and then additional methylmagnesium bromide (13.8 mL, 0.96 g, 19 mmoles) is added. The reaction mixture is stirred at 0° C. for 2 hrs and then at room temperature for 18 hrs. Analysis by TLC showed a single spot suggesting a complete and clean conversion to the methyl ketone. The reaction mixture is quenched with 50 mL of saturated ammonium chloride and then diluted with 250 mL of ethyl acetate. The aqueous layer is removed and then the organic layer is extracted with a fresh portion of saturated ammonium chloride (50 mL). The organic layer is separated, dried, filtered, and then the filtrate is evaporated to provide an oil, which is flash chromatographed (silica gel, 30% ethyl acetate in hexane) to afford the title compound as a white solid.

E) Conversion of Cyclopropyl Aldehyde Moiety (A) into an Alcohol

Example 176

This Example illustrates conversion of 1-{3-[4-(tert-butyl-dimethyl-silanyloxy)-phenyl]-4-phenyl-isoxazol-5-yl}-cyclopropanecarbaldehyde into (1-{3-[4-(tert-butyl-dimethyl-silanyloxy)-phenyl]-4-phenyl-isoxazol-5-yl}-cyclopropyl)-methanol (i.e. A' of Structure 6, Scheme I is transformed from an aldehyde into an alcohol).

To a cold (0° C.) solution of 1-{3-[4-(tert-butyl-dimethyl-silanyloxy)-phenyl]-4-phenyl-isoxazol-5-yl}-cyclopropanecarbaldehyde, which may be produced as in Example 172, (0.73 g, 1.7 mmoles) in 7 mL of anhydrous THF, is added 5 mL of cyclopropylmagnesium bromide (0.36 g, 1.4 mmoles, 0.50 M in THF). The reaction mixture is stirred at 0° C. for 2 hrs and then at room temperature for 18 hrs. Saturated ammonium chloride (25 mL) is added and then the reaction mixture is diluted with 200 mL of ethyl acetate. The aqueous layer is removed and then the organic layer is washed with additional ammonium chloride (50 mL), followed with brine (50 mL). The organic layer is dried (sodium sulfate), filtered, and then the filtrate is evaporated to provide a yellow oil, which is flash chromatographed (silica gel, 20% ethyl acetate in hexane) to give the title compound as a colorless tacky solid.

Example 177

This Example illustrates conversion of 1-[3-(4-methoxy-phenyl)-4-phenyl-isoxazol-5-yl]-cyclopropanecarbaldehyde into (±)-1-{1-[3-(4-methoxy-phenyl)-4-phenyl-isoxazol-5-yl]-cyclopropyl}-ethanol (i.e. A' of Structure 6, Scheme I is transformed from an aldehyde into an alcohol).

To a stirring solution consisting of 1-[3-(4-methoxy-phenyl)-4-phenyl-isoxazol-5-yl]-cyclopropanecarbaldehyde, which may be produced as in Example 170, (23.15 g) in tetrahydrofuran (300 mL) cooled to 0° C. under a nitrogen atmosphere is added a solution consisting of 1.4 M methylmagnesium bromide in toluene-tetrahydrofuran (78 mL) over approximately five minutes. The mixture is allowed to warm slowly to room temperature over 33 hours. The reaction mixture is quenched with saturated aqueous ammonium chloride and is diluted with diethyl ether (700 mL.) The organic phase is washed with portions of saturated aqueous ammonium chloride until the aqueous phase achieved neutral pH. The organic phase is then washed with water (300 mL) and brine solution (300 mL) and is dried over anhydrous sodium sulfate. The dried ether phase is concentrated under reduced pressure to afford the title compound as an oil; MS (APCI+) 336 (MH+.)

Example 178

This Example illustrates conversion of 1-{3-[4-(tert-butyl-dimethyl-silanyloxy)-phenyl]-4-phenyl-isoxazol-5-yl}-cyclopropanecarbaldehyde into (±)-1-(1-{3-[4-(tert-Butyl-dimethyl-silanyloxy)-phenyl]-4-phenyl-isoxazol-5-yl}-cyclopropyl)-ethanol (i.e. A' of Structure 6, Scheme I is transformed from an aldehyde into an alcohol).

To a solution of 1-{3-[4-(tert-butyl-dimethyl-silanyloxy)-phenyl]-4-phenyl-isoxazol-5-yl}-cyclopropanecarbaldehyde, which may be produced as in Example 172, (1.07 g) in THF (13 mL) at 0° C. under nitrogen is added a solution of methylmagnesium bromide (2.7 mL, 1.4 M in 75:25 toluene/THF.) The resulting solution is allowed to warm to ambient temperature over 18 hours. The reaction mixture is diluted with ethyl acetate and 1 M HCl added. The layers are separated and the organics washed with brine. The organic layer is dried (MgSO4), filtered and concentrated under reduced pressure. The resulting residue is purified by flash chromatography (0% to 50% ethyl acetate-hexanes) to afford the title compound as a colorless foam MS (APCI+) m/z 436 (MH+.)

Example 178B

This Example illustrates conversion of 1-[3-(4-methoxy-phenyl)-4-phenyl-isoxazol-5-yl]-cyclopropanecarbaldehyde into (±)-1-{1-[3-(4-methoxy-phenyl)-4-phenyl-isoxazol-5-yl]-cyclopropyl}-propan-1-ol (i.e. A' of Structure 6, Scheme I is transformed from an aldehyde into an alcohol).

A solution of 1-[3-(4-methoxy-phenyl)-4-phenyl-isoxazol-5-yl]-cyclopropanecarbaldehyde (19.41 g), which may be produced as in Example 170, in 300 mL THF is purged with $N_2$ and cooled to 0° C. Ethylmagnesium bromide (1.0 M in THF, 91.17 mL) is added over 15 minutes. The reaction is allowed to slowly warm to room temperature overnight at which time the reaction is quenched with sat. $NH_4Cl$ to pH 7. Add diethyl ether and water. The layers are separated and the ether is washed with sat. $NH_4Cl$, water, and brine, dried over $Na_2SO_4$, filtered, evaporated, and pumped under high vacuum to give the title compound as a gum.

F) Addition of Protecting Group "Pg" to the Unprotected Isoxazole of Structure 6 from Scheme I Example 179

This Example illustrates placing a tert-butyldimethyl-silyl protecting group on the phenol moiety adjacent to the 3-position of the isoxazole ring of an intermediate as described by Structure 6, 1-{3-[4-(tert-butyl-dimethyl-silanyloxy)-phenyl]-4-phenyl-isoxazol-5-yl}-cyclopropanecarboxylic acid methoxy-methyl-amide.

To a solution of 1-[3-(4-hydroxy-phenyl)-4-phenyl-isoxazol-5-yl]-cyclopropanecarboxylic acid methoxy-methyl-amide, which may be produced analogously to Example 154, except N,O-dimethylamine is used in place of morpholine (0.26 g, 0.71 mmoles) in 10 mL of anhydrous DMF is added imidazole (0.21 g, 3.1 mmoles), followed by tetrabutyldimethylsilyl chloride (0.24 g, 1.6 mmoles). The reaction mixture is stirred at room temperature for 18 hrs. The reaction mixture is diluted with 200 mL of ethyl acetate and then the organic solution is washed with saturated sodium bicarbonate (2×50 mL), saturated ammonium chloride (2×50 mL), followed with brine. The organic layer is separated, dried (sodium sulfate), filtered, and then the filtrate is evaporated to give an oil. Purification by flash chromatography (silica gel, 30% ethyl acetate in hexane) provides the title compound as colorless viscous oil.

Example 180

This Example also illustrates placing a tert-butyl-dimethyl silyl protecting group on the phenol moiety adjacent to the 3-position of the isoxazole ring of an intermediate as described by Structure 6, yielding (1-{3-[4-(tert-butyl-dimethyl-silanyloxy)-phenyl]-4-phenyl-isoxazol-5-yl}-cyclopropyl)-morpholin-4-yl-methanone.

To a stirring solution comprised of {1-[3-(4-hydroxy-phenyl)-4-phenyl-isoxazol-5-yl]-cyclopropyl}-morpholin-4-yl-methanone, which may be produced as in Example 154, (20 g), triethylamine (15.7 mL), and 4-dimethylaminopyridine (DMAP, 0.3 g) in tetrahydrofuran (200 mL) at 0° C. under a nitrogen stream is added a solution comprised of tert-butyldimethylsilyl chloride (12 g) in tetrahydrofuran (150 mL) dropwise over one hour. The reaction mixture is allowed to warm to room temperature gradually as it is stirred overnight. The reaction mixture is quenched with the addition of water (300 mL) and is extracted with diethyl ether (300 mL.) The organic phase is dried over anhydrous magnesium sulfate and is concentrated under reduced pressure to afford a yellow oil. The crude product is purified by flash silica gel column chromatography. Elution with a gradient (100% hexanes to 100% ethyl acetate over 3000 mL) on a 400 g Analogix silica cartridge affords an oil. The oily product is subjected to high vacuum overnight at room temperature to afford the solid title compound MS (APCI+) 505 (MH+.) Fractions from the chromatography containing impurities along with desired material are concentrated under reduced pressure. The concentrate is purified by flash silica gel column chromatography. Elution with a gradient (100% hexanes to 100% ethyl acetate) affords additional title compound.

Alternatively, in a 3-neck 1 L flask equipped with an addition funnel, a solution comprised of {1-[3-(4-hydroxy-phenyl)-4-phenyl-isoxazol-5-yl]-cyclopropyl}-morpholin-4-yl-methanone, which may also be produced as in Example 154, (20.3 g), DMAP (1.59 g), and triethylamine (16 mL) in THF (174 mL) is cooled to 0° C. under an atmosphere of nitrogen. A solution of tert-butyldimethylsilyl chloride (12 g) in THF (87 mL) is added in dropwise at 0° C. and the resulting mixture is allowed to warm on its own over 18 hours. The reaction mixture is diluted with ethyl acetate and washed with saturated aqueous ammonium chloride and brine. The organic layer is dried over anhydrous magnesium sulfate, filtered, and concentrated. Purification by flash chromatography (0% to 60% ethyl acetate-hexanes) affords the title compound as a yellow foam (22.9 g); TLC Rf=0.33 (1:1 hexanes-ethyl acetate); MS (APCI+)=505 (MH+.) Alternatively, a gradient of 0% to 50% ethyl acetate-hexanes is used for the chromatography step.

Example 181

This Example illustrates placing a methoxy protecting group on the phenol moiety adjacent to the 3-position of the isoxazole ring, generating an isoxazole intermediate of Structure 6, (R)-(−)-1-{1-[3-(4-methoxy-phenyl)-4-phenyl-isoxazol-5-yl]-cyclopropyl}-ethanol.

Set up a 100 mL round bottom flask with a stir bar. Add 6.00 g of (R)-(−)-4-{5-[1-(1-hydroxy-ethyl)-cyclopropyl]-4-phenyl-isoxazol-3-yl}-phenol, which may be produced as in Example 193, 10.0 mL of THF and then 10.0 mL of 1.89 N NaOH. A clear, yellow solution is formed. Add 2.150 mL of dimethyl sulfate. The mixture is stirred for 2 h 20 min. Turbidity is noticed within 10 min. Add 2.50 mL of 1.89 N NaOH to destroy any excess dimethyl sulfate. Stir for 25 minutes and then transfer to a separatory funnel with 75 mL of MTBE. Mix well and then separate layers. Wash organic layer with 25 mL of water. Dry over magnesium sulfate, filter, and then concentrate under reduced pressure to give clear, yellow oil. Put oil on mechanical pump to give foam. Vacuum dry for 2 hours, to afford the title compound as a glass.

Example 182

This Example illustrates placing a tert-butyldimethylsilyl protecting group on the phenol moiety adjacent to the 3-position of the isoxazole ring, generating an isoxazole intermediate of Structure 6, (1-{3-[4-(tert-butyl-dimethyl-silanyloxy)-phenyl]-4-phenyl-isoxazol-5-yl}-cyclopropanecarboxylic acid methyl ester.

A solution of 1-[3-(4-hydroxy-phenyl)-4-phenyl-isoxazol-5-yl]-cyclopropanecarboxylic acid methyl ester, which may be produced as in Example 187, 188 or 189, (9.60 g), DMAP (0.87 g), and TEA (8.78 mL) in 100 mL THF is purged with $N_2$ and cooled in an ice bath. A solution of tert-butyldimethylsilyl chloride (6.47 g) in 50 mL THF is added over 5 minutes. The reaction is allowed to warm to room temperature overnight at which time it is diluted with ethyl acetate and washed with water and brine. After drying over $Na_2SO_4$ and evaporating, the crude product is purified by flash silica gel chromatography (Analogix 150 g column, eluting with 0-20% ethyl acetate in hexanes) to give the title compound as a gum.

Alternatively, the product obtained is crystallized from petroleum ether or pentane.

Alternatively, 1-[3-(4-hydroxy-phenyl)-4-phenyl-isoxazol-5-yl]-cyclopropanecarboxylic acid ethyl ester may be used in place of the ethyl ester.

Example 183

This Example illustrates placing a benzyl protecting group on the phenol moiety adjacent to the 3-position of the isoxazole ring, generating an isoxazole intermediate of Structure 6, 1-[3-(4-Benzyloxy-phenyl)-4-phenyl-isoxazol-5-yl]-cyclopropanecarboxylic acid ethyl ester A solution of 1-[3-(4-hydroxy-phenyl)-4-phenyl-isoxazol-5-yl]-cyclopropanecarboxylic acid ethyl ester, which may be produced as in Example 205, (1.18 g) in 30 mL DMF is treated with $K_2CO_3$ (2.43 g) and purged with $N_2$. Benzyl bromide (0.42 mL) is added. The reaction is allowed to stir at room temperature overnight. The reaction is diluted with ethyl acetate and washed with water and brine, dried over $Na_2SO_4$, and evaporated to give the title compound as an off-white solid.

G) Removal of Protecting Group "Pg" from Unprotected Isoxazole of Structure 6 from Scheme I

Example 184

This Example illustrate the removal of a methoxy protecting group from the phenol adjacent to the 3-position of the isoxazole, yielding 4-[5-(1-hydroxymethyl-cyclopropyl)-4-phenyl-isoxazol-3-yl]-phenol.

A solution of {1-[3-(4-methoxy-phenyl)-4-phenyl-isoxazol-5-yl]-cyclopropyl}-methanol, which may be produced as in which may be produced as in Example 160 (17.9 g) is dissolved in 200 mL $CH_2Cl_2$ and cooled to −10° C. $BBr_3$ (55.8 g) is added over 10 minutes. After 2 hours, the reaction is further cooled to −20° C. and quenched by cautious addition of sat. $NH_4Cl$. The product precipitates out of the $CH_2Cl_2$ layer. The solid is collected, washed with $CH_2Cl_2$, and dried under vacuum to provide the title compound.

Example 185

This Example illustrates the removal of a tert-butyl-dimethyl-silyanyl protecting group from the phenol adjacent to the 3-position of the isoxazole, yielding 4-[5-(1-hydroxymethyl-cyclopropyl)-4-phenyl-isoxazol-3-yl]-phenol.

A solution of (1-{3-[4-(tert-butyl-dimethyl-silanyloxy)-phenyl]-4-phenyl-isoxazol-5-yl}-cyclopropyl) -methanol, which may be produced as in Example 155, (18.19 g) in 200 mL THF is purged with $N_2$ and treated with tetrabutylammonium fluoride (1.0 $\underline{M}$ in THF, 45.3 mL). After stirring overnight at room temperature, the solution is evaporated to dryness and chromatographed (300 g silica gel column eluting with a gradient of 0 to 50% ethyl acetate in hexanes) to provide material which is recrystallized from methanol and hexanes to give the title compound as a solid; $^1$H NMR (400 MHz, DMSO-$d_6$) δ ppm 0.67 (m, 2 H), 0.78 (m, 2 H), 3.46 (d, J=5.8 Hz, 2 H) 4.94 (m, 1 H) 6.68 (m, 2 H) 7.09 (m, 2 H) 7.29 (m, 5 H) 9.73 (s, 1 H); MS(APCI+) m/z 308 (MH$^+$.)

Example 186

This Example illustrates a number of ways for removing a methoxy protecting group from the phenol adjacent to the 3-position of the isoxazole.

Example 186A

Preparation of {1-[3-(4-Hydroxy-phenyl)-4-phenyl-isoxazol-5-yl]-cyclopropyl}-morpholin-4-yl-methanone Method A1

To a solution of crude {1-[3-(4-methoxy-phenyl)-4-phenyl-isoxazol-5-yl]-cyclopropyl}-morpholin-4-yl-methanone, which may be produced as in Example 153, (13 g, 31 mmoles) in 300 mL of anhydrous toluene is added aluminum chloride (24 g, 177 mmoles). The reaction mixture is heated at reflux for 2 hrs and then cooled to room temperature. Ethyl acetate (600 mL) is added and then ice cubes are added dropwise until the tarry solid dissolves in the biphasic (ethyl acetate/water) mixture. The organic layer is removed and then the aqueous layer is extracted with an additional portion of ethyl acetate (200 mL). The ethyl acetate extracts are combined and washed with 200 mL brine. The organic layer is separated, dried, filtered, and then the filtrate is evaporated to afford an orange-red oil. Precipitation from dichloromethane affords the title compound as a white solid.

Alternatively, the following are substituted in the preceding procedure:

1.) at reflux for 1, 2, or 3 hrs employing 6.1-6.2 eq of aluminum chloride
2.) at room temperature for 15 min, followed by heating at reflux for 30 min employing 3 eq of aluminum chloride.
3.) at room temperature for 2 days in a mixture of methylether in dichloromethane with 3 eq aluminum chloride.
4.) at room temperature for 1 hr, followed by 30 min at 30° C. in dichloromethane with 2.5 eq aluminum chloride and 5 eq of 2-dimethylaminoethanethiol hydrochloride to provide none of the title compound.
5.) purified by flash chromatography on silica gel with 60% ethyl acetate in hexane as eluent
6.) purified by flash chromatography on silica gel with 60% ethyl acetate in hexane as eluent. Followed by trituration in dichloromethane
7.) purified by flash chromatography on silica gel with 0-100% ethyl acetate in hexane, followed with 2% methanol in ethyl acetate as eluents and then trituration in dichloromethane
8.) purified by flash chromatography on silica gel with 0-100% ethyl acetate in hexane
9.) purified by flash chromatography on silica gel with 0-100% ethyl acetate in hexane, followed by 5% methanol in ethyl acetate Method A2:

To a 250 mL round bottom flask is added {1-[3-(4-methoxy-phenyl)-4-phenyl-isoxazol-5-yl]-cyclopropyl}-morpholin-4-yl-methanone, which may be produced as in Example 153, and 10 mL dichloromethane. The solution is cooled in dry ice-isopropanol bath (ca. −30° C.). 2.5 mL 1 $\underline{M}$ boron tribromide in dichloromethane solution is added. After 0.5 hr, little product observed. Another 2.5 mL 1 $\underline{M}$ boron tribromide in dichloromethane solution is added. After 8 molar equivalents added, the mixture is warmed to −5° C. and another 8 molar equivalents boron tribromide are added. The mixture is stirred for two days. 10 mL of 1 $\underline{M}$ boron tribromide in dichloromethane solution is added. The mixture is stirred over the weekend. 1 molar equivalent of sodium iodide is added, and the mixture is stirred for 4 hr: title compound/starting material (HPLC) 58:16.

Method A3:

A mixture of {1-[3-(4-methoxy-phenyl)-4-phenyl-isoxazol-5-yl]-cyclopropyl}-morpholin-4-yl-methanone, which may be produced as in Example 153, (0.2 g) and sodium cyanide (0.12 g) in DMSO (10 mL) is heated at reflux overnight. LCMS shows some conversion to {1-[3-(4-hydroxy-phenyl)-4-phenyl-isoxazol-5-yl]-cyclopropyl}-morpholin-4-yl-methanone.

Method A4:

A mixture of {1-[3-(4-methoxy-phenyl)-4-phenyl-isoxazol-5-yl]-cyclopropyl}-morpholin-4-yl-methanone, which may be produced as in Example 153, and excess anhydrous lithium iodide in 2,4,6-collidine is heated at reflux.

Method A5:

A solution of excess 2-(dimethylamino)ethanethiol hydrochloride in DMF is cooled in an ice bath and then excess sodium tert-butoxide is added. The ice bath is removed and the cloudy solution is stirred at room temperature for 15 min. The limiting reagent, {1-[3-(4-methoxy-phenyl)-4-phenyl-isoxazol-5-yl]-cyclopropyl}-morpholin-4-yl-methanone, in DMF is added and the reaction mixture is heated at reflux.

Example 186B

This example illustrates several alternative methods for removing the methoxy protecting group from 1-{1-[3-(4-methoxy-phenyl)-4-phenyl-isoxazol-5-yl]-cyclopropyl}-ethanone (which may be produced as in Example 173 or 175) to produce 1-{1-[3-(4-hydroxy-phenyl)-4-phenyl-isoxazol-5-yl]-cyclopropyl}-ethanone.

Method B1

A stirring mixture consisting of 1-{1-[3-(4-methoxy-phenyl)-4-phenyl-isoxazol-5-yl]-cyclopropyl}-ethanone (limiting reagent) in a solvent such as toluene, p-xylene or dichloromethane under a nitrogen atmosphere is treated with a Lewis acid (1-4.1 molar equivalents) such as boron trichloride, boron tribromide, boron trifluoride-dimethylsulfide complex, 9-bromo-9-borabicyclo[3.3.0]nonane, or aluminum trichloride. The mixture is cooled to −78° C. or −10° C., kept at room temperature, or heated to reflux.

Method B2

To a stirring mixture consisting of 2-diethylamino-ethanethiol hydrochloride (1.2-6 molar equivalents) and sodium tert-butoxide (2-12 molar equivalents) in N,N-dimethylformamide at 0° C. under a nitrogen atmosphere is added a mixture consisting of 1-{1-[3-(4-methoxy-phenyl)-4-phenyl-isoxazol-5-yl]-cyclopropyl}-ethanone (limiting reagent) in N,N-dimethylformamide. The stirring mixture is heated to reflux.

Method B3:

A mixture consisting of 1-{1-[3-(4-methoxy-phenyl)-4-phenyl-isoxazol-5-yl]-cyclopropyl}-ethanone (limiting reagent), 2-diethylamino-ethanethiol hydrochloride (3 molar equivalents), tetrabutylammonium hydrogen sulfate (0.2 molar equivalents), and 50% sodium hydroxide (excess) in toluene at room temperature is stirred.

Method B4:

A mixture consisting of 1-{1-[3-(4-methoxy-phenyl)-4-phenyl-isoxazol-5-yl]-cyclopropyl}-ethanone (limiting reagent) and pyridinium hydrochloride (1-14 molar equivalents) in a solvent such as N,N-dimethylformamide, dimethylsulfoxide, tetrahydrofuran, toluene, or xylene under a nitrogen atmosphere is stirred at reflux.

Alternatively, the starting materials are melted together with no solvent.

Method B5:

A stirring mixture consisting of 1-{1-[3-(4-methoxy-phenyl)-4-phenyl-isoxazol-5-yl]-cyclopropyl}-ethanone (limiting reagent) and a lithium salt such as lithium chloride (3 molar equivalents), lithium bromide (15 molar equivalents), or lithium iodide (2-5 molar equivalents) in a solvent such as N,N-dimethylformamide or 2,4,6-collidine under a nitrogen atmosphere is heated to reflux.

Method B6:

A mixture consisting of 1-{1-[3-(4-methoxy-phenyl)-4-phenyl-isoxazol-5-yl]-cyclopropyl}-ethanone reagent) and potassium trimethylsilanolate (1.1 molar equivalents) in a solvent such as toluene, dichloromethane, or tetrahydrofuran is stirred at room temperature or at 60° C.

Method B7:

A stirring mixture consisting of 1-{1-[3-(4-methoxy-phenyl)-4-phenyl-isoxazol-5-yl]-cyclopropyl }-ethanone (limiting reagent) and sodium cyanide (5 molar equivalents) in dimethyl sulfoxide is heated at reflux.

Example 187

This Example illustrates a number of ways for removing a methoxy protecting group from the phenol adjacent to the 3-position of the isoxazole, yielding 1-[3-(4-hydroxy-phenyl)-4-phenyl-isoxazol-5-yl]-cyclopropanecarboxylic acid methyl ester.

Method A1:

A solution of 1-[3-(4-methoxy-phenyl)-4-phenyl-isoxazol-5-yl]-cyclopropanecarboxylic acid methyl ester, which may be produced as in Example 160, (20.0 g) in 400 mL $CH_2Cl_2$ is purged with $N_2$ and cooled to an internal temperature of −10° C. A solution of $BBr_3$ (21.65 mL) in 100 mL $CH_2Cl_2$ is added to the reaction mixture over an hour at a rate sufficient to keep the internal temperature below −8° C. The bath is removed, and the reaction is allowed to warm to 5° C. over an hour. The reaction is deemed complete by LCMS and cooled to −10° C. The reaction is quenched with 5% $NaHCO_3$ at a rate sufficient to keep the internal temperature below −9° C. After the quench is complete, the bath is removed and additional water is added to dissolve all solids. The layers are separated, and the aqueous layer is washed with $CH_2Cl_2$. The combined organic extracts are washed with water and brine, dried over $Na_2SO_4$, and evaporated to give the foamy solid title compound.

Method A2:

Dichloromethane (15 mL) is added to aluminum chloride (0.84 g) and then a solution of 1-[3-(4-methoxy-phenyl)-4-phenyl-isoxazol-5-yl]-cyclopropanecarboxylic acid methyl ester which may be produced as in Example 160, (1.0 g) in dichloromethane (10 mL) is added. The resulting homogenous yellow colored solution is stirred at room temperature overnight. LCMS indicates 14% of title compound is formed.

Method A3:

A mixture of 1-[3-(4-methoxy-phenyl)-4-phenyl-isoxazol-5-yl]-cyclopropanecarboxylic acid methyl ester which may be produced as in Example 160, and excess anhydrous lithium iodide in 2,4,6-collidine is heated at reflux.

Method A4:

A solution of excess 2-(dimethylamino)ethanethiol hydrochloride in DMF is cooled in an ice bath and then excess sodium tert-butoxide is added. The ice bath is removed and the cloudy solution is stirred at room temperature for 15 min. The limiting reagent, 1-[3-(4-methoxy-phenyl)-4-phenyl-isoxazol-5-yl]-cyclopropanecarboxylic acid methyl ester, in DMF is added and the reaction mixture is heated at reflux.

Method B

Set up a 25 mL reaction tube with a stir bar. Purge well with nitrogen and then add 575 mg of 2-diethylamino-ethanethiol and 2.0 mL of DMF. Cool in an ice-water bath and add 622 mg of sodium tert-butoxide. Remove cold bath and stir 15 min. Add 533 mg of the substrate (R)-1-{1-[3-(4-methoxy-phenyl)-4-phenyl-isoxazol-5-yl]-cyclopropyl}-ethanol, which may be produced as in Example 181, dissolved in 2.0 mL of DMF. Heat mixture to 100° C. internal. Stir for two hours.

Example 188

This Example illustrates the removal of a tert-butyldimethylsilyl protecting group from the phenol adjacent to the 3-position of the isoxazole, 1-[3-(4-hydroxy-phenyl)-4-phenyl-isoxazol-5-yl]-cyclopropanecarboxylic acid methyl ester.

A solution of 1-{3-[4-(tert-butyl-dimethyl-silanyloxy)-phenyl]-4-phenyl-isoxazol-5-yl}-cyclopropanecarboxylic acid methyl ester, which may be produced as in either Example 143 or 144, (1.00 g) in 10 mL THF is purged with $N_2$ and treated with tetrabutylammonium fluoride (1.0 M in THF, 4.45 mL) and stirred overnight at room temperature. The solution is evaporated to dryness and chromatographed (40 g silica gel column eluting with a gradient of 0 to 50% ethyl acetate in hexanes) to provide the title compound.

Example 189

This Example illustrates the removal of a benzyl protecting group from the phenol adjacent to the 3-position of the isoxazole, yielding 1-[3-(4-hydroxy-phenyl)-4-phenyl-isoxazol-5-yl]-cyclopropanecarboxylic acid methyl ester.

A solution of 1-[3-(4-benzyloxy-phenyl)-4-phenyl-isoxazol-5-yl]-cyclopropanecarboxylic acid methyl ester which may be produced as described in Example 146, (1.33 g) in THF (25 mL) and ethanol (25 mL) is treated with 10% Pd/C (0.2 g, 55% water) and shaken under $H_2$ pressure (17 psi) for 1 hour. The reaction is filtered and concentrated to provide the title compound.

Example 190

This Example illustrates the removal of a tert-butyldimethyl-silyl protecting group from the phenol adjacent to the 3-position of the isoxazole.

Method A1:

To a solution of 1-{3-[4-(tert-butyl-dimethyl-silanyloxy)-phenyl]-4-phenyl-isoxazol-5-yl}-cyclopropanecarboxylic acid methyl ester, which may be produced as in Example 143 or 144, (10.00 g) is added 50% sodium hydroxide (10 mL). The reaction is stirred at 60° C. overnight. The reaction is cooled and concentrated under reduced pressure. The gummy residue is partitioned between ether and water. The aqueous phase is washed with ether before acidifying to pH 5 with concentrated HCl. The aqueous phase is extracted with ethyl acetate, and the combined extracts are washed with water and brine, dried over $Na_2SO_4$, and evaporated to provide the 1-[3-(4-Hydroxy-phenyl)-4-phenyl-isoxazol-5-yl]-cyclopropanecarboxylic acid as a foamy solid.

Method A2:

The white solid 1-{3-[4-(tert-butyl-dimethyl-silanyloxy)-phenyl]-4-phenyl-isoxazol-5-yl}-cyclopropanecarboxylic acid methyl ester, which may be produced as in Example 143 or 144, (41.28 g) is dissolved in tetrahydrofuran (150 mL) and the solution is added to a solution comprised of potassium hydroxide (27.0 g) in water (150 mL). The biphasic mixture is heated for 1.5 hours over steam. The mixture is treated with concentrated aqueous hydrochloric acid to bring the aqueous phase to pH about 0-1, and the biphasic mixture is extracted with diethyl ether. The organic phase is separated from the aqueous phase and is dried over anhydrous magnesium sulfate and vacuum filtered. The filtrate is concentrated under reduced pressure to an off-white amorphous solid with a clear oily residue ring around the outer edges of the solid. The material is dissolved in boiling absolute ethanol (100 mL) over steam. Cooling to room temperature slowly produces no precipitate. Hexanes are added to give a turbid suspension, but scratching with a glass rod afforded no solid. The solvent is evaporated over steam, leaving a yellow oily liquid. This liquid is transferred to an evaporating flask with ethanol rinsing and is subjected to high vacuum at 70° C. to obtain a clear, light-orange foam peppered with some small white solid circles. The material is treated with isopropanol-heptane and is heated over steam for about one minute and then scratched with a glass rod to afford a white precipitate. The precipitate is collected by vacuum filtration, and the solids are rinsed with fresh heptane and minimal isopropanol, and are suction dried to afford 1-[3-(4-hydroxy-phenyl)-4-phenyl-isoxazol-5-yl]-cyclopropanecarboxylic acid as a white powder (32.23 g); MS (APCI+) 322 ($MH^+$), (APCI−) 320 ($M^-$.)

Method A3:

To a solution of 1-{3-[4-(tert-butyl-dimethyl-silanyloxy)-phenyl]-4-phenyl-isoxazol-5-yl}-cyclopropane carboxylic acid methyl ester, which may be produced as in Example 143 or 144, (0.25 g, 0.56 mmoles) in 10 mL of methanol is added lithium hydroxide monohydrate (0.049 g, 1.2 mmoles). The reaction mixture is stirred at room temperature for 18 hrs. The reaction mixture is evaporated to give crude yellow oil, which is dissolved in 50 mL of water. The aqueous solution is acidified with 1 N HCl to pH=2. A white precipitate forms, which redissolves in solution and then fell out of solution after about 30 minutes as a gummy yellow solid. The product is extracted with diethyl ether (2×50 mL) and then the ether extracts are combined and washed with 50 mL of brine. The organic layer is dried (sodium sulfate), filtered, and then evaporated to afford 1-[3-(4-hydroxy-phenyl)-4-phenyl-isoxazol-5-yl]-cyclopropanecarboxylic acid as a crude yellow solid.

Example 191A

This Example illustrates the removal of a tert-butyldimethyl-silyl protecting group from the phenol adjacent to the 3-position of the isoxazole.

To a solution of 1-{3-[4-(tert-butyl-dimethyl-silanyloxy)-phenyl]-4-phenyl-isoxazol-5-yl}-cyclopropane carboxylic acid ethyl ester, which may be produced as in Example 145, (5.2 g, 11 mmoles) in a mixture of 150 mL of methanol and 22 mL of water is added solid sodium hydroxide (0.93 g, 23 mmoles). The reaction mixture is stirred at reflux for 18 hrs. Analyses by TLC indicated that saponification is incomplete. However, the silyl protecting group is completely removed. An additional 2.1 molar equivalents of sodium hydroxide is added and then the reaction mixture is heated at reflux for an additional 18 hrs. The reaction is complete as indicated by TLC. The reaction mixture is evaporated to give crude yellow oil, which is dissolved in 200 mL of water. The aqueous solution is acidified with 1 N HCl to pH=2. A white precipitate forms, which is triturated at room temperature for 1 hr. The mixture is filtered to collect a white solid, which was dried to afford 1-[3-(4-hydroxy-phenyl)-4-phenyl-isoxazol-5-yl]-cyclopropanecarboxylic acid.

Example 191B

This Example illustrates the removal of a benzyl protecting group from the phenol adjacent to the 3-position of the isoxazole.

(R)-1-{1-[3-(4-Benzyloxy-phenyl)-4-phenyl-isoxazol-5-yl]-cyclopropyl}-ethanol, which may be produced as in Example 192 (9.4 g) is dissolved in methanol (150 mL) and 1 g of 5% Pd/$BaSO_4$ catalyst is added. The resulting mixture is stirred for 30 minutes at room temperature under a hydrogen atmosphere (20 psi.) The catalyst is removed by filtration and the resulting filtrate concentrated to dryness. To the resulting residue is added 1:1 hexanes-$CH_2Cl_2$ (200 mL) and the resulting mixture stirred for 15 minutes. The resulting off-white solids are removed by filtration and dried. Isolate (R)-(−)-4-{5-[1-(1-hydroxy-ethyl)-cyclopropyl]-4-phenyl-isoxazol-3-yl}-phenol as a white solid; MS (APCI+) m/z 322 ($MH^+$.) Alternatively, the reaction can be carried out using a 5% palladium on alumina catalyst at 50 psi hydrogen pressure.

H) Reduction of Cyclopropyl Ketone Moiety (A) into an Alcohol

Example 192

This Example illustrates conversion of 1-{1-[3-(4-Benzyloxy-phenyl)-4-phenyl-isoxazol-5-yl]-cyclopropyl}-ethanone into (R)-1-{1-[3-(4-Benzyloxy-phenyl)-4-phenyl-isoxazol-5-yl]-cyclopropyl}-ethanol (i.e. A' of Structure 6, Scheme I is transformed from a ketone into an alcohol).

Method A1:

1-{1-[3-(4-Benzyloxy-phenyl)-4-phenyl-isoxazol-5-yl]-cyclopropyl}-ethanone which may be produced as in Example 167 or 168 (13.2 g) is dissolved in a mixture of toluene (100 mL) and THF (10 mL) (alternatively, either THF or toluene can be used instead of the mixture of toluene and THF). This solution is added dropwise via addition funnel to a stirring solution of $BH_3$-diethylaniline complex (5.16 mL) and (S)—CBS-oxazaborolidine (6.4 mL, 1 $\underline{M}$ in toluene) in 29 mL of toluene at room temperature under an atmosphere of nitrogen. After the addition is complete, the reaction mixture is allowed to stir at room temperature over 30 minutes. The reaction mixture is quenched with saturated aqueous $NH_4Cl$ and ethyl acetate added. The layers are separated and the organics washed with additional $NH_4Cl$ (2×) and brine (2×.) The organic layer is dried ($MgSO_4$), filtered, and concentrated under reduced pressure. The resulting residue is purified by flash chromatography (0% to 100% ethyl acetate-hexanes.) Isolate the title compound as a white tacky foam; MS (APCI+) m/z 412 (MH+.)

Method A2:

1-{1-[3-(4-Benzyloxy-phenyl)-4-phenyl-isoxazol-5-yl]-cyclopropyl}-ethanone, which may be produced as Example 167 or 168, is dissolved in 100 mL of THF in a 1 L 4 necked flask under nitrogen. This solution is diluted with 100 mL of toluene with stirring. 10.0 mL of (S)—CBS catalyst solution (1M in toluene) is added over 3 minutes. Add 8.0 mL of BH3:diethylaniline complex over 4 minutes. Rinse addition funnel with about 10 mL of toluene. Stir for 1 hour 30 minutes. The reaction is quenched over 5 minutes by transferring reaction mixture into 100 mL of half sat. aq. $NH_4Cl$. Rinse reaction flask with 60 mL of toluene. Stir the mixture for 15 min. and then filter through Celite. Rinse and wash with 110 mL of toluene. Transfer to a separatory funnel. Drain aqueous layer. Wash the organic layer with 100 mL of water. Wash the organic layer with 100 mL of 1 N HCl. Wash the organic layer twice with 100 mL of water. Transfer the organic layer into a 1 L 4N flask and rinse with 50 mL of toluene. Heat and distill under vacuum. Collect a total of about 365 mL of distillate. Add 225 mL of 2:1 heptane:MTBE. Stir vigorously for 2.5 hours. Filter solids. Wash solids with 300 mL of 3:1 heptane:MTBE. Alternatively, a 3:1 mixture of heptane and isopropyl alcohol can be used in place of the 2:1 heptane/MTBE mixture for purifying and isolating the product.

Example 193 A-D

This Example illustrates four alternative methods for converting 1-(1-{3-[4-(tert-Butyl-dimethyl-silanyloxy)-phenyl]-4-phenyl-isoxazol-5-yl}-cyclopropyl)-ethanone, which may be produced as taught in Example 162 or 163, into a final product of Formula I, (R)-(−)-4-{5-[1-(1-Hydroxy-ethyl)-cyclopropyl]-4-phenyl-isoxazol-3-yl}-phenol (A' of Structure 6, Scheme I is transformed from a ketone into an alcohol and the protecting group, Pg, is removed).

Example 193A 1-(1-{3-[4-(tert-Butyl-dimethyl-silanyloxy)-phenyl]-4-phenyl-isoxazol-5-yl}-cyclopropyl)-ethanone (56.1 grams) is combined with toluene (400 mL) and stirred to a solution. Borane-N,N-diethylaniline complex, (18.7 grams), tetrahydrofuran (115 mL) and (S)-2-methyl-CBS-oxazaborolidine, 1 M in toluene (25.9 mL) are combined in a separate container and stirred under nitrogen.

The ketone solution is added to the borane solution over 1.5 hours at 22° C. to 25° C. The mixture is stirred for about 30 minutes at 20° C. to 22° C. and then quenched with ammonium chloride solution (250 mL containing 35 grams, 654 mmoles ammonium chloride). The organic layer is separated from the aqueous and filtered. The filtrate is washed with saturated sodium chloride solution (250 mL, 1523 mmoles sodium chloride), dried over magnesium sulfate (approximately 25 grams) and filtered. The filtrate is concentrated by vacuum distillation to a liquid. The liquid is dissolved into methanol and concentrated by vacuum distillation to remove toluene. The remaining liquid is dissolved into hexanes and concentrated by vacuum distillation to a viscous liquid (76.1 grams.)

The viscous liquid is pushed through a bed of silica gel (350 grams) using 90% hexanes/10% ethyl acetate (1 Liter) followed by 70% hexanes/30 parts ethyl acetate (3 Liters). The filtrate is collected in incremental samples (500 mL each). Samples 3-7 are combined and concentrated by vacuum distillation to yield the alcohol intermediate 1-(1-{3-[4-(tert-butyl-dimethyl-silanyloxy)-phenyl]-4-phenyl-isoxazol-5-yl}-cyclopropyl)-ethanol (66.7 grams.)

The alcohol intermediate (57.5 grams), tetrahydrofuran, (115 mL) and tetrafluoroboric acid (68 mL, 48%, 371 mmoles) are combined and stirred at 30° C.-40° C. for 3 hours. Water (50 mL) is added to the slurry. The slurry is cooled to −5° C. and filtered to collect the solids. The solids are washed with 70 mL of cold water and dried to a constant weight under vacuum at 50° C. to afford the solid title compound. The purity is determined by chiral HPLC (99.3%) and chemical HPLC (99.9%.)

Example 193B 1-(1-{3-[4-(tert-Butyl-dimethyl-silanyloxy)-phenyl]-4-phenyl-isoxazol-5-yl}-cyclopropyl)-ethanone (7.9 grams) is combined with toluene (55 mL) and stirred to a solution. Borane-N,N-diethylaniline complex (2.6 grams), tetrahydrofuran (16 mL) and (S)-2-methyl-CBS-oxazaborolidine, 1 M in toluene (3.3 mL) are combined in a separate container and stirred under nitrogen.

The ketone solution is added to the borane solution over 50 minutes at 19° C.-22° C. The mixture is stirred for an additional 2 hour at 20° C.-22° C. Tetrabutylammonium fluoride in THF (1 M, 7.4 mL) is added. The mixture is stirred for 15 minutes and then quenched with ammonium chloride solution (30 mL containing 14 grams, 26 mmoles ammonium chloride). The organic layer is separated from the aqueous The aqueous layer is washed with ethyl acetate (30 mL) and the layers are separated. The organic layers are combined, dried over magnesium sulfate and filtered. The filtrate is concentrated by vacuum distillation to an oil. The oil is dissolved in toluene and vacuum distilled to remove water. The residue is dissolved in methanol and vacuum distilled to remove toluene. The resulting oil is identified as the title compound by HPLC retention time.

Example 193C 1-(1-{3-[4-(tert-Butyl-dimethyl-silanyloxy)-phenyl]-4-phenyl-isoxazol-5-yl}-cyclopropyl)-ethanone (41.75 g, 96.28 mmol) is dissolved in toluene (294 mL) and the solution is added dropwise via addition funnel to a stirring solution of BH3-THF complex (87 mL, 1 M in THF stabilized with 1,2,2,6,6-pentamethylpiperidine, 87 mmol, 0.9 equivalents) and (S)—CBS-oxazaborolidine (19 mL, 1M in toluene, 19 mmol, 0.2 equivalents) at room temperature over a 2 hour period. The mixture is then stirred at room temperature for 30 minutes. The reaction mixture is cooled to 0° C. and a TBAF solution (130 mL, 1 M in THF, 130 mmol, 1.35 equivalents) is added portion-wise via an addition funnel with vigorous stirring. After an additional 30 minutes, the mixture is quenched with ammonium chloride (saturated aqueous, 250 mL) and ethyl acetate (250 mL) is added. The layers are separated and the organics washed with additional saturated aqueous ammonium chloride (2×) and brine (2×). The organic layer is dried ($MgSO_4$), filtered, and concentrated under reduced pressure to afford a white solid. A solution of hexanes/dichloromethane (1:1 v/v, 500 mL) is added to the solids and stirred for five minutes. The white solids are filtered off and dried under reduced pressure to obtain the title compound as a white solid. LC/MS indicates 100% purity; MS (APCI+) m/z 322 (MH+.)

Alternatively, the number of molar equivalents is as follows: BH3-THF complex (0.6 molar equivalents) and (S)—CBS-oxazaborolidine (0.1 molar equivalents.)

Example 193D

A solution of borane (0.75 mL, 1 M in THF stabilized with NaBH$_4$) and (S)—CBS-oxazaborolidine (0.17 mL, 1 M in toluene) in toluene (2 mL) is stirred at ambient temperature under an atmosphere of nitrogen. A solution of 1-(1-{3-[4-(tert-butyl-dimethyl-silanyloxy)-phenyl]-4-phenyl-isoxazol-5-yl}-cyclopropyl)-ethanone (360 mg) in 2 mL THF is slowly added. The resulting solution is allowed to stir at ambient temperature for 1.5 hours. To the crude reaction mixture is carefully added tetrabutylammonium fluoride solution (2.5 mL, 1 M in THF.) After stirring 30 minutes, the reaction mixture is diluted with ethyl acetate (15 mL) and quenched with 1 M HCl (10 mL.) The layers are separated and the organics washed with brine. The organic layer is dried (MgSO$_4$), filtered, and concentrated under reduced pressure to afford a light yellow residue. Dichloromethane is added and the resulting white solids are filtered off and dried. Isolated the title compound with 93% enantiomeric excess (chiral HPLC analysis); TLC Rf=0.30 (1:1 hexanes-ethyl acetate); MS (APCI+) m/z 322 (MH+.)

Example 194

This example illustrates the conversion of 1-{1-[3-(4-hydroxy-phenyl)-4-phenyl-isoxazol-5-yl]-cyclopropyl}-ethanone into a final product of Formula I, (R)-(−)-4-{5-[1-(1-Hydroxy-ethyl)-cyclopropyl]-4-phenyl-isoxazol-3-yl}-phenol (i.e A' is converted from a ketone into an alcohol).
Method A:

A stirring mixture consisting of 1-{-[3-(4-hydroxy-phenyl)-4-phenyl-isoxazol-5-yl]-cyclopropyl}-ethanone with may be produced as in Example 164, a base such as potassium tert-butoxide (0.78 equivalents) or potassium carbonate (0.25 equivalents), a catalyst such as Ru—(S)-BINAP (1 mol %) or Ru—(S)-BINAP-(S)-DIAPEN (1 mol %), in IPA or IPA/THF (4:1) is pressurized with hydrogen gas (50 psi) at room temperature for 16 hours. The mixture is diluted with ethyl acetate and filtered through a plug of Celite. The organic solution is concentrated under reduced pressure and the concentrate is purified by chiral HPLC.
Method B:

A solution of 1-{1-[3-(4-hydroxy-phenyl)-4-phenyl-isoxazol-5-yl]-cyclopropyl}-ethanone, which may be produced as in Example 164 (18 mg) and (S)—CBS-oxazaborolidine (0.051 mL, 1 M in toluene) in THF (0.25 mL) is cooled to −10° C. Borane (0.10 mL, 1 M in THF stabilized with NaBH$_4$) is added. After stirring 5 minutes at −10° C., the solution is diluted with ethyl acetate and 1 M HCl. The layers are separated and the organics washed with brine. The organic layer is dried (MgSO$_4$), filtered, and concentrated under reduced pressure. The resulting residue is purified by flash chromatography (0% to 50% ethyl acetate-hexanes) and the title compound is isolated as a white solid with an 88% enantiomeric excess (chiral HPLC); MS (APCI+) m/z 322 (MH+.)

Preparation of Final Compounds of Formula I

Example 195

This example illustrates the separation of (R)-(−)-4-{5-[1-(1-hydroxy-ethyl)-cyclopropyl]-4-phenyl-isoxazol-3-yl}-phenol from the racemate of this compound.

The racemate (±)-4-{5-[1-(1-hydroxy-ethyl)-cyclopropyl]-4-phenyl-isoxazol-3-yl}-phenol, which may be prepared as in Example 198 (0.190 g) is separated into its enantiomers (SFC Chiralcel AD-H, 30% co-solvent [90% IPA/10% MeOH], 70% $CO_2$)
Enantiomer 1: retention time 4.51 min
Enantiomer 2: retention time 5.53 min
The separated enantiomers are returned as dry samples and recrystallized from ethanol-hexanes.
Enantiomer 1: (R)-(−)-4-{5-[1-(1-Hydroxy-ethyl)-cyclopropyl]-4-phenyl-isoxazol-3-yl}-phenol: 50.2 mg of a white powder
Enantiomeric excess: 97.33%
Specific Rotation (Rudolph Research Analytical Model AutoPol IV): [α]=−34° in MeOH [where cell length=25 mm; C=4.7 mg/mL; observed α=−0.040°; λ=598 nm; t=23.3° C.; [a]=(4000×a)/C].

Example 196

This example illustrates attempts to enhance the enantiomeric purity of (R)-(−)-4-{5-[1-(1-hydroxymethyl)-cyclopropyl]-4-phenyl-isoxazol-3-yl}-phenol, from the racemate of this compound.

Dissolve an admixture of (S) and (R)-(−)-4-[5-(1-hydroxymethyl-cyclopropyl)-4-phenyl-isoxazol-3-yl]-phenol, (which is>than 90% of the (R)-enantiomer) which may be produced as shown immediately above (38 g) in hot acetonitrile (1200 mL) then add hot water (1000 mL) until a small amount of precipitation is observed. The suspension is set aside to cool for 4 hours. Crystals are collected by vacuum filtration and dried in a 60° C. vacuum oven overnight to afford a first crop of (R)-(−)-4-[5-(1-hydroxymethyl-cyclopropyl)-4-phenyl-isoxazol-3-yl]-phenol. The solid that formed in the mother liquor during filtration is collected as a second crop. The first crop is combined with first crops obtained from the recrystallizations of other batches, dissolved up in hot acetonitrile and concentrated under reduced pressure to afford one large homogeneous batch on which analysis is performed. Purity=100% (by certified HPLC analysis) and chiral purity=99.7% (99.4% enantiomeric excess by certified chiral HPLC); melting point 213.5 (C (Thomas Hoover Melting Point Apparatus); Specific rotation (Rudolph Research Analytical Model AutoPol IV): [α]=−32.0° in methanol [where cell path length=25 mm; C=5.0 mg/mL; observed α=−0.040°; λ=598 nm; T=24.1° C.; [α]=(4000×α)/C].

Alternatively, the material is recrystallized using ethanol/hexane or THF/hexane.

Example 197

This example illustrates attempts the conversion of (±)-1-(1-{3-[4-(tert-butyl-dimethyl-silanyloxy)-phenyl]-4-phenyl-isoxazol-5-yl}-cyclopropyl)-ethanol into (S)-(+)-4-{5-[1-(1- hydroxy-ethyl)-cyclopropyl]-4-phenyl-isoxazol-3-yl}-phenol, a product of Formula I.

Method A:

Step 1: Deprotection with TBAF

To a solution of (±)-1-(1-{3-[4-(tert-butyl-dimethyl-silanyloxy)-phenyl]-4-phenyl-isoxazol-5-yl}-cyclopropy)-ethanol, which may be produced as in Example 178A (2.2 g) in 60 mL of anhydrous THF is added tetrabutylammonium fluoride hydrate (2.6 g.) The reaction mixture is stirred at room temperature for 4 hrs. Saturated ammonium chloride (50 mL) is added to the reaction mixture, followed with 300 mL of ethyl acetate. The aqueous layer are separated and then the organic layer is washed with additional saturated ammonium chloride (2×50 mL), followed with brine (50 mL). The organic layer is dried (sodium sulfate), filtered, and the filtrate is evaporated to give a white solid, which is purified by flash chromatography (silica gel, 40% ethyl acetate in hexane) to afford a white solid as (±)-4-{5-{1-(1-hydroxy-ethyl)-cyclopropyl]-4-phenyl-isoxazol-3-yl}-phenol.

Step 2: Chiral Separation

A 1.31 g sample of (±) 4-{5-{1-(1-hydroxy-ethyl)-cyclopropyl]-4-phenyl-isoxazol-3-yl}-phenol is submitted for Preparative Chiral Separation (SFC Chiralcel AD-H, 30% co-solvent [90% IPA/10% MeOH], 70% $CO_2$) to yield the title compound; melting point 220-221° C.; MS (APCI+) m/z 322 (MH$^+$); Specific Rotation (Rudolph Research Analytical Model AutoPol IV): [α]=+24.6° in methanol [where cell length=25 mm; C=7.8 mg/mL; observed α=+0.048°; λ=598 nm; t=23.5° C.; [α]=(4000×α)/C].

Alternatively, the title compound is recrystallized from ethanol-hexanes.

Example 197 B

This example illustrates the preparation of (S)-(±)-4-[5-(1-hydroxymethyl-cyclopropyl)-4-phenyl-isoxazol-3-yl]-phenol.

A racemic mixture (190 mg) of 4-[5-(1-hydroxymethyl-cyclopropyl)-4-phenyl-isoxazol-3-yl]-phenol, which may be prepared as in Example 184 or 206, is applied to a Chiracel OJ 20×250 mm 1 μm particle preparative column and eluted with hexanes-ethanol (85:15) at a flow rate of 15 mL/min to afford the individual enantiomers as white solids. Recrystallization from ethanol-hexanes affords (S)-(+)-4-[5-(1-hydroxymethyl-cyclopropyl)-4-phenyl-isoxazol-3-yl]-phenol with 100% enantiomeric excess (as measured by chiral analytical HPLC). Specific rotation (Rudolph Research Analytical Model AutoPol IV): [α]=36.0° in methanol [where cell path length=25 mm; C=4.8 mg/mL; observed α=0.044°; λ=598 nm; T=23.4° C.; [α]=(4000×α)/C].

Example 198

This Example illustrate the preparation of (±)-4-{5-[1-(1-hydroxy-ethyl)-cyclopropyl]-4-phenyl-isoxazol-3-yl}-phenol from 1-{3-[4-(tert-butyl-dimethyl-silanyloxy)-phenyl]-4-phenyl-isoxazol-5-yl}-cyclopropanecarbaldehyde.

Step 1: Methyl Grignard addition to aldehyde.

To a cold (0° C.) solution of 1-{3-[4-(tert-butyl-dimethyl-silanyloxy)-phenyl]-4-phenyl-isoxazol-5-yl}-cyclopropanecarbaldehyde, which may be produced as in Example 172, (2.5 g) in 22 mL of anhydrous THF, is added 4.8 mL of methylmagnesium bromide (0.79 g, 1.4 M in THF/hexane). The reaction mixture is stirred at 0° C. for 2 hrs and then at room temperature for 18 hrs. Saturated ammonium chloride (50 mL) is added and then the reaction mixture is diluted with 300 mL of ethyl acetate. The aqueous layer is removed and then the organic layer is washed with additional ammonium chloride (50 mL), followed with brine (50 mL). The organic layer is dried (sodium sulfate), filtered, and then the filtrate is evaporated to provide a yellow oil, which is flash chromatographed (silica gel, 20% ethyl acetate in hexane) to give 2.16 g of a colorless tacky solid as (±)-1-(1-{3-[4-(tert-dimethyl-silanyloxy)-phenyl]-4-phenyl-isoxazol-5-yl}-cyclopropyl)-ethanol; MS (APCI+) m/z 436 (MH$^+$.)

Alternatively, the reaction is stirred at 0° C. for 2 hours only.

Step 2: Deprotection with TBAF

To a stirring solution of (±)-1-(1-{3-[4-(tert-butyl-dimethyl-silanyloxy)-phenyl]-4-phenyl-isoxazol-5-yl}-cyclopropyl)-ethanol, produced in the step above, (662 mg) in dry THF (15 mL) is added tetrabutylammonium fluoride (1.7 mL of a 1 M solution in THF) at room temperature for 1 hour. To the reaction is added saturated ammonium chloride (10 mL), water (75 mL), and ethyl acetate (300 mL). The organic phase is separated and washed with water (75 mL) followed by brine (25 mL.) The organic layer is dried over $MgSO_4$, filtered, and concentrated down to a volume of approximately 5-10 mL ethyl acetate. The mixture is triturated with hexane and is filtered to collect a white solid. The solid is washed with hexane and dried under house high vacuum to obtain the title compound as a white solid (HPLC purity: >99%). The material is recrystallized from hot ethanol-hexanes. Upon cooling in the refrigerator, white crystals form. The first crop of (±)-4-{5-[1-(1-hydroxy-ethyl)-cyclopropyl]-4-phenyl-isoxazol-3-yl}-phenol is filtered and dried under house high vacuum (278 mg.)

LC/MS (Phenomenex Develosil Combi RP3, 50×4.6 mm column, 45° C., 50-2% $H_2O$ over 3.5 min, hold 0.5 min) 254 nm, retention time: 1.60 min, purity: 99%, m/z 322 (MH$^+$);

Microanalysis for $C_{20}H_{19}NO_3$

Calculated: C, 74.75; H, 5.96; N, 4.36.

Found: C, 74.44; H, 6.03; N, 4.41.

Example 199

This example illustrate the transformation of (±)-1-{1-[3-(4-methoxy-phenyl)-4-phenyl-isoxazol-5-yl]-cyclopropyl}-ethanol into (±)-4-{5-[1-(1-hydroxy-ethyl)-cyclopropyl]-4-phenyl-isoxazol-3-yl}-phenol.

A stirring mixture consisting of (±)-1-{1-[3-(4-methoxy-phenyl)-4-phenyl-isoxazol-5-yl]-cyclopropyl}-ethanol, which may be produced as in Example 177 (limiting reagent), 2-diethylamino-ethanethiol hydrochloride (1-2.2 molar equivalents), and a base (2-3.5 molar equivalents) such as sodium tert-butoxide or sodium hydride in N,N-dimethylformamide under an argon atmosphere is brought to reflux for one to sixteen hours. The mixture is treated with saturated aqueous ammonium chloride and extracted with ethyl acetate. The organic phase is washed with water and brine solution and is dried over a drying agent such as anhydrous magnesium sulfate or sodium sulfate. The organic solution is concentrated under reduced pressure and the concentrate is purified by flash silica gel column chromatography.

Example 200

This Example illustrates the preparation of (R)-(−)-4-{5-[1-(1-hydroxy-propyl)-cyclopropyl]-4-phenyl-isoxazol-3-yl}-phenol.

Method A1:

1-(1-{3-[4-(tert-Butyl-dimethyl-silanyloxy)-phenyl]-4-phenyl-isoxazol-5-yl}-cyclopropyl)-propan-1-one, which may be produced as in Example 165 (limiting reagent, 36.93 g) is dissolved in toluene (252 mL) and the solution is added dropwise via addition funnel to a stirring solution of borane-THF complex (74 mL, 1M in THF stabilized with 1,2,2,6,6-pentamethylpiperidine) and (S)—CBS-oxazaborolidine (16 mL, 1 M in toluene) at room temperature. Time addition=4 hours. After addition of the last drop, the mixture is stirred at room temperature over 30 minutes. Cool to 0° C. and add TBAF solution (111 mL, 1 M in THF) portion-wise with vigorous stirring. Allow to stir an additional 30 minutes. The mixture is quenched with ammonium chloride (satd aq, 30 mL) and ethyl acetate (30 mL) is added. The layers are separated and the organics washed with additional saturated ammonium chloride (2×) and brine (2×). The organic layer is dried ($MgSO_4$), filtered and concentrated under reduced pressure to afford a white solid. A solution of hexanes-dichloromethane (1:1 v/v, 500 mL) is added to the solids and stirred for five minutes. The white solids are filtered off and dried open over 19 hours. The solids are dried in the drying oven. Isolate a white solid; 97.84% enantiomeric excess by chiral HPLC (98.92% desired isomer). LCMS indicates 99.4% purity. MS ($APCI^+$) 336.2 ($MH^+$.) The product is dissolved in acetonitrile (approximately 650 mL) and heated until complete dissolution. Water is added until cloudiness persisted (approximately 600 mL). The mixture is heated until a clear solution resulted. The solution was then kept at room temperature over 18 hours. The resulting material is collected by filtration and is dried in a drying oven at 70° C. over three days to afford the title compound; melting point 166.3° C.; specific rotation (Rudolph Research Analytical Model AutoPol IV): $[\alpha]=-51.3°$ in methanol [where cell length=25 mm; C=6.4 mg/mL; observed $\alpha=-0.082°$; $\lambda=598$ nm; t=23.6° C.; $[\alpha]=(4000\times\alpha)/C$]. Collected a second crop of title compound as a white solid; melting point 165.4° C.; specific rotation (Rudolph Research Analytical Model AutoPol IV): $[\alpha]=-46.0°$ in methanol [where cell length=25 mm; C=6.0 mg/mL; observed $\alpha=-0.069°$; $\lambda=598$ nm; T=23.6° C.; $[\alpha]=(4000\times\alpha)/C$].

Alternatively, the starting material 1-(1-{3-[4-(tert-butyl-dimethyl-silanyloxy)-phenyl]-4-phenyl-isoxazol-5-yl}-cyclopropyl)-propan-1-one, which may be produced as in Example 165 is dissolved in dichloromethane or tetrahydrofuran instead of toluene, 0.6 molar equivalent of borane-THF is used instead of 0.9 molar equivalent of borane-THF, 0.1 molar equivalent of (S)—CBS-oxazaborolidine is used instead of 0.2 molar equivalent, and catecholborane is used instead of borane-THF complex. The product is also crystallized from the organic extract, which may comprise ethyl acetate, toluene, tetrahydrofuran, dichloromethane, diethyl ether, or a mixture of any of these solvents. The organic mother liquor solution left over from filtration to collect the crystals is worked up as described in Method A3. The crystals are further recrystallized using recrystallization conditions as described in Method A4. Alternate recrystallization solvents include ethanol and isopropanol instead of acetonitrile.

Method A2:

1-(1-{3-[4-(tert-butyl-dimethyl-silanyloxy)-phenyl]-4-phenyl-isoxazol-5-yl}-cyclopropyl)-propan-1-one (2.4 grams) is combined with toluene (17 mL) and stirred to a solution. Borane-N,N-diethylaniline complex, (0.85 grams), tetrahydrofuran (5 mL) and (S)-2-methyl-CBS-oxazaborolidine, 1 $\underline{M}$ in toluene (7.4 mL) are combined in a separate container and stirred under nitrogen.

The ketone solution is added to the borane solution over 50 minutes at 19° C.-22° C. The mixture is stirred for an additional 2 hour at 20° C.-22° C. Tetrabutylammonium fluoride in THF (1 $\underline{M}$, 7.4 mL) is added. The mixture is stirred for 15 minutes and then quenched with ammonium chloride solution (30 mL containing 14 grams, 26 mmoles ammonium chloride.) The organic layer is separated from the aqueous layer. The aqueous layer is washed with ethyl acetate (30 mL) and the layers are separated. The organic layers are combined, dried over magnesium sulfate and filtered. The filtrate is concentrated by vacuum distillation to an oil. The oil is dissolved in toluene and vacuum distilled to remove water. The residue is dissolved in methanol and vacuum distilled to remove toluene. The resulting oil (3.2 g) is identified as the title compound by HPLC retention time. The purity is determined chemical HPLC (84.1%.)

Method A3:

Organic mother liquor solutions from five experiments utilizing Method A1 or A2 are combined and the combined solutes are purified by flash silica gel column chromatography. Elution on an Isco RediSep silica cartridge (120 g of silica) with hexanes to 40% ethyl acetate in hexanes gradient affords a residue that is treated with chloroform. The mixture stood overnight and is concentrated under reduced pressure. The concentrate is triturated with chloroform and the solids are collected by filtration to afford the title compound; LCMS ($APCI^+$) 336 ($MH^+$); chiral HPLC 90.6% enantiomeric excess.

Method A4:

Seven batches (approximately 10.5 g) of title compound obtained by various alternatives of Method A1 are combined with one bath (approximately 2.6 g) of title compound obtained by Method A3. The combined solids are dissolved in boiling ethanol. Fine insoluble particles are removed by filtration through filter paper. The filtrate is concentrated under reduced pressure to an oil. The oil is dissolved in boiling ethanol. Water is added to the hot solution until cloudiness persists, and ethanol is subsequently added to the hot solution until a clear solution forms again. The solution is subsequently allowed to stand at room temperature for one hour affording a milky solution. The mixture is placed in the refrigerator for one hour. The milky solution persists and is concentrated under reduced pressure to afford a solid. The solid is dissolved in boiling ethanol and water is added until just before persistent cloudiness. Upon standing, the mixture affords a solid that is collected by filtration. The solid is dried in the vacuum oven (50° C.) to afford a solid (9.2 g.) The solid is recrystallized again from ethanol-water. The crystals are collected by vacuum filtration and are rinsed with several milliliters of room-temperature absolute ethanol. The solids are suctioned and further dried in the vacuum oven (60° C.) for four hours to afford the solid title compound; melting point 163-164° C.; MS ($APCI^+$) 336 ($MH^+$); microanalysis for $C_{21}H_{21}NO_3$% C(calculated/found) 75.20/75.14, % H, 6.31/6.35, % N (4.18/4. 12); specific rotation (Rudolph Research Analytical Model AutoPol IV): $[\alpha]=-43.7°$ in methanol [where cell length=25 mm; C=6.0 mg/mL; $\lambda=598$ nm; T=25.2° C.; $[\alpha]=(4000\times\alpha)/C$].

Example 201

This Example illustrates the preparation of (S)-(+)-4-{5-[1-(1-hydroxy-propyl)-cyclopropyl]-4-phenyl-isoxazol-3-yl}-phenol.

Step 1: Deprotection with TBAF

To a solution of (±)-1-(1-{3-[4-(tert-butyl-dimethyl-silanyloxy)-phenyl]-4-phenyl-isoxazol-5-yl}-cyclopropyl)-propan-1-ol, which may be produced as in Example 174 (2.1 g) in 60 mL of anhydrous THF is added tetrabutylammonium fluoride hydrate (2.4 g.) The reaction mixture is stirred at room temperature for 4 hrs. Saturated ammonium chloride (50 mL) is added to the reaction mixture, followed with 300 mL of ethyl acetate. The aqueous layer is separated and then the organic layer is washed with additional saturated ammonium chloride (2×50 mL), followed with brine (50 mL.) The organic layer is dried (sodium sulfate), filtered, and the filtrate is evaporated to give a white solid, which was purified by flash chromatography (silica gel, 40% ethyl acetate in hexane) to afford the white solid (±)-4-{5-{1-(1-hydroxy-propyl)-cyclopropyl]-4-phenyl-isoxazol-3-yl}-phenol; MS (APCI+) m/z 336 (MH$^+$.)

Step 2: Separation of enantiomers by Chiral HPLC

A 1.38 g sample of (±)-4-{5-{1-(1-hydroxy-propyl)-cyclopropyl]-4-phenyl-isoxazol-3-yl}-phenol is submitted for Preparative Chiral Separation (SFC Chiralcel AD-H, 30% cosolvent [90% IPA/10% MeOH], 70% CO$_2$). The enantiomers are returned as dry samples. Each sample is dissolved in a mixture of methanol and ethyl acetate and then filtered to remove any possible insoluble material and then dried to afford 558 mg of a white solid as the (−)-enantiomer and 476 mg of a white solid as the (+)-enantiomer (title compound) (+)-4-{5-{1-(1-hydroxy-propyl)-cyclopropyl]-4-phenyl-isoxazol-3-yl}-phenol; melting point 165-166° C.; MS (APCI+) m/z 336 (MH$^+$); Specific Rotation (Rudolph Research Analytical Model AutoPol IV): [α]=+40.5° in methanol [where cell length=25 mm; C=7.4 mg/mL; observed α=+0.075°; λ=598 nm; T=23.5° C.; [α]=(4000×α)/C].

Example 202

This Example illustrates the preparation of (±)-4-{5-[1-(1-Hydroxy-propyl)-cyclopropyl]-4-phenyl-isoxazol-3-yl}-phenol.

Method A:

Step 1: Ethyl Grignard addition to aldehyde

A solution of 1-{3-[4-(tert-butyl-dimethyl-silanyloxy)-phenyl]-4-phenyl-isoxazol-5-yl}-cyclopropanecarbaldehyde, which may be produced as in Example 172 (20.38 g) in 300 mL tetrahydrofuran under an N$_2$ atmosphere is cooled to 0° C. Ethylmagnesium bromide (53.4 mL, 1.0 M/methyl tert-butyl ether) is added over approximately 15 minutes. The reaction is stirred at 0° C. for 1 hour, 10 minutes. Saturated ammonium chloride (~600 mL) is added and the product is extracted into ethyl acetate two times. The combined organic extracts are washed with brine, dried over anhydrous magnesium sulfate, filtered, and concentrated. The crude material is purified by column chromatography (15% followed by 20% ethyl acetate/hexane) to obtain a viscous oil that partially solidified under house vacuum. The material is dried in a 50° C. vacuum oven for approximately 1 hour to give (±)-1-(1-{3-[4-(tert-butyl-dimethyl-silanyloxy)-phenyl]-4-phenyl-isoxazol-5-yl}-cyclopropyl)-propan-1-ol as a waxy off-white solid.

Alternatively, the reaction is warmed to room temperature and stirred for an additional 24 hours.

LCMS (Phenomenex Develosil Combi RP3, 50×4.6 mm column, 45° C., 10-2% H$_2$O over 3.5 min, hold 0.5 min) 214 nm, retention time: 2.292 min, purity: 100%, m/z 450 (MH$^+$.)

Step 2: Deprotection with TBAF

To a solution of (+/−)-1-(1-{3-[4-(tert-butyl-dimethyl-silanyloxy)-phenyl]-4-phenyl-isoxazol-5-yl}-cyclopropyl)-propan-1-ol, which may be produced as above (3.73 g) in 20 mL tetrahydrofuran under an N$_2$ atmosphere is added tetrabutylammonium fluoride (9.1 mL, 1.0 M/tetrahydrofuran.) The reaction is stirred at room temperature for 1 hour. Saturated ammonium chloride is added and the product is extracted into ethyl acetate two times. The combined organic extracts are washed with brine, dried over anhydrous magnesium sulfate, filtered and concentrated. The crude material is purified by column chromatography (35% ethyl acetate/hexane). The title compound, (±)-4-{5-[1-(1-Hydroxy-propyl)-cyclopropyl]-4-phenyl-isoxazol-3-yl}-phenol, is isolated as a white solid. (2.45 g); $^1$H NMR (400 MHz, DMSO-d$_6$) δ ppm 0.62 (2 H, m), 0.83 (5 H, m), 1.33 (1 H, m), 1.50 (1 H, m), 3.25 (1 H, m), 4.84 (1 H, d, J=5.7 Hz), 6.68 (2 H, d, J=8.4 Hz), 7.10 (2 H, d, J=8.4 Hz), 7.30 (2 H, m), 7.38 (3 H, m), 9.75 (1 H, s.)

Method B:

1-{1-[3-(4-Methoxy-phenyl)-4-phenyl-isoxazol-5-yl]-cyclopropyl}-propan-1-ol, which may be produced as in Example 178B (21.09 g) is dissolved in 300 mL CH$_2$Cl$_2$, purged with N$_2$, and cooled to an internal temperature of −10° C. in an ice/methanol bath. BBr$_3$ is added over 5 minutes at a rate sufficient to keep the internal temperature below −5° C. After 1 hour, the internal temperature is lowered to −20° C. by the addition of several pieces of dry ice to the bath. Saturated NH$_4$Cl is added at a rate sufficient to keep the internal temperature below −5° C. Water (100 mL) is added and the mixture is allowed to warm to room temperature overnight.

Method C:

1-[3-(4-Hydroxy-phenyl)-4-phenyl-isoxazol-5-yl]-cyclopropanecarbaldehyde, which may be produced as in Example 171 (1.18 g) is dissolved in 15 mL THF, purged with N$_2$, and cooled to 0° C. in an ice bath. Ethylmagnesium bromide (1.0 M in MTBE, 9.66 mL) is added and the ice bath removed. The reaction is allowed to stir at room temperature overnight.

Miscellaneous Functionalization Reactions

Example 203

This example illustrate the preparation of 1-[4-phenyl-3-(4-triisopropylsilanyloxy-phenyl)-isoxazol-5-yl]-cyclopropanecarboxylic acid ethyl ester, from a commercially available starting material.

Step A)

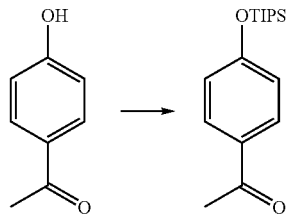

A solution of 1-(4-hydroxyphenyl)-ethanone (50 g) and imidazole (500 g) in 7.5 L THF was purged with N$_2$, treated with triisopropylsilylchloride (779 g) dropwise, and stirred for 20 hours at 35° C. The solids were filtered and washed with THF (2×750 mL.) The filtrate was evaporated under reduced pressure, dissolved in ethyl acetate (5 L), washed with water, sat. NaHCO$_3$, and brine, dried over Na$_2$SO$_4$, and concentrated. The residue was passed through a bed of silica gel washed with hexanes containing 2% triethylamine and eluted with hexanes (3×4 L) and 5% ethyl acetate in hexanes (2×4 L) to give 1060 g of 1-(4-triisopropylsilanyloxy-phenyl)-ethanone.

Step B)

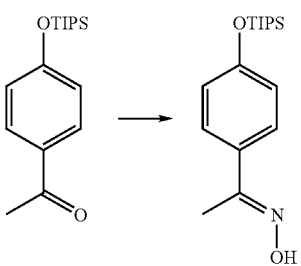

To solution of 1-(4-triisopropylsilanyloxy-phenyl)-ethanone, produced as above, (1060 g) in ethanol (10 L) under an atmosphere of dry N$_2$ was added sodium acetate (371 g) and hydroxylamine hydrochloride (302 g) in portions. The reaction solution was stirred at room temperature then 60° C. for 20 hours, cooled to room temperature, and concentrated. The residue was diluted with 6 L of ethyl acetate, washed with water and brine, dried over Na$_2$SO$_4$ and evaporated. The residue was suspended in 5% ethyl acetate in hexanes (5 L) and filtered through a small bed of silica gel and evaporated to afford 1-(4-triisopropylsilanyloxy-phenyl)-ethanone oxime as a colorless, turbid, semi-solid, 900 g.

Step C)

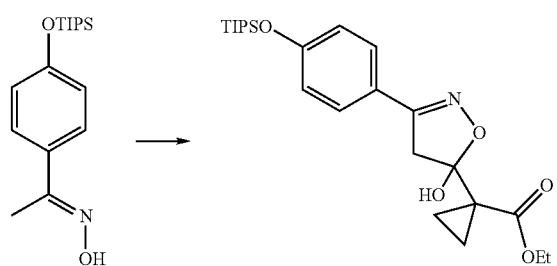

A solution of 1-(4-triisopropylsilanyloxy-phenyl)-ethanone oxime, produced as above, (519 g) in 3.6 L of THF was purged with N$_2$ and cooled to −70° C. Lithium diisopropylamide (2 M in THF, 2.53 L) was added dropwise over 4 hours maintaining a temperature between −70 and −40° C. for another 4 hours. The reaction was cooled to −70° C. and cyclopropane diethylcarboxylate (377 g) was added over 2 hours. The reaction mixture was allowed to warm to ambient temperature overnight and then added to 2.5 L of sat. NH$_4$Cl. The mixture was extracted with ethyl acetate (3 L, then 3×1 L.) The combined organic extracts were washed with water, 1 M HCl (2×1 L), water, and brine, dried over Na$_2$SO$_4$, filtered, and evaporated to give 1.2 Kg of the crude product. The residue was purified by silica gel chromatography eluting with 0 to 25% ethyl acetate in hexanes to provide 320 g of 1-[5-hydroxy-3-(4-triisopropylsilanyloxy-phenyl)-4,5-dihydro-isoxazol-5-yl]-cyclopropanecarboxylic acid ethyl ester as a light-brown liquid after evaporation.

Step D)

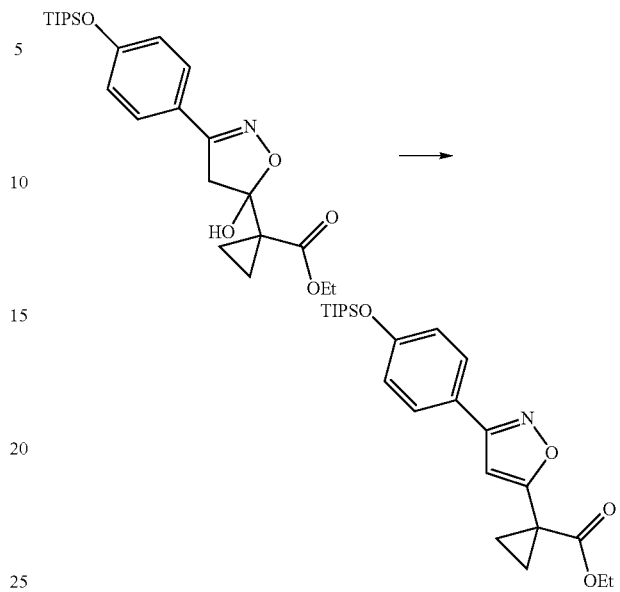

A solution of 1-[5-hydroxy-3-(4-triisopropylsilanyloxy-phenyl)-4,5-dihydro-isoxazol-5-yl]-cyclopropanecarboxylic acid ethyl ester, produced as above, (320 g) in toluene (3 L) containing PTSA (10.0 g) was heated at reflux for 1 hour. The reaction was cooled to room temperature, diluted with ether (500 mL), poured into cold sat. NaHCO$_3$ (500 mL), and stirred. The layers were separated, and the organic layer was washed with brine, dried over Na$_2$SO$_4$, and concentrated to a thick paste which upon fast chromatography over silica gel using 5% ethyl acetate in hexanes afforded 1-[3-(4-triisopropylsilanyloxy-phenyl)-isoxazol-5-yl]-cyclopropanecarboxylic acid ethyl ester (298 g) as a light-brown thick liquid.

Step E)

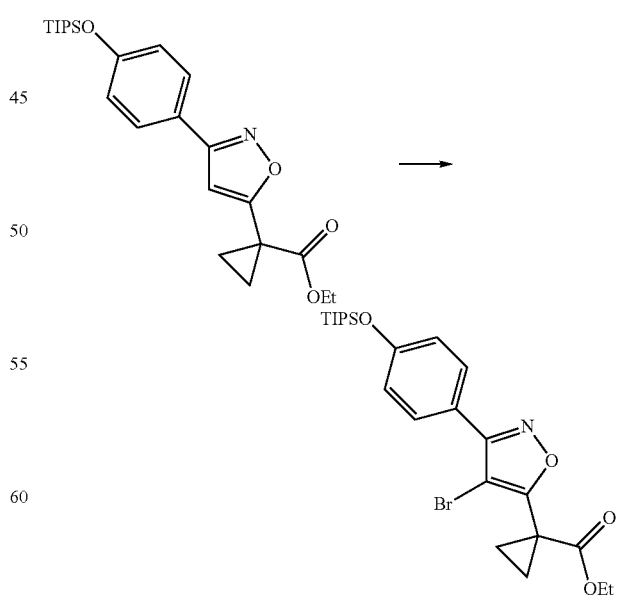

A solution of 1-[3-(4-triisopropylsilanyloxy-phenyl)-isoxazol-5-yl]-cyclopropanecarboxylic acid ethyl ester (288 g) in 3 L DMF was cooled to 5° C. under an atmosphere of $N_2$. The reaction solution was treated with N-bromosuccinimide (131.5 g) and allowed to slowly warm to room temperature over 20 hours. The reaction mixture was concentrated under reduced pressure. The residue was dissolved in ethyl acetate (2 L), cooled to −15° C., and quenched with 10% sodium metabisulfite solution (150 mL) with stirring. The organic layer was separated, washed with sat. $NaHCO_3$ (250 mL) and brine (250 mL), dried over $Na_2SO_4$, filtered, and evaporated. The residue was purified by column chromatography (0 to 20% ethyl acetate in hexanes) to afford 1-[4-bromo-3-(4-triisopropylsilanyloxy-phenyl)-isoxazol-5-yl]-cyclopropanecarboxylic acid ethyl ester (285 g) as a light-brown thick liquid.

Example 204

This Example illustrates the preparation of {1-[4-bromo-3-(4-triisopropylsilanyloxy-phenyl)-isoxazol-5-yl]-cyclopropyl}-methanol.

Example 204A

To a stirring solution comprised of 1-[4-bromo-3-(4-triisopropylsilanyloxy-phenyl)-isoxazol-5-yl]-cyclopropanecarboxylic acid ethyl ester which may be produced as in Example 203 (10 g) in dichloromethane (150 mL) at −78° C. under a nitrogen stream is added the 1.0 $\underline{M}$ diisobutylaluminum hydride (DIBAL-H) in hexane solution (41 mL.) The reaction mixture is gradually warmed to room temperature as the dry ice in the cold bath dissipates overnight (14 hours.) The reaction mixture is cooled to 0° C. with an ice-water bath and to the stirring yellow solution under a positive nitrogen stream is slowly added methanol (60 mL) via syringe over about a ten minute period. The cloudy suspension is then poured into a saturated aqueous sodium bicarbonate solution (350 mL) and the mixture is stirred vigorously in a 1 L Erlenmeyer flask for 30 minutes. The biphasic mixture is diluted with additional dichloromethane (300 mL) and is de-emulsified with the addition of 50% wt/v aqueous potassium sodium tartrate solution (200 mL.) The organic phase is separated and dried over anhydrous magnesium sulfate and is concentrated to afford a cloudy oil (10.00 g.) This crude product is purified by flash silica chromatography. Elution through a 330-g RediSep silica cartridge with a gradient (100% hexanes to 30% ethyl acetate over 200l mL, then 30% to 75% ethyl acetate over another 200l mL) affords the clear oil (7.06 g.) The purified product is reconstituted in chloroform and is reconcentrated under reduced pressure to afford the title compound as an oil. $^1$H-NMR (400 MHz; $CDCl_3$) δ 7.68 (m, 2H), 6.95 (m, 2H), 3.81 (s, 2H), 1.86 (broad s, 1H), 1.27 (m, 5H), 1.10 (d, 18 H, J=7.2 Hz), 1.04 (m, 2H); MS (APCI$^+$) 466 (MH$^+$.)

Example 204B

A solution of 1-[4-bromo-3-(4-triisopropylsilanyloxy-phenyl)-isoxazol-5-yl]-cyclopropanecarboxylic acid ethyl ester, produced as in Example 203, (2.10 g) in 20 mL THF is purged with $N_2$ and cooled to −10° C. Lithium aluminum hydride (1.0 $\underline{M}$ in THF, 8.26 mL) is added over 5 minutes. After 30 minutes, the reaction is carefully quenched with sat. $NH_4Cl$ followed by water and ethyl acetate. LC/MS indicates no desired product, only the 4-des Br product, 1-[3-(4-triisopropylsilanyloxy-phenyl)-isoxazol-5-yl]-cyclopropanecarboxylic acid ethyl ester.

Example 205

This Example illustrates the preparation of 1-[4-phenyl-3-(4-triisopropylsilanyloxy-phenyl)-isoxazol-5-yl]-cyclopropanecarboxylic acid ethyl ester.

To a microwave vial charged with phenylboronic acid (0.0240 g) and a magnetic stir bar is added a solution consisting of 1-[4-bromo-3-(4-triisopropylsilanyloxy-phenyl)-isoxazol-5-yl]-cyclopropanecarboxylic acid ethyl ester, which may be produced as in Example 203 in (0.100 g) in absolute ethanol (0.5 mL) followed by a 2.5 $\underline{M}$ sodium carbonate solution and palladium(0) tetrakis-triphenylphosphine (0.0114 g.) The vial is sealed and the mixture loaded into the microwave. The mixture is stirred with an internal temperature of 150° C. for seven minutes. The solvent is removed under reduced pressure and the product is purified by chromatography such as flash silica gel column chromatography or by preparatory HPLC (reverse phase.)

Example 206

This Example illustrates the preparation of 4-[5-(1-hydroxymethyl-cyclopropyl)-4-phenyl-isoxazol-3-yl]-phenol.

To a microwave vial charged with phenylboronic acid (0.0183 g) and a magnetic stir bar is added a solution consisting of {1-[4-bromo-3-(4-triisopropylsilanyloxy-phenyl)-isoxazol-5-yl]-cyclopropyl}-methanol, which may be produced as in Example 204, (0.0700 g) in absolute ethanol (2 mL) followed by a 2.5 $\underline{M}$ sodium carbonate solution (0.33 mL) and palladium(0) tetrakis-triphenylphosphine (approximately 9 mg.) The vial is sealed and the mixture loaded into the microwave. The mixture is stirred with an internal temperature of 150° C. for seven minutes. The solvent is removed under reduced pressure and the product is purified by chromatography such as flash silica gel column chromatography or by preparatory HPLC (reverse phase.)

Example 207

Preparation of racemic 1-{1-[3-(4-Benzyloxy-phenyl)-4-phenyl-isoxazol-5-yl]-cyclopropyl}-ethanol from 1-{1-[3-(4-Benzyloxy-phenyl)-4-phenyl-isoxazol-5-yl]-cyclopropyl}-ethanone

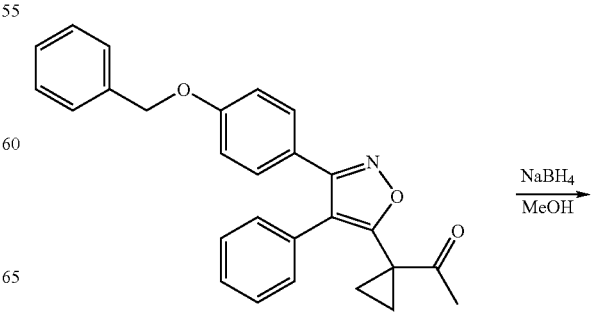

-continued

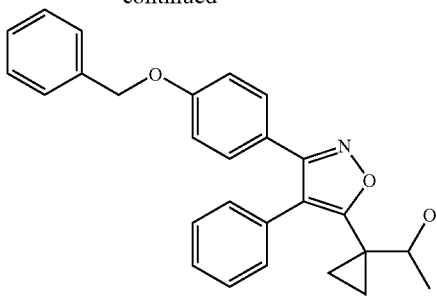

A 20 mL glass vial is charged with a stir bar, 0.735 g of the ketone substrate, which may be produced as in Example 167 or 168, and 7.4 mL of methanol. The mixture is stirred and 0.121 g of sodium borohydride is added in portions. The mixture is stirred overnight. Another 0.197 g of sodium borohydride is added in portions and then the mixture is stirred for an additional 5 hours. The reaction is quenched by the addition of 10 mL of water and then transferred to a separatory funnel with 50 mL of MTBE and 25 mL of water. The layers are separated and the organic layer is washed twice with 25 mL of water. The organic layer is concentrated at the Rotavap. The white solids are redissolved in 50 mL of MTBE and then concentrated at the Rotavap again for 0.72 g.

What is claimed is:

1. (±)-4-{5-[1-(1-Hydroxy-ethyl)-cyclopropyl]-4-phenyl-isoxazol-3-yl}-phenol, or a pharmaceutically acceptable salt thereof.

2. (R)-(−)-4-{5-[1-(1-Hydroxy-ethyl)-cyclopropyl]-4-phenyl-isoxazol-3-yl}-phenol, or a pharmaceutically acceptable salt thereof.

3. (S)-(+)-4-{5-[1-(1-Hydroxy-ethyl)-cyclopropyl]-4-phenyl-isoxazol-3-yl}-phenol, or a pharmaceutically acceptable salt thereof.

4. A pharmaceutical composition comprising a compound according to claim 2 in admixture with at least one pharmaceutically acceptable excipient.

5. A topical pharmaceutical composition comprising a compound according to claim 2 in admixture with at least one pharmaceutically acceptable excipient suitable for topical application.

* * * * *